US012668620B2

(12) United States Patent     (10) Patent No.:   US 12,668,620 B2

Moran et al.      (45) Date of Patent:    Jun. 30, 2026

(54) NEUTRALIZING MONOCLONAL ANTI-VP1 ANTIBODIES TO BK VIRUS

(71) Applicant: Icahn School of Medicine at Mount Sinai, New York, NY (US)

(72) Inventors: Thomas M. Moran, New York, NY (US); Thomas A. Kraus, New York, NY (US); James A. Duty, New York, NY (US); Domenico Tortorella, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 460 days.

(21) Appl. No.: 18/549,974

(22) PCT Filed: Mar. 11, 2022

(86) PCT No.: PCT/US2022/020050

§ 371 (c)(1),
(2) Date: Sep. 11, 2023

(87) PCT Pub. No.: WO2022/192740

PCT Pub. Date: Sep. 15, 2022

(65) Prior Publication Data

US 2025/0304658 A1     Oct. 2, 2025

Related U.S. Application Data

(60) Provisional application No. 63/160,678, filed on Mar. 12, 2021.

(51) Int. Cl.
| | |
|---|---|
| *C07K 16/084* | (2026.01) |
| *A61K 31/343* | (2006.01) |
| *A61K 31/366* | (2006.01) |
| *A61K 31/52* | (2006.01) |
| *A61K 31/5377* | (2006.01) |
| *A61K 38/13* | (2006.01) |
| *A61K 39/00* | (2006.01) |
| *A61P 31/20* | (2006.01) |

(52) U.S. Cl.
CPC .......... *C07K 16/084* (2013.01); *A61K 31/343* (2013.01); *A61K 31/366* (2013.01); *A61K 31/52* (2013.01); *A61K 31/5377* (2013.01); *A61K 38/13* (2013.01); *A61P 31/20* (2018.01); *A61K 2039/54* (2013.01); *C07K 2317/41* (2013.01); *C07K 2317/52* (2013.01); *C07K 2317/565* (2013.01); *C07K 2317/567* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2010/0254975 A1 | 10/2010 | Hsu et al. | |
| 2014/0087362 A1 | 3/2014 | Szalay et al. | |
| 2016/0090427 A1* | 3/2016 | Lee ..................... | C07K 16/22 |
| | | | 435/69.6 |
| 2019/0161553 A1 | 5/2019 | Sather et al. | |
| 2020/0190167 A1 | 6/2020 | Abend et al. | |
| 2020/0384109 A1 | 12/2020 | Abend et al. | |

FOREIGN PATENT DOCUMENTS

| | | | | |
|---|---|---|---|---|
| WO | WO-2006116269 A2 * | 11/2006 | ............... | A61P 3/08 |
| WO | WO-2010107752 A2 * | 9/2010 | ............. | A61P 19/02 |
| WO | WO-2013138241 A1 * | 9/2013 | ............. | C07K 16/40 |
| WO | 2017046676 A1 | 3/2017 | | |
| WO | WO-2017184619 A2 * | 10/2017 | ............. | A61P 37/04 |
| WO | WO-2018112474 A1 * | 6/2018 | ........... | G01N 33/564 |
| WO | WO-2019190931 A1 * | 10/2019 | .......... | C07K 16/205 |
| WO | WO-2022046888 A1 * | 3/2022 | .......... | C07K 16/104 |
| WO | WO-2022170126 A2 * | 8/2022 | .......... | C07K 16/104 |

OTHER PUBLICATIONS

Kovacs Steven J et al: "2367 A 1-15 First-in-Human Study of MAU868, a Novel Neutralizing Antibody Against BK Virus", 62nd Ash Annual Meeting and Exposition, Dec. 6, 2020 (Dec. 6, 2020), pp. 1-1.

Partial Supplementary Search Report for European Patent Application No. 22768138.4 dated Feb. 7, 2025.

International Search Report and Written Opinion dated Aug. 18, 2022 for PCT/US2022/020050, 14 pages.

* cited by examiner

*Primary Examiner* — Julie Wu

*Assistant Examiner* — Amy M. Chattin

(74) *Attorney, Agent, or Firm* — Fox Rothschild LLP

(57) ABSTRACT

Provided herein are monoclonal antibodies targeting VP1 of polyomaviruses including BK virus. Also provided are methods of treating or preventing polyomavirus infections using one or more antibodies.

20 Claims, 11 Drawing Sheets

Specification includes a Sequence Listing.

| Sample of screening | Neutralization | | | | Flow cytometry | | | | | Screening by flow and neutralization |
|---|---|---|---|---|---|---|---|---|---|---|
| | BK1 | BK2 | BK3 | BK4 | BK1 | BK2 | BK3 | BK4 | Median | |
| 1E8 | 16.8 | 5.4 | 1.5 | 1.5 | 10,870 | 7,709 | 5,518 | 12,747 | 1,119 | |
| 2A10 | 1.8 | 2.6 | 1.6 | 1.4 | 12,625 | 15,381 | 13,850 | 14,292 | 1,808 | |
| 2F11 | 15.1 | 2.2 | 0.9 | 0.6 | 9,047 | 11,853 | 10,618 | 14,461 | 2,223 | |
| 3D6 | 1.1 | 1.6 | 1.5 | 1.5 | 19,386 | 16,748 | 11,029 | 19,423 | 3,220 | |
| 3F9 | 2.1 | 1.9 | 17.6 | 0.6 | 9,246 | 11,910 | 2,517 | 13,240 | 1,217 | |
| 3G5 | 1.3 | 18.8 | 17.8 | 0.4 | 23,013 | 6,918 | 2,758 | 15,894 | 1,459 | |
| 4D11 | 0.7 | 20.7 | 20.3 | 1.0 | 9,420 | 10,091 | 1,680 | 8,108 | 1,080 | |
| 4F1 | 2.0 | 1.0 | 0.8 | 0.8 | 12,488 | 15,598 | 13,548 | 16,660 | 2,088 | |
| 6E1 | 2.4 | 18.8 | 21.1 | 1.0 | 16,972 | 8,274 | 3,649 | 13,525 | 1,746 | |
| 8D11 | 1.2 | 17.7 | 20.7 | 1.3 | 17,542 | 9,733 | 4,703 | 13,395 | 3,110 | |
| 10F7 | 14.4 | 1.5 | 0.3 | 1.5 | 5,741 | 13,960 | 9,204 | 17,245 | 1,128 | |
| 11C11 | 1.0 | 3.0 | 22.2 | 1.5 | 12,063 | 19,388 | 2,134 | 12,340 | 1,386 | |
| 12C10 | 1.5 | 1.3 | 19.6 | 1.4 | 10,848 | 15,407 | 1,951 | 15,087 | 1,332 | |
| 12D10 | 1.3 | 1.7 | 26.6 | 0.9 | 12,267 | 15,596 | 1,928 | 13,614 | 1,907 | |
| 12H1 | 1.4 | 1.8 | 22.5 | 1.4 | 8,340 | 13,018 | 1,832 | 12,142 | 1,195 | |

FIG. 9

Cross neutralizing mAb. supernatant

| | | | | | | | | | | | |
|---|---|---|---|---|---|---|---|---|---|---|---|
| Four Genotypes | 2A10 | 1.8 | 2.6 | 1.6 | 1.4 | | 12,625 | 15,361 | 13,850 | 14,292 | 1,808 |
| | 3D6 | 1.1 | 1.6 | 1.5 | 1.5 | | 19,386 | 16,748 | 11,029 | 19,423 | 3,220 |
| | 4F1 | 2.0 | 1.0 | 0.8 | 0.8 | | 12,438 | 15,598 | 13,548 | 16,660 | 2,088 |
| 2, 3, and 4 neut | 1OF7 | 14.4 | 1.5 | 0.3 | 1.5 | | 5,741 | 13,960 | 9,204 | 17,245 | 1,128 |
| | 1E8 | 16.8 | 5.41 | 1.5 | 1.5 | | 10,870 | 7,709 | 5,518 | 12,747 | 1,119 |
| | 2F11 | 15.1 | 2.2 | 0.9 | 0.6 | | 9,047 | 11,853 | 10,618 | 14,461 | 2,223 |
| 1, 2, and 4 neut | 3F9 | 2.1 | 1.9 | 17.6 | 0.6 | | 9,246 | 11,910 | 2,517 | 13,240 | 1,217 |
| | 11C11 | 1.0 | 3.0 | 22.2 | 1.5 | | 12,063 | 19,398 | 2,134 | 12,340 | 1,386 |
| | 12C10 | 1.5 | 1.3 | 19.6 | 1.4 | | 10,848 | 15,407 | 1,951 | 15,087 | 1,332 |
| | 12D10 | 1.3 | 1.7 | 26.6 | 0.9 | | 12,267 | 15,596 | 1,928 | 13,614 | 1,907 |
| | 12H1 | 1.4 | 1.8 | 22.5 | 1.4 | | 8,340 | 13,018 | 1,832 | 12,142 | 1,195 |
| 1 and 4 neut | 3G5 | 1.3 | 18.8 | 17.8 | 0.4 | | 23,013 | 6,918 | 2,758 | 15,894 | 1,459 |
| | 4D11 | 0.7 | 20.7 | 20.3 | 1.0 | | 9,420 | 10,091 | 1,680 | 8,108 | 1,080 |
| | 6E1 | 2.4 | 18.8 | 21.1 | 1.0 | | 16,972 | 8,274 | 3,649 | 13,525 | 1,746 |
| | 8D11 | 1.2 | 17.7 | 20.7 | 1.3 | | 17,542 | 9,793 | 4,703 | 13,395 | 3,110 |

SEQUENCE LISTING

```
<160> NUMBER OF SEQ ID NOS: 529

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Phe Thr Phe Ser Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 2

Ile Asp Ser Ser Ala Gly Ala Ile
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Ala Arg Glu Arg Arg Asp Gly His Lys Ile Phe Asp Cys
1               5               10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Gln Asn Ile Leu Tyr Ser Ser Asn Asn Lys Asn Tyr
1               5               10

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Trp Ser Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Tyr Tyr Ser Ser Pro Tyr Asn
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Gln Val Gln Leu Val Glu Ser Gly Gly Asp Leu Val Lys Pro Gly Gly
1               5               10              15

Ser Leu Arg Leu Ser Cys Val Ala Ser Gly Phe Thr Phe Ser Asp Tyr
            20              25              30

Tyr Met Asn Trp Ile Arg Leu Pro Pro Gly Lys Gly Leu Glu Trp Val
        35              40              45

Ser Tyr Ile Asp Ser Ser Ala Gly Ala Ile Tyr Tyr Ala Asp Ser Val
    50              55              60
```

```
Arg Gly Arg Phe Thr Val Ser Arg Asp Asp Ala Lys Asn Ser Leu Phe
65                  70                  75                  80

Leu His Met Asn Ser Leu Arg Ala Asp Asp Thr Ala Val Tyr Tyr Cys
                    85                  90                  95

Ala Arg Glu Arg Arg Asp Gly His Lys Ile Phe Asp Cys Trp Gly Pro
                100                 105                 110

Gly Thr Leu Val Thr Val Ser Ser
            115                 120

<210> SEQ ID NO 8
<211> LENGTH: 113
<212> TYPE: PRT
<213> ORGANISM: Artificial Sequence
<220> FEATURE:
<223> OTHER INFORMATION: Synthetic

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
                20                  25                  30

Ser Asn Asn Lys Asn Tyr Leu Ala Trp Tyr Gln Gln Lys Ala Gly Gln
            35                  40                  45

Pro Pro Lys Leu Leu Ile Phe Trp Ser Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
            100                 105                 110

Lys

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Phe Thr Phe Ser Asp Tyr Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Ile Asp Ser Ser Ala Gly Ala Ile
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic
```

```
<400> SEQUENCE: 11

Ala Arg Glu Arg Arg Asp Gly His Lys Ile Phe Asp Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Asn Ile Leu Tyr Ser Ser Asn Asn Lys Asn Tyr
1               5                   10

<210> SEQ ID NO 13
<211> LENGTH: 3
<212> TYPE: PRT
<213> ORGANISM: Artificial Sequence
<220> FEATURE:
<223> OTHER INFORMATION: Synthetic

<400> SEQUENCE: 13

Trp Ser Ser
1

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Gln Gln Tyr Tyr Ser Ser Pro Tyr Asn
1               5

<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

Gln Val His Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Met Pro Pro Gly Lys Gly Leu Glu Trp Ile
        35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Leu Phe
65                  70                  75                  80

Leu His Met Asn Asn Leu Arg Ala Asp Asp Thr Ala Val Tyr Tyr Cys
                85                  90                  95

Ala Arg Glu Arg Arg Asp Gly His Lys Ile Phe Asp Cys Trp Gly Pro
            100                 105                 110

Gly Thr Leu Val Thr Val Ser Ser
        115                 120
```

-continued

<210> SEQ ID NO 16
<211> LENGTH: 113
<212> TYPE: PRT
<213> ORGANISM: Artificial Sequence
<220> FEATURE:
<223> OTHER INFORMATION: Synthetic

<400> SEQUENCE: 16

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asn Asn Lys Asn Tyr Leu Ala Trp Tyr Gln Gln Lys Ala Gly Gln
        35                  40                  45

Pro Pro Lys Leu Leu Ile Phe Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
            100                 105                 110

Lys
```

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

```
Gly Tyr Ser Phe Thr Tyr Tyr Trp
1               5
```

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

```
Ile Tyr Pro Gly Asp Ser Asp Thr
1               5
```

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

```
Thr Thr His Ala Arg Asn Trp Asn Asn Val Ala Tyr
1               5                   10
```

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Asn Ile Asn Thr Phe
1               5

<210> SEQ ID NO 21
<211> LENGTH: 3
<212> TYPE: PRT
<213> ORGANISM: Artificial Sequence
<220> FEATURE:
<223> OTHER INFORMATION: Synthetic

<400> SEQUENCE: 21

Ala Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Gln Gln Ser Ser Ser Thr Pro Trp Thr
1               5

<210> SEQ ID NO 23
<211> LENGTH: 119
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Tyr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Thr His Ala Arg Asn Trp Asn Asn Val Ala Tyr Trp Gly Gln Gly
            100                 105                 110

Thr Leu Val Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

-continued

```
Asp Arg Leu Thr Ile Thr Cys Arg Ala Ser Gln Asn Ile Asn Thr Phe
            20                  25                  30

Leu Asn Trp Tyr Gln Gln Asn Pro Gly Lys Ala Pro Lys Val Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Thr Pro Trp
                85                  90                  95

Thr Phe Gly Gln Gly Thr Lys Val Glu Ile Lys
            100                 105
```

```
<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Gly Phe Thr Phe Ser Gly Phe Ala
1               5
```

```
<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Ile Ser Gly Ser Gly Asp Ile Thr
1               5
```

```
<210> SEQ ID NO 27
<211> LENGTH: 16
<212> TYPE: PRT
<213> ORGANISM: Artificial Sequence
<220> FEATURE:
<223> OTHER INFORMATION: Synthetic

<400> SEQUENCE: 27

Ala Lys Asp Pro Tyr Asn Trp Asn His Gly Val Tyr Gly Met Asp Val
1               5                   10                  15
```

```
<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Tyr
1               5
```

```
<210> SEQ ID NO 29
<211> LENGTH: 3
<212> TYPE: PRT
<213> ORGANISM: Artificial Sequence
<220> FEATURE:
<223> OTHER INFORMATION: Synthetic

<400> SEQUENCE: 29
```

Gly Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gln Gln Ser Phe Asn Ala Pro Leu Thr
1               5

<210> SEQ ID NO 31
<211> LENGTH: 123
<212> TYPE: PRT
<213> ORGANISM: Artificial Sequence
<220> FEATURE:
<223> OTHER INFORMATION: Synthetic

<400> SEQUENCE: 31

Glu Val Gln Leu Leu Glu Ser Gly Gly Gly Leu Ala Gln Pro Gly Lys
1               5                   10                  15

Ser Leu Arg Leu Ser Cys Ala Ala Ser Gly Phe Thr Phe Ser Gly Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Ile Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Gly Ala Glu Asp Thr Ala Val Tyr Tyr Cys
                85                  90                  95

Ala Lys Asp Pro Tyr Asn Trp Asn His Gly Val Tyr Gly Met Asp Val
            100                 105                 110

Trp Gly Gln Gly Thr Thr Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Phe Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Ser Phe Asn Ala Pro Leu
                85                  90                  95

-continued

```
Thr Phe Gly Gly Gly Thr Lys Val Glu Ile Lys
        100                 105

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Gly Phe Thr Phe Ser Asp Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Ile Asp Ser Ser Ala Gly Ala Ile
1               5

<210> SEQ ID NO 35
<211> LENGTH: 13
<212> TYPE: PRT
<213> ORGANISM: Artificial Sequence
<220> FEATURE:
<223> OTHER INFORMATION: Synthetic

<400> SEQUENCE: 35

Ala Arg Glu Arg Arg Asp Gly His Lys Ile Phe Asp Trp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Gln Asn Ile Leu Tyr Thr Ser Asn Asn Lys Asn Tyr
1               5                   10

<210> SEQ ID NO 37
<211> LENGTH: 3
<212> TYPE: PRT
<213> ORGANISM: Artificial Sequence
<220> FEATURE:
<223> OTHER INFORMATION: Synthetic

<400> SEQUENCE: 37

Trp Ser Ser
1

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

His Gln Tyr Tyr Ser Ser Pro Tyr Thr
```

```
1                5
```

<210> SEQ ID NO 39
<211> LENGTH: 120
<212> TYPE: PRT
<213> ORGANISM: Artificial Sequence
<220> FEATURE:
<223> OTHER INFORMATION: Synthetic

<400> SEQUENCE: 39

```
Gln Val Gln Leu Val Glu Ser Gly Gly Gly Leu Val Lys Pro Gly Gly
1                5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Arg Gly Leu Gln Trp Ile
        35                  40                  45

Ser Tyr Ile Asp Ser Ser Ala Gly Ala Ile Tyr Tyr Ala Asp Ser Val
        50                  55                  60

Lys Gly Arg Phe Thr Val Ser Arg Asp Asp Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Arg Arg Asp Gly His Lys Ile Phe Asp Trp Trp Gly Gln
            100                 105                 110

Gly Thr Leu Val Thr Val Ser Ser
        115                 120
```

<210> SEQ ID NO 40
<211> LENGTH: 113
<212> TYPE: PRT
<213> ORGANISM: Artificial Sequence
<220> FEATURE:
<223> OTHER INFORMATION: Synthetic

<400> SEQUENCE: 40

```
Asp Ile Val Met Thr Gln Ser Pro Asp Ser Leu Ala Val Ser Leu Gly
1                5                   10                  15

Glu Arg Ala Thr Ile Asn Cys Lys Ser Ser Gln Asn Ile Leu Tyr Thr
            20                  25                  30

Ser Asn Asn Lys Asn Tyr Leu Gly Trp Tyr Gln Gln Lys Ala Gly Gln
        35                  40                  45

Pro Pro Lys Leu Leu Ile Tyr Trp Ser Ser Thr Arg Asn Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Pro Tyr Thr Phe Gly Gln Gly Thr Asn Leu Glu Ile
            100                 105                 110

Lys
```

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

```
Gly Tyr Ser Phe Thr Asn Tyr Trp
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Ile Tyr Pro Gly Asp Ser Asp Thr
1               5

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Ala Thr His Ala Arg Ser Trp Asn Tyr Val Ala Tyr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Val Asn Asn Phe
1               5

<210> SEQ ID NO 45
<211> LENGTH: 3
<212> TYPE: PRT
<213> ORGANISM: Artificial Sequence
<220> FEATURE:
<223> OTHER INFORMATION: Synthetic

<400> SEQUENCE: 45

Ala Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Gln Gln Ser Asn Thr Thr Pro Trp Thr
1               5

<210> SEQ ID NO 47
<211> LENGTH: 119
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Gln Ser Gly Ala Glu Val Lys Lys Pro Gly Glu
```

-continued

```
1               5                    10                   15

Ser Leu Lys Ile Ser Cys Lys Gly Ser Gly Tyr Ser Phe Thr Asn Tyr
                20                   25                   30

Trp Ile Gly Trp Val Arg Gln Met Pro Gly Lys Gly Leu Glu Trp Met
            35                   40                   45

Gly Ile Ile Tyr Pro Gly Asp Ser Asp Thr Arg Tyr Ser Pro Ser Phe
    50                   55                   60

Gln Gly Gln Val Thr Leu Ser Ala Asp Lys Ser Ile Ser Thr Ala Tyr
65                   70                   75                   80

Leu Gln Trp Asn Ser Leu Lys Ala Ser Asp Thr Ala Met Tyr Tyr Cys
                85                   90                   95

Ala Thr His Ala Arg Ser Trp Asn Tyr Val Ala Tyr Trp Gly Gln Gly
            100                  105                  110

Thr Leu Val Thr Val Ala Ser
        115
```

<210> SEQ ID NO 48
<211> LENGTH: 107
<212> TYPE: PRT
<213> ORGANISM: Artificial Sequence
<220> FEATURE:
<223> OTHER INFORMATION: Synthetic

<400> SEQUENCE: 48

```
Asp Ile Gln Met Thr Gln Ser Pro Ser Ser Leu Ser Ala Ser Val Gly
1               5                    10                   15

Asp Arg Val Thr Ile Thr Cys Arg Ala Ser Gln Ser Val Asn Asn Phe
                20                   25                   30

Leu Asn Trp Tyr Gln Gln Lys Pro Gly Thr Ala Pro Lys Leu Leu Ile
            35                   40                   45

Tyr Ala Ala Ser Ser Leu Gln Gly Gly Val Pro Ser Arg Phe Ser Gly
    50                   55                   60

Ser Gly Ser Gly Thr Asp Phe Thr Leu Thr Ile Ser Ser Leu Gln Pro
65                   70                   75                   80

Glu Asp Phe Ala Thr Tyr Tyr Cys Gln Gln Ser Asn Thr Thr Pro Trp
                85                   90                   95

Thr Phe Gly Gln Gly Thr Lys Val Glu Ile Lys
            100                  105
```

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

```
Gly Phe Thr Phe Ser Asp Tyr Tyr
1               5
```

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

```
Ile Asp Ser Ser Ala Gly Ala Ile
1               5
```

```
<210> SEQ ID NO 51
<211> LENGTH: 13
<212> TYPE: PRT
<213> ORGANISM: Artificial Sequence
<220> FEATURE:
<223> OTHER INFORMATION: Synthetic

<400> SEQUENCE: 51

Ala Arg Glu Arg Arg Asp Gly His Lys Ile Phe Asp Cys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Gln Asn Ile Leu Tyr Ser Ser Asn Asn Lys Asn Tyr
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Synthetic

<400> SEQUENCE: 53

Trp Ser Ser
1

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Gln Gln Tyr Tyr Ser Ser Pro Tyr Asn
1               5

<210> SEQ ID NO 55
<211> LENGTH: 120
<212> TYPE: PRT
<213> ORGANISM: Artificial Sequence
<220> FEATURE:
<223> OTHER INFORMATION: Synthetic

<400> SEQUENCE: 55

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Lys Gly Leu Glu Trp Ile
        35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Leu Phe
65                  70                  75                  80

Leu His Met Asn Ser Leu Arg Ala Asp Asp Thr Ala Val Tyr Tyr Cys
```

-continued

```
                     85                      90                      95

Ala Arg Glu Arg Arg Asp Gly His Lys Ile Phe Asp Cys Trp Gly Pro
                    100                     105                     110

Gly Thr Leu Val Thr Val Ser Ser
            115                 120

<210> SEQ ID NO 56
<211> LENGTH: 113
<212> TYPE: PRT
<213> ORGANISM: Artificial Sequence
<220> FEATURE:
<223> OTHER INFORMATION: Synthetic

<400> SEQUENCE: 56

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
                20                  25                  30

Ser Asn Asn Lys Asn Tyr Leu Ala Trp Tyr Gln Gln Lys Thr Gly Gln
        35                  40                  45

Pro Pro Lys Leu Leu Ile Phe Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
            100                 105                 110

Lys

<210> SEQ ID NO 57
<211> LENGTH: 8
<212> TYPE: PRT
<213> ORGANISM: Artificial Sequence
<220> FEATURE:
<223> OTHER INFORMATION: Synthetic

<400> SEQUENCE: 57

Gly Phe Thr Phe Asp Asp Tyr Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic

<400> SEQUENCE: 58

Ile Ser Trp Ser Gly Val Thr Met
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Ala Arg Gly Asp Gly Thr Asn Ala Phe Asp Ile
1               5                   10
```

<210> SEQ ID NO 60
<211> LENGTH: 12
<212> TYPE: PRT
<213> ORGANISM: Artificial Sequence
<220> FEATURE:
<223> OTHER INFORMATION: Synthetic

<400> SEQUENCE: 60

Gln Ser Val Leu Tyr Lys Ser Asn Asn Lys Asn Tyr
1               5                   10

<210> SEQ ID NO 61
<211> LENGTH: 3
<212> TYPE: PRT
<213> ORGANISM: Artificial Sequence
<220> FEATURE:
<223> OTHER INFORMATION: Synthetic

<400> SEQUENCE: 61

Trp Ala Ser
1

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Gln Gln Tyr Tyr Ser Val Pro Leu Thr
1               5

<210> SEQ ID NO 63
<211> LENGTH: 118
<212> TYPE: PRT
<213> ORGANISM: Artificial Sequence
<220> FEATURE:
<223> OTHER INFORMATION: Synthetic

<400> SEQUENCE: 63

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Gly Pro Gly Lys Gly Leu Glu Trp Val
        35                  40                  45

Ser Gly Ile Ser Trp Ser Gly Val Thr Met Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Arg Met Asn Ser Leu Arg Ala Asp Asp Thr Ala Phe Tyr Tyr Cys
                85                  90                  95

Ala Arg Gly Asp Gly Thr Asn Ala Phe Asp Ile Trp Gly His Gly Thr
            100                 105                 110

Met Val Thr Val Ser Ser
        115

<210> SEQ ID NO 64
<211> LENGTH: 113
<212> TYPE: PRT
<213> ORGANISM: Artificial Sequence
<220> FEATURE:
<223> OTHER INFORMATION: Synthetic

<400> SEQUENCE: 64

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Lys
            20                  25                  30

Ser Asn Asn Lys Asn Tyr Leu Asp Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Val Pro Leu Thr Phe Gly Gly Gly Thr Lys Val Glu Ile
            100                 105                 110

Lys

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Gly Phe Thr Phe Ser Asp Tyr Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Ile Asp Ser Ser Ala Gly Ala Ile
1               5

<210> SEQ ID NO 67
<211> LENGTH: 13
<212> TYPE: PRT
<213> ORGANISM: Artificial Sequence
<220> FEATURE:
<223> OTHER INFORMATION: Synthetic

<400> SEQUENCE: 67

Ala Arg Glu Arg Arg Asp Gly His Lys Ile Phe Asp Cys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Gln Asn Ile Leu Tyr Ser Ser Asn Asn Lys Asn Tyr
1               5                   10

```
<210> SEQ ID NO 69
<211> LENGTH: 3
<212> TYPE: PRT
<213> ORGANISM: Artificial Sequence
<220> FEATURE:
<223> OTHER INFORMATION: Synthetic

<400> SEQUENCE: 69

Trp Ser Ser
1

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Gln Gln Tyr Tyr Ser Ser Pro Tyr Asn
1               5

<210> SEQ ID NO 71
<211> LENGTH: 120
<212> TYPE: PRT
<213> ORGANISM: Artificial Sequence
<220> FEATURE:
<223> OTHER INFORMATION: Synthetic

<400> SEQUENCE: 71

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Lys Gly Leu Glu Trp Ile
        35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Leu Phe
65                  70                  75                  80

Leu His Met Asn Asn Leu Arg Ala Asp Asp Thr Ala Val Tyr Tyr Cys
                85                  90                  95

Ala Arg Glu Arg Arg Asp Gly His Lys Ile Phe Asp Cys Trp Gly Pro
            100                 105                 110

Gly Thr Leu Val Thr Val Ser Ser
        115                 120

<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asn Asn Lys Asn Tyr Leu Ala Trp Tyr Gln Gln Lys Ala Gly Gln
        35                  40                  45
```

```
Pro Pro Lys Leu Leu Ile Phe Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
            100                 105                 110

Lys

<210> SEQ ID NO 73
<211> LENGTH: 8
<212> TYPE: PRT
<213> ORGANISM: Artificial Sequence
<220> FEATURE:
<223> OTHER INFORMATION: Synthetic

<400> SEQUENCE: 73

Gly Phe Thr Phe Ser Asp Tyr Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic

<400> SEQUENCE: 74

Ile Asp Ser Ser Ala Gly Ala Ile
1               5

<210> SEQ ID NO 75
<211> LENGTH: 13
<212> TYPE: PRT
<213> ORGANISM: Artificial Sequence
<220> FEATURE:
<223> OTHER INFORMATION: Synthetic

<400> SEQUENCE: 75

Ala Arg Glu Arg Arg Asp Gly His Lys Ile Phe Asp Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic

<400> SEQUENCE: 76

Gln Asn Ile Leu Tyr Ser Ser Asn Asn Lys Asn Tyr
1               5                   10

<210> SEQ ID NO 77
<211> LENGTH: 3
<212> TYPE: PRT
<213> ORGANISM: Artificial Sequence
<220> FEATURE:
<223> OTHER INFORMATION: Synthetic

<400> SEQUENCE: 77

Trp Ser Ser
1
```

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

His Gln Tyr Tyr Ser Ser Pro Tyr Asn
1               5

<210> SEQ ID NO 79
<211> LENGTH: 120
<212> TYPE: PRT
<213> ORGANISM: Artificial Sequence
<220> FEATURE:
<223> OTHER INFORMATION: Synthetic

<400> SEQUENCE: 79

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Arg Gly Leu Glu Trp Ile
            35                  40                  45

Ser Tyr Ile Asp Ser Ser Ala Gly Ala Ile Tyr Tyr Ala Asp Ser Val
        50                  55                  60

Lys Gly Arg Phe Thr Val Ser Arg Asp Asp Ala Lys Lys Ser Leu Phe
65                  70                  75                  80

Leu Tyr Met Asn Ser Leu Arg Ala Asp Asp Thr Ala Val Tyr Tyr Cys
                85                  90                  95

Ala Arg Glu Arg Arg Asp Gly His Lys Ile Phe Asp Tyr Trp Gly Pro
            100                 105                 110

Gly Thr Leu Val Thr Val Ser Ser
        115                 120

<210> SEQ ID NO 80
<211> LENGTH: 113
<212> TYPE: PRT
<213> ORGANISM: Artificial Sequence
<220> FEATURE:
<223> OTHER INFORMATION: Synthetic

<400> SEQUENCE: 80

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asn Asn Lys Asn Tyr Leu Ala Trp Tyr Gln Gln Lys Ala Gly Gln
        35                  40                  45

Pro Pro Lys Leu Leu Ile Phe Trp Ser Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Pro Tyr Asn Phe Gly Arg Gly Thr Thr Leu Glu Ile
            100                 105                 110

Lys

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Gly Phe Thr Phe Ser Ser Phe Ala
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Ile Ser Gly Ser Gly Gly Ser Thr
1               5

<210> SEQ ID NO 83
<211> LENGTH: 16
<212> TYPE: PRT
<213> ORGANISM: Artificial Sequence
<220> FEATURE:
<223> OTHER INFORMATION: Synthetic

<400> SEQUENCE: 83

Ala Lys Asp Lys Arg Asn Trp Asn Tyr Gly Ile Asp Ser Phe Asp Phe
1               5                   10                  15

<210> SEQ ID NO 84
<211> LENGTH: 6
<212> TYPE: PRT
<213> ORGANISM: Artificial Sequence
<220> FEATURE:
<223> OTHER INFORMATION: Synthetic

<400> SEQUENCE: 84

Gln Ser Ile Ser Gly Tyr
1               5

<210> SEQ ID NO 85
<211> LENGTH: 3
<212> TYPE: PRT
<213> ORGANISM: Artificial Sequence
<220> FEATURE:
<223> OTHER INFORMATION: Synthetic

<400> SEQUENCE: 85

Ala Thr Ser
1

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

His Gln Ser His Ser Pro Pro Phe Thr
1               5

-continued

<210> SEQ ID NO 87
<211> LENGTH: 123
<212> TYPE: PRT
<213> ORGANISM: Artificial Sequence
<220> FEATURE:
<223> OTHER INFORMATION: Synthetic

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Asp Lys Arg Asn Trp Asn Tyr Gly Ile Asp Ser Phe Asp Phe
            100                 105                 110

Trp Gly Gln Gly Thr Met Val Thr Val Ser Ser
        115                 120

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Ser Leu Ser Ala Ser Val Gly
1               5                   10                  15

Gly Arg Val Thr Ile Thr Cys Arg Thr Ser Gln Ser Ile Ser Gly Tyr
            20                  25                  30

Leu Asn Trp Tyr Gln Gln Lys Ala Gly Lys Ala Pro Lys Leu Leu Ile
        35                  40                  45

Tyr Ala Thr Ser Asn Leu Gln Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys His Gln Ser His Ser Pro Pro Phe
                85                  90                  95

Thr Phe Gly Pro Gly Thr Lys Val Ala Phe Lys
            100                 105

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Gly Phe Thr Phe Ser Ser Tyr Glu
1               5

```
<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Ile Ser Ser Gly Gly Ser Ser Ile
1               5

<210> SEQ ID NO 91
<211> LENGTH: 15
<212> TYPE: PRT
<213> ORGANISM: Artificial Sequence
<220> FEATURE:
<223> OTHER INFORMATION: Synthetic

<400> SEQUENCE: 91

Ala Arg Val Gly Gly Ser Tyr Tyr Tyr Ser Tyr Ala Met Asp Val
1               5                   10                  15

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Asp Ile Ser Ser Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Synthetic

<400> SEQUENCE: 93

Ala Ala Ser
1

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Gln Gln Pro His Asn Ser Pro Phe Ser
1               5

<210> SEQ ID NO 95
<211> LENGTH: 122
<212> TYPE: PRT
<213> ORGANISM: Artificial Sequence
<220> FEATURE:
<223> OTHER INFORMATION: Synthetic

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30

Glu Met Asn Trp Val Arg Gln Ala Pro Gly Lys Gly Leu Glu Trp Val
        35                  40                  45

Ser Tyr Ile Ser Ser Gly Gly Ser Ser Ile Lys Tyr Ala Asp Ser Val
    50                  55                  60

Arg Gly Arg Phe Ala Phe Ser Arg Asp Asn Ala Glu Asn Ser Val His
65                  70                  75                  80

Leu Gln Met Asn Ser Leu Arg Ala Glu Asp Thr Ala Val Tyr Tyr Cys
                85                  90                  95

Ala Arg Val Gly Gly Ser Tyr Tyr Tyr Ser Tyr Ala Met Asp Val Trp
            100                 105                 110

Gly Gln Gly Thr Ala Val Thr Val Ser Ser
            115                 120
```

```
<210> SEQ ID NO 96
<211> LENGTH: 107
<212> TYPE: PRT
<213> ORGANISM: Artificial Sequence
<220> FEATURE:
<223> OTHER INFORMATION: Synthetic

<400> SEQUENCE: 96

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Thr Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Pro His Asn Ser Pro Phe
                85                  90                  95

Ser Phe Gly Pro Gly Thr Lys Val Asp Val Lys
            100                 105
```

```
<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Gly Phe Thr Phe Ser Asp Tyr Tyr
1               5
```

```
<210> SEQ ID NO 98
<211> LENGTH: 8
<212> TYPE: PRT
<213> ORGANISM: Artificial Sequence
<220> FEATURE:
<223> OTHER INFORMATION: Synthetic

<400> SEQUENCE: 98

Ile Asp Ser Ser Ala Gly Ala Ile
1               5
```

```
<210> SEQ ID NO 99
```

<211> LENGTH: 13
<212> TYPE: PRT
<213> ORGANISM: Artificial Sequence
<220> FEATURE:
<223> OTHER INFORMATION: Synthetic

<400> SEQUENCE: 99

Val Arg Glu Arg Arg Asp Gly His Lys Ile Phe Asp Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100

Gln Asn Ile Leu Tyr Ser Ser Asn Asn Lys Asn Tyr
1               5                   10

<210> SEQ ID NO 101
<211> LENGTH: 3
<212> TYPE: PRT
<213> ORGANISM: Artificial Sequence
<220> FEATURE:
<223> OTHER INFORMATION: Synthetic

<400> SEQUENCE: 101

Trp Ser Ser
1

<210> SEQ ID NO 102
<211> LENGTH: 9
<212> TYPE: PRT
<213> ORGANISM: Artificial Sequence
<220> FEATURE:
<223> OTHER INFORMATION: Synthetic

<400> SEQUENCE: 102

Gln Gln Tyr Tyr Ser Ser Pro Tyr Asn
1               5

<210> SEQ ID NO 103
<211> LENGTH: 120
<212> TYPE: PRT
<213> ORGANISM: Artificial Sequence
<220> FEATURE:
<223> OTHER INFORMATION: Synthetic

<400> SEQUENCE: 103

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Lys Gly Leu Glu Trp Ile
        35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Leu Phe
65                  70                  75                  80

Leu His Met Asn Ser Leu Arg Ala Asp Asp Thr Ala Val Tyr Tyr Cys
                85                  90                  95

Val Arg Glu Arg Arg Asp Gly His Lys Ile Phe Asp Tyr Trp Gly Pro

-continued

```
            100                 105                 110

Gly Thr Leu Val Thr Val Ser Ser
        115                 120

<210> SEQ ID NO 104
<211> LENGTH: 113
<212> TYPE: PRT
<213> ORGANISM: Artificial Sequence
<220> FEATURE:
<223> OTHER INFORMATION: Synthetic

<400> SEQUENCE: 104

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asn Asn Lys Asn Tyr Leu Ala Trp Tyr Gln Gln Lys Ala Gly Gln
        35                  40                  45

Pro Pro Lys Leu Leu Ile Phe Trp Ser Ser Ile Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
            100                 105                 110

Lys

<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Gly Phe Thr Phe Ser Gly Phe Ala
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic

<400> SEQUENCE: 106

Ile Ser Gly Ser Gly Asp Ile Thr
1               5

<210> SEQ ID NO 107
<211> LENGTH: 16
<212> TYPE: PRT
<213> ORGANISM: Artificial Sequence
<220> FEATURE:
<223> OTHER INFORMATION: Synthetic

<400> SEQUENCE: 107

Gly Lys Asp Pro Tyr Asn Trp Asn His Gly Val Tyr Gly Met Asp Val
1               5                   10                  15

<210> SEQ ID NO 108
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Thr Tyr
1               5

<210> SEQ ID NO 109
<211> LENGTH: 3
<212> TYPE: PRT
<213> ORGANISM: Artificial Sequence
<220> FEATURE:
<223> OTHER INFORMATION: Synthetic

<400> SEQUENCE: 109

Gly Ala Ser
1

<210> SEQ ID NO 110
<211> LENGTH: 9
<212> TYPE: PRT
<213> ORGANISM: Artificial Sequence
<220> FEATURE:
<223> OTHER INFORMATION: Synthetic

<400> SEQUENCE: 110

Gln Gln Ser Tyr Asn Ile Pro Leu Thr
1               5

<210> SEQ ID NO 111
<211> LENGTH: 123
<212> TYPE: PRT
<213> ORGANISM: Artificial Sequence
<220> FEATURE:
<223> OTHER INFORMATION: Synthetic

<400> SEQUENCE: 111

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Gly Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Ile Thr Tyr Tyr Gly Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Asp Ala Asp Thr Ala Val Tyr Tyr Cys
                85                  90                  95

Gly Lys Asp Pro Tyr Asn Trp Asn His Gly Val Tyr Gly Met Asp Val
            100                 105                 110

Trp Gly Gln Gly Thr Thr Val Thr Val Ser Ser
        115                 120

<210> SEQ ID NO 112
<211> LENGTH: 107
<212> TYPE: PRT
<213> ORGANISM: Artificial Sequence
<220> FEATURE:
<223> OTHER INFORMATION: Synthetic
```

```
<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Phe Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Ser Leu Thr Ile Ser Ser Leu His Pro
65                  70                  75                  80

Gly Asp Phe Ala Thr Tyr Tyr Cys Gln Gln Ser Tyr Asn Ile Pro Leu
                85                  90                  95

Thr Phe Gly Gly Gly Thr Lys Val Glu Ile Lys
            100                 105

<210> SEQ ID NO 113
<211> LENGTH: 8
<212> TYPE: PRT
<213> ORGANISM: Artificial Sequence
<220> FEATURE:
<223> OTHER INFORMATION: Synthetic

<400> SEQUENCE: 113

Gly Phe Ala Phe His Thr Tyr Asp
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Val Val Gly Ser Gly Ile Asn Thr
1               5

<210> SEQ ID NO 115
<211> LENGTH: 12
<212> TYPE: PRT
<213> ORGANISM: Artificial Sequence
<220> FEATURE:
<223> OTHER INFORMATION: Synthetic

<400> SEQUENCE: 115

Ala Lys Asp Ser Ser Ser Trp Phe Ser Leu His Tyr
1               5                   10

<210> SEQ ID NO 116
<211> LENGTH: 6
<212> TYPE: PRT
<213> ORGANISM: Artificial Sequence
<220> FEATURE:
<223> OTHER INFORMATION: Synthetic

<400> SEQUENCE: 116

Gln Ser Ile Ser Asn Trp
1               5

<210> SEQ ID NO 117
<211> LENGTH: 3
<212> TYPE: PRT
```

-continued

```
<213> ORGANISM: Artificial Sequence
<220> FEATURE:
<223> OTHER INFORMATION: Synthetic

<400> SEQUENCE: 117

Lys Ala Ser
1

<210> SEQ ID NO 118
<211> LENGTH: 9
<212> TYPE: PRT
<213> ORGANISM: Artificial Sequence
<220> FEATURE:
<223> OTHER INFORMATION: Synthetic

<400> SEQUENCE: 118

Gln Gln Tyr Arg Ser Tyr Ala Tyr Thr
1               5

<210> SEQ ID NO 119
<211> LENGTH: 119
<212> TYPE: PRT
<213> ORGANISM: Artificial Sequence
<220> FEATURE:
<223> OTHER INFORMATION: Synthetic

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe His Thr Tyr
            20                  25                  30

Asp Met Thr Trp Val Arg Gln Ala Pro Gly Lys Gly Leu Glu Trp Val
        35                  40                  45

Ser Gly Val Val Gly Ser Gly Ile Asn Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Ser Ser Trp Phe Ser Leu His Tyr Trp Gly Gln Gly
            100                 105                 110

Thr Leu Val Thr Val Ser Ser
        115

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                      70                      75                      80

Asp Asp Phe Ala Ser Tyr Tyr Cys Gln Gln Tyr Arg Ser Tyr Ala Tyr
                        85                      90                      95

Thr Phe Gly Gln Gly Thr Lys Leu Glu Ile Thr
            100                     105

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Gly Phe Thr Phe Ser Asp Tyr Tyr
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Ile Asp Ser Ser Ala Gly Ala Thr
1               5

<210> SEQ ID NO 123
<211> LENGTH: 13
<212> TYPE: PRT
<213> ORGANISM: Artificial Sequence
<220> FEATURE:
<223> OTHER INFORMATION: Synthetic

<400> SEQUENCE: 123

Ala Arg Glu Arg Arg Ser Gly His Lys Ile Phe Asp Cys
1               5                       10

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Gln Asn Ile Leu Tyr Ser Ser Asn Asn Lys Asn Tyr
1               5                       10

<210> SEQ ID NO 125
<211> LENGTH: 3
<212> TYPE: PRT
<213> ORGANISM: Artificial Sequence
<220> FEATURE:
<223> OTHER INFORMATION: Synthetic

<400> SEQUENCE: 125

Trp Ser Ser
1

<210> SEQ ID NO 126
<211> LENGTH: 9
<212> TYPE: PRT
<213> ORGANISM: Artificial Sequence
<220> FEATURE:
```

<223> OTHER INFORMATION: Synthetic

<400> SEQUENCE: 126

Gln Gln Tyr Tyr Ser Ser Pro Tyr Asn
1               5

<210> SEQ ID NO 127
<211> LENGTH: 120
<212> TYPE: PRT
<213> ORGANISM: Artificial Sequence
<220> FEATURE:
<223> OTHER INFORMATION: Synthetic

<400> SEQUENCE: 127

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
                20                  25                  30

Tyr Met Asn Trp Ile Arg Leu Pro Pro Gly Lys Gly Leu Glu Trp Ile
            35                  40                  45

Ser Tyr Ile Asp Ser Ser Ala Gly Ala Thr Tyr Tyr Ala Asp Ser Val
        50                  55                  60

Lys Gly Arg Phe Thr Val Ser Arg Asp Asp Ala Lys Asn Ser Leu Phe
65                  70                  75                  80

Leu His Met Asn Ser Leu Arg Ala Glu Asp Thr Ala Val Tyr Tyr Cys
                85                  90                  95

Ala Arg Glu Arg Arg Ser Gly His Lys Ile Phe Asp Cys Trp Gly Pro
                100                 105                 110

Gly Thr Leu Val Thr Val Ser Ser
            115                 120

<210> SEQ ID NO 128
<211> LENGTH: 113
<212> TYPE: PRT
<213> ORGANISM: Artificial Sequence
<220> FEATURE:
<223> OTHER INFORMATION: Synthetic

<400> SEQUENCE: 128

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
                20                  25                  30

Ser Asn Asn Lys Asn Tyr Leu Ala Trp Tyr Gln Gln Lys Ala Gly Gln
            35                  40                  45

Pro Pro Lys Leu Leu Ile Phe Trp Ser Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
                100                 105                 110

Lys

<210> SEQ ID NO 129
<211> LENGTH: 8
<212> TYPE: PRT
<213> ORGANISM: Artificial Sequence

```
<220> FEATURE:
<223> OTHER INFORMATION: Synthetic

<400> SEQUENCE: 129

Gly Phe Thr Phe Ser Asp Tyr Tyr
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic

<400> SEQUENCE: 130

Ile Asp Ser Ser Ala Gly Ala Ile
1               5

<210> SEQ ID NO 131
<211> LENGTH: 13
<212> TYPE: PRT
<213> ORGANISM: Artificial Sequence
<220> FEATURE:
<223> OTHER INFORMATION: Synthetic

<400> SEQUENCE: 131

Ala Arg Glu Arg Arg Asp Gly His Lys Ile Phe Asp Tyr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Gln Asn Ile Leu Tyr Ser Ser Asn Asn Lys Asn Tyr
1               5                   10

<210> SEQ ID NO 133
<211> LENGTH: 3
<212> TYPE: PRT
<213> ORGANISM: Artificial Sequence
<220> FEATURE:
<223> OTHER INFORMATION: Synthetic

<400> SEQUENCE: 133

Trp Ser Ser
1

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

Gln Gln Tyr Tyr Ser Ser Pro Tyr Asn
1               5

<210> SEQ ID NO 135
<211> LENGTH: 120
<212> TYPE: PRT
<213> ORGANISM: Artificial Sequence
<220> FEATURE:
```

<223> OTHER INFORMATION: Synthetic

<400> SEQUENCE: 135

```
Gln Val His Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Asn Trp Ile Arg Leu Pro Pro Gly Lys Gly Leu Glu Trp Ile
        35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Met Phe
65                  70                  75                  80

Leu His Met Asn Ser Leu Arg Ala Asp Asp Thr Ala Val Tyr Tyr Cys
                85                  90                  95

Ala Arg Glu Arg Arg Asp Gly His Lys Ile Phe Asp Tyr Trp Gly Pro
                100                 105                 110

Gly Thr Leu Val Thr Val Ser Ser
        115                 120
```

<210> SEQ ID NO 136
<211> LENGTH: 113
<212> TYPE: PRT
<213> ORGANISM: Artificial Sequence
<220> FEATURE:
<223> OTHER INFORMATION: Synthetic

<400> SEQUENCE: 136

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Ile Leu Tyr Ser
            20                  25                  30

Ser Asn Asn Lys Asn Tyr Leu Ala Trp Tyr Gln Gln Lys Ala Gly Gln
        35                  40                  45

Pro Pro Lys Leu Leu Ile Phe Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
                100                 105                 110

Lys
```

<210> SEQ ID NO 137
<211> LENGTH: 8
<212> TYPE: PRT
<213> ORGANISM: Artificial Sequence
<220> FEATURE:
<223> OTHER INFORMATION: Synthetic

<400> SEQUENCE: 137

```
Gly Phe Thr Phe Ser Asp Tyr Tyr
1               5
```

<210> SEQ ID NO 138
<211> LENGTH: 8
<212> TYPE: PRT
<213> ORGANISM: Artificial Sequence -continued
<220> FEATURE:
<223> OTHER INFORMATION: Synthetic

<400> SEQUENCE: 138

Ile Asp Ser Ser Ala Gly Ala Ile
1               5

<210> SEQ ID NO 139
<211> LENGTH: 13
<212> TYPE: PRT
<213> ORGANISM: Artificial Sequence
<220> FEATURE:
<223> OTHER INFORMATION: Synthetic

<400> SEQUENCE: 139

Ala Arg Glu Arg Arg Glu Gly His Lys Ile Phe Asp Phe
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Gln Asn Ile Leu Tyr Ser Ser Asn Asn Lys Asn Tyr
1               5                   10

<210> SEQ ID NO 141
<211> LENGTH: 3
<212> TYPE: PRT
<213> ORGANISM: Artificial Sequence
<220> FEATURE:
<223> OTHER INFORMATION: Synthetic

<400> SEQUENCE: 141

Trp Ser Ser
1

<210> SEQ ID NO 142
<211> LENGTH: 9
<212> TYPE: PRT
<213> ORGANISM: Artificial Sequence
<220> FEATURE:
<223> OTHER INFORMATION: Synthetic

<400> SEQUENCE: 142

Gln Gln Tyr Tyr Ser Ser Pro Tyr Asn
1               5

<210> SEQ ID NO 143
<211> LENGTH: 120
<212> TYPE: PRT
<213> ORGANISM: Artificial Sequence
<220> FEATURE:
<223> OTHER INFORMATION: Synthetic

<400> SEQUENCE: 143

Gln Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Ser Asp Tyr
                20                  25                  30

Tyr Met Asn Trp Ile Arg Leu Pro Pro Gly Lys Gly Leu Glu Trp Ile
            35                  40                  45

Ser Tyr Ile Asp Ser Ser Ala Gly Ala Ile Tyr Tyr Ala Asp Ser Val
    50                  55                  60

Lys Gly Arg Phe Thr Val Ser Arg Asp Asp Ala Lys Asn Ser Leu Phe
65                  70                  75                  80

Leu His Met Asn Ser Leu Arg Ala Asp Asp Thr Ala Val Tyr Tyr Cys
                85                  90                  95

Ala Arg Glu Arg Arg Glu Gly His Lys Ile Phe Asp Phe Trp Gly Pro
                100                 105                 110

Gly Thr Leu Val Thr Val Ser Ser
        115                 120

<210> SEQ ID NO 144
<211> LENGTH: 113
<212> TYPE: PRT
<213> ORGANISM: Artificial Sequence
<220> FEATURE:
<223> OTHER INFORMATION: Synthetic

<400> SEQUENCE: 144

Asp Ile Val Met Thr Gln Ser Pro Asp Ser Leu Ala Leu Ser Leu Gly
1                   5                   10                  15

Glu Arg Ala Thr Ile Asn Cys Lys Ser Ser Gln Asn Ile Leu Tyr Ser
                20                  25                  30

Ser Asn Asn Lys Asn Tyr Leu Ala Cys Tyr Gln Gln Lys Ala Gly Gln
        35                  40                  45

Pro Pro Lys Leu Leu Ile Phe Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Tyr Asn Phe Gly Arg Gly Thr Thr Leu Glu Ile
                100                 105                 110

Lys

<210> SEQ ID NO 145
<211> LENGTH: 8
<212> TYPE: PRT
<213> ORGANISM: Artificial Sequence
<220> FEATURE:
<223> OTHER INFORMATION: Synthetic

<400> SEQUENCE: 145

Gly Phe Thr Phe His Asn Tyr Ala
1                   5

<210> SEQ ID NO 146
<211> LENGTH: 8
<212> TYPE: PRT
<213> ORGANISM: Artificial Sequence
<220> FEATURE:
<223> OTHER INFORMATION: Synthetic

<400> SEQUENCE: 146

Ile Ser Gly Ser Gly Gly Thr Ala
1                   5

<210> SEQ ID NO 147
<211> LENGTH: 14
<212> TYPE: PRT
<213> ORGANISM: Artificial Sequence -continued
<220> FEATURE:
<223> OTHER INFORMATION: Synthetic

<400> SEQUENCE: 147

Ala Lys Asp Arg Phe Leu Glu Trp Val Glu Gly Phe Asp Ser
1               5                   10

<210> SEQ ID NO 148
<211> LENGTH: 6
<212> TYPE: PRT
<213> ORGANISM: Artificial Sequence
<220> FEATURE:
<223> OTHER INFORMATION: Synthetic

<400> SEQUENCE: 148

Gln Ser Ile Gly Ser Phe
1               5

<210> SEQ ID NO 149
<211> LENGTH: 3
<212> TYPE: PRT
<213> ORGANISM: Artificial Sequence
<220> FEATURE:
<223> OTHER INFORMATION: Synthetic

<400> SEQUENCE: 149

Ala Ala Ser
1

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

Gln Gln Ser Tyr Asn Thr Pro Leu Thr
1               5

<210> SEQ ID NO 151
<211> LENGTH: 121
<212> TYPE: PRT
<213> ORGANISM: Artificial Sequence
<220> FEATURE:
<223> OTHER INFORMATION: Synthetic

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Leu Tyr Tyr Cys
                85                  90                  95

Ala Lys Asp Arg Phe Leu Glu Trp Val Glu Gly Phe Asp Ser Trp Gly
            100                 105                 110

Gln Gly Thr Leu Val Thr Val Ser Ser

-continued

```
          115                 120

<210> SEQ ID NO 152
<211> LENGTH: 107
<212> TYPE: PRT
<213> ORGANISM: Artificial Sequence
<220> FEATURE:
<223> OTHER INFORMATION: Synthetic

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Phe
            20                  25                  30

Leu Ile Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys
            100                 105

<210> SEQ ID NO 153
<211> LENGTH: 8
<212> TYPE: PRT
<213> ORGANISM: Artificial Sequence
<220> FEATURE:
<223> OTHER INFORMATION: Synthetic

<400> SEQUENCE: 153

Gly Phe Thr Phe Ser Ser Tyr Glu
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic

<400> SEQUENCE: 154

Ile Ser Ser Gly Gly Ser Ser Ile
1               5

<210> SEQ ID NO 155
<211> LENGTH: 15
<212> TYPE: PRT
<213> ORGANISM: Artificial Sequence
<220> FEATURE:
<223> OTHER INFORMATION: Synthetic

<400> SEQUENCE: 155

Ala Arg Val Gly Gly Ser Tyr Tyr Tyr Ser Tyr Ala Met Asp Val
1               5                   10                  15

<210> SEQ ID NO 156
<211> LENGTH: 6
<212> TYPE: PRT
<213> ORGANISM: Artificial Sequence
<220> FEATURE:
<223> OTHER INFORMATION: Synthetic
```

<400> SEQUENCE: 156

Gln Asp Ile Ser Ser Tyr
1               5

<210> SEQ ID NO 157
<211> LENGTH: 3
<212> TYPE: PRT
<213> ORGANISM: Artificial Sequence
<220> FEATURE:
<223> OTHER INFORMATION: Synthetic

<400> SEQUENCE: 157

Ala Ala Ser
1

<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Gln Gln Pro Asn Asn Tyr Pro Phe Ser
1               5

<210> SEQ ID NO 159
<211> LENGTH: 122
<212> TYPE: PRT
<213> ORGANISM: Artificial Sequence
<220> FEATURE:
<223> OTHER INFORMATION: Synthetic

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Gly Gly Ser Ser Ile Lys Tyr Ala Asp Ser Val
    50                  55                  60

Arg Gly Arg Phe Thr Phe Ser Arg Asp Asn Ala Glu Asn Ser Val His
65                  70                  75                  80

Leu Gln Met Asn Ser Leu Arg Gly Glu Asp Thr Ala Val Tyr Tyr Cys
                85                  90                  95

Ala Arg Val Gly Gly Ser Tyr Tyr Tyr Ser Tyr Ala Met Asp Val Trp
            100                 105                 110

Gly Gln Gly Thr Ala Val Thr Val Ser Ser
        115                 120

<210> SEQ ID NO 160
<211> LENGTH: 107
<212> TYPE: PRT
<213> ORGANISM: Artificial Sequence
<220> FEATURE:
<223> OTHER INFORMATION: Synthetic

<400> SEQUENCE: 160

Asp Ile Gln Leu Thr Gln Ser Pro Ser Phe Leu Ser Ala Ser Val Gly
1               5                   10                  15

```
Asp Arg Val Thr Ile Thr Cys Trp Ala Ser Gln Asp Ile Ser Ser Tyr
        20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Pro Asn Asn Tyr Pro Phe
                85                  90                  95

Ser Phe Gly Pro Gly Thr Lys Val Asp Val Lys
            100                 105
```

```
<210> SEQ ID NO 161
<211> LENGTH: 8
<212> TYPE: PRT
<213> ORGANISM: Artificial Sequence
<220> FEATURE:
<223> OTHER INFORMATION: Synthetic

<400> SEQUENCE: 161

Gly Phe Thr Phe Ser Ser Tyr Glu
1               5
```

```
<210> SEQ ID NO 162
<211> LENGTH: 8
<212> TYPE: PRT
<213> ORGANISM: Artificial Sequence
<220> FEATURE:
<223> OTHER INFORMATION: Synthetic

<400> SEQUENCE: 162

Ile Ser Ser Gly Gly Ser Ser Ile
1               5
```

```
<210> SEQ ID NO 163
<211> LENGTH: 15
<212> TYPE: PRT
<213> ORGANISM: Artificial Sequence
<220> FEATURE:
<223> OTHER INFORMATION: Synthetic

<400> SEQUENCE: 163

Ala Arg Val Gly Gly Ser Tyr Tyr Tyr Ser Tyr Ala Met Asp Val
1               5                   10                  15
```

```
<210> SEQ ID NO 164
<211> LENGTH: 6
<212> TYPE: PRT
<213> ORGANISM: Artificial Sequence
<220> FEATURE:
<223> OTHER INFORMATION: Synthetic

<400> SEQUENCE: 164

Gln Asp Ile Ser Ser Tyr
1               5
```

```
<210> SEQ ID NO 165
<211> LENGTH: 3
<212> TYPE: PRT
<213> ORGANISM: Artificial Sequence
<220> FEATURE:
<223> OTHER INFORMATION: Synthetic

<400> SEQUENCE: 165
```

-continued

```
Ala Ala Ser
1

<210> SEQ ID NO 166
<211> LENGTH: 9
<212> TYPE: PRT
<213> ORGANISM: Artificial Sequence
<220> FEATURE:
<223> OTHER INFORMATION: Synthetic

<400> SEQUENCE: 166

Gln Gln Pro Asn Asn Tyr Pro Phe Ser
1               5

<210> SEQ ID NO 167
<211> LENGTH: 122
<212> TYPE: PRT
<213> ORGANISM: Artificial Sequence
<220> FEATURE:
<223> OTHER INFORMATION: Synthetic

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Gly Gly Ser Ser Ile Lys Tyr Ala Asp Ser Val
    50                  55                  60

Arg Gly Arg Phe Thr Phe Ser Arg Asp Asn Ala Glu Asn Ser Val Phe
65                  70                  75                  80

Leu Gln Met Asn Ser Leu Arg Gly Glu Asp Thr Ala Val Tyr Tyr Cys
                85                  90                  95

Ala Arg Val Gly Gly Ser Tyr Tyr Tyr Ser Tyr Ala Met Asp Val Trp
            100                 105                 110

Gly Gln Gly Thr Ala Val Thr Val Ser Ser
        115                 120

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Pro Asn Asn Tyr Pro Phe
                85                  90                  95
```

Ser Phe Gly Pro Gly Thr Lys Val Asp Val Lys
        100                 105

<210> SEQ ID NO 169
<211> LENGTH: 8
<212> TYPE: PRT
<213> ORGANISM: Artificial Sequence
<220> FEATURE:
<223> OTHER INFORMATION: Synthetic

<400> SEQUENCE: 169

Gly Phe Thr Phe Ser Ser Phe Ala
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic

<400> SEQUENCE: 170

Ile Ser Ala Ser Gly Gly Thr Thr
1               5

<210> SEQ ID NO 171
<211> LENGTH: 14
<212> TYPE: PRT
<213> ORGANISM: Artificial Sequence
<220> FEATURE:
<223> OTHER INFORMATION: Synthetic

<400> SEQUENCE: 171

Ala Lys Asp Arg Phe Leu Glu Trp Val Glu Gly Phe Asp Pro
1               5                   10

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Ser Ile Gly Arg Phe
1               5

<210> SEQ ID NO 173
<211> LENGTH: 3
<212> TYPE: PRT
<213> ORGANISM: Artificial Sequence
<220> FEATURE:
<223> OTHER INFORMATION: Synthetic

<400> SEQUENCE: 173

Ala Thr Ser
1

<210> SEQ ID NO 174
<211> LENGTH: 9
<212> TYPE: PRT
<213> ORGANISM: Artificial Sequence
<220> FEATURE:
<223> OTHER INFORMATION: Synthetic

<400> SEQUENCE: 174

Gln Gln Ser Tyr Ile Thr Pro Leu Thr 1               5

<210> SEQ ID NO 175
<211> LENGTH: 121
<212> TYPE: PRT
<213> ORGANISM: Artificial Sequence
<220> FEATURE:
<223> OTHER INFORMATION: Synthetic

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Gly Ile Ser Ala Ser Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Glu Tyr Tyr Cys
                85                  90                  95

Ala Lys Asp Arg Phe Leu Glu Trp Val Glu Gly Phe Asp Pro Trp Gly
            100                 105                 110

Gln Gly Ile Leu Val Thr Val Ser Pro
        115                 120

<210> SEQ ID NO 176
<211> LENGTH: 107
<212> TYPE: PRT
<213> ORGANISM: Artificial Sequence
<220> FEATURE:
<223> OTHER INFORMATION: Synthetic

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Phe
            20                  25                  30

Leu Ile Trp Tyr Gln Gln Lys Pro Gly Lys Ala Pro Lys Leu Leu Leu
        35                  40                  45

Tyr Ala Thr Ser Ser Leu Gln Ser Gly Val Pro Ala Arg Phe Thr Gly
    50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Ser Tyr Ile Thr Pro Leu
                85                  90                  95

Thr Phe Gly Gly Gly Thr Lys Val Glu Ile Lys
            100                 105

<210> SEQ ID NO 177
<211> LENGTH: 8
<212> TYPE: PRT
<213> ORGANISM: Artificial Sequence
<220> FEATURE:
<223> OTHER INFORMATION: Synthetic

<400> SEQUENCE: 177

Gly Phe Thr Phe Ser Ser Phe Ala
1               5

```
<210> SEQ ID NO 178
<211> LENGTH: 8
<212> TYPE: PRT
<213> ORGANISM: Artificial Sequence
<220> FEATURE:
<223> OTHER INFORMATION: Synthetic

<400> SEQUENCE: 178

Ile Ser Ala Ser Gly Gly Thr Thr
1               5

<210> SEQ ID NO 179
<211> LENGTH: 14
<212> TYPE: PRT
<213> ORGANISM: Artificial Sequence
<220> FEATURE:
<223> OTHER INFORMATION: Synthetic

<400> SEQUENCE: 179

Ala Lys Asp Arg Phe Leu Glu Trp Val Glu Gly Phe Asp Pro
1               5                   10

<210> SEQ ID NO 180
<211> LENGTH: 6
<212> TYPE: PRT
<213> ORGANISM: Artificial Sequence
<220> FEATURE:
<223> OTHER INFORMATION: Synthetic

<400> SEQUENCE: 180

Gln Ser Ile Gly Arg Phe
1               5

<210> SEQ ID NO 181
<211> LENGTH: 3
<212> TYPE: PRT
<213> ORGANISM: Artificial Sequence
<220> FEATURE:
<223> OTHER INFORMATION: Synthetic

<400> SEQUENCE: 181

Ala Thr Ser
1

<210> SEQ ID NO 182
<211> LENGTH: 9
<212> TYPE: PRT
<213> ORGANISM: Artificial Sequence
<220> FEATURE:
<223> OTHER INFORMATION: Synthetic

<400> SEQUENCE: 182

Gln Gln Ser Tyr Ile Thr Pro Leu Thr
1               5

<210> SEQ ID NO 183
<211> LENGTH: 121
<212> TYPE: PRT
<213> ORGANISM: Artificial Sequence
<220> FEATURE:
<223> OTHER INFORMATION: Synthetic

<400> SEQUENCE: 183

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Phe
        20                  25                  30

Ala Met Ser Trp Val Arg Gln Ala Pro Gly Lys Gly Leu Glu Trp Val
        35                  40                  45

Ser Gly Ile Ser Ala Ser Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Glu Tyr Tyr Cys
                85                  90                  95

Ala Lys Asp Arg Phe Leu Glu Trp Val Glu Gly Phe Asp Pro Trp Gly
            100                 105                 110

Gln Gly Ile Leu Val Thr Val Ser Pro
        115                 120
```

<210> SEQ ID NO 184
<211> LENGTH: 107
<212> TYPE: PRT
<213> ORGANISM: Artificial Sequence
<220> FEATURE:
<223> OTHER INFORMATION: Synthetic

<400> SEQUENCE: 184

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Phe
            20                  25                  30

Leu Ile Trp Tyr Gln Gln Lys Pro Gly Lys Ala Pro Lys Leu Leu Leu
        35                  40                  45

Tyr Ala Thr Ser Ser Leu Gln Ser Gly Val Pro Ala Arg Phe Thr Gly
    50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Ser Tyr Ile Thr Pro Leu
                85                  90                  95

Thr Phe Gly Gly Gly Thr Lys Val Glu Ile Lys
            100                 105
```

<210> SEQ ID NO 185
<211> LENGTH: 25
<212> TYPE: PRT
<213> ORGANISM: Artificial Sequence
<220> FEATURE:
<223> OTHER INFORMATION: Synthetic

<400> SEQUENCE: 185

```
Gln Val Gln Leu Val Glu Ser Gly Gly Asp Leu Val Lys Pro Gly Gly
1               5                   10                  15

Ser Leu Arg Leu Ser Cys Val Ala Ser
            20                  25
```

<210> SEQ ID NO 186
<211> LENGTH: 17
<212> TYPE: PRT
<213> ORGANISM: Artificial Sequence
<220> FEATURE:
<223> OTHER INFORMATION: Synthetic

<400> SEQUENCE: 186

```
Met Asn Trp Ile Arg Leu Pro Pro Gly Lys Gly Leu Glu Trp Val Ser
```

-continued

```
1               5              10             15

Tyr

<210> SEQ ID NO 187
<211> LENGTH: 38
<212> TYPE: PRT
<213> ORGANISM: Artificial Sequence
<220> FEATURE:
<223> OTHER INFORMATION: Synthetic

<400> SEQUENCE: 187

Tyr Tyr Ala Asp Ser Val Arg Gly Arg Phe Thr Val Ser Arg Asp Asp
1               5              10             15

Ala Lys Asn Ser Leu Phe Leu His Met Asn Ser Leu Arg Ala Asp Asp
            20             25             30

Thr Ala Val Tyr Tyr Cys
        35

<210> SEQ ID NO 188
<211> LENGTH: 11
<212> TYPE: PRT
<213> ORGANISM: Artificial Sequence
<220> FEATURE:
<223> OTHER INFORMATION: Synthetic

<400> SEQUENCE: 188

Trp Gly Pro Gly Thr Leu Val Thr Val Ser Ser
1               5              10

<210> SEQ ID NO 189
<211> LENGTH: 26
<212> TYPE: PRT
<213> ORGANISM: Artificial Sequence
<220> FEATURE:
<223> OTHER INFORMATION: Synthetic

<400> SEQUENCE: 189

Asp Ile Val Met Thr Gln Ser Pro Asp Ser Leu Ala Val Ser Leu Gly
1               5              10             15

Glu Arg Ala Thr Ile Asn Cys Lys Ser Ser
            20             25

<210> SEQ ID NO 190
<211> LENGTH: 17
<212> TYPE: PRT
<213> ORGANISM: Artificial Sequence
<220> FEATURE:
<223> OTHER INFORMATION: Synthetic

<400> SEQUENCE: 190

Leu Ala Trp Tyr Gln Gln Lys Ala Gly Gln Pro Pro Lys Leu Leu Ile
1               5              10             15

Phe

<210> SEQ ID NO 191
<211> LENGTH: 36
<212> TYPE: PRT
<213> ORGANISM: Artificial Sequence
<220> FEATURE:
<223> OTHER INFORMATION: Synthetic

<400> SEQUENCE: 191

Thr Arg Glu Ser Gly Val Pro Asp Arg Phe Ser Gly Ser Gly Ser Gly
1               5              10             15
```

```
Thr Asp Phe Thr Leu Thr Ile Asn Ser Leu Gln Ala Glu Asp Val Ala
            20                  25                  30

Val Tyr Tyr Cys
        35

<210> SEQ ID NO 192
<211> LENGTH: 10
<212> TYPE: PRT
<213> ORGANISM: Artificial Sequence
<220> FEATURE:
<223> OTHER INFORMATION: Synthetic

<400> SEQUENCE: 192

Phe Gly Arg Gly Thr Thr Leu Glu Ile Lys
1               5                   10

<210> SEQ ID NO 193
<211> LENGTH: 25
<212> TYPE: PRT
<213> ORGANISM: Artificial Sequence
<220> FEATURE:
<223> OTHER INFORMATION: Synthetic

<400> SEQUENCE: 193

Gln Val His Leu Val Glu Ser Gly Gly Asp Leu Val Lys Pro Gly Gly
1               5                   10                  15

Ser Leu Arg Leu Ser Cys Val Ala Ser
            20                  25

<210> SEQ ID NO 194
<211> LENGTH: 17
<212> TYPE: PRT
<213> ORGANISM: Artificial Sequence
<220> FEATURE:
<223> OTHER INFORMATION: Synthetic

<400> SEQUENCE: 194

Met Asn Trp Ile Arg Met Pro Pro Gly Lys Gly Leu Glu Trp Ile Ser
1               5                   10                  15

Tyr

<210> SEQ ID NO 195
<211> LENGTH: 38
<212> TYPE: PRT
<213> ORGANISM: Artificial Sequence
<220> FEATURE:
<223> OTHER INFORMATION: Synthetic

<400> SEQUENCE: 195

Tyr Tyr Ala Asp Ser Val Lys Gly Arg Phe Thr Val Ser Arg Asp Asp
1               5                   10                  15

Ala Lys Asn Ser Leu Phe Leu His Met Asn Asn Leu Arg Ala Asp Asp
            20                  25                  30

Thr Ala Val Tyr Tyr Cys
        35

<210> SEQ ID NO 196
<211> LENGTH: 36
<212> TYPE: PRT
<213> ORGANISM: Artificial Sequence
<220> FEATURE:
<223> OTHER INFORMATION: Synthetic

<400> SEQUENCE: 196
```

```
Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 197
<211> LENGTH: 25
<212> TYPE: PRT
<213> ORGANISM: Artificial Sequence
<220> FEATURE:
<223> OTHER INFORMATION: Synthetic

<400> SEQUENCE: 197

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 198
<211> LENGTH: 17
<212> TYPE: PRT
<213> ORGANISM: Artificial Sequence
<220> FEATURE:
<223> OTHER INFORMATION: Synthetic

<400> SEQUENCE: 198

Ile Gly Trp Val Arg Gln Met Pro Gly Lys Gly Leu Glu Trp Met Gly
1               5                   10                  15

Ile

<210> SEQ ID NO 199
<211> LENGTH: 38
<212> TYPE: PRT
<213> ORGANISM: Artificial Sequence
<220> FEATURE:
<223> OTHER INFORMATION: Synthetic

<400> SEQUENCE: 199

Arg Tyr Ser Pro Ser Phe Gln Gly Gln Val Thr Ile Ser Ala Asp Lys
1               5                   10                  15

Ser Ile Ser Thr Ala Tyr Leu Gln Trp Ser Ser Leu Lys Ala Ser Asp
            20                  25                  30

Thr Ala Met Tyr Tyr Cys
        35

<210> SEQ ID NO 200
<211> LENGTH: 11
<212> TYPE: PRT
<213> ORGANISM: Artificial Sequence
<220> FEATURE:
<223> OTHER INFORMATION: Synthetic

<400> SEQUENCE: 200

Trp Gly Gln Gly Thr Leu Val Thr Val Ser Ser
1               5                   10

<210> SEQ ID NO 201
<211> LENGTH: 26
<212> TYPE: PRT
<213> ORGANISM: Artificial Sequence
<220> FEATURE:
```

```
<223> OTHER INFORMATION: Synthetic

<400> SEQUENCE: 201

Asp Ile Gln Met Thr Gln Ser Pro Ser Ser Leu Ser Ala Ser Val Gly
1               5                   10                  15

Asp Arg Leu Thr Ile Thr Cys Arg Ala Ser
            20                  25

<210> SEQ ID NO 202
<211> LENGTH: 17
<212> TYPE: PRT
<213> ORGANISM: Artificial Sequence
<220> FEATURE:
<223> OTHER INFORMATION: Synthetic

<400> SEQUENCE: 202

Leu Asn Trp Tyr Gln Gln Asn Pro Gly Lys Ala Pro Lys Val Leu Ile
1               5                   10                  15

Tyr

<210> SEQ ID NO 203
<211> LENGTH: 36
<212> TYPE: PRT
<213> ORGANISM: Artificial Sequence
<220> FEATURE:
<223> OTHER INFORMATION: Synthetic

<400> SEQUENCE: 203

Ser Leu Glu Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 204
<211> LENGTH: 10
<212> TYPE: PRT
<213> ORGANISM: Artificial Sequence
<220> FEATURE:
<223> OTHER INFORMATION: Synthetic

<400> SEQUENCE: 204

Phe Gly Gln Gly Thr Lys Val Glu Ile Lys
1               5                   10

<210> SEQ ID NO 205
<211> LENGTH: 25
<212> TYPE: PRT
<213> ORGANISM: Artificial Sequence
<220> FEATURE:
<223> OTHER INFORMATION: Synthetic

<400> SEQUENCE: 205

Glu Val Gln Leu Leu Glu Ser Gly Gly Gly Leu Ala Gln Pro Gly Lys
1               5                   10                  15

Ser Leu Arg Leu Ser Cys Ala Ala Ser
            20                  25

<210> SEQ ID NO 206
<211> LENGTH: 17
<212> TYPE: PRT
<213> ORGANISM: Artificial Sequence
<220> FEATURE:
```

<223> OTHER INFORMATION: Synthetic

<400> SEQUENCE: 206

Met Ser Trp Val Arg Gln Ala Pro Gly Lys Gly Leu Glu Trp Val Ser
1               5                   10                  15

Gly

<210> SEQ ID NO 207
<211> LENGTH: 38
<212> TYPE: PRT
<213> ORGANISM: Artificial Sequence
<220> FEATURE:
<223> OTHER INFORMATION: Synthetic

<400> SEQUENCE: 207

Tyr Tyr Ala Asp Ser Val Lys Gly Arg Phe Thr Ile Ser Arg Asp Asn
1               5                   10                  15

Ser Lys Ser Thr Leu Tyr Leu Gln Met Asn Ser Leu Gly Ala Glu Asp
            20                  25                  30

Thr Ala Val Tyr Tyr Cys
        35

<210> SEQ ID NO 208
<211> LENGTH: 11
<212> TYPE: PRT
<213> ORGANISM: Artificial Sequence
<220> FEATURE:
<223> OTHER INFORMATION: Synthetic

<400> SEQUENCE: 208

Trp Gly Gln Gly Thr Thr Val Thr Val Ser Ser
1               5                   10

<210> SEQ ID NO 209
<211> LENGTH: 26
<212> TYPE: PRT
<213> ORGANISM: Artificial Sequence
<220> FEATURE:
<223> OTHER INFORMATION: Synthetic

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 210
<211> LENGTH: 17
<212> TYPE: PRT
<213> ORGANISM: Artificial Sequence
<220> FEATURE:
<223> OTHER INFORMATION: Synthetic

<400> SEQUENCE: 210

Leu Asn Trp Tyr Gln Gln Lys Pro Gly Lys Ala Pro Lys Phe Leu Ile
1               5                   10                  15

Tyr

<210> SEQ ID NO 211
<211> LENGTH: 36
<212> TYPE: PRT
<213> ORGANISM: Artificial Sequence
<220> FEATURE:
<223> OTHER INFORMATION: Synthetic

```
<220> FEATURE:
<221> NAME/KEY: misc_feature
<222> LOCATION: (17)..(17)
<223> OTHER INFORMATION: Xaa can be any naturally occurring amino acid

<400> SEQUENCE: 211

Ser Leu Gln Ser Gly Val Pro Ser Arg Phe Ser Gly Ser Gly Cys Gly
1               5                   10                  15

Xaa Asp Phe Thr Leu Thr Ile Ser Ser Leu Gln Arg Glu Asp Phe Ala
            20                  25                  30

Ala Tyr Tyr Cys
        35

<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Phe Gly Gly Gly Thr Lys Val Glu Ile Lys
1               5                   10

<210> SEQ ID NO 213
<211> LENGTH: 25
<212> TYPE: PRT
<213> ORGANISM: Artificial Sequence
<220> FEATURE:
<223> OTHER INFORMATION: Synthetic

<400> SEQUENCE: 213

Gln Val Gln Leu Val Glu Ser Gly Gly Gly Leu Val Lys Pro Gly Gly
1               5                   10                  15

Ser Leu Arg Leu Ser Cys Val Ala Ser
            20                  25

<210> SEQ ID NO 214
<211> LENGTH: 17
<212> TYPE: PRT
<213> ORGANISM: Artificial Sequence
<220> FEATURE:
<223> OTHER INFORMATION: Synthetic

<400> SEQUENCE: 214

Met Asn Trp Ile Arg Leu Pro Pro Gly Arg Gly Leu Gln Trp Ile Ser
1               5                   10                  15

Tyr

<210> SEQ ID NO 215
<211> LENGTH: 38
<212> TYPE: PRT
<213> ORGANISM: Artificial Sequence
<220> FEATURE:
<223> OTHER INFORMATION: Synthetic

<400> SEQUENCE: 215

Tyr Tyr Ala Asp Ser Val Lys Gly Arg Phe Thr Val Ser Arg Asp Asp
1               5                   10                  15

Ala Lys Asn Ser Leu Tyr Leu Gln Met Asn Ser Leu Arg Ala Asp Asp
            20                  25                  30

Thr Ala Val Tyr Tyr Cys
        35
```

-continued

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Leu Gly Trp Tyr Gln Gln Lys Ala Gly Gln Pro Pro Lys Leu Leu Ile
1               5                   10                  15

Tyr

<210> SEQ ID NO 217
<211> LENGTH: 36
<212> TYPE: PRT
<213> ORGANISM: Artificial Sequence
<220> FEATURE:
<223> OTHER INFORMATION: Synthetic

<400> SEQUENCE: 217

Thr Arg Asn Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 218
<211> LENGTH: 10
<212> TYPE: PRT
<213> ORGANISM: Artificial Sequence
<220> FEATURE:
<223> OTHER INFORMATION: Synthetic

<400> SEQUENCE: 218

Phe Gly Gln Gly Thr Asn Leu Glu Ile Lys
1               5                   10

<210> SEQ ID NO 219
<211> LENGTH: 38
<212> TYPE: PRT
<213> ORGANISM: Artificial Sequence
<220> FEATURE:
<223> OTHER INFORMATION: Synthetic

<400> SEQUENCE: 219

Arg Tyr Ser Pro Ser Phe Gln Gly Gln Val Thr Leu Ser Ala Asp Lys
1               5                   10                  15

Ser Ile Ser Thr Ala Tyr Leu Gln Trp Asn Ser Leu Lys Ala Ser Asp
            20                  25                  30

Thr Ala Met Tyr Tyr Cys
        35

<210> SEQ ID NO 220
<211> LENGTH: 11
<212> TYPE: PRT
<213> ORGANISM: Artificial Sequence
<220> FEATURE:
<223> OTHER INFORMATION: Synthetic

<400> SEQUENCE: 220

Trp Gly Gln Gly Thr Leu Val Thr Val Ala Ser
1               5                   10

```
<210> SEQ ID NO 221
<211> LENGTH: 17
<212> TYPE: PRT
<213> ORGANISM: Artificial Sequence
<220> FEATURE:
<223> OTHER INFORMATION: Synthetic

<400> SEQUENCE: 221

Leu Asn Trp Tyr Gln Gln Lys Pro Gly Thr Ala Pro Lys Leu Leu Ile
1               5                   10                  15

Tyr

<210> SEQ ID NO 222
<211> LENGTH: 36
<212> TYPE: PRT
<213> ORGANISM: Artificial Sequence
<220> FEATURE:
<223> OTHER INFORMATION: Synthetic

<400> SEQUENCE: 222

Ser Leu Gln Gly Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 223
<211> LENGTH: 17
<212> TYPE: PRT
<213> ORGANISM: Artificial Sequence
<220> FEATURE:
<223> OTHER INFORMATION: Synthetic

<400> SEQUENCE: 223

Met Asn Trp Ile Arg Leu Pro Pro Gly Lys Gly Leu Glu Trp Ile Ser
1               5                   10                  15

Tyr

<210> SEQ ID NO 224
<211> LENGTH: 38
<212> TYPE: PRT
<213> ORGANISM: Artificial Sequence
<220> FEATURE:
<223> OTHER INFORMATION: Synthetic

<400> SEQUENCE: 224

Tyr Tyr Ala Asp Ser Val Lys Gly Arg Phe Thr Val Ser Arg Asp Asp
1               5                   10                  15

Ala Lys Asn Ser Leu Phe Leu His Met Asn Ser Leu Arg Ala Asp Asp
            20                  25                  30

Thr Ala Val Tyr Tyr Cys
        35

<210> SEQ ID NO 225
<211> LENGTH: 17
<212> TYPE: PRT
<213> ORGANISM: Artificial Sequence
<220> FEATURE:
<223> OTHER INFORMATION: Synthetic

<400> SEQUENCE: 225

Leu Ala Trp Tyr Gln Gln Lys Thr Gly Gln Pro Pro Lys Leu Leu Ile
```

-continued

```
1               5               10              15

Phe

<210> SEQ ID NO 226
<211> LENGTH: 25
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Asp Leu Val Gln Pro Gly Arg
1               5               10              15

Ser Leu Arg Leu Ser Cys Ala Ala Ser
            20              25

<210> SEQ ID NO 227
<211> LENGTH: 17
<212> TYPE: PRT
<213> ORGANISM: Artificial Sequence
<220> FEATURE:
<223> OTHER INFORMATION: Synthetic

<400> SEQUENCE: 227

Met His Trp Val Arg Gln Gly Pro Gly Lys Gly Leu Glu Trp Val Ser
1               5               10              15

Gly

<210> SEQ ID NO 228
<211> LENGTH: 38
<212> TYPE: PRT
<213> ORGANISM: Artificial Sequence
<220> FEATURE:
<223> OTHER INFORMATION: Synthetic

<400> SEQUENCE: 228

Gly Tyr Ala Asp Ser Val Lys Gly Arg Phe Thr Ile Ser Arg Asp Asn
1               5               10              15

Ala Lys Asn Ser Leu Tyr Leu Arg Met Asn Ser Leu Arg Ala Asp Asp
            20              25              30

Thr Ala Phe Tyr Tyr Cys
        35

<210> SEQ ID NO 229
<211> LENGTH: 11
<212> TYPE: PRT
<213> ORGANISM: Artificial Sequence
<220> FEATURE:
<223> OTHER INFORMATION: Synthetic

<400> SEQUENCE: 229

Trp Gly His Gly Thr Met Val Thr Val Ser Ser
1               5               10

<210> SEQ ID NO 230
<211> LENGTH: 17
<212> TYPE: PRT
<213> ORGANISM: Artificial Sequence
<220> FEATURE:
<223> OTHER INFORMATION: Synthetic

<400> SEQUENCE: 230

Leu Asp Trp Tyr Gln Gln Lys Pro Gly Gln Pro Pro Lys Leu Leu Ile
1               5               10              15
```

-continued

Tyr

```
<210> SEQ ID NO 231
<211> LENGTH: 36
<212> TYPE: PRT
<213> ORGANISM: Artificial Sequence
<220> FEATURE:
<223> OTHER INFORMATION: Synthetic

<400> SEQUENCE: 231

Ser Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 232
<211> LENGTH: 17
<212> TYPE: PRT
<213> ORGANISM: Artificial Sequence
<220> FEATURE:
<223> OTHER INFORMATION: Synthetic

<400> SEQUENCE: 232

Met Asn Trp Ile Arg Leu Pro Pro Gly Arg Gly Leu Glu Trp Ile Ser
1               5                   10                  15

Tyr

<210> SEQ ID NO 233
<211> LENGTH: 38
<212> TYPE: PRT
<213> ORGANISM: Artificial Sequence
<220> FEATURE:
<223> OTHER INFORMATION: Synthetic

<400> SEQUENCE: 233

Tyr Tyr Ala Asp Ser Val Lys Gly Arg Phe Thr Val Ser Arg Asp Asp
1               5                   10                  15

Ala Lys Lys Ser Leu Phe Leu Tyr Met Asn Ser Leu Arg Ala Asp Asp
            20                  25                  30

Thr Ala Val Tyr Tyr Cys
        35

<210> SEQ ID NO 234
<211> LENGTH: 25
<212> TYPE: PRT
<213> ORGANISM: Artificial Sequence
<220> FEATURE:
<223> OTHER INFORMATION: Synthetic

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 235
<211> LENGTH: 38
<212> TYPE: PRT
<213> ORGANISM: Artificial Sequence
<220> FEATURE:
<223> OTHER INFORMATION: Synthetic
```

-continued

```
<400> SEQUENCE: 235

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Ile Tyr Tyr Cys
        35

<210> SEQ ID NO 236
<211> LENGTH: 11
<212> TYPE: PRT
<213> ORGANISM: Artificial Sequence
<220> FEATURE:
<223> OTHER INFORMATION: Synthetic

<400> SEQUENCE: 236

Trp Gly Gln Gly Thr Met Val Thr Val Ser Ser
1               5                   10

<210> SEQ ID NO 237
<211> LENGTH: 26
<212> TYPE: PRT
<213> ORGANISM: Artificial Sequence
<220> FEATURE:
<223> OTHER INFORMATION: Synthetic

<400> SEQUENCE: 237

Asp Ile Gln Met Thr Gln Ser Pro Ser Ser Leu Ser Ala Ser Val Gly
1               5                   10                  15

Gly Arg Val Thr Ile Thr Cys Arg Thr Ser
            20                  25

<210> SEQ ID NO 238
<211> LENGTH: 17
<212> TYPE: PRT
<213> ORGANISM: Artificial Sequence
<220> FEATURE:
<223> OTHER INFORMATION: Synthetic

<400> SEQUENCE: 238

Leu Asn Trp Tyr Gln Gln Lys Ala Gly Lys Ala Pro Lys Leu Leu Ile
1               5                   10                  15

Tyr

<210> SEQ ID NO 239
<211> LENGTH: 36
<212> TYPE: PRT
<213> ORGANISM: Artificial Sequence
<220> FEATURE:
<223> OTHER INFORMATION: Synthetic

<400> SEQUENCE: 239

Asn Leu Gln Ser Gly Val Pro Ser Arg Phe Thr Gly Ser Gly Ser Gly
1               5                   10                  15

Thr Asp Phe Thr Leu Thr Ile Ser Ser Leu Gln Pro Glu Asp Phe Ala
            20                  25                  30

Ala Tyr Tyr Cys
        35

<210> SEQ ID NO 240
<211> LENGTH: 10
<212> TYPE: PRT
```

<213> ORGANISM: Artificial Sequence
<220> FEATURE:
<223> OTHER INFORMATION: Synthetic

<400> SEQUENCE: 240

Phe Gly Pro Gly Thr Lys Val Ala Phe Lys
1               5                   10

<210> SEQ ID NO 241
<211> LENGTH: 25
<212> TYPE: PRT
<213> ORGANISM: Artificial Sequence
<220> FEATURE:
<223> OTHER INFORMATION: Synthetic

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 242
<211> LENGTH: 17
<212> TYPE: PRT
<213> ORGANISM: Artificial Sequence
<220> FEATURE:
<223> OTHER INFORMATION: Synthetic

<400> SEQUENCE: 242

Met Asn Trp Val Arg Gln Ala Pro Gly Lys Gly Leu Glu Trp Val Ser
1               5                   10                  15

Tyr

<210> SEQ ID NO 243
<211> LENGTH: 38
<212> TYPE: PRT
<213> ORGANISM: Artificial Sequence
<220> FEATURE:
<223> OTHER INFORMATION: Synthetic

<400> SEQUENCE: 243

Lys Tyr Ala Asp Ser Val Arg Gly Arg Phe Ala Phe Ser Arg Asp Asn
1               5                   10                  15

Ala Glu Asn Ser Val His Leu Gln Met Asn Ser Leu Arg Ala Glu Asp
            20                  25                  30

Thr Ala Val Tyr Tyr Cys
        35

<210> SEQ ID NO 244
<211> LENGTH: 11
<212> TYPE: PRT
<213> ORGANISM: Artificial Sequence
<220> FEATURE:
<223> OTHER INFORMATION: Synthetic

<400> SEQUENCE: 244

Trp Gly Gln Gly Thr Ala Val Thr Val Ser Ser
1               5                   10

<210> SEQ ID NO 245
<211> LENGTH: 26
<212> TYPE: PRT
<213> ORGANISM: Artificial Sequence
<220> FEATURE:
<223> OTHER INFORMATION: Synthetic

<400> SEQUENCE: 245

Asp Ile Gln Leu Thr Gln Ser Pro Ser Phe Leu Ser Ala Ser Val Gly
1               5                   10                  15

Asp Arg Val Thr Ile Thr Cys Trp Ala Ser
            20                  25

<210> SEQ ID NO 246
<211> LENGTH: 17
<212> TYPE: PRT
<213> ORGANISM: Artificial Sequence
<220> FEATURE:
<223> OTHER INFORMATION: Synthetic

<400> SEQUENCE: 246

Leu Ala Trp Tyr Gln Gln Lys Pro Gly Lys Ala Pro Lys Leu Leu Ile
1               5                   10                  15

Tyr

<210> SEQ ID NO 247
<211> LENGTH: 36
<212> TYPE: PRT
<213> ORGANISM: Artificial Sequence
<220> FEATURE:
<223> OTHER INFORMATION: Synthetic

<400> SEQUENCE: 247

Thr Leu Gln Ser Gly Val Pro Ser Arg Phe Thr Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 248
<211> LENGTH: 10
<212> TYPE: PRT
<213> ORGANISM: Artificial Sequence
<220> FEATURE:
<223> OTHER INFORMATION: Synthetic

<400> SEQUENCE: 248

Phe Gly Pro Gly Thr Lys Val Asp Val Lys
1               5                   10

<210> SEQ ID NO 249
<211> LENGTH: 36
<212> TYPE: PRT
<213> ORGANISM: Artificial Sequence
<220> FEATURE:
<223> OTHER INFORMATION: Synthetic

<400> SEQUENCE: 249

Ile Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35

<210> SEQ ID NO 250
<211> LENGTH: 25
<212> TYPE: PRT

<213> ORGANISM: Artificial Sequence
<220> FEATURE:
<223> OTHER INFORMATION: Synthetic

<400> SEQUENCE: 250

Glu Val Gln Leu Leu Glu Ser Gly Gly Gly Leu Ile Gln Pro Gly Gly
1               5                   10                  15

Ser Leu Arg Leu Ser Cys Ala Ala Ser
            20                  25

<210> SEQ ID NO 251
<211> LENGTH: 38
<212> TYPE: PRT
<213> ORGANISM: Artificial Sequence
<220> FEATURE:
<223> OTHER INFORMATION: Synthetic

<400> SEQUENCE: 251

Tyr Tyr Gly Asp Ser Val Lys Gly Arg Phe Thr Ile Ser Arg Asp Asn
1               5                   10                  15

Ser Lys Ser Thr Leu Tyr Leu Gln Met Asn Ser Leu Arg Asp Ala Asp
            20                  25                  30

Thr Ala Val Tyr Tyr Cys
        35

<210> SEQ ID NO 252
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be any naturally occurring amino acid

<400> SEQUENCE: 252

Ser Leu Gln Ser Gly Val Pro Ser Arg Phe Ser Gly Ser Gly Cys Gly
1               5                   10                  15

Thr Asp Phe Ser Leu Thr Ile Ser Ser Xaa His Pro Gly Asp Phe Ala
            20                  25                  30

Thr Tyr Tyr Cys
        35

<210> SEQ ID NO 253
<211> LENGTH: 17
<212> TYPE: PRT
<213> ORGANISM: Artificial Sequence
<220> FEATURE:
<223> OTHER INFORMATION: Synthetic

<400> SEQUENCE: 253

Met Thr Trp Val Arg Gln Ala Pro Gly Lys Gly Leu Glu Trp Val Ser
1               5                   10                  15

Gly

<210> SEQ ID NO 254
<211> LENGTH: 38
<212> TYPE: PRT
<213> ORGANISM: Artificial Sequence
<220> FEATURE:
<223> OTHER INFORMATION: Synthetic

<400> SEQUENCE: 254

```
Tyr Tyr Ala Asp Ser Val Lys Gly Arg Phe Thr Ile Ser Arg Asp Asn
1               5                   10                  15

Ser Lys Ser Thr Leu Tyr Leu Gln Met Asn Ser Leu Arg Ala Glu Asp
            20                  25                  30

Thr Ala Val Tyr Tyr Cys
        35

<210> SEQ ID NO 255
<211> LENGTH: 26
<212> TYPE: PRT
<213> ORGANISM: Artificial Sequence
<220> FEATURE:
<223> OTHER INFORMATION: Synthetic

<400> SEQUENCE: 255

Asp Ile Gln Met Thr Gln Ser Pro Ser Thr Leu Ser Ala Ser Val Gly
1               5                   10                  15

Asp Arg Val Thr Ile Thr Cys Arg Ala Ser
            20                  25

<210> SEQ ID NO 256
<211> LENGTH: 36
<212> TYPE: PRT
<213> ORGANISM: Artificial Sequence
<220> FEATURE:
<223> OTHER INFORMATION: Synthetic

<400> SEQUENCE: 256

Ser Leu Glu Ser Gly Val Pro Ser Arg Phe Ser Gly Ser Gly Ser Gly
1               5                   10                  15

Thr Asp Phe Thr Leu Thr Ile Ser Ser Leu Gln Pro Asp Asp Phe Ala
            20                  25                  30

Ser Tyr Tyr Cys
        35

<210> SEQ ID NO 257
<211> LENGTH: 10
<212> TYPE: PRT
<213> ORGANISM: Artificial Sequence
<220> FEATURE:
<223> OTHER INFORMATION: Synthetic

<400> SEQUENCE: 257

Phe Gly Gln Gly Thr Lys Leu Glu Ile Thr
1               5                   10

<210> SEQ ID NO 258
<211> LENGTH: 38
<212> TYPE: PRT
<213> ORGANISM: Artificial Sequence
<220> FEATURE:
<223> OTHER INFORMATION: Synthetic

<400> SEQUENCE: 258

Tyr Tyr Ala Asp Ser Val Lys Gly Arg Phe Thr Val Ser Arg Asp Asp
1               5                   10                  15

Ala Lys Asn Ser Leu Phe Leu His Met Asn Ser Leu Arg Ala Glu Asp
            20                  25                  30

Thr Ala Val Tyr Tyr Cys
        35

<210> SEQ ID NO 259
<211> LENGTH: 38
```

-continued

```
<212> TYPE: PRT
<213> ORGANISM: Artificial Sequence
<220> FEATURE:
<223> OTHER INFORMATION: Synthetic

<400> SEQUENCE: 259

Tyr Tyr Ala Asp Ser Val Lys Gly Arg Phe Thr Val Ser Arg Asp Asp
1               5                   10                  15

Ala Lys Asn Ser Met Phe Leu His Met Asn Ser Leu Arg Ala Asp Asp
            20                  25                  30

Thr Ala Val Tyr Tyr Cys
        35

<210> SEQ ID NO 260
<211> LENGTH: 26
<212> TYPE: PRT
<213> ORGANISM: Artificial Sequence
<220> FEATURE:
<223> OTHER INFORMATION: Synthetic

<400> SEQUENCE: 260

Asp Ile Val Met Thr Gln Ser Pro Asp Ser Leu Ala Leu Ser Leu Gly
1               5                   10                  15

Glu Arg Ala Thr Ile Asn Cys Lys Ser Ser
            20                  25

<210> SEQ ID NO 261
<211> LENGTH: 17
<212> TYPE: PRT
<213> ORGANISM: Artificial Sequence
<220> FEATURE:
<223> OTHER INFORMATION: Synthetic

<400> SEQUENCE: 261

Leu Ala Cys Tyr Gln Gln Lys Ala Gly Gln Pro Pro Lys Leu Leu Ile
1               5                   10                  15

Phe

<210> SEQ ID NO 262
<211> LENGTH: 38
<212> TYPE: PRT
<213> ORGANISM: Artificial Sequence
<220> FEATURE:
<223> OTHER INFORMATION: Synthetic

<400> SEQUENCE: 262

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Asp Asp
            20                  25                  30

Thr Ala Leu Tyr Tyr Cys
        35

<210> SEQ ID NO 263
<211> LENGTH: 17
<212> TYPE: PRT
<213> ORGANISM: Artificial Sequence
<220> FEATURE:
<223> OTHER INFORMATION: Synthetic

<400> SEQUENCE: 263

Leu Ile Trp Tyr Gln Gln Lys Pro Gly Lys Ala Pro Lys Leu Leu Ile
1               5                   10                  15
```

-continued

Tyr

```
<210> SEQ ID NO 264
<211> LENGTH: 36
<212> TYPE: PRT
<213> ORGANISM: Artificial Sequence
<220> FEATURE:
<223> OTHER INFORMATION: Synthetic

<400> SEQUENCE: 264

Ser Leu Gln Ser Gly Val Pro Ser Arg Phe Ser Gly Ser Gly Ser Gly
1               5                   10                  15

Thr Asp Phe Thr Leu Ile Ile Ser Ser Leu Gln Pro Glu Asp Phe Ala
            20                  25                  30

Thr Tyr Tyr Cys
        35

<210> SEQ ID NO 265
<211> LENGTH: 38
<212> TYPE: PRT
<213> ORGANISM: Artificial Sequence
<220> FEATURE:
<223> OTHER INFORMATION: Synthetic

<400> SEQUENCE: 265

Lys Tyr Ala Asp Ser Val Arg Gly Arg Phe Thr Phe Ser Arg Asp Asn
1               5                   10                  15

Ala Glu Asn Ser Val His Leu Gln Met Asn Ser Leu Arg Gly Glu Asp
            20                  25                  30

Thr Ala Val Tyr Tyr Cys
        35

<210> SEQ ID NO 266
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Xaa can be any naturally occurring amino acid

<400> SEQUENCE: 266

Thr Leu Gln Ser Gly Val Pro Ser Arg Phe Ser Gly Ser Gly Xaa Gly
1               5                   10                  15

Thr Glu Phe Thr Leu Thr Ile Ser Ser Leu Gln Arg Glu Asp Phe Ala
            20                  25                  30

Thr Tyr Tyr Cys
        35

<210> SEQ ID NO 267
<211> LENGTH: 38
<212> TYPE: PRT
<213> ORGANISM: Artificial Sequence
<220> FEATURE:
<223> OTHER INFORMATION: Synthetic

<400> SEQUENCE: 267

Lys Tyr Ala Asp Ser Val Arg Gly Arg Phe Thr Phe Ser Arg Asp Asn
1               5                   10                  15

Ala Glu Asn Ser Val Phe Leu Gln Met Asn Ser Leu Arg Gly Glu Asp
            20                  25                  30
```

-continued

```
Thr Ala Val Tyr Tyr Cys
        35

<210> SEQ ID NO 268
<211> LENGTH: 36
<212> TYPE: PRT
<213> ORGANISM: Artificial Sequence
<220> FEATURE:
<223> OTHER INFORMATION: Synthetic

<400> SEQUENCE: 268

Thr Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 269
<211> LENGTH: 25
<212> TYPE: PRT
<213> ORGANISM: Artificial Sequence
<220> FEATURE:
<223> OTHER INFORMATION: Synthetic

<400> SEQUENCE: 269

Glu Val Gln Leu Leu Glu Ser Gly Gly Gly Leu Val Gln Pro Gly Gly
1               5                   10                  15

Ser Leu Arg Leu Ser Cys Ala Val Ser
            20                  25

<210> SEQ ID NO 270
<211> LENGTH: 38
<212> TYPE: PRT
<213> ORGANISM: Artificial Sequence
<220> FEATURE:
<223> OTHER INFORMATION: Synthetic

<400> SEQUENCE: 270

Asn Tyr Ala Asp Ser Val Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Glu Tyr Tyr Cys
        35

<210> SEQ ID NO 271
<211> LENGTH: 11
<212> TYPE: PRT
<213> ORGANISM: Artificial Sequence
<220> FEATURE:
<223> OTHER INFORMATION: Synthetic

<400> SEQUENCE: 271

Trp Gly Gln Gly Ile Leu Val Thr Val Ser Pro
1               5                   10

<210> SEQ ID NO 272
<211> LENGTH: 17
<212> TYPE: PRT
<213> ORGANISM: Artificial Sequence
<220> FEATURE:
<223> OTHER INFORMATION: Synthetic

<400> SEQUENCE: 272
```

-continued

```
Leu Ile Trp Tyr Gln Gln Lys Pro Gly Lys Ala Pro Lys Leu Leu Leu
1               5                   10                  15

Tyr

<210> SEQ ID NO 273
<211> LENGTH: 36
<212> TYPE: PRT
<213> ORGANISM: Artificial Sequence
<220> FEATURE:
<223> OTHER INFORMATION: Synthetic

<400> SEQUENCE: 273

Ser Leu Gln Ser Gly Val Pro Ala Arg Phe Thr Gly Ser Gly Ser Gly
1               5                   10                  15

Thr Asp Phe Thr Leu Thr Ile Gly Ser Leu Gln Pro Glu Asp Phe Ala
                20                  25                  30

Thr Tyr Tyr Cys
        35

<210> SEQ ID NO 274
<211> LENGTH: 330
<212> TYPE: PRT
<213> ORGANISM: Artificial Sequence
<220> FEATURE:
<223> OTHER INFORMATION: Synthetic

<400> SEQUENCE: 274

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

-continued

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 275
<211> LENGTH: 326
<212> TYPE: PRT
<213> ORGANISM: Artificial Sequence
<220> FEATURE:
<223> OTHER INFORMATION: Synthetic

<400> SEQUENCE: 275

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 276
<211> LENGTH: 377
<212> TYPE: PRT
<213> ORGANISM: Artificial Sequence
<220> FEATURE:
<223> OTHER INFORMATION: Synthetic

<400> SEQUENCE: 276

Ala Ser Thr Lys Gly Pro Ser Val Phe Pro Leu Ala Pro Cys Ser Arg
1                5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300
```

```
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375
```

<210> SEQ ID NO 277
<211> LENGTH: 327
<212> TYPE: PRT
<213> ORGANISM: Artificial Sequence
<220> FEATURE:
<223> OTHER INFORMATION: Synthetic

<400> SEQUENCE: 277

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 278
<211> LENGTH: 353
<212> TYPE: PRT
<213> ORGANISM: Artificial Sequence
<220> FEATURE:
<223> OTHER INFORMATION: Synthetic

<400> SEQUENCE: 278
```

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
            245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
            275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320
```

```
Pro Leu Ala Phe Thr Gln Lys Thr Ile Asp Arg Leu Ala Gly Lys Pro
            325                 330                 335

Thr His Val Asn Val Ser Val Val Met Ala Glu Val Asp Gly Thr Cys
            340                 345                 350

Tyr

<210> SEQ ID NO 279
<211> LENGTH: 340
<212> TYPE: PRT
<213> ORGANISM: Artificial Sequence
<220> FEATURE:
<223> OTHER INFORMATION: Synthetic

<400> SEQUENCE: 279

Ala Ser Pro Thr Ser Pro Lys Val Phe Pro Leu Ser Leu Asp Ser Thr
1               5                  10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
            85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
            130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
            210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
            245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
            275                 280                 285

Ala Glu Asp Trp Lys Lys Gly Glu Thr Phe Ser Cys Met Val Gly His
        290                 295                 300

Glu Ala Leu Pro Leu Ala Phe Thr Gln Lys Thr Ile Asp Arg Met Ala
305                 310                 315                 320
```

```
Gly Lys Pro Thr His Ile Asn Val Ser Val Val Met Ala Glu Ala Asp
            325                 330                 335

Gly Thr Cys Tyr
            340

<210> SEQ ID NO 280
<211> LENGTH: 384
<212> TYPE: PRT
<213> ORGANISM: Artificial Sequence
<220> FEATURE:
<223> OTHER INFORMATION: Synthetic

<400> SEQUENCE: 280

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
            85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
            115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
            165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
    275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Arg Ser Thr Thr Phe Trp Ala
            325                 330                 335
```

-continued

```
Trp Ser Val Leu Arg Val Pro Ala Pro Pro Ser Pro Gln Pro Ala Thr
        340             345             350

Tyr Thr Cys Val Val Ser His Glu Asp Ser Arg Thr Leu Leu Asn Ala
        355             360             365

Ser Arg Ser Leu Glu Val Ser Tyr Val Thr Asp His Gly Pro Met Lys
    370             375             380

<210> SEQ ID NO 281
<211> LENGTH: 453
<212> TYPE: PRT
<213> ORGANISM: Artificial Sequence
<220> FEATURE:
<223> OTHER INFORMATION: Synthetic

<400> SEQUENCE: 281

Gly Ser Ala Ser Ala Pro Thr Leu Phe Pro Leu Val Ser Cys Glu Asn
1               5               10              15

Ser Pro Ser Asp Thr Ser Ser Val Ala Val Gly Cys Leu Ala Gln Asp
            20              25              30

Phe Leu Pro Asp Ser Ile Thr Phe Ser Trp Lys Tyr Lys Asn Asn Ser
        35              40              45

Asp Ile Ser Ser Thr Arg Gly Phe Pro Ser Val Leu Arg Gly Gly Lys
    50              55              60

Tyr Ala Ala Thr Ser Gln Val Leu Leu Pro Ser Lys Asp Val Met Gln
65              70              75              80

Gly Thr Asp Glu His Val Val Cys Lys Val Gln His Pro Asn Gly Asn
            85              90              95

Lys Glu Lys Asn Val Pro Leu Pro Val Ile Ala Glu Leu Pro Pro Lys
            100             105             110

Val Ser Val Phe Val Pro Pro Arg Asp Gly Phe Phe Gly Asn Pro Arg
        115             120             125

Lys Ser Lys Leu Ile Cys Gln Ala Thr Gly Phe Ser Pro Arg Gln Ile
    130             135             140

Gln Val Ser Trp Leu Arg Glu Gly Lys Gln Val Gly Ser Gly Val Thr
145             150             155             160

Thr Asp Gln Val Gln Ala Glu Ala Lys Glu Ser Gly Pro Thr Thr Tyr
            165             170             175

Lys Val Thr Ser Thr Leu Thr Ile Lys Glu Ser Asp Trp Leu Gly Gln
            180             185             190

Ser Met Phe Thr Cys Arg Val Asp His Arg Gly Leu Thr Phe Gln Gln
        195             200             205

Asn Ala Ser Ser Met Cys Val Pro Asp Gln Asp Thr Ala Ile Arg Val
    210             215             220

Phe Ala Ile Pro Pro Ser Phe Ala Ser Ile Phe Leu Thr Lys Ser Thr
225             230             235             240

Lys Leu Thr Cys Leu Val Thr Asp Leu Thr Thr Tyr Asp Ser Val Thr
            245             250             255

Ile Ser Trp Thr Arg Gln Asn Gly Glu Ala Val Lys Thr His Thr Asn
            260             265             270

Ile Ser Glu Ser His Pro Asn Ala Thr Phe Ser Ala Val Gly Glu Ala
        275             280             285

Ser Ile Cys Glu Asp Asp Trp Asn Ser Gly Glu Arg Phe Thr Cys Thr
    290             295             300

Val Thr His Thr Asp Leu Pro Ser Pro Leu Lys Gln Thr Ile Ser Arg
305             310             315             320
```

-continued

```
Pro Lys Gly Val Ala Leu His Arg Pro Asp Val Tyr Leu Leu Pro Pro
            325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
        370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
            405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
            435                 440                 445

Ala Gly Thr Cys Tyr
        450

<210> SEQ ID NO 282
<211> LENGTH: 428
<212> TYPE: PRT
<213> ORGANISM: Artificial Sequence
<220> FEATURE:
<223> OTHER INFORMATION: Synthetic

<400> SEQUENCE: 282

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
            85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
            115                 120                 125

Pro Thr Ile Gln Leu Leu Cys Leu Val Ser Gly Tyr Thr Pro Gly Thr
        130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
            165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
            195                 200                 205

Cys Ala Asp Ser Asn Pro Arg Gly Val Ser Ala Tyr Leu Ser Arg Pro
        210                 215                 220
```

```
Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
                275                 280                 285

Arg Asp Trp Ile Glu Gly Glu Thr Tyr Gln Cys Arg Val Thr His Pro
                290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
                340                 345                 350

Glu Asp Ile Ser Val Gln Trp Leu His Asn Glu Val Gln Leu Pro Asp
                355                 360                 365

Ala Arg His Ser Thr Thr Gln Pro Arg Lys Thr Lys Gly Ser Gly Phe
                370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
                420                 425
```

```
<210> SEQ ID NO 283
<211> LENGTH: 324
<212> TYPE: PRT
<213> ORGANISM: Artificial Sequence
<220> FEATURE:
<223> OTHER INFORMATION: Synthetic

<400> SEQUENCE: 283
```

```
Ala Lys Thr Thr Pro Pro Ser Val Tyr Pro Leu Ala Pro Gly Ser Ala
1                   5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val His Thr Phe Pro Ala Val Leu Gln Ser Asp Leu Tyr Thr Leu
                50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
                115                 120                 125

Thr Ile Thr Leu Thr Pro Lys Val Thr Cys Val Val Val Asp Ile Ser
                130                 135                 140

Lys Asp Asp Pro Glu Val Gln Phe Ser Trp Phe Val Asp Asp Val Glu
145                 150                 155                 160
```

```
Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
        210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asn Thr Asn Gly Ser Tyr Phe Val Tyr Ser Lys Leu Asn
                275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys

<210> SEQ ID NO 284
<211> LENGTH: 330
<212> TYPE: PRT
<213> ORGANISM: Artificial Sequence
<220> FEATURE:
<223> OTHER INFORMATION: Synthetic

<400> SEQUENCE: 284

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
                100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
        130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
```

-continued

```
              195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
                275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 285
<211> LENGTH: 335
<212> TYPE: PRT
<213> ORGANISM: Artificial Sequence
<220> FEATURE:
<223> OTHER INFORMATION: Synthetic

<400> SEQUENCE: 285

Lys Thr Thr Pro Pro Ser Val Tyr Pro Leu Ala Pro Gly Cys Gly Asp
1               5                   10                  15

Thr Thr Gly Ser Ser Val Thr Leu Gly Cys Leu Val Lys Gly Tyr Phe
                20                  25                  30

Pro Glu Ser Val Thr Val Thr Trp Asn Ser Gly Ser Leu Ser Ser Ser
        35                  40                  45

Val His Thr Phe Pro Ala Leu Leu Gln Ser Gly Leu Tyr Thr Met Ser
    50                  55                  60

Ser Ser Val Thr Val Pro Ser Ser Thr Trp Pro Ser Gln Thr Val Thr
65                  70                  75                  80

Cys Ser Val Ala His Pro Ala Ser Ser Thr Thr Val Asp Lys Lys Leu
                85                  90                  95

Glu Pro Ser Gly Pro Ile Ser Thr Ile Asn Pro Cys Pro Pro Cys Lys
                100                 105                 110

Glu Cys His Lys Cys Pro Ala Pro Asn Leu Glu Gly Gly Pro Ser Val
        115                 120                 125

Phe Ile Phe Pro Pro Asn Ile Lys Asp Val Leu Met Ile Ser Leu Thr
    130                 135                 140

Pro Lys Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
                180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
    210                 215                 220

Ser Lys Ile Lys Gly Leu Val Arg Ala Pro Gln Val Tyr Ile Leu Pro
```

```
225                 230                 235                 240

Pro Pro Ala Glu Gln Leu Ser Arg Lys Asp Val Ser Leu Thr Cys Leu
            245                 250                 255

Val Val Gly Phe Asn Pro Gly Asp Ile Ser Val Glu Trp Thr Ser Asn
            260                 265                 270

Gly His Thr Glu Glu Asn Tyr Lys Asp Thr Ala Pro Val Leu Asp Ser
            275                 280                 285

Asp Gly Ser Tyr Phe Ile Tyr Ser Lys Leu Asn Met Lys Thr Ser Lys
        290                 295                 300

Trp Glu Lys Thr Asp Ser Phe Ser Cys Asn Val Arg His Glu Gly Leu
305                 310                 315                 320

Lys Asn Tyr Tyr Leu Lys Lys Thr Ile Ser Arg Ser Pro Gly Lys
                325                 330                 335

<210> SEQ ID NO 286
<211> LENGTH: 335
<212> TYPE: PRT
<213> ORGANISM: Artificial Sequence
<220> FEATURE:
<223> OTHER INFORMATION: Synthetic

<400> SEQUENCE: 286

Ala Lys Thr Thr Ala Pro Ser Val Tyr Pro Leu Val Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
        50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro His Gln
            100                 105                 110

Arg Val Pro Pro Cys Ala Ala Pro Asp Leu Leu Gly Gly Pro Ser Val
            115                 120                 125

Phe Ile Phe Pro Pro Lys Ile Lys Asp Val Leu Met Ile Ser Leu Ser
        130                 135                 140

Pro Met Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
            165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
        210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
            245                 250                 255

Ile Thr Gly Phe Leu Pro Ala Glu Ile Ala Val Asp Trp Thr Ser Asn
```

-continued

```
              260                 265                 270

Gly Arg Thr Glu Gln Asn Tyr Lys Asn Thr Ala Thr Val Leu Asp Ser
          275                 280                 285

Asp Gly Ser Tyr Phe Met Tyr Ser Lys Leu Arg Val Gln Lys Ser Thr
      290                 295                 300

Trp Glu Arg Gly Ser Leu Phe Ala Cys Ser Val Val His Glu Val Leu
305                 310                 315                 320

His Asn His Leu Thr Thr Lys Thr Ile Ser Arg Ser Leu Gly Lys
              325                 330                 335

<210> SEQ ID NO 287
<211> LENGTH: 344
<212> TYPE: PRT
<213> ORGANISM: Artificial Sequence
<220> FEATURE:
<223> OTHER INFORMATION: Synthetic

<400> SEQUENCE: 287

Glu Ser Ala Arg Asn Pro Thr Ile Tyr Pro Leu Thr Leu Pro Pro Ala
1               5                  10                  15

Leu Ser Ser Asp Pro Val Ile Ile Gly Cys Leu Ile His Asp Tyr Phe
              20                  25                  30

Pro Ser Gly Thr Met Asn Val Thr Trp Gly Lys Ser Gly Lys Asp Ile
          35                  40                  45

Thr Thr Val Asn Phe Pro Pro Ala Leu Ala Ser Gly Gly Arg Tyr Thr
      50                  55                  60

Met Ser Asn Gln Leu Thr Leu Pro Ala Val Glu Cys Pro Glu Gly Glu
65                  70                  75                  80

Ser Val Lys Cys Ser Val Gln His Asp Ser Asn Pro Val Gln Glu Leu
              85                  90                  95

Asp Val Asn Cys Ser Gly Pro Thr Pro Pro Pro Ile Thr Ile Pro
              100                 105                 110

Ser Cys Gln Pro Ser Leu Ser Leu Gln Arg Pro Ala Leu Glu Asp Leu
          115                 120                 125

Leu Leu Gly Ser Asp Ala Ser Ile Thr Cys Thr Leu Asn Gly Leu Arg
      130                 135                 140

Asn Pro Glu Gly Ala Val Phe Thr Trp Glu Pro Ser Thr Gly Lys Asp
145                 150                 155                 160

Ala Val Gln Lys Lys Ala Val Gln Asn Ser Cys Gly Cys Tyr Ser Val
              165                 170                 175

Ser Ser Val Leu Pro Gly Cys Ala Glu Arg Trp Asn Ser Gly Ala Ser
              180                 185                 190

Phe Lys Cys Thr Val Thr His Pro Glu Ser Gly Thr Leu Thr Gly Thr
          195                 200                 205

Ile Ala Lys Val Thr Val Asn Thr Phe Pro Pro Gln Val His Leu Leu
      210                 215                 220

Pro Pro Pro Ser Glu Glu Leu Ala Leu Asn Glu Leu Leu Ser Leu Thr
225                 230                 235                 240

Cys Leu Val Arg Ala Phe Asn Pro Lys Glu Val Leu Val Arg Trp Leu
              245                 250                 255

His Gly Asn Glu Glu Leu Ser Pro Glu Ser Tyr Leu Val Phe Glu Pro
              260                 265                 270

Leu Lys Glu Pro Gly Glu Gly Ala Thr Thr Tyr Leu Val Thr Ser Val
          275                 280                 285

Leu Arg Val Ser Ala Glu Thr Trp Lys Gln Gly Asp Gln Tyr Ser Cys
```

```
                290                 295                 300

Met Val Gly His Glu Ala Leu Pro Met Asn Phe Thr Gln Lys Thr Ile
305                 310                 315                 320

Asp Arg Leu Ser Gly Lys Pro Thr Asn Val Ser Val Ser Val Ile Met
                325                 330                 335

Ser Glu Gly Asp Gly Ile Cys Tyr
            340

<210> SEQ ID NO 288
<211> LENGTH: 454
<212> TYPE: PRT
<213> ORGANISM: Artificial Sequence
<220> FEATURE:
<223> OTHER INFORMATION: Synthetic

<400> SEQUENCE: 288

Ser Gln Ser Phe Pro Asn Val Phe Pro Leu Val Ser Cys Glu Ser Pro
1               5                   10                  15

Leu Ser Asp Lys Asn Leu Val Ala Met Gly Cys Leu Ala Arg Asp Phe
            20                  25                  30

Leu Pro Ser Thr Ile Ser Phe Thr Trp Asn Tyr Gln Asn Asn Thr Glu
        35                  40                  45

Val Ile Gln Gly Ile Arg Thr Phe Pro Thr Leu Arg Thr Gly Gly Lys
    50                  55                  60

Tyr Leu Ala Thr Ser Gln Val Leu Leu Ser Pro Lys Ser Ile Leu Glu
65                  70                  75                  80

Gly Ser Asp Glu Tyr Leu Val Cys Lys Ile His Tyr Gly Gly Lys Asn
                85                  90                  95

Arg Asp Leu His Val Pro Ile Pro Ala Val Ala Glu Met Asn Pro Asn
            100                 105                 110

Val Asn Val Phe Val Pro Pro Arg Asp Gly Phe Ser Gly Pro Ala Pro
        115                 120                 125

Arg Lys Ser Lys Leu Ile Cys Glu Ala Thr Asn Phe Thr Pro Lys Pro
    130                 135                 140

Ile Thr Val Ser Trp Leu Lys Asp Gly Lys Leu Val Glu Ser Gly Phe
145                 150                 155                 160

Thr Thr Asp Pro Val Thr Ile Glu Asn Lys Gly Ser Thr Pro Gln Thr
            165                 170                 175

Tyr Lys Val Ile Ser Thr Leu Thr Ile Ser Glu Ile Asp Trp Leu Asn
            180                 185                 190

Leu Asn Val Tyr Thr Cys Arg Val Asp His Arg Gly Leu Thr Phe Leu
        195                 200                 205

Lys Asn Val Ser Ser Thr Cys Ala Ala Ser Pro Ser Thr Asp Ile Leu
    210                 215                 220

Thr Phe Thr Ile Pro Pro Ser Phe Ala Asp Ile Phe Leu Ser Lys Ser
225                 230                 235                 240

Ala Asn Leu Thr Cys Leu Val Ser Asn Leu Ala Thr Tyr Glu Thr Leu
            245                 250                 255

Asn Ile Ser Trp Ala Ser Gln Ser Gly Glu Pro Leu Glu Thr Lys Ile
            260                 265                 270

Lys Ile Met Glu Ser His Pro Asn Gly Thr Phe Ser Ala Lys Gly Val
        275                 280                 285

Ala Ser Val Cys Val Glu Asp Trp Asn Asn Arg Lys Glu Phe Val Cys
    290                 295                 300

Thr Val Thr His Arg Asp Leu Pro Ser Pro Gln Lys Lys Phe Ile Ser
```

-continued

```
305                310                315                320

Lys Pro Asn Glu Val His Lys His Pro Pro Ala Val Tyr Leu Leu Pro
                325                330                335

Pro Ala Arg Glu Gln Leu Asn Leu Arg Glu Ser Ala Thr Val Thr Cys
            340                345                350

Leu Val Lys Gly Phe Ser Pro Ala Asp Ile Ser Val Gln Trp Leu Gln
            355                360                365

Arg Gly Gln Leu Leu Pro Gln Glu Lys Tyr Val Thr Ser Ala Pro Met
            370                375                380

Pro Glu Pro Gly Ala Pro Gly Phe Tyr Phe Thr His Ser Ile Leu Thr
385                390                395                400

Val Thr Glu Glu Glu Trp Asn Ser Gly Glu Thr Tyr Thr Cys Val Val
                405                410                415

Gly His Glu Ala Leu Pro His Leu Val Thr Glu Arg Thr Val Asp Lys
                420                425                430

Ser Thr Gly Lys Pro Thr Leu Tyr Asn Val Ser Leu Ile Met Ser Asp
            435                440                445

Thr Gly Gly Thr Cys Tyr
        450

<210> SEQ ID NO 289
<211> LENGTH: 257
<212> TYPE: PRT
<213> ORGANISM: Artificial Sequence
<220> FEATURE:
<223> OTHER INFORMATION: Synthetic

<400> SEQUENCE: 289

Asp Lys Lys Glu Pro Asp Met Phe Leu Leu Ser Glu Cys Lys Ala Pro
1                5                10                15

Glu Glu Asn Glu Lys Ile Asn Leu Gly Cys Leu Val Ile Gly Ser Gln
                20                25                30

Pro Leu Lys Ile Ser Trp Glu Pro Lys Lys Ser Ser Ile Val Glu His
            35                40                45

Val Phe Pro Ser Glu Met Arg Asn Gly Asn Tyr Thr Met Val Leu Gln
        50                55                60

Val Thr Val Leu Ala Ser Glu Leu Asn Leu Asn His Thr Cys Thr Ile
65                70                75                80

Asn Lys Pro Lys Arg Lys Glu Lys Pro Phe Lys Phe Pro Glu Ser Trp
                85                90                95

Asp Ser Gln Ser Ser Lys Arg Val Thr Pro Thr Leu Gln Ala Lys Asn
            100                105                110

His Ser Thr Glu Ala Thr Lys Ala Ile Thr Thr Lys Lys Asp Ile Glu
            115                120                125

Gly Ala Met Ala Pro Ser Asn Leu Thr Val Asn Ile Leu Thr Thr Ser
        130                135                140

Thr His Pro Glu Met Ser Ser Trp Leu Leu Cys Glu Val Ser Gly Phe
145                150                155                160

Phe Pro Glu Asn Ile His Leu Met Trp Leu Gly Val His Ser Lys Met
                165                170                175

Lys Ser Thr Asn Phe Val Thr Ala Asn Pro Thr Ala Gln Pro Gly Gly
            180                185                190

Thr Phe Gln Thr Trp Ser Val Leu Arg Leu Pro Val Ala Leu Ser Ser
            195                200                205

Ser Leu Asp Thr Tyr Thr Cys Val Val Glu His Glu Ala Ser Lys Thr
```

```
              210                 215                 220

Lys Leu Asn Ala Ser Lys Ser Leu Ala Ile Ser Gly Cys Tyr His Leu
225                 230                 235                 240

Leu Pro Glu Ser Asp Gly Pro Ser Arg Arg Pro Asp Gly Pro Ala Leu
                    245                 250                 255

Ala

<210> SEQ ID NO 290
<211> LENGTH: 421
<212> TYPE: PRT
<213> ORGANISM: Artificial Sequence
<220> FEATURE:
<223> OTHER INFORMATION: Synthetic

<400> SEQUENCE: 290

Ser Ile Arg Asn Pro Gln Leu Tyr Pro Leu Lys Pro Cys Lys Gly Thr
1                   5                   10                  15

Ala Ser Met Thr Leu Gly Cys Leu Val Lys Asp Tyr Phe Pro Asn Pro
                20                  25                  30

Val Thr Val Thr Trp Tyr Ser Asp Ser Leu Asn Met Ser Thr Val Asn
            35                  40                  45

Phe Pro Ala Leu Gly Ser Glu Leu Lys Val Thr Thr Ser Gln Val Thr
        50                  55                  60

Ser Trp Gly Lys Ser Ala Lys Asn Phe Thr Cys His Val Thr His Pro
65                  70                  75                  80

Pro Ser Phe Asn Glu Ser Arg Thr Ile Leu Val Arg Pro Val Asn Ile
                85                  90                  95

Thr Glu Pro Thr Leu Glu Leu Leu His Ser Ser Cys Asp Pro Asn Ala
                100                 105                 110

Phe His Ser Thr Ile Gln Leu Tyr Cys Phe Ile Tyr Gly His Ile Leu
            115                 120                 125

Asn Asp Val Ser Val Ser Trp Leu Met Asp Asp Arg Glu Ile Thr Asp
        130                 135                 140

Thr Leu Ala Gln Thr Val Leu Ile Lys Glu Glu Gly Lys Leu Ala Ser
145                 150                 155                 160

Thr Cys Ser Lys Leu Asn Ile Thr Glu Gln Gln Trp Met Ser Glu Ser
                165                 170                 175

Thr Phe Thr Cys Lys Val Thr Ser Gln Gly Val Asp Tyr Leu Ala His
                180                 185                 190

Thr Arg Arg Cys Pro Asp His Glu Pro Arg Gly Val Ile Thr Tyr Leu
            195                 200                 205

Ile Pro Pro Ser Pro Leu Asp Leu Tyr Gln Asn Gly Ala Pro Lys Leu
        210                 215                 220

Thr Cys Leu Val Val Asp Leu Glu Ser Glu Lys Asn Val Asn Val Thr
225                 230                 235                 240

Trp Asn Gln Glu Lys Lys Thr Ser Val Ser Ala Ser Gln Trp Tyr Thr
                245                 250                 255

Lys His His Asn Asn Ala Thr Thr Ser Ile Thr Ser Ile Leu Pro Val
                260                 265                 270

Val Ala Lys Asp Trp Ile Glu Gly Tyr Gly Tyr Gln Cys Ile Val Asp
            275                 280                 285

His Pro Asp Phe Pro Lys Pro Ile Val Arg Ser Ile Thr Lys Thr Pro
        290                 295                 300

Gly Gln Arg Ser Ala Pro Glu Val Tyr Val Phe Pro Pro Pro Glu Glu
305                 310                 315                 320
```

```
Glu Ser Glu Asp Lys Arg Thr Leu Thr Cys Leu Ile Gln Asn Phe Phe
                325                 330                 335

Pro Glu Asp Ile Ser Val Gln Trp Leu Gly Asp Gly Lys Leu Ile Ser
                340                 345                 350

Asn Ser Gln His Ser Thr Thr Thr Pro Leu Lys Ser Asn Gly Ser Asn
                355                 360                 365

Gln Gly Phe Phe Ile Phe Ser Arg Leu Glu Val Ala Lys Thr Leu Trp
            370                 375                 380

Thr Gln Arg Lys Gln Phe Thr Cys Gln Val Ile His Glu Ala Leu Gln
385                 390                 395                 400

Lys Pro Arg Lys Leu Glu Lys Thr Ile Ser Thr Ser Leu Gly Asn Thr
                405                 410                 415

Ser Leu Arg Pro Ser
                420

<210> SEQ ID NO 291
<211> LENGTH: 107
<212> TYPE: PRT
<213> ORGANISM: Artificial Sequence
<220> FEATURE:
<223> OTHER INFORMATION: Synthetic

<400> SEQUENCE: 291

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 292
<211> LENGTH: 106
<212> TYPE: PRT
<213> ORGANISM: Artificial Sequence
<220> FEATURE:
<223> OTHER INFORMATION: Synthetic

<400> SEQUENCE: 292

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
```

-continued

```
                        85                  90                  95

Glu Lys Thr Val Ala Pro Thr Glu Cys Ser
            100                 105

<210> SEQ ID NO 293
<211> LENGTH: 106
<212> TYPE: PRT
<213> ORGANISM: Artificial Sequence
<220> FEATURE:
<223> OTHER INFORMATION: Synthetic

<400> SEQUENCE: 293

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 294
<211> LENGTH: 106
<212> TYPE: PRT
<213> ORGANISM: Artificial Sequence
<220> FEATURE:
<223> OTHER INFORMATION: Synthetic

<400> SEQUENCE: 294

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 295
<211> LENGTH: 106
<212> TYPE: PRT
<213> ORGANISM: Artificial Sequence
<220> FEATURE:
<223> OTHER INFORMATION: Synthetic

<400> SEQUENCE: 295

Gly Gln Pro Lys Ala Ala Pro Ser Val Thr Leu Phe Pro Pro Ser Ser
1               5                   10                  15
```

-continued

```
Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
            35                  40                  45

Val Asn Thr Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

```
<210> SEQ ID NO 296
<211> LENGTH: 106
<212> TYPE: PRT
<213> ORGANISM: Artificial Sequence
<220> FEATURE:
<223> OTHER INFORMATION: Synthetic

<400> SEQUENCE: 296

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
            35                  40                  45

Val Lys Val Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

```
<210> SEQ ID NO 297
<211> LENGTH: 107
<212> TYPE: PRT
<213> ORGANISM: Artificial Sequence
<220> FEATURE:
<223> OTHER INFORMATION: Synthetic

<400> SEQUENCE: 297

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
```

```
                100                 105

<210> SEQ ID NO 298
<211> LENGTH: 106
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 298

Xaa Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 299
<211> LENGTH: 105
<212> TYPE: PRT
<213> ORGANISM: Artificial Sequence
<220> FEATURE:
<223> OTHER INFORMATION: Synthetic

<400> SEQUENCE: 299

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105

<210> SEQ ID NO 300
<211> LENGTH: 104
<212> TYPE: PRT
<213> ORGANISM: Artificial Sequence
<220> FEATURE:
<223> OTHER INFORMATION: Synthetic

<400> SEQUENCE: 300

Gln Pro Lys Ser Thr Pro Thr Leu Thr Met Phe Pro Pro Ser Pro Glu
```

```
1           5              10             15
```

Glu Leu Gln Glu Asn Lys Ala Thr Leu Val Cys Leu Ile Ser Asn Phe
            20              25             30

Ser Pro Ser Gly Val Thr Val Ala Trp Lys Ala Asn Gly Thr Pro Ile
        35              40             45

Thr Gln Gly Val Asp Thr Ser Asn Pro Thr Lys Glu Asp Asn Lys Tyr
    50              55             60

Met Ala Ser Ser Phe Leu His Leu Thr Ser Asp Gln Trp Arg Ser His
65              70              75             80

Asn Ser Phe Thr Cys Gln Val Thr His Glu Gly Asp Thr Val Glu Lys
                85              90             95

Ser Leu Ser Pro Ala Glu Cys Leu
            100

<210> SEQ ID NO 301
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 301

Xaa Gln Pro Lys Ala Thr Pro Ser Val Asn Leu Phe Pro Pro Ser Ser
1           5              10             15

Glu Glu Leu Lys Thr Lys Lys Ala Thr Leu Val Cys Met Ile Thr Glu
            20              25             30

Phe Tyr Ala Ala Ala Val Arg Val Ala Trp Lys Ala Asp Gly Thr Pro
            35              40             45

Phe Thr Gln Gly Val Glu Thr Thr Gln Pro Pro Lys Gln Arg Asp Asn
    50              55             60

Met Ala Ser Ser Tyr Leu Leu Phe Thr Ala Glu Ala Trp Glu Ser His
65              70              75             80

Ser Ser Tyr Ser Cys His Val Thr His Glu Gly Asn Thr Val Glu Lys
                85              90             95

Ser Leu Ser Arg Ala Glu Cys Ser
            100

<210> SEQ ID NO 302
<211> LENGTH: 24
<212> TYPE: DNA
<213> ORGANISM: Artificial Sequence
<220> FEATURE:
<223> OTHER INFORMATION: Synthetic

<400> SEQUENCE: 302
ggattcacct tcagtgacta ctac                                    24

<210> SEQ ID NO 303
<211> LENGTH: 24
<212> TYPE: DNA
<213> ORGANISM: Artificial Sequence
<220> FEATURE:
<223> OTHER INFORMATION: Synthetic

<400> SEQUENCE: 303
attgatagta gtgctggtgc catt                                    24
```

-continued

```
<210> SEQ ID NO 304
<211> LENGTH: 39
<212> TYPE: DNA
<213> ORGANISM: Artificial Sequence
<220> FEATURE:
<223> OTHER INFORMATION: Synthetic

<400> SEQUENCE: 304
gcgagagagc gtagagatgg ccacaaaatc tttgactgt                              39

<210> SEQ ID NO 305
<211> LENGTH: 36
<212> TYPE: DNA
<213> ORGANISM: Artificial Sequence
<220> FEATURE:
<223> OTHER INFORMATION: Synthetic

<400> SEQUENCE: 305
cagaatattt tgtacagttc caacaataag aactac                                36

<210> SEQ ID NO 306
<211> LENGTH: 9
<212> TYPE: DNA
<213> ORGANISM: Artificial Sequence
<220> FEATURE:
<223> OTHER INFORMATION: Synthetic

<400> SEQUENCE: 306 tggtcatct                                                              9

<210> SEQ ID NO 307
<211> LENGTH: 27
<212> TYPE: DNA
<213> ORGANISM: Artificial Sequence
<220> FEATURE:
<223> OTHER INFORMATION: Synthetic

<400> SEQUENCE: 307
cagcaatatt acagtagtcc gtataat                                          27

<210> SEQ ID NO 308
<211> LENGTH: 360
<212> TYPE: DNA
<213> ORGANISM: Artificial Sequence
<220> FEATURE:
<223> OTHER INFORMATION: Synthetic

<400> SEQUENCE: 308
caggtgcagc tggtggagtc tgggggagac ttggtcaagc ctggagggtc cctgagactc      60
tcctgtgtag cctcgggatt caccttcagt gactactaca tgaactggat ccgcctgcct     120
ccagggaagg gcctggagtg ggtttcatac attgatagta gtgctggtgc catttactat     180
gcagactctg tgaggggccg attcaccgtc tccaggacg acgccaagaa ttcactattt      240
ctgcacatga acagcctgag agccgatgac acggccgttt attactgtgc gagagagcgt     300
agagatggcc acaaaatctt tgactgttgg ggcccgggaa ccctggtcac cgtctcttca     360

<210> SEQ ID NO 309
<211> LENGTH: 339
<212> TYPE: DNA
<213> ORGANISM: Artificial Sequence
<220> FEATURE:
<223> OTHER INFORMATION: Synthetic

<400> SEQUENCE: 309
```

-continued

```
gacatcgtga tgacccagtc tccagactcc ctggctgtgt ctctgggcga gagggccacc    60
atcaactgca agtccagcca gaatattttg tacagttcca acaataagaa ctacttagct   120
tggtaccagc agaaagcagg acagcctcct aagttgctca tttttctggtc atctacccgg   180 gaatccgggg tccctgaccg attcagtggc agcgggtctg ggacagattt cactctcacc   240
atcaacagcc tgcaggctga agatgtggca gtttattact gtcagcaata ttacagtagt   300
ccgtataatt ttggccgggg gaccacactg gagatcaaa                           339
```

```
<210> SEQ ID NO 310
<211> LENGTH: 36
<212> TYPE: DNA
<213> ORGANISM: Artificial Sequence
<220> FEATURE:
<223> OTHER INFORMATION: Synthetic

<400> SEQUENCE: 310
cagaatattt tatacagttc caacaataag aactat                              36
```

```
<210> SEQ ID NO 311
<211> LENGTH: 360
<212> TYPE: DNA
<213> ORGANISM: Artificial Sequence
<220> FEATURE:
<223> OTHER INFORMATION: Synthetic

<400> SEQUENCE: 311
caggtgcacc tggtggagtc tggggggagac ttggtcaagc ctggagggtc cctgagactc    60
tcctgtgtag cctctggatt caccttcagt gactactaca tgaactggat ccgtatgcct   120
ccagggaagg gcctggagtg gatttcatac attgatagta gtgctggtgc catttactat   180
gcagactctg tgaagggccg attcaccgtc tccagggacg acgccaagaa ctcactgttt   240
ctacacatga acaacctgag agccgatgac acggccgttt attactgtgc gagagagcgt   300
agagatggcc acaaaatctt tgactgttgg ggcccgggaa ccctggtcac cgtctcctca   360
```

```
<210> SEQ ID NO 312
<211> LENGTH: 339
<212> TYPE: DNA
<213> ORGANISM: Artificial Sequence
<220> FEATURE:
<223> OTHER INFORMATION: Synthetic

<400> SEQUENCE: 312
gacatcgtga tgacccagtc tccagactcc ctggctgtgt ctctgggcga gagggccacc    60
atcaactgca agtccagcca gaatatttta tacagttcca acaataagaa ctatttagct   120
tggtaccagc agaaagcagg acagcctcct aagttgctca tttttctggtc atctacccgg   180 gaatccggggg tccctgaccg attcagtggc agcgggtctg ggacagattt cactctcacc   240
atcagcagcc tgcaggctga agatgtggca gtttattact gtcagcaata ttacagtagt   300
ccgtataatt ttggccgggg gaccacactg gagatcaaa                           339
```

```
<210> SEQ ID NO 313
<211> LENGTH: 24
<212> TYPE: DNA
<213> ORGANISM: Artificial Sequence
<220> FEATURE:
<223> OTHER INFORMATION: Synthetic

<400> SEQUENCE: 313
```

-continued

```
ggatacagtt ttacatacta ctgg                                              24

<210> SEQ ID NO 314
<211> LENGTH: 24
<212> TYPE: DNA
<213> ORGANISM: Artificial Sequence
<220> FEATURE:
<223> OTHER INFORMATION: Synthetic

<400> SEQUENCE: 314
atctatcctg gtgactctga tacc                                              24

<210> SEQ ID NO 315
<211> LENGTH: 36
<212> TYPE: DNA
<213> ORGANISM: Artificial Sequence
<220> FEATURE:
<223> OTHER INFORMATION: Synthetic

<400> SEQUENCE: 315
actacacatg cgcgcaactg gaacaacgtg gcctac                                 36

<210> SEQ ID NO 316
<211> LENGTH: 18
<212> TYPE: DNA
<213> ORGANISM: Artificial Sequence
<220> FEATURE:
<223> OTHER INFORMATION: Synthetic

<400> SEQUENCE: 316
cagaacatta acaccttt                                                     18

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 gctgcatcc                                                                9

<210> SEQ ID NO 318
<211> LENGTH: 27
<212> TYPE: DNA
<213> ORGANISM: Artificial Sequence
<220> FEATURE:
<223> OTHER INFORMATION: Synthetic

<400> SEQUENCE: 318
caacagagtt ctagtacccc gtggacg                                           27

<210> SEQ ID NO 319
<211> LENGTH: 357
<212> TYPE: DNA
<213> ORGANISM: Artificial Sequence
<220> FEATURE:
<223> OTHER INFORMATION: Synthetic

<400> SEQUENCE: 319
gaggtgcagc tggtgcagtc tggagcagag gtgaaaaagc ccggggagtc tctgaagatc       60
tcctgtaagg gttctggata cagttttaca tactactgga tcggctgggt gcgccagatg      120
cccgggaaag gcctggagtg gatggggatc atctatcctg gtgactctga taccagatac      180
agcccgtcct tccaaggcca ggtcaccatc tcagccgaca gtccatcag taccgcctat      240
```

-continued

```
ttgcagtgga gcagcctgaa ggcctcggac accgccatgt attactgtac tacacatgcg        300
cgcaactgga acaacgtggc ctactggggc cagggaaccc tggtcaccgt ctcctca          357

<210> SEQ ID NO 320
<211> LENGTH: 322
<212> TYPE: DNA
<213> ORGANISM: Artificial Sequence
<220> FEATURE:
<223> OTHER INFORMATION: Synthetic

<400> SEQUENCE: 320
gacatccaga tgacccagtc tccatcctcc ctgtctgcat ctgtcggaga cagactcacc         60
atcacttgcc gggcaagtca gaacattaac acctttttaa attggtatca acagaaccca        120
gggaaagccc ctaaggtcct gatctatgct gcatccagtt tggaaagtgg ggtcccatca        180
aggttcagtg gcagtggatc tgggacagat ttcactctca ccatcagcag tctgcaacct        240
gaagattttg caacttacta ctgtcaacag agttctagta ccccgtggac gttcggccaa        300
gggaccaagg tggaaatcaa ac                                                   322

<210> SEQ ID NO 321
<211> LENGTH: 24
<212> TYPE: DNA
<213> ORGANISM: Artificial Sequence
<220> FEATURE:
<223> OTHER INFORMATION: Synthetic

<400> SEQUENCE: 321
ggattcacct ttagtggctt cgcc                                                  24

<210> SEQ ID NO 322
<211> LENGTH: 24
<212> TYPE: DNA
<213> ORGANISM: Artificial Sequence
<220> FEATURE:
<223> OTHER INFORMATION: Synthetic

<400> SEQUENCE: 322
attagtggga gtggtgatat caca                                                  24

<210> SEQ ID NO 323
<211> LENGTH: 48
<212> TYPE: DNA
<213> ORGANISM: Artificial Sequence
<220> FEATURE:
<223> OTHER INFORMATION: Synthetic

<400> SEQUENCE: 323
gcgaaagacc catataactg gaaccacggg gtctacggca tggacgtc                        48

<210> SEQ ID NO 324
<211> LENGTH: 18
<212> TYPE: DNA
<213> ORGANISM: Artificial Sequence
<220> FEATURE:
<223> OTHER INFORMATION: Synthetic

<400> SEQUENCE: 324
cagagcatta gcagctat                                                         18

<210> SEQ ID NO 325
<211> LENGTH: 9
<212> TYPE: DNA
```

<213> ORGANISM: Artificial Sequence
<220> FEATURE:
<223> OTHER INFORMATION: Synthetic

<400> SEQUENCE: 325 ggtgcatcc                                                                                          9

<210> SEQ ID NO 326
<211> LENGTH: 27
<212> TYPE: DNA
<213> ORGANISM: Artificial Sequence
<220> FEATURE:
<223> OTHER INFORMATION: Synthetic

<400> SEQUENCE: 326
caacagagtt tcaatgcccc tctcact                                                                      27

<210> SEQ ID NO 327
<211> LENGTH: 369
<212> TYPE: DNA
<213> ORGANISM: Artificial Sequence
<220> FEATURE:
<223> OTHER INFORMATION: Synthetic

<400> SEQUENCE: 327
gaggtgcagc ttttggagtc ggggggaggc ttggcacagc cggggaagtc cctgagactc      60
tcctgtgcag cctctggatt cacctttagt ggcttcgcca tgagctgggt ccgccaggct     120
cctgggaagg ggctggagtg ggtctcaggt attagtggga gtggtgatat cacatactat     180
gcagactccg tgaagggccg gttcaccatt tccagagaca attccaagag tacgctgtat     240
cttcaaatga acagcctggg agccgaggac acggccgtgt attactgtgc gaaagaccca     300
tataactgga accacggggt ctacggcatg gacgtctggg gccaagggac cacggtcacc     360
gtctcctca                                                                                         369

<210> SEQ ID NO 328
<211> LENGTH: 321
<212> TYPE: DNA
<213> ORGANISM: Artificial Sequence
<220> FEATURE:
<223> OTHER INFORMATION: Synthetic

<400> SEQUENCE: 328
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaaattcct gatctatggt gcatccagtt tgcaaagtgg ggtcccatca     180
aggttcagtg gcagtggatc tgggactgat ttcactctca ccatcagcag tctgcaacct     240
gaagatttcg cagcttacta ctgtcaacag agtttcaatg cccctctcac tttcggcggc     300
gggaccaagg tggagatcaa a                                                                            321

<210> SEQ ID NO 329
<211> LENGTH: 39
<212> TYPE: DNA
<213> ORGANISM: Artificial Sequence
<220> FEATURE:
<223> OTHER INFORMATION: Synthetic

<400> SEQUENCE: 329
gcgagagaac gtagagatgg ccacaaaatc tttgactgg                                                         39

-continued

```
<210> SEQ ID NO 330
<211> LENGTH: 36
<212> TYPE: DNA
<213> ORGANISM: Artificial Sequence
<220> FEATURE:
<223> OTHER INFORMATION: Synthetic

<400> SEQUENCE: 330
cagaatattt tatacacttc caacaataag aactac                                 36

<210> SEQ ID NO 331
<211> LENGTH: 27
<212> TYPE: DNA
<213> ORGANISM: Artificial Sequence
<220> FEATURE:
<223> OTHER INFORMATION: Synthetic

<400> SEQUENCE: 331
catcagtatt acagtagtcc gtacact                                           27

<210> SEQ ID NO 332
<211> LENGTH: 360
<212> TYPE: DNA
<213> ORGANISM: Artificial Sequence
<220> FEATURE:
<223> OTHER INFORMATION: Synthetic

<400> SEQUENCE: 332
caggtgcagc tggtggagtc tggggggaggc ttggtcaagc ctggagggtc cctgagactc      60
tcctgcgtag cctctggatt caccttcagt gactactaca tgaactggat ccgcctgcct     120
ccagggaggg ggctgcagtg gatttcatac attgatagta gtgctggtgc catttactac     180
gcagactctg tgaagggccg attcaccgtc tccagggacg acgccaagaa ttcactttat     240
ctgcaaatga acagcctgag agccgatgac acggccgttt attactgtgc gagagaacgt     300
agagatggcc acaaaatctt tgactggtgg ggccagggaa ccctggtcac cgtctcctca     360

<210> SEQ ID NO 333
<211> LENGTH: 339
<212> TYPE: DNA
<213> ORGANISM: Artificial Sequence
<220> FEATURE:
<223> OTHER INFORMATION: Synthetic

<400> SEQUENCE: 333
gacatcgtga tgacccagtc tccagactcc ctggctgtgt ctctgggcga gagggccacc      60
atcaactgca agtccagcca gaatatttta tacacttcca acaataagaa ctacttaggt     120
tggtaccagc agaaagcagg acagcctcct aaactgctca tttactggtc atctacccgg     180
aattccgggg tccctgaccg cttcagtggc agcgggtctg ggacagattt cactctcacc     240
atcagcagcc tgcaggctga ggatgtggca gtttattact gtcatcagta ttacagtagt     300
ccgtacactt ttggccaggg gaccaacctg gagatcaaa                             339

<210> SEQ ID NO 334
<211> LENGTH: 24
<212> TYPE: DNA
<213> ORGANISM: Artificial Sequence
<220> FEATURE:
<223> OTHER INFORMATION: Synthetic

<400> SEQUENCE: 334
ggatacagtt ttaccaacta ctgg                                              24
```

-continued

```
<210> SEQ ID NO 335
<211> LENGTH: 36
<212> TYPE: DNA
<213> ORGANISM: Artificial Sequence
<220> FEATURE:
<223> OTHER INFORMATION: Synthetic

<400> SEQUENCE: 335
gcgacacatg cgcgcagctg gaactacgtg gcctac                              36

<210> SEQ ID NO 336
<211> LENGTH: 18
<212> TYPE: DNA
<213> ORGANISM: Artificial Sequence
<220> FEATURE:
<223> OTHER INFORMATION: Synthetic

<400> SEQUENCE: 336
cagagcgtca acaacttt                                                  18

<210> SEQ ID NO 337
<211> LENGTH: 27
<212> TYPE: DNA
<213> ORGANISM: Artificial Sequence
<220> FEATURE:
<223> OTHER INFORMATION: Synthetic

<400> SEQUENCE: 337
caacagagta acactacccc gtggacg                                        27

<210> SEQ ID NO 338
<211> LENGTH: 358
<212> TYPE: DNA
<213> ORGANISM: Artificial Sequence
<220> FEATURE:
<223> OTHER INFORMATION: Synthetic

<400> SEQUENCE: 338
gaggtgcagc tggtgcagtc tggagcagag gtgaaaaagc ccgggggagtc tctgaagatc     60 tcctgtaagg gttctggata cagtttttacc aactactgga tcggctgggt gcgccagatg    120
cccgggaaag gcctggagtg gatggggatc atctatcctg gtgactctga taccagatac    180
agcccgtcct tccaaggcca ggtcaccctc tcagccgaca gtccatcag taccgcctac     240 ctacagtgga acagcctgaa ggcctcggac accgccatgt attactgtgc gacacatgcg    300
cgcagctgga actacgtggc ctactggggc cagggaaccc tggtcaccgt cgcctcat     358

<210> SEQ ID NO 339
<211> LENGTH: 321
<212> TYPE: DNA
<213> ORGANISM: Artificial Sequence
<220> FEATURE:
<223> OTHER INFORMATION: Synthetic

<400> SEQUENCE: 339
gacatccaga tgacccagtc tccatcctcc ctgtctgcat ctgtaggaga cagagtcacc     60
atcacttgcc gggcaagtca gagcgtcaac aactttttaa attggtatca gcagaaacca    120
gggacagccc ctaaactcct gatctatgct gcatccagtt tgcaaggtgg ggtcccatca    180
aggttcagtg gcagtggctc tgggacagat ttcactctca ccatcagcag tctgcaacct    240
gaagattttg caacttacta ctgtcaacag agtaacacta ccccgtggac gttcggccaa    300
gggaccaagg tggaaatcaa a                                             321
```

<210> SEQ ID NO 340
<211> LENGTH: 36
<212> TYPE: DNA
<213> ORGANISM: Artificial Sequence
<220> FEATURE:
<223> OTHER INFORMATION: Synthetic

<400> SEQUENCE: 340
cagaatattt tatacagttc caacaataag aactac                               36

<210> SEQ ID NO 341
<211> LENGTH: 360
<212> TYPE: DNA
<213> ORGANISM: Artificial Sequence
<220> FEATURE:
<223> OTHER INFORMATION: Synthetic

<400> SEQUENCE: 341
caggtgcagc tggtggagtc tggggggagac ttggtcaagc ctggagggtc cctgagactc    60
tcctgtgtag cctctggatt caccttcagt gactactaca tgaactggat ccgcctgcct    120
ccagggaagg gcctggagtg gatttcctac attgatagta gtgctggtgc catttactat    180
gcagactctg tgaagggccg attcaccgtc tccagggacg acgccaagaa ctcactattt    240
ctgcacatga acagcctgag agccgatgac acggccgttt attactgtgc gagagagcgt    300
agagatggcc acaaaatctt tgactgttgg ggcccgggaa ccctggtcac cgtctcctca    360

<210> SEQ ID NO 342
<211> LENGTH: 339
<212> TYPE: DNA
<213> ORGANISM: Artificial Sequence
<220> FEATURE:
<223> OTHER INFORMATION: Synthetic

<400> SEQUENCE: 342
gacatcgtga tgacccagtc tccagactcc ctggctgtgt ctctgggcga gagggccacc    60
atcaactgca agtccagcca gaatatttta tacagttcca acaataagaa ctacttagct    120
tggtaccagc agaaaacagg acagcctcct aagttgctca ttttctggtc atctacccgg    180
gaatccgggg tccctgaccg attcagtggc agcgggtctg ggacagattt cactctcacc    240
atcagcagcc tgcaggctga ggatgtggca gtttattact gtcagcaata ttacagtagt    300
ccgtataatt ttggccgggg gaccacactg gagatcaaa                          339

<210> SEQ ID NO 343
<211> LENGTH: 24
<212> TYPE: DNA
<213> ORGANISM: Artificial Sequence
<220> FEATURE:
<223> OTHER INFORMATION: Synthetic

<400> SEQUENCE: 343
ggattcacct ttgatgatta tgcc                                           24

<210> SEQ ID NO 344
<211> LENGTH: 24
<212> TYPE: DNA
<213> ORGANISM: Artificial Sequence
<220> FEATURE:
<223> OTHER INFORMATION: Synthetic

<400> SEQUENCE: 344
attagttgga gtggtgttac catg                                                    24

<210> SEQ ID NO 345
<211> LENGTH: 33
<212> TYPE: DNA
<213> ORGANISM: Artificial Sequence
<220> FEATURE:
<223> OTHER INFORMATION: Synthetic

<400> SEQUENCE: 345
gcaagagggg atggaaccaa tgcttttgat atc                                          33

<210> SEQ ID NO 346
<211> LENGTH: 36
<212> TYPE: DNA
<213> ORGANISM: Artificial Sequence
<220> FEATURE:
<223> OTHER INFORMATION: Synthetic

<400> SEQUENCE: 346
cagagtgttt tgtacaagtc caacaataag aactac                                       36

<210> SEQ ID NO 347
<211> LENGTH: 9
<212> TYPE: DNA
<213> ORGANISM: Artificial Sequence
<220> FEATURE:
<223> OTHER INFORMATION: Synthetic

<400> SEQUENCE: 347 tgggcatct                                                                      9

<210> SEQ ID NO 348
<211> LENGTH: 27
<212> TYPE: DNA
<213> ORGANISM: Artificial Sequence
<220> FEATURE:
<223> OTHER INFORMATION: Synthetic

<400> SEQUENCE: 348
cagcaatatt atagtgttcc gctcact                                                 27

<210> SEQ ID NO 349
<211> LENGTH: 354
<212> TYPE: DNA
<213> ORGANISM: Artificial Sequence
<220> FEATURE:
<223> OTHER INFORMATION: Synthetic

<400> SEQUENCE: 349
gaagtgcagt tggtggagtc tgggggagac ttggtacagc ctggcaggtc cctgagactc           60
tcctgtgcag cctctggatt cacctttgat gattatgcca tgcactgggt ccggcaaggt          120
ccagggaagg gcctggagtg ggtctcaggc attagttgga gtggtgttac catgggctat         180
gcggactctg tgaagggccg attcaccatt tccagagaca cgccaagaa ctccctgtac          240 ctgcgaatga acagtctgag agctgacgac acggccttct attactgtgc aagaggggat         300
ggaaccaatg cttttgatat ctggggccac gggacaatgg tcaccgtctc ttca              354

<210> SEQ ID NO 350
<211> LENGTH: 339
<212> TYPE: DNA
<213> ORGANISM: Artificial Sequence
<220> FEATURE:
<223> OTHER INFORMATION: Synthetic

```
<400> SEQUENCE: 350
gacatcgtga tgacccagtc tccagactcc ctggctgtgt ctctgggcga gagggccacc      60
atcaactgca agtccagcca gagtgttttg tacaagtcca acaataagaa ctacttggat     120
tggtatcagc agaaaccagg acagcctcct aagctgctca tttattgggc atcttcccgg     180
gaatccgggg tccctgaccg attcagtggc agcgggtctg ggacagattt cactctgacc     240
atcagcagcc tgcaggctga agatgtggca gtttattact gtcagcaata ttatagtgtt     300
ccgctcactt tcggcggagg gaccaaggtg gagatcaaa                            339

<210> SEQ ID NO 351
<211> LENGTH: 360
<212> TYPE: DNA
<213> ORGANISM: Artificial Sequence
<220> FEATURE:
<223> OTHER INFORMATION: Synthetic

<400> SEQUENCE: 351
caggtgcagc tggtggagtc tgggggagac ttggtcaagc ctggagggtc cctgagactc      60
tcctgtgtag cctctggatt caccttcagt gactactaca tgaactggat ccgcctgcct     120
ccagggaagg gcctggagtg gatttcatac attgatagta gtgctggtgc catttactat     180
gcagactctg tgaagggccg attcaccgtc tccaggacg acgccaagaa ctcactattt      240
ctacacatga acaacctgag agccgatgac acggccgttt attactgtgc gagagagcgt     300
agagatggcc acaaaatctt tgactgttgg ggcccgggaa ccctggtcac cgtctcctca     360

<210> SEQ ID NO 352
<211> LENGTH: 339
<212> TYPE: DNA
<213> ORGANISM: Artificial Sequence
<220> FEATURE:
<223> OTHER INFORMATION: Synthetic

<400> SEQUENCE: 352
gacatcgtga tgacccagtc tccagactcc ctggctgtgt ctctgggcga gagggccacc      60
atcaactgca agtccagcca gaatatttta tacagttcca acaataagaa ctacttagct     120
tggtaccagc agaaagcagg acagcctcct aagttgctca ttttctggtc atctacccgg     180
gaatccgggg tccctgaccg attcagtggc agcgggtctg ggacagattt cactctcacc     240
atcagcagcc tgcaggctga agatgtggca gtttattact gtcagcaata ttacagtagt     300
ccgtataatt ttggccgggg gaccacactg gagatcaaa                            339

<210> SEQ ID NO 353
<211> LENGTH: 39
<212> TYPE: DNA
<213> ORGANISM: Artificial Sequence
<220> FEATURE:
<223> OTHER INFORMATION: Synthetic

<400> SEQUENCE: 353
gcgagagagc gtagagatgg ccacaaaatc tttgactat                             39

<210> SEQ ID NO 354
<211> LENGTH: 27
<212> TYPE: DNA
<213> ORGANISM: Artificial Sequence
<220> FEATURE:
<223> OTHER INFORMATION: Synthetic
```

-continued

```
<400> SEQUENCE: 354
caccaatatt acagtagtcc gtataat                                          27

<210> SEQ ID NO 355
<211> LENGTH: 360
<212> TYPE: DNA
<213> ORGANISM: Artificial Sequence
<220> FEATURE:
<223> OTHER INFORMATION: Synthetic

<400> SEQUENCE: 355
caggtgcagc tggtggagtc tggggggagac ttggtcaagc ctggagggtc cctgagactc      60
tcctgtgtag cctctggatt caccttcagt gactactaca tgaactggat ccgcctgcct     120
ccagggaggg gcctggagtg gatttcatac attgatagta gtgctggtgc catttactat     180
gcagactctg tgaagggccg attcaccgtc tccagggacg acgccaagaa gtcactattt     240
ctgtacatga acagcctgag agccgatgac acggccgttt attactgtgc gagagagcgt     300
agagatggcc acaaaatctt tgactattgg ggcccgggaa ccctggtcac cgtctcctca     360

<210> SEQ ID NO 356
<211> LENGTH: 339
<212> TYPE: DNA
<213> ORGANISM: Artificial Sequence
<220> FEATURE:
<223> OTHER INFORMATION: Synthetic

<400> SEQUENCE: 356
gacatcgtga tgacccagtc tccagactcc ctggctgtgt ctctgggcga gagggccacc      60
atcaactgca gtccagcca gaatatttta tacagttcca acaataagaa ctacttagct     120
tggtaccagc agaaagcagg acagcctcct aagttgctca ttttctggtc atctacccgg     180
gaatccgggg tccctgaccg attcagtggc agcgggtctg ggacagattt cactctcacc     240
atcagcagcc tgcaggctga agatgtggca gtttattact gtcaccaata ttacagtagt     300
ccgtataatt ttggccgggg gaccacactg gagatcaaa                            339

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
ggattcacct ttagcagctt tgcc                                            24

<210> SEQ ID NO 358
<211> LENGTH: 24
<212> TYPE: DNA
<213> ORGANISM: Artificial Sequence
<220> FEATURE:
<223> OTHER INFORMATION: Synthetic

<400> SEQUENCE: 358
attagtggta gtggtggtag caca                                            24

<210> SEQ ID NO 359
<211> LENGTH: 48
<212> TYPE: DNA
<213> ORGANISM: Artificial Sequence
<220> FEATURE:
<223> OTHER INFORMATION: Synthetic
```

-continued

```
<400> SEQUENCE: 359
gcgaaagata aaaggaactg gaactacggg attgattctt ttgatttc              48

<210> SEQ ID NO 360
<211> LENGTH: 18
<212> TYPE: DNA
<213> ORGANISM: Artificial Sequence
<220> FEATURE:
<223> OTHER INFORMATION: Synthetic

<400> SEQUENCE: 360
cagagcatta gcggctat                                              18

<210> SEQ ID NO 361
<211> LENGTH: 9
<212> TYPE: DNA
<213> ORGANISM: Artificial Sequence
<220> FEATURE:
<223> OTHER INFORMATION: Synthetic

<400> SEQUENCE: 361 gctacatcc                                                         9

<210> SEQ ID NO 362
<211> LENGTH: 27
<212> TYPE: DNA
<213> ORGANISM: Artificial Sequence
<220> FEATURE:
<223> OTHER INFORMATION: Synthetic

<400> SEQUENCE: 362
catcagagtc acagtccccc attcact                                    27

<210> SEQ ID NO 363
<211> LENGTH: 369
<212> TYPE: DNA
<213> ORGANISM: Artificial Sequence
<220> FEATURE:
<223> OTHER INFORMATION: Synthetic

<400> SEQUENCE: 363
gaggtgcagt tgttggagtc tgggggaggc ttggtacagc ctggggggtc cctgagactc   60
tcctgtgcag cctctggatt cacctttagc agctttgcca tgagctgggt ccgccaggct  120
ccagggaagg ggctggagtg ggtctcaggt attagtggta gtggtggtag cacatactac  180
gcagactccg tgaagggccg gttcaccatc tccagagaca attccaagaa cacgctgtat  240
ctgcaaatga acagcctgag agccgaggac acggccatat attactgtgc gaaagataaa  300
aggaactgga actacgggat tgattctttt gatttctggg gccaagggac gatggtcacc  360
gtctcttca                                                        369

<210> SEQ ID NO 364
<211> LENGTH: 321
<212> TYPE: DNA
<213> ORGANISM: Artificial Sequence
<220> FEATURE:
<223> OTHER INFORMATION: Synthetic

<400> SEQUENCE: 364
gacatccaga tgacccagtc tccgtcctcc ctgtctgcat ctgtaggagg cagagtcacc   60
atcacttgcc ggacaagtca gagcattagc ggctatttaa attggtatca gcagaaagca  120
```

-continued

```
gggaaagccc ctaaactcct gatctatgct acatccaatt tgcaaagtgg ggtcccatca        180
aggttcactg gcagtggctc tgggacagat ttcactctca ccatcagcag tctgcaacct        240
gaagattttg cagcttacta ctgtcatcag agtcacagtc ccccattcac tttcggccct        300
gggaccaaag tggctttcaa a                                                   321

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
ggattcacct tcagtagtta tgaa                                                24

<210> SEQ ID NO 366
<211> LENGTH: 24
<212> TYPE: DNA
<213> ORGANISM: Artificial Sequence
<220> FEATURE:
<223> OTHER INFORMATION: Synthetic

<400> SEQUENCE: 366
attagtagtg gtggtagttc tata                                                24

<210> SEQ ID NO 367
<211> LENGTH: 45
<212> TYPE: DNA
<213> ORGANISM: Artificial Sequence
<220> FEATURE:
<223> OTHER INFORMATION: Synthetic

<400> SEQUENCE: 367
gcgagagtgg gtggaagcta ctactactcc tacgctatgg acgtc                         45

<210> SEQ ID NO 368
<211> LENGTH: 18
<212> TYPE: DNA
<213> ORGANISM: Artificial Sequence
<220> FEATURE:
<223> OTHER INFORMATION: Synthetic

<400> SEQUENCE: 368
caggacatta gcagttat                                                       18

<210> SEQ ID NO 369
<211> LENGTH: 27
<212> TYPE: DNA
<213> ORGANISM: Artificial Sequence
<220> FEATURE:
<223> OTHER INFORMATION: Synthetic

<400> SEQUENCE: 369
caacagcctc ataattcccc attcagt                                             27

<210> SEQ ID NO 370
<211> LENGTH: 366
<212> TYPE: DNA
<213> ORGANISM: Artificial Sequence
<220> FEATURE:
<223> OTHER INFORMATION: Synthetic

<400> SEQUENCE: 370
gaggtgcagt tggtggagtc tgggg, g, gc ttggtccagc ctggagggtc cctgagactc        60
```

-continued

```
tcctgtgcag cctctggatt caccttcagt agttatgaaa tgaactgggt ccgccaggct          120
ccagggaagg gactggagtg ggtttcatac attagtagtg gtggtagttc tataaaatac          180
gcagactctg tgaggggccg attcgccttc tccagagaca cgccgagaa ctcagtgcat          240 ctgcaaatga acagcctgag agccgaggac acggctgttt attactgtgc gagagtgggg          300
ggaagctact actactccta cgctatggac gtctgggggcc aagggaccgc ggtcaccgtc          360
tcctca                                                                     366
```

```
<210> SEQ ID NO 371
<211> LENGTH: 321
<212> TYPE: DNA
<213> ORGANISM: Artificial Sequence
<220> FEATURE:
<223> OTHER INFORMATION: Synthetic

<400> SEQUENCE: 371
gacatccagt tgacccagtc tccatccttc ctgtctgcat ctgtaggaga cagagtcacc           60
atcacttgct gggccagtca ggacattagc agttatttag cctggtatca gcaaaaacca          120
gggaaagccc ctaagctcct gatctatgct gcatccactt tgcaaagtgg ggtcccatca          180
aggttcaccg gcagtggatc tgggacagaa ttcactctca caatcagcag cctgcagcct          240
gaagattttg caacttatta ctgtcaacag cctcataatt ccccattcag tttcggccct          300
gggaccaaag tggatgtcaa a                                                     321
```

```
<210> SEQ ID NO 372
<211> LENGTH: 39
<212> TYPE: DNA
<213> ORGANISM: Artificial Sequence
<220> FEATURE:
<223> OTHER INFORMATION: Synthetic

<400> SEQUENCE: 372
gtgagagagc gtagagatgg ccacaaaatc tttgactat                                  39
```

```
<210> SEQ ID NO 373
<211> LENGTH: 360
<212> TYPE: DNA
<213> ORGANISM: Artificial Sequence
<220> FEATURE:
<223> OTHER INFORMATION: Synthetic

<400> SEQUENCE: 373
caggtgcagc tggtggagtc tgggggagac ttggtcaagc ctggagggtc cctgagactc           60
tcctgtgtag cctctggatt caccttcagt gactactaca tgaactggat ccgcctgcct          120
ccagggaagg gcctggagtg gatttcatac attgatagta gtgctggtgc catttactat          180
gcagactctg tgaagggccg attcaccgtc tccagggacg acgccaagaa ctcactattt          240
ctgcacatga acagcctgag agccgatgac acggccgttt attactgtgt gagagagcgt          300
agagatggcc acaaaatctt tgactattgg ggcccgggaa ccctggtcac cgtctcctcc          360
```

```
<210> SEQ ID NO 374
<211> LENGTH: 339
<212> TYPE: DNA
<213> ORGANISM: Artificial Sequence
<220> FEATURE:
<223> OTHER INFORMATION: Synthetic

<400> SEQUENCE: 374
```

-continued

```
gacatcgtga tgacccagtc tccagactcc ctggctgtgt ctctgggcga gagggccacc        60
atcaactgca agtccagcca gaatatttta tacagttcca acaataagaa ctacttagct       120
tggtaccagc agaaagcagg acagcctcct aagttgctca ttttctggtc atctattcgg       180
gaatccgggg tccctgaccg attcagtggc agcgggtctg ggacagattt cactctcacc       240
atcagcagcc tgcaggctga agatgtggca gtttattatt gtcagcaata ttacagtagt       300
ccgtataatt ttggccgggg gaccacactg gagatcaaa                              339

<210> SEQ ID NO 375
<211> LENGTH: 48
<212> TYPE: DNA
<213> ORGANISM: Artificial Sequence
<220> FEATURE:
<223> OTHER INFORMATION: Synthetic

<400> SEQUENCE: 375
gggaaagatc catataactg gaatcacggg gtctacggca tggacgtc                      48

<210> SEQ ID NO 376
<211> LENGTH: 18
<212> TYPE: DNA
<213> ORGANISM: Artificial Sequence
<220> FEATURE:
<223> OTHER INFORMATION: Synthetic

<400> SEQUENCE: 376
cagagcatta gcacctat                                                       18

<210> SEQ ID NO 377
<211> LENGTH: 9
<212> TYPE: DNA
<213> ORGANISM: Artificial Sequence
<220> FEATURE:
<223> OTHER INFORMATION: Synthetic

<400> SEQUENCE: 377 ggtgcttcc                                                                  9

<210> SEQ ID NO 378
<211> LENGTH: 27
<212> TYPE: DNA
<213> ORGANISM: Artificial Sequence
<220> FEATURE:
<223> OTHER INFORMATION: Synthetic

<400> SEQUENCE: 378
caacagagtt acaatatccc tctcact                                             27

<210> SEQ ID NO 379
<211> LENGTH: 369
<212> TYPE: DNA
<213> ORGANISM: Artificial Sequence
<220> FEATURE:
<223> OTHER INFORMATION: Synthetic

<400> SEQUENCE: 379
gaggtgcagc tgttggaatc tgggggaggc ctgatacaac cggggggggtc cctgagactc        60 tcctgtgcag cctctggatt cacctttagt ggcttcgcca tgagctgggt ccgccaggct       120
cctgggaagg ggctggagtg ggtctcaggt attagtggga gtggtgatat cacatactat       180
ggagactccg tgaagggccg gttcaccatt tccagagaca attccaagag tacgctgtat       240
ctgcaaatga acagcctgag agacgcggac acggccgtat attattgtgg gaaagatcca       300
```

```
tataactgga atcacggggt ctacggcatg gacgtctggg gccaagggac cacggtcacc    360
gtctcctca                                                           369

<210> SEQ ID NO 380
<211> LENGTH: 321
<212> TYPE: DNA
<213> ORGANISM: Artificial Sequence
<220> FEATURE:
<223> OTHER INFORMATION: Synthetic

<400> SEQUENCE: 380
gacatccaga tgacccagtc tccatcctcc ctgtctgcat ccgtaggaga cagagtcacc     60
atcacttgcc gggcaagtca gagcattagc acctatttaa attggtatca gcagaagcca    120
gggaaagccc ctaagttcct gatctatggt gcttccagtt tgcaaagtgg ggtcccatca    180
aggttcagtg gcagtggatc tgggacagat ttctctctca ccatcagcag tctgcaccct    240
ggagacttcg caacttacta ctgtcaacag agttacaata tccctctcac tttcggcgga    300
gggaccaagg tggagatcaa a                                             321

<210> SEQ ID NO 381
<211> LENGTH: 24
<212> TYPE: DNA
<213> ORGANISM: Artificial Sequence
<220> FEATURE:
<223> OTHER INFORMATION: Synthetic

<400> SEQUENCE: 381
ggattcgcct ttcacaccta tgac                                           24

<210> SEQ ID NO 382
<211> LENGTH: 24
<212> TYPE: DNA
<213> ORGANISM: Artificial Sequence
<220> FEATURE:
<223> OTHER INFORMATION: Synthetic

<400> SEQUENCE: 382
gttgttggta gtggtattaa caca                                           24

<210> SEQ ID NO 383
<211> LENGTH: 36
<212> TYPE: DNA
<213> ORGANISM: Artificial Sequence
<220> FEATURE:
<223> OTHER INFORMATION: Synthetic

<400> SEQUENCE: 383
gcgaaagata gcagcagttg gttttccctc cactac                              36

<210> SEQ ID NO 384
<211> LENGTH: 18
<212> TYPE: DNA
<213> ORGANISM: Artificial Sequence
<220> FEATURE:
<223> OTHER INFORMATION: Synthetic

<400> SEQUENCE: 384
cagagcataa gtaactgg                                                  18

<210> SEQ ID NO 385
<211> LENGTH: 9
<212> TYPE: DNA
```

-continued

```
<213> ORGANISM: Artificial Sequence
<220> FEATURE:
<223> OTHER INFORMATION: Synthetic

<400> SEQUENCE: 385 aaggcgtct                                                                9

<210> SEQ ID NO 386
<211> LENGTH: 27
<212> TYPE: DNA
<213> ORGANISM: Artificial Sequence
<220> FEATURE:
<223> OTHER INFORMATION: Synthetic

<400> SEQUENCE: 386
caacagtata gaagttatgc gtacact                                           27

<210> SEQ ID NO 387
<211> LENGTH: 357
<212> TYPE: DNA
<213> ORGANISM: Artificial Sequence
<220> FEATURE:
<223> OTHER INFORMATION: Synthetic

<400> SEQUENCE: 387
gaggtgcagt tgttggagtc tggggggaggc ttggtacagc ctggggggtc cctgagactc    60
tcctgtgcag cctctggatt cgcctttcac acctatgaca tgacctgggt ccgccaggct   120
ccagggaagg gactggagtg ggtctcaggt gttgttggta gtggtattaa cacatactac   180
gcagactccg tgaagggccg gttcaccatt tccagagaca attccaagag cacgctctat   240
ctgcaaatga acagtctgag agccgaggac acggccgtat attactgtgc gaaagatagc   300
agcagttggt tttccctcca ctactggggc cagggaaccc tggtcaccgt ctcctca      357

<210> SEQ ID NO 388
<211> LENGTH: 321
<212> TYPE: DNA
<213> ORGANISM: Artificial Sequence
<220> FEATURE:
<223> OTHER INFORMATION: Synthetic

<400> SEQUENCE: 388
gacatccaga tgacccagtc tccttccacc ctgtctgcat ctgtaggaga cagagtcacc    60
atcacttgcc gggccagtca gagcataagt aactggttgg cctggtatca gcagaaacca   120
gggaaagccc ctaaactcct gatctataag gcgtctagtt tagaaagtgg ggtcccatca   180
aggttcagcg gcagtggatc tgggacagat ttcactctca ccatcagcag cctgcagcct   240
gatgattttg caagttatta ctgccaacag tatagaagtt atgcgtacac ttttggccag   300
gggaccaagc tggagatcac a                                              321

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
ggattcacct tcagtgacta ttac                                           24

<210> SEQ ID NO 390
<211> LENGTH: 24
```

```
<212> TYPE: DNA
<213> ORGANISM: Artificial Sequence
<220> FEATURE:
<223> OTHER INFORMATION: Synthetic

<400> SEQUENCE: 390
attgatagta gtgctggtgc cact                                                    24

<210> SEQ ID NO 391
<211> LENGTH: 39
<212> TYPE: DNA
<213> ORGANISM: Artificial Sequence
<220> FEATURE:
<223> OTHER INFORMATION: Synthetic

<400> SEQUENCE: 391
gcgagagagc gtagaagtgg ccacaaaatc tttgactgt                                    39

<210> SEQ ID NO 392
<211> LENGTH: 360
<212> TYPE: DNA
<213> ORGANISM: Artificial Sequence
<220> FEATURE:
<223> OTHER INFORMATION: Synthetic

<400> SEQUENCE: 392
caggtgcagt tggtggagtc tgggggagac ttggtcaagc ctggagggtc cctgagactc            60
tcctgtgtag cctctggatt caccttcagt gactattaca tgaactggat ccgcctgcct           120
ccagggaagg gcctggagtg gatttcatac attgatagta gtgctggtgc cacttactat          180
gcagactctg tgaagggccg attcaccgtc tccagggacg acgccaagaa ttcactattt          240
ctgcacatga acagtctgag agccgaggac acggccgttt attactgtgc gagagagcgt          300
agaagtggcc acaaaatctt tgactgttgg ggcccgggaa ccctggtcac cgtctcctca          360

<210> SEQ ID NO 393
<211> LENGTH: 24
<212> TYPE: DNA
<213> ORGANISM: Artificial Sequence
<220> FEATURE:
<223> OTHER INFORMATION: Synthetic

<400> SEQUENCE: 393
attgatagta gcgctggtgc catt                                                    24

<210> SEQ ID NO 394
<211> LENGTH: 360
<212> TYPE: DNA
<213> ORGANISM: Artificial Sequence
<220> FEATURE:
<223> OTHER INFORMATION: Synthetic

<400> SEQUENCE: 394
caggtgcacc tggtggagtc tgggggagac ttggtcaagc ctggagggtc cctgagactc            60
tcctgtgtag cctctggatt caccttcagt gactactaca tgaactggat ccgcctgcct           120
ccagggaagg gcctggagtg gatttcatac attgatagta gcgctggtgc catttactat          180
gcagactctg tgaagggccg attcaccgtc tccagggacg acgccaagaa ctcaatgttt          240
ctgcacatga acagcctgag agccgatgac acggccgttt attactgtgc gagagagcgt          300
agagatggcc acaaaatctt tgactattgg ggcccgggaa ccctggtcac cgtctcctca          360

<210> SEQ ID NO 395
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 395
ggtttcacct tcagtgacta ctac                                            24

<210> SEQ ID NO 396
<211> LENGTH: 39
<212> TYPE: DNA
<213> ORGANISM: Artificial Sequence
<220> FEATURE:
<223> OTHER INFORMATION: Synthetic

<400> SEQUENCE: 396
gcgagagagc ggagagaagg ccacaaaatc tttgacttt                            39

<210> SEQ ID NO 397
<211> LENGTH: 360
<212> TYPE: DNA
<213> ORGANISM: Artificial Sequence
<220> FEATURE:
<223> OTHER INFORMATION: Synthetic

<400> SEQUENCE: 397
caggtgcaac tggtggagtc tgggggagac ttggtcaagc ctggagggtc cctgagactc     60
tcctgtgtag cctctggttt caccttcagt gactactaca tgaactggat ccgcctgcct    120
ccagggaagg gcctggagtg gatttcatac attgatagta gtgctggtgc catttactat    180
gcagactctg tgaaggggcg attcaccgtc tccagggacg acgccaagaa ctcattattt    240
ctgcacatga acagcctgag agccgatgac acggccgttt attactgtgc gagagagcgg    300
agagaaggcc acaaaatctt tgacttttgg ggcccgggaa ccctggtcac cgtctcctca    360

<210> SEQ ID NO 398
<211> LENGTH: 339
<212> TYPE: DNA
<213> ORGANISM: Artificial Sequence
<220> FEATURE:
<223> OTHER INFORMATION: Synthetic

<400> SEQUENCE: 398
gacatcgtga tgacccagtc tccagactcc ctggctctgt ctctgggcga gagggccacc     60
attaactgca gtccagcca gaatatttta tacagttcca acaataagaa ctacttagct    120
tgttaccaac agaaagcagg acagcctcct aagttgctca ttttctggtc atctacccgg    180
gaatccgggg tccctgaccg attcagtggc agcgggtctg ggacagattt cactctcacc    240
atcagcagcc tgcaggctga agatgtggca gtttattact gtcagcaata ttacagtagt    300
ccgtataatt tcggccgggg gaccacactg gagatcaaa                           339

<210> SEQ ID NO 399
<211> LENGTH: 24
<212> TYPE: DNA
<213> ORGANISM: Artificial Sequence
<220> FEATURE:
<223> OTHER INFORMATION: Synthetic

<400> SEQUENCE: 399
ggcttcacct ttcacaacta tgcc                                            24
```

<210> SEQ ID NO 400
<211> LENGTH: 24
<212> TYPE: DNA
<213> ORGANISM: Artificial Sequence
<220> FEATURE:
<223> OTHER INFORMATION: Synthetic

<400> SEQUENCE: 400
attagtggta gtggtggtac cgca                                    24

<210> SEQ ID NO 401
<211> LENGTH: 42
<212> TYPE: DNA
<213> ORGANISM: Artificial Sequence
<220> FEATURE:
<223> OTHER INFORMATION: Synthetic

<400> SEQUENCE: 401
gcgaaagacc gatttttgga gtgggtagag gggttcgact cc                42

<210> SEQ ID NO 402
<211> LENGTH: 18
<212> TYPE: DNA
<213> ORGANISM: Artificial Sequence
<220> FEATURE:
<223> OTHER INFORMATION: Synthetic

<400> SEQUENCE: 402
cagagcattg gcagcttt                                           18

<210> SEQ ID NO 403
<211> LENGTH: 27
<212> TYPE: DNA
<213> ORGANISM: Artificial Sequence
<220> FEATURE:
<223> OTHER INFORMATION: Synthetic

<400> SEQUENCE: 403
caacagagtt acaataccccc gctcact                                27

<210> SEQ ID NO 404
<211> LENGTH: 363
<212> TYPE: DNA
<213> ORGANISM: Artificial Sequence
<220> FEATURE:
<223> OTHER INFORMATION: Synthetic

<400> SEQUENCE: 404
gaggtgcagc tgttggagtc tgggggaggc ttggtacagc ctggggggtc cctgagactc    60
tcctgtgcag cctctggctt cacctttcac aactatgcca tgagctgggt ccgccaggct   120
ccagggaagg ggctggagtg ggtctcaggt attagtggta gtggtggtac cgcatactac   180
gcagactccg tgaagggccg gttcaccatt tccagagaca attccaagaa cacgctgtat   240
ctgcaaatga acagcctgag agccgacgac acggccttat attactgtgc gaaagaccga   300
tttttggagt gggtagaggg gttcgactcc tggggccagg gaaccctggt caccgtctcc   360
tca                                                                 363

<210> SEQ ID NO 405
<211> LENGTH: 321
<212> TYPE: DNA
<213> ORGANISM: Artificial Sequence
<220> FEATURE:
<223> OTHER INFORMATION: Synthetic

<400> SEQUENCE: 405
gacatccaga tgacccagtc tccatcctcc ctgtctgcat ctgtaggaga cagagtcacc    60
atcacttgcc gggcaagtca gagcattggc agctttttaa tttggtatca gcagaaacca   120
gggaaagccc ctaagctcct gatttatgct gcatccagtt tgcaaagtgg ggtcccatca   180
aggttcagtg gcagtggatc tgggacagat ttcactctca ttatcagcag tctgcaacct   240
gaagattttg caacttatta ctgtcaacag agttacaata ccccgctcac tttcggcgga   300
gggaccaaag tggagatcaa a                                               321

<210> SEQ ID NO 406
<211> LENGTH: 24
<212> TYPE: DNA
<213> ORGANISM: Artificial Sequence
<220> FEATURE:
<223> OTHER INFORMATION: Synthetic

<400> SEQUENCE: 406
attagtagtg gtggtagttc cata                                            24

<210> SEQ ID NO 407
<211> LENGTH: 27
<212> TYPE: DNA
<213> ORGANISM: Artificial Sequence
<220> FEATURE:
<223> OTHER INFORMATION: Synthetic

<400> SEQUENCE: 407
caacagccta ataattaccc attcagt                                         27

<210> SEQ ID NO 408
<211> LENGTH: 366
<212> TYPE: DNA
<213> ORGANISM: Artificial Sequence
<220> FEATURE:
<223> OTHER INFORMATION: Synthetic

<400> SEQUENCE: 408
gaggtgcagt tggtggagtc tgggggaggc ttggtccagc ctggagggtc cctgagactc    60
tcctgtgcag cctctggatt caccttcagt agttatgaaa tgaactgggt ccgccaggct   120
ccagggaagg gactggagtg ggtttcatac attagtagtg gtggtagttc cataaaatac   180
gcagactctg tgaggggccg attcaccttc tccagagaca acgccgagaa ctcagtgcat   240
ctgcaaatga acagcctgag aggcgaggac acggctgttt attactgtgc gagagtgggt   300
ggaagctact actactccta cgctatggac gtctggggcc aagggaccgc ggtcaccgtc   360
tcctca                                                                366

<210> SEQ ID NO 409
<211> LENGTH: 321
<212> TYPE: DNA
<213> ORGANISM: Artificial Sequence
<220> FEATURE:
<223> OTHER INFORMATION: Synthetic

<400> SEQUENCE: 409
gacatccagt tgacccagtc tccatccttc ctgtctgcat ctgtaggaga cagagtcacc    60
atcacttgct gggccagtca ggacattagc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240

-continued

```
gaagattttg caacttatta ctgtcaacag cctaataatt acccattcag tttcggccct       300
gggaccaaag tggatgtcaa a                                                  321

<210> SEQ ID NO 410
<211> LENGTH: 366
<212> TYPE: DNA
<213> ORGANISM: Artificial Sequence
<220> FEATURE:
<223> OTHER INFORMATION: Synthetic

<400> SEQUENCE: 410
gaggtgcagt tggtggagtc tgggggaggc ttggtccagc ctggagggtc cctgagactc        60
tcctgtgcag cctctggatt caccttcagt agttatgaaa tgaactgggt ccgccaggct       120
ccagggaagg gactggagtg ggtttcatac attagtagtg gtggtagttc cataaaatac       180
gcagactctg tgaggggccg attcaccttc tccagagaca acgccgagaa ctcagtgttt       240
ctccaaatga acagcctgag aggcgaggac acggctgttt attactgtgc gagagtgggt       300
ggaagctact actactccta cgctatggac gtctggggcc aagggaccgc ggtcaccgtc       360
tcctca                                                                  366

<210> SEQ ID NO 411
<211> LENGTH: 321
<212> TYPE: DNA
<213> ORGANISM: Artificial Sequence
<220> FEATURE:
<223> OTHER INFORMATION: Synthetic

<400> SEQUENCE: 411
gacatccagt tgacccagtc tccatccttc ctgtctgcat ctgtaggaga cagagtcacc        60
atcacttgct gggccagtca ggacattagc agttatttag cctggtatca gcaaaaacca       120
gggaaagccc ctaagctcct gatctatgct gcatccactt tacaaagtgg ggtcccatca       180
aggttcagcg gcagtggatc tgggacagaa ttcactctca caatcagcag cctgcagcct       240
gaagattttg caacttatta ctgtcaacag cctaataatt acccattcag tttcggccct       300
gggaccaaag tggatgtcaa a                                                  321

<210> SEQ ID NO 412
<211> LENGTH: 24
<212> TYPE: DNA
<213> ORGANISM: Artificial Sequence
<220> FEATURE:
<223> OTHER INFORMATION: Synthetic

<400> SEQUENCE: 412
attagtgcta gtggcggtac caca                                               24

<210> SEQ ID NO 413
<211> LENGTH: 42
<212> TYPE: DNA
<213> ORGANISM: Artificial Sequence
<220> FEATURE:
<223> OTHER INFORMATION: Synthetic

<400> SEQUENCE: 413
gcgaaagacc gatttttgga gtgggtagag gggttcgacc cc                           42

<210> SEQ ID NO 414
<211> LENGTH: 18
<212> TYPE: DNA
```

<213> ORGANISM: Artificial Sequence
<220> FEATURE:
<223> OTHER INFORMATION: Synthetic

<400> SEQUENCE: 414
cagagcattg gcaggttt                                                    18

<210> SEQ ID NO 415
<211> LENGTH: 27
<212> TYPE: DNA
<213> ORGANISM: Artificial Sequence
<220> FEATURE:
<223> OTHER INFORMATION: Synthetic

<400> SEQUENCE: 415
caacagagtt acattacccc gctcact                                          27

<210> SEQ ID NO 416
<211> LENGTH: 363
<212> TYPE: DNA
<213> ORGANISM: Artificial Sequence
<220> FEATURE:
<223> OTHER INFORMATION: Synthetic

<400> SEQUENCE: 416
gaggtgcagt tgttggagtc tgggggaggc ttggtacagc ctggggggtc cctgagactc      60
tcctgtgcag tctctggatt cacctttagc agctttgcca tgagctgggt ccgccaggct     120
ccagggaagg gcctggagtg ggtctcgggt attagtgcta gtggcggtac cacaaattac     180
gcagactccg tgaaaggccg gttcaccatc tccagagaca attccaagaa cacgctctat     240
ctgcaaatga gcagcctgag agccgaggac acggccgaat attactgtgc gaaagaccga     300
tttttggagt gggtagaggg gttcgacccc tggggccagg gaatcctggt caccgtctcc     360
cca                                                                   363

<210> SEQ ID NO 417
<211> LENGTH: 321
<212> TYPE: DNA
<213> ORGANISM: Artificial Sequence
<220> FEATURE:
<223> OTHER INFORMATION: Synthetic

<400> SEQUENCE: 417
gacatccaga tgacccagtc tccatcctcc ctgtctgcat ctgtaggaga cagagtcacc      60
atcacttgcc gggcaagtca gagcattggc aggtttttaa tttggtatca gcagaaacca     120
gggaaagccc ctaaactcct gctttatgct acatccagtt tgcaaagtgg ggtcccagca     180
aggttcactg gcagtgggtc tgggacagat ttcactctca ccatcggcag tctgcaacct     240
gaagattttg caacttacta ctgtcaacag agttacatta ccccgctcac tttcggcgga     300
gggaccaagg tggagatcaa a                                               321

<210> SEQ ID NO 418
<211> LENGTH: 363
<212> TYPE: DNA
<213> ORGANISM: Artificial Sequence
<220> FEATURE:
<223> OTHER INFORMATION: Synthetic

<400> SEQUENCE: 418
gaggtgcagt tgttggagtc tgggggaggc ttggtacagc ctggggggtc cctgagactc      60
tcctgtgcag cctctggatt cacctttagc agctttgcca tgagctgggt ccgccaggct     120

-continued

```
ccagggaagg gcctggagtg ggtctcgggt attagtgcta gtggcggtac cacaaattac      180
gcagactccg tgaaaggccg gttcaccatc tccagagaca attccaagaa cacgctctat      240
ctgcaaatga gcagcctgag agccgaggac acggccgaat attactgtgc gaaagaccga      300
tttttggagt gggtagaggg gttcgacccc tggggccagg gaatcctggt caccgtctcc      360
cca                                                                    363

<210> SEQ ID NO 419
<211> LENGTH: 321
<212> TYPE: DNA
<213> ORGANISM: Artificial Sequence
<220> FEATURE:
<223> OTHER INFORMATION: Synthetic

<400> SEQUENCE: 419
gacatccaga tgacccagtc tccatcctcc ctgtctgcat ctgtaggaga cagagtcacc       60
atcacttgcc gggcaagtca gagcattggc aggtttttaa tttggtatca gcagaaacca      120
gggaaagccc ctaagctcct gctctatgct acatccagtt tgcaaagtgg ggtcccagca      180
aggttcactg gcagtgggtc tgggacagat ttcactctca ccatcggcag tctgcaacct      240
gaagattttg caacttacta ctgtcaacag agttacatta ccccgctcac tttcggcgga      300
gggaccaagg tggagatcaa a                                                321

<210> SEQ ID NO 420
<211> LENGTH: 75
<212> TYPE: DNA
<213> ORGANISM: Artificial Sequence
<220> FEATURE:
<223> OTHER INFORMATION: Synthetic

<400> SEQUENCE: 420
caggtgcagc tggtggagtc tggggggagac ttggtcaagc ctggagggtc cctgagactc       60
tcctgtgtag cctcg                                                        75

<210> SEQ ID NO 421
<211> LENGTH: 51
<212> TYPE: DNA
<213> ORGANISM: Artificial Sequence
<220> FEATURE:
<223> OTHER INFORMATION: Synthetic

<400> SEQUENCE: 421
atgaactgga tccgcctgcc tccagggaag ggcctggagt gggtttcata c                51

<210> SEQ ID NO 422
<211> LENGTH: 114
<212> TYPE: DNA
<213> ORGANISM: Artificial Sequence
<220> FEATURE:
<223> OTHER INFORMATION: Synthetic

<400> SEQUENCE: 422
tactatgcag actctgtgag gggccgattc accgtctcca gggacgacgc caagaattca       60
ctatttctgc acatgaacag cctgagagcc gatgacacgg ccgtttatta ctgt            114

<210> SEQ ID NO 423
<211> LENGTH: 33
<212> TYPE: DNA
<213> ORGANISM: Artificial Sequence
<220> FEATURE:
```

-continued

<223> OTHER INFORMATION: Synthetic

<400> SEQUENCE: 423
tggggcccgg gaaccctggt caccgtctct tca                                      33

<210> SEQ ID NO 424
<211> LENGTH: 78
<212> TYPE: DNA
<213> ORGANISM: Artificial Sequence
<220> FEATURE:
<223> OTHER INFORMATION: Synthetic

<400> SEQUENCE: 424
gacatcgtga tgacccagtc tccagactcc ctggctgtgt ctctgggcga gagggccacc        60
atcaactgca agtccagc                                                       78

<210> SEQ ID NO 425
<211> LENGTH: 51
<212> TYPE: DNA
<213> ORGANISM: Artificial Sequence
<220> FEATURE:
<223> OTHER INFORMATION: Synthetic

<400> SEQUENCE: 425
ttagcttggt accagcagaa agcaggacag cctcctaagt tgctcatttt c                  51

<210> SEQ ID NO 426
<211> LENGTH: 108
<212> TYPE: DNA
<213> ORGANISM: Artificial Sequence
<220> FEATURE:
<223> OTHER INFORMATION: Synthetic

<400> SEQUENCE: 426
acccgggaat ccggggtccc tgaccgattc agtggcagcg ggtctgggac agatttcact        60
ctcaccatca acagcctgca ggctgaagat gtggcagttt attactgt                     108

<210> SEQ ID NO 427
<211> LENGTH: 30
<212> TYPE: DNA
<213> ORGANISM: Artificial Sequence
<220> FEATURE:
<223> OTHER INFORMATION: Synthetic

<400> SEQUENCE: 427
tttggccggg ggaccacact ggagatcaaa                                          30

<210> SEQ ID NO 428
<211> LENGTH: 75
<212> TYPE: DNA
<213> ORGANISM: Artificial Sequence
<220> FEATURE:
<223> OTHER INFORMATION: Synthetic

<400> SEQUENCE: 428
caggtgcacc tggtggagtc tggggggagac ttggtcaagc ctggagggtc cctgagactc        60
tcctgtgtag cctct                                                          75

<210> SEQ ID NO 429
<211> LENGTH: 51
<212> TYPE: DNA
<213> ORGANISM: Artificial Sequence
<220> FEATURE:
<223> OTHER INFORMATION: Synthetic -continued

<400> SEQUENCE: 429
atgaactgga tccgtatgcc tccagggaag ggcctggagt ggatttcata c          51

<210> SEQ ID NO 430
<211> LENGTH: 114
<212> TYPE: DNA
<213> ORGANISM: Artificial Sequence
<220> FEATURE:
<223> OTHER INFORMATION: Synthetic

<400> SEQUENCE: 430
tactatgcag actctgtgaa gggccgattc accgtctcca gggacgacgc caagaactca          60
ctgtttctac acatgaacaa cctgagagcc gatgacacgg ccgtttatta ctgt          114

<210> SEQ ID NO 431
<211> LENGTH: 33
<212> TYPE: DNA
<213> ORGANISM: Artificial Sequence
<220> FEATURE:
<223> OTHER INFORMATION: Synthetic

<400> SEQUENCE: 431
tggggcccgg gaaccctggt caccgtctcc tca          33

<210> SEQ ID NO 432
<211> LENGTH: 108
<212> TYPE: DNA
<213> ORGANISM: Artificial Sequence
<220> FEATURE:
<223> OTHER INFORMATION: Synthetic

<400> SEQUENCE: 432
acccgggaat ccggggtccc tgaccgattc agtggcagcg ggtctgggac agatttcact          60
ctcaccatca gcagcctgca ggctgaagat gtggcagttt attactgt          108

<210> SEQ ID NO 433
<211> LENGTH: 75
<212> TYPE: DNA
<213> ORGANISM: Artificial Sequence
<220> FEATURE:
<223> OTHER INFORMATION: Synthetic

<400> SEQUENCE: 433
gaggtgcagc tggtgcagtc tggagcagag gtgaaaaagc ccggggagtc tctgaagatc          60
tcctgtaagg gttct          75

<210> SEQ ID NO 434
<211> LENGTH: 51
<212> TYPE: DNA
<213> ORGANISM: Artificial Sequence
<220> FEATURE:
<223> OTHER INFORMATION: Synthetic

<400> SEQUENCE: 434
atcggctggg tgcgccagat gcccgggaaa ggcctggagt ggatggggat c          51

<210> SEQ ID NO 435
<211> LENGTH: 114
<212> TYPE: DNA
<213> ORGANISM: Artificial Sequence
<220> FEATURE:
<223> OTHER INFORMATION: Synthetic -continued

```
<400> SEQUENCE: 435
agatacagcc cgtccttcca aggccaggtc accatctcag ccgacaagtc catcagtacc      60
gcctatttgc agtggagcag cctgaaggcc tcggacaccg ccatgtatta ctgt           114

<210> SEQ ID NO 436
<211> LENGTH: 33
<212> TYPE: DNA
<213> ORGANISM: Artificial Sequence
<220> FEATURE:
<223> OTHER INFORMATION: Synthetic

<400> SEQUENCE: 436
tggggccagg gaaccctggt caccgtctcc tca                                   33

<210> SEQ ID NO 437
<211> LENGTH: 78
<212> TYPE: DNA
<213> ORGANISM: Artificial Sequence
<220> FEATURE:
<223> OTHER INFORMATION: Synthetic

<400> SEQUENCE: 437
gacatccaga tgacccagtc tccatcctcc ctgtctgcat ctgtcggaga cagactcacc      60
atcacttgcc gggcaagt                                                    78

<210> SEQ ID NO 438
<211> LENGTH: 51
<212> TYPE: DNA
<213> ORGANISM: Artificial Sequence
<220> FEATURE:
<223> OTHER INFORMATION: Synthetic

<400> SEQUENCE: 438
ttaaattggt atcaacagaa cccagggaaa gcccctaagg tcctgattta t              51

<210> SEQ ID NO 439
<211> LENGTH: 108
<212> TYPE: DNA
<213> ORGANISM: Artificial Sequence
<220> FEATURE:
<223> OTHER INFORMATION: Synthetic

<400> SEQUENCE: 439
agtttggaaa gtggggtccc atcaaggttc agtggcagtg gatctgggac agatttcact      60
ctcaccatca gcagtctgca acctgaagat tttgcaactt actactgt                  108

<210> SEQ ID NO 440
<211> LENGTH: 30
<212> TYPE: DNA
<213> ORGANISM: Artificial Sequence
<220> FEATURE:
<223> OTHER INFORMATION: Synthetic

<400> SEQUENCE: 440
ttcggccaag ggaccaaggt ggaaatcaaa                                       30

<210> SEQ ID NO 441
<211> LENGTH: 75
<212> TYPE: DNA
<213> ORGANISM: Artificial Sequence
<220> FEATURE:
<223> OTHER INFORMATION: Synthetic

<400> SEQUENCE: 441
```

```
gaggtgcagc ttttggagtc ggggggaggc ttggcacagc cggggaagtc cctgagactc        60
tcctgtgcag cctct                                                          75
```

<210> SEQ ID NO 442
<211> LENGTH: 51
<212> TYPE: DNA
<213> ORGANISM: Artificial Sequence
<220> FEATURE:
<223> OTHER INFORMATION: Synthetic

<400> SEQUENCE: 442

```
atgagctggg tccgccaggc tcctgggaag gggctggagt gggtctcagg t                 51
```

<210> SEQ ID NO 443
<211> LENGTH: 114
<212> TYPE: DNA
<213> ORGANISM: Artificial Sequence
<220> FEATURE:
<223> OTHER INFORMATION: Synthetic

<400> SEQUENCE: 443

```
tactatgcag actccgtgaa gggccggttc accatttcca gagacaattc caagagtacg        60
ctgtatcttc aaatgaacag cctgggagcc gaggacacgg ccgtgtatta ctgt            114
```

<210> SEQ ID NO 444
<211> LENGTH: 33
<212> TYPE: DNA
<213> ORGANISM: Artificial Sequence
<220> FEATURE:
<223> OTHER INFORMATION: Synthetic

<400> SEQUENCE: 444

```
tggggccaag gaccacggt caccgtctcc tca                                      33
```

<210> SEQ ID NO 445
<211> LENGTH: 78
<212> TYPE: DNA
<213> ORGANISM: Artificial Sequence
<220> FEATURE:
<223> OTHER INFORMATION: Synthetic

<400> SEQUENCE: 445

```
gacatccaga tgacccagtc tccatcctcc ctgtctgcat ctgtaggaga cagagtcacc        60
atcacttgcc gggcaagt                                                       78
```

<210> SEQ ID NO 446
<211> LENGTH: 51
<212> TYPE: DNA
<213> ORGANISM: Artificial Sequence
<220> FEATURE:
<223> OTHER INFORMATION: Synthetic

<400> SEQUENCE: 446

```
ttaaattggt atcagcagaa accagggaaa gcccctaaat tcctgattta t                 51
```

<210> SEQ ID NO 447
<211> LENGTH: 108
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (50)..(50)

-continued

```
<223> OTHER INFORMATION: n is a, c, g, or t

<400> SEQUENCE: 447
agtttgcaaa gtggggtccc atcaaggttc agtggcagtg gatgtgggan tgatttcact      60
ctcaccatca gcagtctgca acgtgaagat ttcgcagctt actactgt                  108

<210> SEQ ID NO 448
<211> LENGTH: 31
<212> TYPE: DNA
<213> ORGANISM: Artificial Sequence
<220> FEATURE:
<223> OTHER INFORMATION: Synthetic

<400> SEQUENCE: 448
ttcggcgggg ggaccaaggt ggagatcaaa c                                     31

<210> SEQ ID NO 449
<211> LENGTH: 75
<212> TYPE: DNA
<213> ORGANISM: Artificial Sequence
<220> FEATURE:
<223> OTHER INFORMATION: Synthetic

<400> SEQUENCE: 449
caggtgcagc tggtggagtc tggggggaggc ttggtcaagc ctggagggtc cctgagactc      60
tcctgcgtag cctct                                                       75

<210> SEQ ID NO 450
<211> LENGTH: 51
<212> TYPE: DNA
<213> ORGANISM: Artificial Sequence
<220> FEATURE:
<223> OTHER INFORMATION: Synthetic

<400> SEQUENCE: 450
atgaactgga tccgcctgcc tccagggagg gggctgcagt ggatttcata c               51

<210> SEQ ID NO 451
<211> LENGTH: 114
<212> TYPE: DNA
<213> ORGANISM: Artificial Sequence
<220> FEATURE:
<223> OTHER INFORMATION: Synthetic

<400> SEQUENCE: 451
tactacgcag actctgtgaa gggccgattc accgtctcca gggacgacgc caagaattca      60
ctttatctgc aaatgaacag cctgagagcc gatgacacgg ccgtttatta ctgt          114

<210> SEQ ID NO 452
<211> LENGTH: 51
<212> TYPE: DNA
<213> ORGANISM: Artificial Sequence
<220> FEATURE:
<223> OTHER INFORMATION: Synthetic

<400> SEQUENCE: 452
ttaggttggt accagcagaa agcaggacag cctcctaaac tgctcattta c               51

<210> SEQ ID NO 453
<211> LENGTH: 108
<212> TYPE: DNA
<213> ORGANISM: Artificial Sequence
<220> FEATURE:
<223> OTHER INFORMATION: Synthetic
```

<400> SEQUENCE: 453
acccggaatt ccgggqtccc tgaccgcttc agtggcagcg ggtctgggac agatttcact        60
ctcaccatca gcagcctgca ggctgaggat gtggcagttt attactgt                    108

<210> SEQ ID NO 454
<211> LENGTH: 30
<212> TYPE: DNA
<213> ORGANISM: Artificial Sequence
<220> FEATURE:
<223> OTHER INFORMATION: Synthetic

<400> SEQUENCE: 454
tttggccagg ggaccaacct ggagatcaaa                                         30

<210> SEQ ID NO 455
<211> LENGTH: 114
<212> TYPE: DNA
<213> ORGANISM: Artificial Sequence
<220> FEATURE:
<223> OTHER INFORMATION: Synthetic

<400> SEQUENCE: 455
agatacagcc cgtccttcca aggccaggtc accctctcag ccgacaagtc catcagtacc        60
gcctacctac agtggaacag cctgaaggcc tcggacaccg ccatgtatta ctgt             114

<210> SEQ ID NO 456
<211> LENGTH: 34
<212> TYPE: DNA
<213> ORGANISM: Artificial Sequence
<220> FEATURE:
<223> OTHER INFORMATION: Synthetic

<400> SEQUENCE: 456
tggggccagg gaaccctggt caccgtcgcc tcat                                    34

<210> SEQ ID NO 457
<211> LENGTH: 51
<212> TYPE: DNA
<213> ORGANISM: Artificial Sequence
<220> FEATURE:
<223> OTHER INFORMATION: Synthetic

<400> SEQUENCE: 457
ttaaattggt atcagcagaa accagggaca gcccctaaac tcctgattta t                51

<210> SEQ ID NO 458
<211> LENGTH: 108
<212> TYPE: DNA
<213> ORGANISM: Artificial Sequence
<220> FEATURE:
<223> OTHER INFORMATION: Synthetic

<400> SEQUENCE: 458
agtttgcaag gtggggtccc atcaaggttc agtggcagtg gctctgggac agatttcact        60
ctcaccatca gcagtctgca acctgaagat tttgcaactt actactgt                    108

<210> SEQ ID NO 459
<211> LENGTH: 75
<212> TYPE: DNA
<213> ORGANISM: Artificial Sequence
<220> FEATURE:
<223> OTHER INFORMATION: Synthetic -continued

```
<400> SEQUENCE: 459
caggtgcagc tggtggagtc tggggggagac ttggtcaagc ctggagggtc cctgagactc      60
tcctgtgtag cctct                                                        75

<210> SEQ ID NO 460
<211> LENGTH: 51
<212> TYPE: DNA
<213> ORGANISM: Artificial Sequence
<220> FEATURE:
<223> OTHER INFORMATION: Synthetic

<400> SEQUENCE: 460
atgaactgga tccgcctgcc tccagggaag ggcctggagt ggatttccta c               51

<210> SEQ ID NO 461
<211> LENGTH: 114
<212> TYPE: DNA
<213> ORGANISM: Artificial Sequence
<220> FEATURE:
<223> OTHER INFORMATION: Synthetic

<400> SEQUENCE: 461
tactatgcag actctgtgaa gggccgattc accgtctcca gggacgacgc caagaactca      60
ctatttctgc acatgaacag cctgagagcc gatgacacgg ccgtttatta ctgt          114

<210> SEQ ID NO 462
<211> LENGTH: 51
<212> TYPE: DNA
<213> ORGANISM: Artificial Sequence
<220> FEATURE:
<223> OTHER INFORMATION: Synthetic

<400> SEQUENCE: 462
ttagcttggt accagcagaa aacaggacag cctcctaagt tgctcatttt c               51

<210> SEQ ID NO 463
<211> LENGTH: 108
<212> TYPE: DNA
<213> ORGANISM: Artificial Sequence
<220> FEATURE:
<223> OTHER INFORMATION: Synthetic

<400> SEQUENCE: 463
acccgggaat ccggggtccc tgaccgattc agtggcagcg ggtctgggac agatttcact      60
ctcaccatca gcagcctgca ggctgaggat gtggcagttt attactgt                 108

<210> SEQ ID NO 464
<211> LENGTH: 75
<212> TYPE: DNA
<213> ORGANISM: Artificial Sequence
<220> FEATURE:
<223> OTHER INFORMATION: Synthetic

<400> SEQUENCE: 464
gaagtgcagt tggtggagtc tggggggagac ttggtacagc ctggcaggtc cctgagactc      60
tcctgtgcag cctct                                                        75

<210> SEQ ID NO 465
<211> LENGTH: 51
<212> TYPE: DNA
<213> ORGANISM: Artificial Sequence
<220> FEATURE:
<223> OTHER INFORMATION: Synthetic
```

<400> SEQUENCE: 465
atgcactggg tccggcaagg tccagggaag ggcctggagt gggtctcagg c                51

<210> SEQ ID NO 466
<211> LENGTH: 114
<212> TYPE: DNA
<213> ORGANISM: Artificial Sequence
<220> FEATURE:
<223> OTHER INFORMATION: Synthetic

<400> SEQUENCE: 466
ggctatgcgg actctgtgaa gggccgattc accatttcca gagacaacgc caagaactcc       60
ctgtacctgc gaatgaacag tctgagagct gacgacacgg ccttctatta ctgt            114

<210> SEQ ID NO 467
<211> LENGTH: 33
<212> TYPE: DNA
<213> ORGANISM: Artificial Sequence
<220> FEATURE:
<223> OTHER INFORMATION: Synthetic

<400> SEQUENCE: 467
tggggccacg ggacaatggt caccgtctct tca                                    33

<210> SEQ ID NO 468
<211> LENGTH: 51
<212> TYPE: DNA
<213> ORGANISM: Artificial Sequence
<220> FEATURE:
<223> OTHER INFORMATION: Synthetic

<400> SEQUENCE: 468
ttggattggt atcagcagaa accaggacag cctcctaagc tgctcattta t                51

<210> SEQ ID NO 469
<211> LENGTH: 108
<212> TYPE: DNA
<213> ORGANISM: Artificial Sequence
<220> FEATURE:
<223> OTHER INFORMATION: Synthetic

<400> SEQUENCE: 469
tcccgggaat ccggggtccc tgaccgattc agtggcagcg ggtctgggac agatttcact       60
ctgaccatca gcagcctgca ggctgaagat gtggcagttt attactgt                   108

<210> SEQ ID NO 470
<211> LENGTH: 30
<212> TYPE: DNA
<213> ORGANISM: Artificial Sequence
<220> FEATURE:
<223> OTHER INFORMATION: Synthetic

<400> SEQUENCE: 470
ttcggcggag ggaccaaggt ggagatcaaa                                        30

<210> SEQ ID NO 471
<211> LENGTH: 51
<212> TYPE: DNA
<213> ORGANISM: Artificial Sequence
<220> FEATURE:
<223> OTHER INFORMATION: Synthetic

<400> SEQUENCE: 471

-continued

```
atgaactgga tccgcctgcc tccagggaag ggcctggagt ggatttcata c                51

<210> SEQ ID NO 472
<211> LENGTH: 114
<212> TYPE: DNA
<213> ORGANISM: Artificial Sequence
<220> FEATURE:
<223> OTHER INFORMATION: Synthetic

<400> SEQUENCE: 472
tactatgcag actctgtgaa gggccgattc accgtctcca gggacgacgc caagaactca        60
ctatttctac acatgaacaa cctgagagcc gatgacacgg ccgttttatta ctgt           114

<210> SEQ ID NO 473
<211> LENGTH: 51
<212> TYPE: DNA
<213> ORGANISM: Artificial Sequence
<220> FEATURE:
<223> OTHER INFORMATION: Synthetic

<400> SEQUENCE: 473
atgaactgga tccgcctgcc tccagggagg ggcctggagt ggatttcata c                51

<210> SEQ ID NO 474
<211> LENGTH: 114
<212> TYPE: DNA
<213> ORGANISM: Artificial Sequence
<220> FEATURE:
<223> OTHER INFORMATION: Synthetic

<400> SEQUENCE: 474
tactatgcag actctgtgaa gggccgattc accgtctcca gggacgacgc caagaagtca        60
ctatttctgt acatgaacag cctgagagcc gatgacacgg ccgttttatta ctgt           114

<210> SEQ ID NO 475
<211> LENGTH: 75
<212> TYPE: DNA
<213> ORGANISM: Artificial Sequence
<220> FEATURE:
<223> OTHER INFORMATION: Synthetic

<400> SEQUENCE: 475
gaggtgcagt tgttggagtc tggggggaggc ttggtacagc ctggggggtc cctgagactc        60
tcctgtgcag cctct                                                        75

<210> SEQ ID NO 476
<211> LENGTH: 51
<212> TYPE: DNA
<213> ORGANISM: Artificial Sequence
<220> FEATURE:
<223> OTHER INFORMATION: Synthetic

<400> SEQUENCE: 476
atgagctggg tccgccaggc tccagggaag gggctggagt gggtctcagg t                51

<210> SEQ ID NO 477
<211> LENGTH: 114
<212> TYPE: DNA
<213> ORGANISM: Artificial Sequence
<220> FEATURE:
<223> OTHER INFORMATION: Synthetic

<400> SEQUENCE: 477
tactacgcag actccgtgaa gggccggttc accatctcca gagacaattc caagaacacg        60
```

-continued

```
ctgtatctgc aaatgaacag cctgagagcc gaggacacgg ccatatatta ctgt          114

<210> SEQ ID NO 478
<211> LENGTH: 33
<212> TYPE: DNA
<213> ORGANISM: Artificial Sequence
<220> FEATURE:
<223> OTHER INFORMATION: Synthetic

<400> SEQUENCE: 478
tggggccaag ggacgatggt caccgtctct tca                                  33

<210> SEQ ID NO 479
<211> LENGTH: 78
<212> TYPE: DNA
<213> ORGANISM: Artificial Sequence
<220> FEATURE:
<223> OTHER INFORMATION: Synthetic

<400> SEQUENCE: 479
gacatccaga tgacccagtc tccgtcctcc ctgtctgcat ctgtaggagg cagagtcacc     60
atcacttgcc ggacaagt                                                   78

<210> SEQ ID NO 480
<211> LENGTH: 51
<212> TYPE: DNA
<213> ORGANISM: Artificial Sequence
<220> FEATURE:
<223> OTHER INFORMATION: Synthetic

<400> SEQUENCE: 480
ttaaattggt atcagcagaa agcagggaaa gcccctaaac tcctgatcta t              51

<210> SEQ ID NO 481
<211> LENGTH: 108
<212> TYPE: DNA
<213> ORGANISM: Artificial Sequence
<220> FEATURE:
<223> OTHER INFORMATION: Synthetic

<400> SEQUENCE: 481
aatttgcaaa gtggggtccc atcaaggttc actggcagtg gctctgggac agatttcact     60
ctcaccatca gcagtctgca acctgaagat tttgcagctt actactgt                 108

<210> SEQ ID NO 482
<211> LENGTH: 30
<212> TYPE: DNA
<213> ORGANISM: Artificial Sequence
<220> FEATURE:
<223> OTHER INFORMATION: Synthetic

<400> SEQUENCE: 482
ttcggccctg ggaccaaagt ggctttcaaa                                      30

<210> SEQ ID NO 483
<211> LENGTH: 75
<212> TYPE: DNA
<213> ORGANISM: Artificial Sequence
<220> FEATURE:
<223> OTHER INFORMATION: Synthetic

<400> SEQUENCE: 483
gaggtgcagt tggtggagtc tgggggaggc ttggtccagc ctggagggtc cctgagactc     60
```
tcctgtgcag cctct                                                          75

<210> SEQ ID NO 484
<211> LENGTH: 51
<212> TYPE: DNA
<213> ORGANISM: Artificial Sequence
<220> FEATURE:
<223> OTHER INFORMATION: Synthetic

<400> SEQUENCE: 484
atgaactggg tccgccaggc tccagggaag ggactggagt gggtttcata c               51

<210> SEQ ID NO 485
<211> LENGTH: 114
<212> TYPE: DNA
<213> ORGANISM: Artificial Sequence
<220> FEATURE:
<223> OTHER INFORMATION: Synthetic

<400> SEQUENCE: 485
aaatacgcag actctgtgag gggccgattc gccttctcca gagacaacgc cgagaactca      60
gtgcatctgc aaatgaacag cctgagagcc gaggacacgg ctgtttatta ctgt            114

<210> SEQ ID NO 486
<211> LENGTH: 33
<212> TYPE: DNA
<213> ORGANISM: Artificial Sequence
<220> FEATURE:
<223> OTHER INFORMATION: Synthetic

<400> SEQUENCE: 486
tggggccaag ggaccgcggt caccgtctcc tca                                     33

<210> SEQ ID NO 487
<211> LENGTH: 78
<212> TYPE: DNA
<213> ORGANISM: Artificial Sequence
<220> FEATURE:
<223> OTHER INFORMATION: Synthetic

<400> SEQUENCE: 487
gacatccagt tgacccagtc tccatccttc ctgtctgcat ctgtaggaga cagagtcacc      60
atcacttgct gggccagt                                                      78

<210> SEQ ID NO 488
<211> LENGTH: 51
<212> TYPE: DNA
<213> ORGANISM: Artificial Sequence
<220> FEATURE:
<223> OTHER INFORMATION: Synthetic

<400> SEQUENCE: 488
ttagcctggt atcagcaaaa accagggaaa gcccctaagc tcctgatcta t               51

<210> SEQ ID NO 489
<211> LENGTH: 108
<212> TYPE: DNA
<213> ORGANISM: Artificial Sequence
<220> FEATURE:
<223> OTHER INFORMATION: Synthetic

<400> SEQUENCE: 489
actttgcaaa gtggggtccc atcaaggttc accggcagtg gatctgggac agaattcact      60
ctcacaatca gcagcctgca gcctgaagat tttgcaactt attactgt                    108

<210> SEQ ID NO 490
<211> LENGTH: 30
<212> TYPE: DNA
<213> ORGANISM: Artificial Sequence
<220> FEATURE:
<223> OTHER INFORMATION: Synthetic

<400> SEQUENCE: 490
ttcggccctg ggaccaaagt ggatgtcaaa                                              30

<210> SEQ ID NO 491
<211> LENGTH: 33
<212> TYPE: DNA
<213> ORGANISM: Artificial Sequence
<220> FEATURE:
<223> OTHER INFORMATION: Synthetic

<400> SEQUENCE: 491
tggggcccgg gaaccctggt caccgtctcc tcc                                          33

<210> SEQ ID NO 492
<211> LENGTH: 108
<212> TYPE: DNA
<213> ORGANISM: Artificial Sequence
<220> FEATURE:
<223> OTHER INFORMATION: Synthetic

<400> SEQUENCE: 492
attcgggaat ccggggtccc tgaccgattc agtggcagcg ggtctgggac agatttcact           60
ctcaccatca gcagcctgca ggctgaagat gtggcagttt attattgt                        108

<210> SEQ ID NO 493
<211> LENGTH: 75
<212> TYPE: DNA
<213> ORGANISM: Artificial Sequence
<220> FEATURE:
<223> OTHER INFORMATION: Synthetic

<400> SEQUENCE: 493
gaggtgcagc tgttggaatc tgggggaggc ctgatacaac cggggggggtc cctgagactc          60 tcctgtgcag cctct                                                            75

<210> SEQ ID NO 494
<211> LENGTH: 114
<212> TYPE: DNA
<213> ORGANISM: Artificial Sequence
<220> FEATURE:
<223> OTHER INFORMATION: Synthetic

<400> SEQUENCE: 494
tactatggag actccgtgaa gggccggttc accatttcca gagacaattc caagagtacg           60
ctgtatctgc aaatgaacag cctgagagac gcggacacgg ccgtatatta ttgt                114

<210> SEQ ID NO 495
<211> LENGTH: 78
<212> TYPE: DNA
<213> ORGANISM: Artificial Sequence
<220> FEATURE:
<223> OTHER INFORMATION: Synthetic

<400> SEQUENCE: 495
gacatccaga tgacccagtc tccatcctcc ctgtctgcat ccgtaggaga cagagtcacc          60

-continued atcacttgcc gggcaagt                                                                  78

<210> SEQ ID NO 496
<211> LENGTH: 51
<212> TYPE: DNA
<213> ORGANISM: Artificial Sequence
<220> FEATURE:
<223> OTHER INFORMATION: Synthetic

<400> SEQUENCE: 496
ttaaattggt atcagcagaa gccagggaaa gcccctaagt tcctgattta t                            51

<210> SEQ ID NO 497
<211> LENGTH: 108
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (76)..(76)
<223> OTHER INFORMATION: n is a, c, g, or t

<400> SEQUENCE: 497
agtttgcaaa gtggggtccc atcaaggttc agtggcagtg gatgtgggac agatttctct              60
ctcaccatca gcagtntgca ccctggagac ttcgcaactt actactgt                            108

<210> SEQ ID NO 498
<211> LENGTH: 51
<212> TYPE: DNA
<213> ORGANISM: Artificial Sequence
<220> FEATURE:
<223> OTHER INFORMATION: Synthetic

<400> SEQUENCE: 498
atgacctggg tccgccaggc tccagggaag ggactggagt gggtctcagg t                            51

<210> SEQ ID NO 499
<211> LENGTH: 114
<212> TYPE: DNA
<213> ORGANISM: Artificial Sequence
<220> FEATURE:
<223> OTHER INFORMATION: Synthetic

<400> SEQUENCE: 499
tactacgcag actccgtgaa gggccggttc accatttcca gagacaattc caagagcacg              60
ctctatctgc aaatgaacag tctgagagcc gaggacacgg ccgtatatta ctgt                    114

<210> SEQ ID NO 500
<211> LENGTH: 78
<212> TYPE: DNA
<213> ORGANISM: Artificial Sequence
<220> FEATURE:
<223> OTHER INFORMATION: Synthetic

<400> SEQUENCE: 500
gacatccaga tgacccagtc tccttccacc ctgtctgcat ctgtaggaga cagagtcacc              60
atcacttgcc gggccagt                                                                  78

<210> SEQ ID NO 501
<211> LENGTH: 51
<212> TYPE: DNA
<213> ORGANISM: Artificial Sequence
<220> FEATURE:
<223> OTHER INFORMATION: Synthetic -continued

<400> SEQUENCE: 501
ttggcctggt atcagcagaa accagggaaa gcccctaaac tcctgatcta t                    51

<210> SEQ ID NO 502
<211> LENGTH: 108
<212> TYPE: DNA
<213> ORGANISM: Artificial Sequence
<220> FEATURE:
<223> OTHER INFORMATION: Synthetic

<400> SEQUENCE: 502
agtttagaaa gtggggtccc atcaaggttc agcggcagtg gatctgggac agatttcact          60
ctcaccatca gcagcctgca gcctgatgat tttgcaagtt attactgc                       108

<210> SEQ ID NO 503
<211> LENGTH: 30
<212> TYPE: DNA
<213> ORGANISM: Artificial Sequence
<220> FEATURE:
<223> OTHER INFORMATION: Synthetic

<400> SEQUENCE: 503
tttggccagg ggaccaagct ggagatcaca                                           30

<210> SEQ ID NO 504
<211> LENGTH: 75
<212> TYPE: DNA
<213> ORGANISM: Artificial Sequence
<220> FEATURE:
<223> OTHER INFORMATION: Synthetic

<400> SEQUENCE: 504
caggtgcagt tggtggagtc tggggagac ttggtcaagc ctggagggtc cctgagactc           60
tcctgtgtag cctct                                                           75

<210> SEQ ID NO 505
<211> LENGTH: 114
<212> TYPE: DNA
<213> ORGANISM: Artificial Sequence
<220> FEATURE:
<223> OTHER INFORMATION: Synthetic

<400> SEQUENCE: 505
tactatgcag actctgtgaa gggccgattc accgtctcca gggacgacgc caagaattca          60
ctatttctgc acatgaacag tctgagagcc gaggacacgg ccgtttatta ctgt               114

<210> SEQ ID NO 506
<211> LENGTH: 114
<212> TYPE: DNA
<213> ORGANISM: Artificial Sequence
<220> FEATURE:
<223> OTHER INFORMATION: Synthetic

<400> SEQUENCE: 506
tactatgcag actctgtgaa gggccgattc accgtctcca gggacgacgc caagaactca          60
atgtttctgc acatgaacag cctgagagcc gatgacacgg ccgtttatta ctgt               114

<210> SEQ ID NO 507
<211> LENGTH: 75
<212> TYPE: DNA
<213> ORGANISM: Artificial Sequence
<220> FEATURE:

```
<223> OTHER INFORMATION: Synthetic

<400> SEQUENCE: 507
caggtgcaac tggtggagtc tgggggagac ttggtcaagc ctggagggtc cctgagactc       60
tcctgtgtag cctct                                                        75

<210> SEQ ID NO 508
<211> LENGTH: 114
<212> TYPE: DNA
<213> ORGANISM: Artificial Sequence
<220> FEATURE:
<223> OTHER INFORMATION: Synthetic

<400> SEQUENCE: 508
tactatgcag actctgtgaa ggggcgattc accgtctcca gggacgacgc caagaactca       60
ttatttctgc acatgaacag cctgagagcc gatgacacgg ccgtttatta ctgt           114

<210> SEQ ID NO 509
<211> LENGTH: 78
<212> TYPE: DNA
<213> ORGANISM: Artificial Sequence
<220> FEATURE:
<223> OTHER INFORMATION: Synthetic

<400> SEQUENCE: 509
gacatcgtga tgacccagtc tccagactcc ctggctctgt ctctgggcga gagggccacc       60
attaactgca agtccagc                                                     78

<210> SEQ ID NO 510
<211> LENGTH: 51
<212> TYPE: DNA
<213> ORGANISM: Artificial Sequence
<220> FEATURE:
<223> OTHER INFORMATION: Synthetic

<400> SEQUENCE: 510
ttagcttgtt accaacagaa agcaggacag cctcctaagt tgctcatttt c                51

<210> SEQ ID NO 511
<211> LENGTH: 30
<212> TYPE: DNA
<213> ORGANISM: Artificial Sequence
<220> FEATURE:
<223> OTHER INFORMATION: Synthetic

<400> SEQUENCE: 511
ttcggccggg ggaccacact ggagatcaaa                                        30

<210> SEQ ID NO 512
<211> LENGTH: 75
<212> TYPE: DNA
<213> ORGANISM: Artificial Sequence
<220> FEATURE:
<223> OTHER INFORMATION: Synthetic

<400> SEQUENCE: 512
gaggtgcagc tgttggagtc tgggggaggc ttggtacagc ctgggggatc cctgagactc       60
tcctgtgcag cctct                                                        75

<210> SEQ ID NO 513
<211> LENGTH: 114
<212> TYPE: DNA
<213> ORGANISM: Artificial Sequence
```

-continued

```
<220> FEATURE:
<223> OTHER INFORMATION: Synthetic

<400> SEQUENCE: 513
tactacgcag actccgtgaa gggccggttc accatttcca gagacaattc caagaacacg        60
ctgtatctgc aaatgaacag cctgagagcc gacgacacgg ccttatatta ctgt            114

<210> SEQ ID NO 514
<211> LENGTH: 51
<212> TYPE: DNA
<213> ORGANISM: Artificial Sequence
<220> FEATURE:
<223> OTHER INFORMATION: Synthetic

<400> SEQUENCE: 514
ttaatttggt atcagcagaa accagggaaa gcccctaagc tcctgattta t                 51

<210> SEQ ID NO 515
<211> LENGTH: 108
<212> TYPE: DNA
<213> ORGANISM: Artificial Sequence
<220> FEATURE:
<223> OTHER INFORMATION: Synthetic

<400> SEQUENCE: 515
agtttgcaaa gtggggtccc atcaaggttc agtggcagtg gatctgggac agatttcact        60
ctcattatca gcagtctgca acctgaagat tttgcaactt attactgt                   108

<210> SEQ ID NO 516
<211> LENGTH: 30
<212> TYPE: DNA
<213> ORGANISM: Artificial Sequence
<220> FEATURE:
<223> OTHER INFORMATION: Synthetic

<400> SEQUENCE: 516
ttcggcggag ggaccaaagt ggagatcaaa                                         30

<210> SEQ ID NO 517
<211> LENGTH: 114
<212> TYPE: DNA
<213> ORGANISM: Artificial Sequence
<220> FEATURE:
<223> OTHER INFORMATION: Synthetic

<400> SEQUENCE: 517
aaatacgcag actctgtgag gggccgattc accttctcca gagacaacgc cgagaactca        60
gtgcatctgc aaatgaacag cctgagaggc gaggacacgg ctgtttatta ctgt            114

<210> SEQ ID NO 518
<211> LENGTH: 51
<212> TYPE: DNA
<213> ORGANISM: Artificial Sequence
<220> FEATURE:
<223> OTHER INFORMATION: Synthetic

<400> SEQUENCE: 518
ttagcctggt atcagcaaaa accagggaaa gcccctaagc tcctgattta t                 51

<210> SEQ ID NO 519
<211> LENGTH: 108
<212> TYPE: DNA
<213> ORGANISM: Artificial Sequence
<220> FEATURE:
```

-continued

<223> OTHER INFORMATION: Synthetic
<220> FEATURE:
<221> NAME/KEY: misc_feature
<222> LOCATION: (44)..(44)
<223> OTHER INFORMATION: n is a, c, g, or t

<400> SEQUENCE: 519
actttgcaaa gtggggtccc atcaaggttc agcggcagtg gatntgggac agaattcact      60
ctcacaatca gcagcttgca gcgtgaagat tttgcaactt attactgt               108

<210> SEQ ID NO 520
<211> LENGTH: 114
<212> TYPE: DNA
<213> ORGANISM: Artificial Sequence
<220> FEATURE:
<223> OTHER INFORMATION: Synthetic

<400> SEQUENCE: 520
aaatacgcag actctgtgag gggccgattc accttctcca gagacaacgc cgagaactca      60
gtgtttctcc aaatgaacag cctgagaggc gaggacacgg ctgtttatta ctgt         114

<210> SEQ ID NO 521
<211> LENGTH: 108
<212> TYPE: DNA
<213> ORGANISM: Artificial Sequence
<220> FEATURE:
<223> OTHER INFORMATION: Synthetic

<400> SEQUENCE: 521
actttacaaa gtggggtccc atcaaggttc agcggcagtg gatctgggac agaattcact      60
ctcacaatca gcagcctgca gcctgaagat tttgcaactt attactgt               108

<210> SEQ ID NO 522
<211> LENGTH: 75
<212> TYPE: DNA
<213> ORGANISM: Artificial Sequence
<220> FEATURE:
<223> OTHER INFORMATION: Synthetic

<400> SEQUENCE: 522
gaggtgcagt tgttggagtc tgggggaggc ttggtacagc ctggggggtc cctgagactc      60
tcctgtgcag tctct                                                    75

<210> SEQ ID NO 523
<211> LENGTH: 51
<212> TYPE: DNA
<213> ORGANISM: Artificial Sequence
<220> FEATURE:
<223> OTHER INFORMATION: Synthetic

<400> SEQUENCE: 523
atgagctggg tccgccaggc tccagggaag ggcctggagt gggtctcggg t              51

<210> SEQ ID NO 524
<211> LENGTH: 114
<212> TYPE: DNA
<213> ORGANISM: Artificial Sequence
<220> FEATURE:
<223> OTHER INFORMATION: Synthetic

<400> SEQUENCE: 524
aattacgcag actccgtgaa aggccggttc accatctcca gagacaattc caagaacacg      60
ctctatctgc aaatgagcag cctgagagcc gaggacacgg ccgaatatta ctgt         114

<210> SEQ ID NO 525
<211> LENGTH: 33
<212> TYPE: DNA
<213> ORGANISM: Artificial Sequence
<220> FEATURE:
<223> OTHER INFORMATION: Synthetic

<400> SEQUENCE: 525
tggggccagg gaatcctggt caccgtctcc cca                                    33

<210> SEQ ID NO 526
<211> LENGTH: 51
<212> TYPE: DNA
<213> ORGANISM: Artificial Sequence
<220> FEATURE:
<223> OTHER INFORMATION: Synthetic

<400> SEQUENCE: 526
ttaatttggt atcagcagaa accagggaaa gccctaaac tcctgcttta t               51

<210> SEQ ID NO 527
<211> LENGTH: 108
<212> TYPE: DNA
<213> ORGANISM: Artificial Sequence
<220> FEATURE:
<223> OTHER INFORMATION: Synthetic

<400> SEQUENCE: 527
agtttgcaaa gtggggtccc agcaaggttc actggcagtg ggtctgggac agatttcact      60
ctcaccatcg gcagtctgca acctgaagat tttgcaactt actactgt                  108

<210> SEQ ID NO 528
<211> LENGTH: 51
<212> TYPE: DNA
<213> ORGANISM: Artificial Sequence
<220> FEATURE:
<223> OTHER INFORMATION: Synthetic

<400> SEQUENCE: 528
ttaatttggt atcagcagaa accagggaaa gccctaagc tcctgctcta t               51

<210> SEQ ID NO 529
<211> LENGTH: 362
<212> TYPE: PRT
<213> ORGANISM: Unknown
<220> FEATURE:
<223> OTHER INFORMATION: Synthetic

<400> SEQUENCE: 529

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

-continued

```
Pro Asn Leu Asn Glu Asp Leu Thr Cys Gly Asn Leu Leu Met Trp Glu
            100             105             110

Ala Val Thr Val Gln Thr Glu Val Ile Gly Ile Thr Ser Met Leu Asn
            115             120             125

Leu His Ala Gly Ser Gln Lys Val His Glu His Gly Gly Gly Lys Pro
    130             135             140

Ile Gln Gly Ser Asn Phe His Phe Phe Ala Val Gly Gly Glu Pro Leu
145             150             155             160

Glu Met Gln Gly Val Leu Met Asn Tyr Arg Ser Lys Tyr Pro Asp Gly
                165             170             175

Thr Ile Thr Pro Lys Asn Pro Thr Ala Gln Ser Gln Val Met Asn Thr
            180             185             190

Asp His Lys Ala Tyr Leu Asp Lys Asn Asn Ala Tyr Pro Val Glu Cys
            195             200             205

Trp Val Pro Asp Pro Ser Arg Asn Glu Asn Ala Arg Tyr Phe Gly Thr
    210             215             220

Phe Thr Gly Gly Glu Asn Val Pro Pro Val Leu His Val Thr Asn Thr
225             230             235             240

Ala Thr Thr Val Leu Leu Asp Glu Gln Gly Val Gly Pro Leu Cys Lys
            245             250             255

Ala Asp Ser Leu Tyr Val Ser Ala Ala Asp Ile Cys Gly Leu Phe Thr
            260             265             270

Asn Ser Ser Gly Thr Gln Gln Trp Arg Gly Leu Ala Arg Tyr Phe Lys
            275             280             285

Ile Arg Leu Arg Lys Arg Ser Val Lys Asn Pro Tyr Pro Ile Ser Phe
    290             295             300

Leu Leu Ser Asp Leu Ile Asn Arg Arg Thr Gln Arg Val Asp Gly Gln
305             310             315             320

Pro Met Tyr Gly Met Glu Ser Gln Val Glu Glu Val Arg Val Phe Asp
            325             330             335

Gly Thr Glu Arg Leu Pro Gly Asp Pro Asp Met Ile Arg Tyr Ile Asp
            340             345             350

Lys Gln Gly Gln Leu Gln Thr Lys Met Leu
    355             360
```

NEUTRALIZING MONOCLONAL ANTI-VP1 ANTIBODIES TO BK VIRUS

CROSS REFERENCE TO RELATED APPLICATIONS

This application claims the benefit under 35 U.S.C. § 119(e) of U.S. Provisional Application No. 63/160,678, filed Mar. 12, 2021, entitled "NEUTRALIZING MONO-CLONAL ANTIBODIES TO BK VIRUS," the entire disclosure of which is hereby incorporated by reference in their entireties.

SEQUENCE LISTING SUBMITTED AS ASCII TEXT FILE VIA EFS-WEB

The present Application contains a Sequence Listing which has been submitted in ASCII format via EFS-Web and is hereby incorporated by reference in its entirety. The ASCII version, created on Jan. 30, 2024, is named SeqList-084284-00283 and is 237,612 bytes in size. By this statement, the Sequence Listing constitutes a part of the instant Specification.

BACKGROUND OF THE INVENTION

BK virus (BKV) is a dsDNA polyomavirus that is the causative agent of polyomavirus-associated nephropathy (PyVAN) and polyomavirus-associated hemorrhagic cystitis (PyVHC) following kidney transplantation and allogeneic hematopoietic stem cell transplantation, respectively. BK virus consists of genetically distinct genotypes that can give rise to differences in serotypes. Both PyVAN and PyVHC occur almost exclusively in immunosuppressed patients and at present the only treatment is a reduction in immunosup-pression that dramatically increases the risk of graft failures. New approaches for treating BK viral disease would be a welcome advance in the art, including in the areas of cancer therapy and organ transplantation.

SUMMARY OF THE INVENTION

The present disclosure provides, in some aspects, isolated antibodies and antigen binding fragments for treating BK viral disease. In particular aspects and without being bound by theory, the isolated antibodies and antigen binding frag-ments disclosed herein neutralize BK virus by binding to the capsid protein VP1, thereby inhibiting its interaction with sialic acid moieties on host cells and preventing viral infection. BK virus infection is common, but self-limiting, in healthy individuals, with infected individuals producing antibodies that limit viral replication. When individuals become immunocompromised, such as after the develop-ment of conditions such as AIDS, or treatment with immu-nosuppressive agents, such as in the course of cancer treat-ment or following organ transplant, loss of antibodies or normal immune system function allows BK virus to repli-cate to a greater extent. This uncontrolled BK virus repli-cation causes multiple adverse effects, including cystitis, nephropathy, urethral stenosis, and colitis. Inhibiting BK virus replication using monoclonal antibodies thus presents a useful method of preventing viral pathogenesis in immu-nocompromised individuals and those receiving immuno-suppressive therapies.

Furthermore, four distinct serotypes of BK virus have been identified, and transplantation of a kidney containing one serotype of BK virus into a recipient without antibodies specific to that serotype is likely to result in transplant rejection. Thus, identifying the BK viral serotype(s) present in a donated kidney, and administering antibodies specific to that serotype(s) to the prospective recipient before, during, and/or after transplantation, serves as one method of reduc-ing the risk of transplant rejection. Additionally, some antibodies or combinations of antibodies provided herein neutralize more than a single serotype of BK virus, including up to all four serotypes of BK virus, and such antibodies or combinations of antibodies are thus useful for preventing or limiting BK virus replication even when the serotype of BK virus infection is not known.

In some aspects, the present disclosure provides an iso-lated antibody or antigen binding fragment thereof, com-prising, a heavy chain variable region (VH) having three complementarity determining regions (CDRs) of HCDR1, HCDR2, and HCDR3, and a light chain variable region (VL) having three CDRs of LCDR1, LCDR2, and LCDR3, wherein:

(a) HCDR1 comprises at least 90% sequence identity to SEQ ID NO: 1, 9, 17, 25, 33, 41, 49, 57, 65, 73, 81, 89, 97, 105, 113, 121, 129, 137, 145, 153, 161, 169, or 177;

(b) HCDR2 comprises at least 90% sequence identity to SEQ ID NO: 2, 10, 18, 26, 34, 42, 50, 58, 66, 74, 82, 90, 98, 106, 114, 122, 130, 138, 146, 154, 162, 170, or 178;

(c) HCDR3 comprises at least 90% sequence identity to SEQ ID NO: 3, 11, 19, 27, 35, 43, 51, 59, 67, 75, 83, 91, 99, 107, 115, 123, 131, 139, 147, 155, 163, 171, or 179;

(d) LCDR1 comprises at least 90% sequence identity to SEQ ID NO: 4, 12, 20, 28, 36, 44, 52, 60, 68, 76, 84, 92, 100, 108, 116, 124, 132, 140, 148, 156, 164, 172, or 180;

(e) LCDR2 comprises at least 90% sequence identity to SEQ ID NO: 5, 13, 21, 29, 37, 45, 53, 61, 69, 77, 85, 93, 101, 109, 117, 125, 133, 141, 149, 157, 165, 173, or 181; and (f) LCDR3 comprises at least 90% sequence identity to SEQ ID NO: 6, 14, 22, 30, 38, 46, 54, 62, 70, 78, 86, 94, 102, 110, 118, 126, 134, 142, 150, 158, 166, 174, or 182.

In some aspects, the present disclosure provides a com-position comprising two more antibodies, wherein a second antibody comprises at least one CDR sequence which is distinct from at least one CDR sequence of a first antibody.

In some embodiments, the isolated antibody or antigen binding fragments provided herein comprise the following sets of CDR sequences:

(a) HCDR1 comprises SEQ ID NO: 1 or a sequence having at least 90% sequence therewith, HCDR2 com-prises SEQ ID NO: 2 or a sequence having at least 90% sequence therewith, HCDR3 comprises SEQ ID NO: 3 or a sequence having at least 90% sequence therewith, LCDR1 comprises SEQ ID NO: 4 or a sequence having at least 90% sequence therewith, LCDR2 comprises SEQ ID NO: 5 or a sequence having at least 90% sequence therewith, and LCDR3 comprises SEQ ID NO: 6 or a sequence having at least 90% sequence therewith;

(b) HCDR1 comprises SEQ ID NO: 9 or a sequence having at least 90% sequence therewith, HCDR2 com-prises SEQ ID NO: 10 or a sequence having at least 90% sequence therewith, HCDR3 comprises SEQ ID NO: 11 or a sequence having at least 90% sequence therewith, LCDR1 comprises SEQ ID NO: 12 or a sequence having at least 90% sequence therewith, LCDR2 comprises SEQ ID NO: 13 or a sequence having at least 90% sequence therewith, and LCDR3 comprises SEQ ID NO: 14 or a sequence having at least 90% sequence therewith;

(c) HCDR1 comprises SEQ ID NO: 17 or a sequence having at least 90% sequence therewith, HCDR2 comprises SEQ ID NO: 18 or a sequence having at least 90% sequence therewith, HCDR3 comprises SEQ ID NO: 19 or a sequence having at least 90% sequence therewith, LCDR1 comprises SEQ ID NO: 20 or a sequence having at least 90% sequence therewith, LCDR2 comprises SEQ ID NO: 21 or a sequence having at least 90% sequence therewith, and LCDR3 comprises SEQ ID NO: 22 or a sequence having at least 90% sequence therewith;

(d) HCDR1 comprises SEQ ID NO: 25 or a sequence having at least 90% sequence therewith, HCDR2 comprises SEQ ID NO: 26 or a sequence having at least 90% sequence therewith, HCDR3 comprises SEQ ID NO: 27 or a sequence having at least 90% sequence therewith, LCDR1 comprises SEQ ID NO: 28 or a sequence having at least 90% sequence therewith, LCDR2 comprises SEQ ID NO: 29 or a sequence having at least 90% sequence therewith, and LCDR3 comprises SEQ ID NO: 30 or a sequence having at least 90% sequence therewith;

(e) HCDR1 comprises SEQ ID NO: 33 or a sequence having at least 90% sequence therewith, HCDR2 comprises SEQ ID NO: 34 or a sequence having at least 90% sequence therewith, HCDR3 comprises SEQ ID NO: 35 or a sequence having at least 90% sequence therewith, LCDR1 comprises SEQ ID NO: 36 or a sequence having at least 90% sequence therewith, LCDR2 comprises SEQ ID NO: 37 or a sequence having at least 90% sequence therewith, and LCDR3 comprises SEQ ID NO: 38 or a sequence having at least 90% sequence therewith;

(f) HCDR1 comprises SEQ ID NO: 41 or a sequence having at least 90% sequence therewith, HCDR2 comprises SEQ ID NO: 42 or a sequence having at least 90% sequence therewith, HCDR3 comprises SEQ ID NO: 43 or a sequence having at least 90% sequence therewith, LCDR1 comprises SEQ ID NO: 44 or a sequence having at least 90% sequence therewith, LCDR2 comprises SEQ ID NO: 45 or a sequence having at least 90% sequence therewith, and LCDR3 comprises SEQ ID NO: 46 or a sequence having at least 90% sequence therewith;

(g) HCDR1 comprises SEQ ID NO: 49 or a sequence having at least 90% sequence therewith, HCDR2 comprises SEQ ID NO: 50 or a sequence having at least 90% sequence therewith, HCDR3 comprises SEQ ID NO: 51 or a sequence having at least 90% sequence therewith, LCDR1 comprises SEQ ID NO: 52 or a sequence having at least 90% sequence therewith, LCDR2 comprises SEQ ID NO: 53 or a sequence having at least 90% sequence therewith, and LCDR3 comprises SEQ ID NO: 54 or a sequence having at least 90% sequence therewith;

(h) HCDR1 comprises SEQ ID NO: 65 or a sequence having at least 90% sequence therewith, HCDR2 comprises SEQ ID NO: 66 or a sequence having at least 90% sequence therewith, HCDR3 comprises SEQ ID NO: 67 or a sequence having at least 90% sequence therewith, LCDR1 comprises SEQ ID NO: 68 or a sequence having at least 90% sequence therewith, LCDR2 comprises SEQ ID NO: 69 or a sequence having at least 90% sequence therewith, and LCDR3 comprises SEQ ID NO: 70 or a sequence having at least 90% sequence therewith;

(i) HCDR1 comprises SEQ ID NO: 73 or a sequence having at least 90% sequence therewith, HCDR2 comprises SEQ ID NO: 74 or a sequence having at least 90% sequence therewith, HCDR3 comprises SEQ ID NO: 75 or a sequence having at least 90% sequence therewith, LCDR1 comprises SEQ ID NO: 76 or a sequence having at least 90% sequence therewith, LCDR2 comprises SEQ ID NO: 77 or a sequence having at least 90% sequence therewith, and LCDR3 comprises SEQ ID NO: 79 or a sequence having at least 90% sequence therewith;

(j) HCDR1 comprises SEQ ID NO: 81 or a sequence having at least 90% sequence therewith, HCDR2 comprises SEQ ID NO: 82 or a sequence having at least 90% sequence therewith, HCDR3 comprises SEQ ID NO: 83 or a sequence having at least 90% sequence therewith, LCDR1 comprises SEQ ID NO: 84 or a sequence having at least 90% sequence therewith, LCDR2 comprises SEQ ID NO: 85 or a sequence having at least 90% sequence therewith, and LCDR3 comprises SEQ ID NO: 86 or a sequence having at least 90% sequence therewith;

(k) HCDR1 comprises SEQ ID NO: 89 or a sequence having at least 90% sequence therewith, HCDR2 comprises SEQ ID NO: 90 or a sequence having at least 90% sequence therewith, HCDR3 comprises SEQ ID NO: 91 or a sequence having at least 90% sequence therewith, LCDR1 comprises SEQ ID NO: 92 or a sequence having at least 90% sequence therewith, LCDR2 comprises SEQ ID NO: 93 or a sequence having at least 90% sequence therewith, and LCDR3 comprises SEQ ID NO: 94 or a sequence having at least 90% sequence therewith;

(l) HCDR1 comprises SEQ ID NO: 97 or a sequence having at least 90% sequence therewith, HCDR2 comprises SEQ ID NO: 98 or a sequence having at least 90% sequence therewith, HCDR3 comprises SEQ ID NO: 99 or a sequence having at least 90% sequence therewith, LCDR1 comprises SEQ ID NO: 100 or a sequence having at least 90% sequence therewith, LCDR2 comprises SEQ ID NO: 101 or a sequence having at least 90% sequence therewith, and LCDR3 comprises SEQ ID NO: 102 or a sequence having at least 90% sequence therewith;

(m) HCDR1 comprises SEQ ID NO: 105 or a sequence having at least 90% sequence therewith, HCDR2 comprises SEQ ID NO: 106 or a sequence having at least 90% sequence therewith, HCDR3 comprises SEQ ID NO: 107 or a sequence having at least 90% sequence therewith, LCDR1 comprises SEQ ID NO: 108 or a sequence having at least 90% sequence therewith, LCDR2 comprises SEQ ID NO: 109 or a sequence having at least 90% sequence therewith, and LCDR3 comprises SEQ ID NO: 110 or a sequence having at least 90% sequence therewith;

(n) HCDR1 comprises SEQ ID NO: 113 or a sequence having at least 90% sequence therewith, HCDR2 comprises SEQ ID NO: 114 or a sequence having at least 90% sequence therewith, HCDR3 comprises SEQ ID NO: 115 or a sequence having at least 90% sequence therewith, LCDR1 comprises SEQ ID NO: 116 or a sequence having at least 90% sequence therewith, LCDR2 comprises SEQ ID NO: 117 or a sequence having at least 90% sequence therewith, and LCDR3 comprises SEQ ID NO: 118 or a sequence having at least 90% sequence therewith;

(o) HCDR1 comprises SEQ ID NO: 121 or a sequence having at least 90% sequence therewith, HCDR2 comprises SEQ ID NO: 122 or a sequence having at least 90% sequence therewith, HCDR3 comprises SEQ ID NO: 123 or a sequence having at least 90% sequence therewith, LCDR1 comprises SEQ ID NO: 124 or a sequence having at least 90% sequence therewith, LCDR2 comprises SEQ ID NO: 125 or a sequence having at least 90% sequence therewith, and LCDR3 comprises SEQ ID NO: 126 or a sequence having at least 90% sequence therewith;

(p) HCDR1 comprises SEQ ID NO: 129 or a sequence having at least 90% sequence therewith, HCDR2 comprises SEQ ID NO: 130 or a sequence having at least 90% sequence therewith, HCDR3 comprises SEQ ID NO: 131 or a sequence having at least 90% sequence therewith, LCDR1 comprises SEQ ID NO: 132 or a sequence having at least 90% sequence therewith, LCDR2 comprises SEQ ID NO: 133 or a sequence having at least 90% sequence therewith, and LCDR3 comprises SEQ ID NO: 134 or a sequence having at least 90% sequence therewith;

(q) HCDR1 comprises SEQ ID NO: 137 or a sequence having at least 90% sequence therewith, HCDR2 comprises SEQ ID NO: 138 or a sequence having at least 90% sequence therewith, HCDR3 comprises SEQ ID NO: 139 or a sequence having at least 90% sequence therewith, LCDR1 comprises SEQ ID NO: 140 or a sequence having at least 90% sequence therewith, LCDR2 comprises SEQ ID NO: 141 or a sequence having at least 90% sequence therewith, and LCDR3 comprises SEQ ID NO: 142 or a sequence having at least 90% sequence therewith;

(r) HCDR1 comprises SEQ ID NO: 145 or a sequence having at least 90% sequence therewith, HCDR2 comprises SEQ ID NO: 146 or a sequence having at least 90% sequence therewith, HCDR3 comprises SEQ ID NO: 147 or a sequence having at least 90% sequence therewith, LCDR1 comprises SEQ ID NO: 148 or a sequence having at least 90% sequence therewith, LCDR2 comprises SEQ ID NO: 149 or a sequence having at least 90% sequence therewith, and LCDR3 comprises SEQ ID NO: 150 or a sequence having at least 90% sequence therewith;

(s) HCDR1 comprises SEQ ID NO: 153 or a sequence having at least 90% sequence therewith, HCDR2 comprises SEQ ID NO: 154 or a sequence having at least 90% sequence therewith, HCDR3 comprises SEQ ID NO: 155 or a sequence having at least 90% sequence therewith, LCDR1 comprises SEQ ID NO: 156 or a sequence having at least 90% sequence therewith, LCDR2 comprises SEQ ID NO: 157 or a sequence having at least 90% sequence therewith, and LCDR3 comprises SEQ ID NO: 158 or a sequence having at least 90% sequence therewith;

(t) HCDR1 comprises SEQ ID NO: 161 or a sequence having at least 90% sequence therewith, HCDR2 comprises SEQ ID NO: 162 or a sequence having at least 90% sequence therewith, HCDR3 comprises SEQ ID NO: 163 or a sequence having at least 90% sequence therewith, LCDR1 comprises SEQ ID NO: 164 or a sequence having at least 90% sequence therewith, LCDR2 comprises SEQ ID NO: 165 or a sequence having at least 90% sequence therewith, and LCDR3 comprises SEQ ID NO: 166 or a sequence having at least 90% sequence therewith;

(u) HCDR1 comprises SEQ ID NO: 169 or a sequence having at least 90% sequence therewith, HCDR2 comprises SEQ ID NO: 170 or a sequence having at least 90% sequence therewith, HCDR3 comprises SEQ ID NO: 171 or a sequence having at least 90% sequence therewith, LCDR1 comprises SEQ ID NO: 172 or a sequence having at least 90% sequence therewith, LCDR2 comprises SEQ ID NO: 173 or a sequence having at least 90% sequence therewith, and LCDR3 comprises SEQ ID NO: 174 or a sequence having at least 90% sequence therewith; or (v) HCDR1 comprises SEQ ID NO: 177 or a sequence having at least 90% sequence therewith, HCDR2 comprises SEQ ID NO: 178 or a sequence having at least 90% sequence therewith, HCDR3 comprises SEQ ID NO: 179 or a sequence having at least 90% sequence therewith, LCDR1 comprises SEQ ID NO: 180 or a sequence having at least 90% sequence therewith, LCDR2 comprises SEQ ID NO: 181 or a sequence having at least 90% sequence therewith, and LCDR3 comprises SEQ ID NO: 182 or a sequence having at least 90% sequence therewith.

In some aspects, the present disclosure provides a composition comprising two more antibodies, wherein a first antibody comprises any of the antibodies (a)-(v) according to the preceding paragraph, and wherein a second antibody does not consist of the first antibody.

In some embodiments, wherein a first antibody comprises any of the antibodies (a)-(v) according to the above paragraph, and wherein a second antibody comprises any of the antibodies (a)-(v) and does not consist of the first antibody.

In some aspects, the present disclosure provides an isolated antibody or antigen binding fragment thereof, comprising, a heavy chain variable region (VH) and a light chain variable region (VL), wherein:

(a) VH comprises at least 90% sequence identity to SEQ ID NO: 7, 15, 23, 31, 39, 47, 55, 63, 71, 79, 87, 95, 103, 111, 119, 127, 135, 143, 151, 159, 167, 175, or 183; and (b) VL comprises at least 90% sequence identity to SEQ ID NO: 8, 16, 24, 32, 40, 48, 56, 64, 72, 80, 88, 96, 104, 112, 120, 128, 136, 144, 152, 160, 168, 176, or 184.

In some aspects, the present disclosure provides a composition comprising two or more antibodies as described in the preceding paragraph, wherein a second antibody comprises (a) at least one VH sequence which is distinct from at least one VH sequence of a first antibody, or (b) at least one VL sequence which is distinct from at least one VL sequence of a first antibody.

In some embodiments of the isolated antibody or antigen binding fragment provided herein:

(aa) VH comprises SEQ ID NO: 7, and VL comprises SEQ ID NO: 8;

(bb) VH comprises SEQ ID NO: 15, and VL comprises SEQ ID NO: 16;

(cc) VH comprises SEQ ID NO: 31, and VL comprises SEQ ID NO: 32;

(dd) VH comprises SEQ ID NO: 39, and VL comprises SEQ ID NO: 40;

(ee) VH comprises SEQ ID NO: 47, and VL comprises SEQ ID NO: 48;

(ff) VH comprises SEQ ID NO: 55, and VL comprises SEQ ID NO: 56;

(gg) VH comprises SEQ ID NO: 63, and VL comprises SEQ ID NO: 64;

(hh) VH comprises SEQ ID NO: 71, and VL comprises SEQ ID NO: 72;

(ii) VH comprises SEQ ID NO: 79, and VL comprises SEQ ID NO: 80;

(jj) VH comprises SEQ ID NO: 87, and VL comprises SEQ ID NO: 88;

(kk) VH comprises SEQ ID NO: 95, and VL comprises SEQ ID NO: 96;

(ll) VH comprises SEQ ID NO: 103, and VL comprises SEQ ID NO: 104;

(mm) VH comprises SEQ ID NO: 111, and VL comprises SEQ ID NO: 112;

(nn) VH comprises SEQ ID NO: 119, and VL comprises SEQ ID NO: 120;

(oo) VH comprises SEQ ID NO: 127, and VL comprises SEQ ID NO: 128;

(pp) VH comprises SEQ ID NO: 135, and VL comprises SEQ ID NO: 136;

(qq) VH comprises SEQ ID NO: 143, and VL comprises SEQ ID NO: 144;

(rr) VH comprises SEQ ID NO: 151, and VL comprises SEQ ID NO: 152;

(ss) VH comprises SEQ ID NO: 159, and VL comprises SEQ ID NO: 160;

(tt) VH comprises SEQ ID NO: 167, and VL comprises SEQ ID NO: 168;

(uu) VH comprises SEQ ID NO: 175, and VL comprises SEQ ID NO: 176; or (vv) VH comprises SEQ ID NO: 183, and VL comprises SEQ ID NO: 184.

In some aspects, the present disclosure provides a composition comprising two more antibodies, wherein a first antibody comprises any of the antibodies (aa)-(vv) according to the preceding paragraph, and wherein a second antibody does not consist of the first antibody.

In some embodiments, wherein a first antibody comprises any of the antibodies (aa)-(vv) according to the above paragraph, and wherein a second antibody comprises any of the antibodies (aa)-(vv) and does not consist of the first antibody.

In some aspects, the present disclosure provides an isolated antibody or antigen binding fragment thereof, wherein, when bound to BK virus VP1 protein, the antibody binds to at least one of the following residues: S80, D82, R83, or R170 of SEQ ID NO: 529 or to a corresponding residue of an amino acid sequence having at least 85% sequence identity with SEQ ID NO: 529, and wherein the antibody inhibits or otherwise blocks binding of BK virus VP1 to sialic acid. In various embodiments, the isolated antibody or antigen binding fragment inhibits BK virus from binding to sialic acid by at least 1%, at least 2%, at least 4%, at least 8%, at least 10%, at least 20%, at least 30%, at least 40%, at least 50%, at least 60%, at least 60%, at least 70%, at least 80%, at least 90%, at least 95%, at least 99%, or up to 100% as compared to the level of binding of BK virus to sialic acid in the absence of the isolated antibody or antigen binding fragment.

In some aspects, the present disclosure provides a composition comprising two more antibodies, wherein a first antibody comprises any of the antibodies according to any of the preceding paragraphs, and wherein a second antibody does not consist of the first antibody.

In some embodiments, wherein a first antibody comprises any of the antibodies according to the above paragraphs, and wherein a second antibody comprises any of the antibodies according to the above paragraph and does not consist of the first antibody.

In some aspects, the present disclosure provides an isolated antibody or antigen binding fragment thereof, wherein (a) the antibody is capable of inhibiting infection by a virus comprising VP1 of BK virus serotype 1, a virus comprising VP1 of BK virus serotype 2, a virus comprising VP1 of BK virus serotype 3, and a virus comprising VP1 of BK virus serotype 4, wherein an antibody capable of inhibiting infection by a virus is an antibody that inhibits infection of a target cell by a virus, as determined by a method comprising the steps of:

(i) contacting the virus with the antibody or a control protein; (ii) incubating the virus with target cells; and (iii) determining the proportion of the target cells infected by the virus, or the amount of viral RNA or DNA present in the target cells, at the end of step (ii); wherein determination of a lesser proportion of target cells infected by the virus, or a lesser amount of pseudoviral RNA or DNA present in the target cells, in the presence of the antibody, relative to the amount of target cells infected or amount of viral RNA or DNA in the absence of the antibody, is indicative of inhibition of infection by the virus; and (b) the antibody is capable of binding to an epitope that is present on VP1 of BK virus serotype 1, VP1 of BK virus serotype 2, VP1 of BK virus serotype 3, and VP1 of BK virus serotype 4.

In some aspects, the present disclosure provides a composition comprises two more antibodies, wherein a first antibody comprises any of the antibodies according to the above paragraphs (e.g., the antibodies designated (a)-(v) or (aa) to (vv)), and wherein a second antibody does not consist of the first antibody.

In some embodiments, wherein a first antibody comprises any of the antibodies according to the above paragraphs (e.g., the antibodies designated (a)-(v) or (aa) to (vv)), and wherein a second antibody comprises any of the antibodies according to the above paragraphs and does not consist of the first antibody.

In some embodiments of the antibody or antigen binding fragment provided herein, the antibody has a dissociation constant ($K_D$) from BK virus VP1 protein selected from the group consisting of at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

In some embodiments, the antibody or antigen binding fragment further comprises: heavy chain framework regions HFR1, HFR2, HFR3, and HFR4; and light chain framework regions LFR1, LFR2, LFR3, and LFR4.

In some embodiments, the HFR1 region comprises the amino acid sequence of any one of SEQ ID NOs: 185, 193, 197, 205, 213, 226, 234, 241, 250, or 269, the HFR2 region comprises the amino acid sequence of any one of SEQ ID NOs: 186, 194, 198, 206, 214, 223, 227, 232, 242, or 253, the HFR3 region comprises the amino acid sequence of any one of SEQ ID NOs: 187, 195, 199, 207, 215, 219, 224, 228, 233, 235, 243, 251, 254, 258, 259, 262, 265, 267, or 270, the HFR4 region comprises the amino acid sequence of any one of SEQ ID NOs: 188, 200, 208, 220, 229, 236, 244, or 271, the LFR1 region comprises the amino acid sequence of any one of SEQ ID NOs: 189, 201, 209, 237, 245, 255, or 260, the LFR2 region comprises the amino acid sequence of any one of SEQ ID NOs: 190, 202, 210, 216, 221, 225, 230, 238, 246, 261, 263, or 272, the LFR3 region comprises SEQ ID NOs: 191, 196, 203, 211, 217, 222, 230, 239, 247, 249, 252, 256, 264, 266, 268, or 273, and the LFR4 region comprises the amino acid sequence of any one of SEQ ID NOs: 192, 204, 212, 218, 240, 248, or 257.

In some embodiments, the antibody or antigen binding fragment further comprises a heavy chain constant (CH) domain and a light chain constant (CL) domain, wherein:

(a) the CH domain is selected from the group consisting of IgG, IgG1, IgG2, IgG2a, IgG2b, IgG2c, IgG3, IgG4, IgA, IgA1, IgA2, IgD, IgM, and IgE constant domains, and comprises a sequence having at least 80%, 85%, 90%, 95%, 96%, 97%, 98%, 99%, or up to 100% sequence identity with one of SEQ ID NOs: 274-290; and (b) the CL domain is selected from the group consisting of Ig kappa and Ig lambda constant domains, and comprises a sequence having at least 80%, 85%, 90%, 95%, 96%, 97%, 98%, 99%, or up to 100% sequence identity with one of SEQ ID NOs: 291-301.

In some embodiments, the antibody is a monoclonal antibody, a chimeric antibody, a humanized antibody, a human engineered antibody, a human antibody, a single chain antibody (scFv), or an antibody fragment.

In some embodiments, the antibody has reduced glycosylation, no glycosylation, or is hypofucosylated.

In some aspects, the present disclosure provides a pharmaceutical composition comprising an antibody or antigen binding fragment and a pharmaceutically acceptable excipient. In some embodiments, the pharmaceutically acceptable carrier contains histidine or a sugar. In some embodiments, the sugar is sucrose.

In some aspects, the present disclosure provides a composition comprising a plurality of antibodies or antigen binding fragments, wherein least 0.05%, 0.1%, 0.5%, 1%, 2%, 3%, 5%, or more of the antibodies in the composition have an alpha 2,3-linked sialic acid residue.

In some aspects, the present disclosure provides a composition comprising a plurality of antibodies or antigen binding fragments, wherein none of the antibodies comprise a bisecting Glc-NAc.

In embodiments, the pharmaceutical composition is prepared as a lyophilisate.

In some aspects, the present disclosure provides a method of neutralizing a BK virus infection comprising administering an effective amount of an antibody or composition comprising an antibody to a subject in need thereof. In some embodiments, the subject in need is diagnosed with BK virus infection or BK viremia.

In some embodiments, the present disclosure provides a method of treating or reducing the likelihood of a BK virus or JC virus associated disorder, comprising administering an effective amount of the antibody or the composition comprising an antibody to a subject in need thereof, and wherein the disorder is: transplant rejection, graft-versus-host disease (GvHD), nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, immune reconstitution inflammatory syndrome (IRIS).

In some embodiments, the antibody is administered via injection or infusion. In some embodiments, the antibody or composition is reconstituted prior to injection or infusion.

These and other aspects and embodiments will be described in greater detail herein. The description of some exemplary embodiments of the disclosure are provided for illustration purposes only and not meant to be limiting. Additional compositions and methods are also embraced by this disclosure.

In some embodiments, the therapeutic agent is an immunosuppressive agent. In some embodiments, the immunosuppressive agent is a monophosphate dehydrogenase inhibitor, a purine synthesis inhibitor, a calcineurin inhibitor, or an mTOR inhibitor. In some embodiments, the immunosuppressive agent is mycophenolate mofetil (MMF), mycophenolate sodium, azathioprine, tacrolimus, sirolimus, or cyclosporine.

In some embodiments, the therapeutic agent is an additional anti-VP1 antibody.

In some aspects, the present disclosure provides a nucleic acid encoding an antibody or antigen binding fragment described in the above paragraphs.

In some aspects, the present disclosure provides a vector comprising the nucleic acid.

In some aspects the present disclosure provides an isolated host cell comprising the vector.

In some aspects, the present disclosure provides a process for producing an antibody or antigen binding fragment comprising cultivating the host cell and recovering the antibody from the culture.

In some aspects, the present disclosure provides a diagnostic reagent comprising an antibody or antigen binding fragment, which is labeled. In some embodiments, the label is selected from the group consisting of a radiolabel, a fluorophore, a chromophore, an imaging agent, and a metal ion.

In some aspects, the present disclosure provides method of reducing the risk of transplant rejection in a transplant recipient receiving a donor organ, comprising (i) determining serotype of BK virus present in the donor organ, (ii) selecting an antibody or composition comprising an antibody that neutralizes the serotype of BK virus present in the donor organ, and (iii) administering the selected antibody to the transplant recipient via injection or infusion.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, Drawings, Examples, and Claims.

BRIEF DESCRIPTION OF THE DRAWINGS

FIG. 9: Neutralization and flow cytometric analysis of selected supernatants containing antibodies. Upper portion of table shows neutralization of four pseudoviruses expressing VP1 from each serotype by supernatants containing monoclonal antibodies, and flow cytometry analysis of cells transfected with one of four nucleic acids encoding a different BK virus VP1 serotype, by staining transfected cells with the same supernatants. Neutralization numbers represent percent of infected cells when supernatants were used in neutralization assay. Flow cytometry numbers represent MFI of cells stained using the supernatants transfected with BK I-IV VP I or mock transfected (median). In the lower portion of the table, supernatants are grouped by the similarities of their binding profiles. These results are performed with undiluted culture supernatants with unknown protein concentrations.

DETAILED DESCRIPTION OF CERTAIN EMBODIMENTS

Definitions

Figure 1:
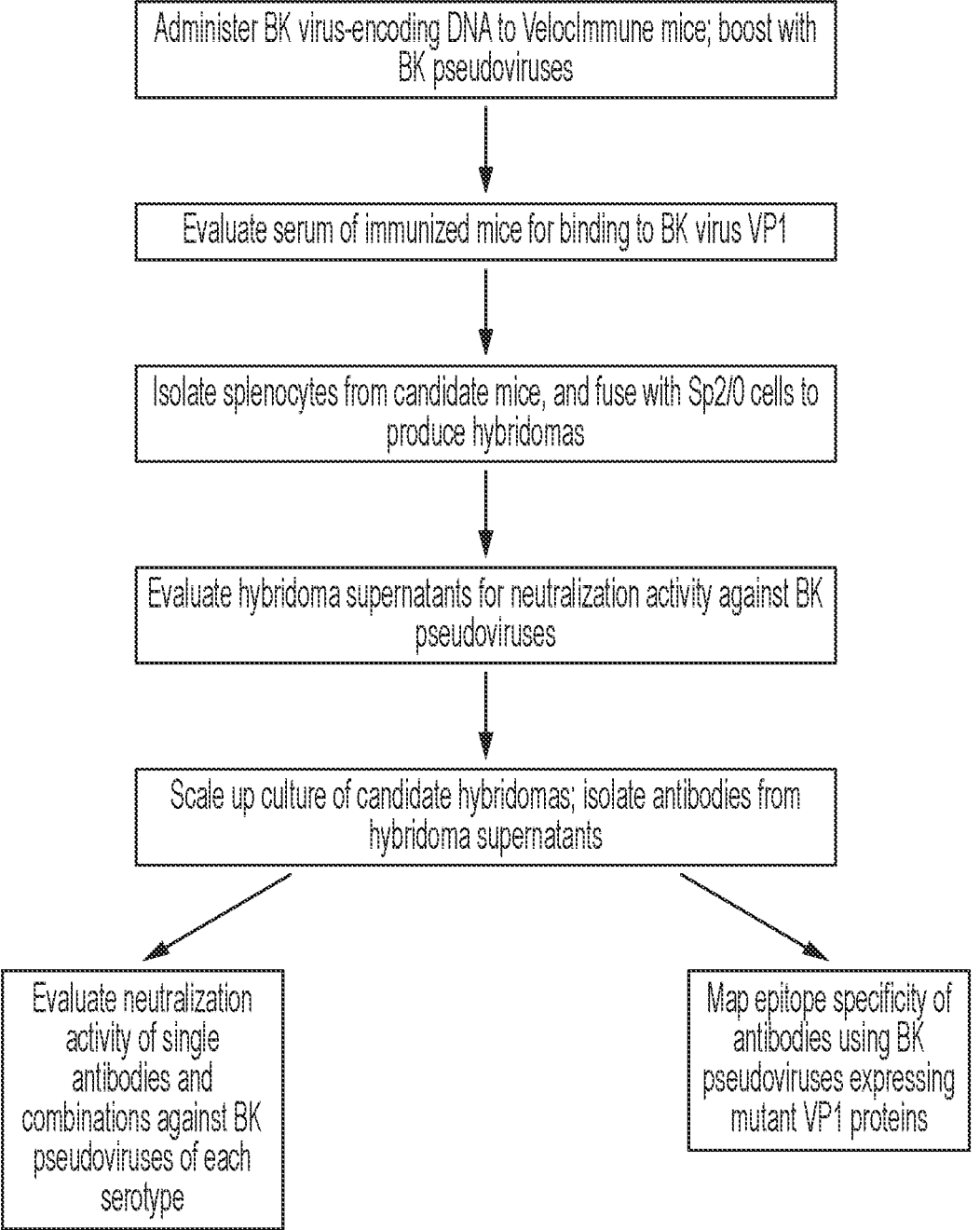
FIG. 1: Generation, isolation, and evaluation of monoclonal antibodies to BK virus. DNA encoding BK virus VP1, VP2, and VP3 was administered to mice as a primary immunization, then pseudoviruses containing BK virus VP1, VP2, and VP3 were administered to mice as a booster dose. Splenocytes were fused with Sp2/0 cells to form hybridomas, which were cultured to produce antibodies, and monoclonal antibodies were isolated from hybridoma supernatants. Isolated monoclonal antibodies were evaluated, either independently or in combination with other antibodies, for neutralization activity against pseudoviruses containing VP1 proteins of different serotypes.

As used herein, "antibody" refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies include, but are not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

As used herein, "complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well-known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262: 732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

As used herein, "antigen binding fragment" refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Nat. Acad. Sci. 85:5879-5883, 1988). Such single chain antibodies are also intended to be encompassed within the term "antigen-binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

As used herein, "monoclonal antibody" refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

As used herein, a "human antibody" includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

As used herein, "polypeptide" and "protein" refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

As used herein, "BK virus" and "BKV" refer to a member of the family Polyomaviridae, genus Orthopolyomavirus. Polyomaviruses are icosahedral, non-enveloped, double-stranded DNA viruses with a genome of approximately 5,000 base pairs. They measure approximately 40-45 nM in diameter (Bennett et al., Microbes and Infection. 2012:14 (9):672-683).

As used herein, "JC virus" and "JCV" refer to a member of the family Polyomaviridae, genus Orthopolyomavirus. JC virus is related to BK virus, and is also an icosahedral, non-enveloped, double-stranded DNA virus with a genome of approximately 5,000 base pairs. They measure approximately 40-45 nM in diameter (Johne et al., Arch. Virol. 2011; 156(9):1627-1634).

As used herein, "serotype" refers to a subset of a virus defined by the immune response generated by viruses of that subset. When exposed to a virus of a given serotype, a host, such as a mouse or human, generates antibodies that bind to that virus and to other viruses of the same serotype, but not necessarily to other viruses of different serotypes. The serotype of a virus can be determined by contacting the virus with antibodies generated in response to viruses of each known serotype, and determining which antibodies bind to the virus. If antibodies generated in response to serotype 1 bind to the virus in question, the virus is said to be of serotype 1.

Sequence identity can be determined using the methods described herein, for example, aligning two sequences using BLAST, ALIGN, CLUSTAL, CLUSTALW, or another alignment software or algorithm known in the art. Percent (%) sequence identity, with respect to a reference amino acid sequence, refers to the percentage of amino acids in a candidate sequence that are identical to the amino acids in the reference amino acid sequence, after aligning the sequences and introducing gaps, if necessary, to achieve maximum percent sequence identity. The percent sequence identity between a candidate amino acid sequence (A) and amino acid sequence (B) can be calculated as follows: % sequence identity=100 times X/Y, where X is the number of amino acids in A that are identical to the amino acids in the corresponding positions in B, after alignment, and Y is the total number of amino acids in B. In some embodiments, the amino acid sequence comprises at least 90%, at least 91%, at least 92%, at least 93%, at least 94%, at least 95%, at least 96%, at least 97%, at least 98%, or at least 99% sequence identity to a reference sequence.

As used herein, "neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein "subject" refers to human and non-human animals. Non-human animals include all vertebrates, e.g., mammals and non-mammals, such as non-human primates, sheep, dog, cow, chickens, amphibians, and reptiles.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved.

A "prophylactically effective dosage," and a "therapeutically effective dosage," of the molecules of the present disclosure can prevent the onset of, or result in a decrease in severity of, respectively, disease symptoms, including symptoms associated polyomavirus infection.

Antibodies

The present disclosure provides, in some aspects, isolated antibodies and antibody fragments (e.g., antigen-binding fragments) that bind to VP1 of a polyomavirus, such as BK virus. An antibody is a soluble form of a B cell receptor, expressed by B cells, that is capable of binding to an epitope or antigen. An antibody is capable of binding to an epitope if the antibody non-transiently associates with the epitope or antigen in a noncovalent manner, such as through hydrogen bonding. The exact strength of binding will depend on the structure of the antibody and the epitope or antigen in question. Methods of determining whether an antibody binds to an epitope or antigen are well known in the art.

In some embodiments, an antibody or antigen-binding fragment thereof comprises one or more heavy chains and one or more light chains. In some embodiments, an antibody or antigen-binding fragment comprises two heavy chains and two light chains, wherein a first light chain is linked to a first heavy chain by a disulfide bond, a second light chain is linked to a second heavy chain by a disulfide bond, and the first and second heavy chains are linked by a disulfide bond. A heavy chain, in some embodiments, comprises a variable domain (VH), comprising three complementarity determining regions (CDRs), and one or more constant domains (CH). A light chain, in some embodiments, comprises a variable domain comprising CDRs (VL) and one or more constant domains.

In some embodiments, the structure of an antibody, and consequently whether the antibody is capable of binding to an epitope or antigen, is determined in part by the amino acid sequences of the CDRs, VH domain, and/or VL domain. The nucleic acid sequence encoding an antibody, and thus the amino acid sequence of the antibody, is determined during B cell development, such that any two B cells often express antibodies with different amino acid sequences. B cells develop from hematopoietic stem cells in the bone marrow, during which the genome of the cell undergoes recombination that results in the formation of the nucleic acid sequence encoding the VH domain and the nucleic acid sequence encoding the VL domain. Prior to the recombination that forms the nucleic acid encoding the VH domain, the genome of a hematopoietic stem cell comprises multiple heavy chain variable (V) segments, multiple heavy chain diversity (D) segments, and multiple heavy chain joining (J) segments. In a developing B cell, the chromosome is recombined such that the DNA between one D and one J segment is excised from the chromosome, forming a DJ complex comprising the D segment and J segment. Next, the chromosome is recombined such that the DNA between one V segment and the DJ complex is excised from the chromosome, forming a VDJ complex comprising the V segment and the DJ complex. The recombination that forms the nucleic acid encoding the VL domain occurs in a similar manner, except that the nucleic acid encoding the VL domain comprises a V segment and a J segment, but not a D segment, and thus formation of the nucleic acid encoding VL domain requires only one recombination step that forms a VJ complex from a V segment and a J segment. Prior to this recombination, the genome of a hematopoietic stem cell comprises multiple light chain variable (V) segments and multiple joining (J) segments. Following the formation of the heavy chain VDJ complex, the chromosome comprising the light chain V and J segments is recombined to excise DNA between one V segment and J segment, forming a VJ complex.

In some embodiments, the present disclosure provides an antibody or antigen-binding fragment thereof comprising a heavy chain variable region (VH) having three complementarity determining regions (CDRs) of HCDR1, HCDR2, and HCDR3, and a light chain variable region (VL) having three CDRs of LCDR1, LCDR2, and LCDR3. Representative amino acid sequences of the CDRs of antibodies provided herein are shown in Table 1, nucleotide sequences are shown in Table 5. In some embodiments, (a) HCDR1 comprises at least 90% sequence identity to any one of SEQ ID NO: 1, 9, 17, 25, 33, 41, 49, 57, 65, 73, 81, 89, 97, 105, 113, 121, 129, 137, 145, 153, 161, 169, or 177;

(b) HCDR2 comprises at least 90% sequence identity to any one of SEQ ID NO: 2, 10, 18, 26, 34, 42, 50, 58, 66, 74, 82, 90, 98, 106, 114, 122, 130, 138, 146, 154, 162, 170, or 178;

(c) HCDR3 comprises at least 90% sequence identity to any one of SEQ ID NO: 3, 11, 19, 27, 35, 43, 51, 59, 67, 75, 83, 91, 99, 107, 115, 123, 131, 139, 147, 155, 163, 171, or 179;

(d) LCDR1 comprises at least 90% sequence identity to any one of SEQ ID NO: 4, 12, 20, 28, 36, 44, 52, 60, 68, 76, 84, 92, 100, 108, 116, 124, 132, 140, 148, 156, 164, 172, or 180;

(e) LCDR2 comprises at least 90% sequence identity to any one of SEQ ID NO: 5, 13, 21, 29, 37, 45, 53, 61, 69, 77, 85, 93, 101, 109, 117, 125, 133, 141, 149, 157, 165, 173, or 181; and (f) LCDR3 comprises at least 90% sequence identity to any one of SEQ ID NO: 6, 14, 22, 30, 38, 46, 54, 62, 70, 78, 86, 94, 102, 110, 118, 126, 134, 142, 150, 158, 166, 174, or 182.

In some embodiments, HCDR1 comprises SEQ ID NO: 1, HCDR2 comprises SEQ ID NO: 2, HCDR3 comprises SEQ ID NO: 3, LCDR1 comprises SEQ ID NO: 4, LCDR2 comprises SEQ ID NO: 5, and LCDR3 comprises SEQ ID NO: 6, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 9, HCDR2 comprises SEQ ID NO: 10, HCDR3 comprises SEQ ID NO: 11, LCDR1 comprises SEQ ID NO: 12, LCDR2 comprises SEQ ID NO: 13, and LCDR3 comprises SEQ ID NO: 14, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 17, HCDR2 comprises SEQ ID NO: 18, HCDR3 comprises SEQ ID NO: 19, LCDR1 comprises SEQ ID NO: 20, LCDR2 comprises SEQ ID NO: 21, and LCDR3 comprises SEQ ID NO: 22, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 25, HCDR2 comprises SEQ ID NO: 26, HCDR3 comprises SEQ ID NO: 27, LCDR1 comprises SEQ ID NO: 28, LCDR2 comprises SEQ ID NO: 29, and LCDR3 comprises SEQ ID NO: 30, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 33, HCDR2 comprises SEQ ID NO: 34, HCDR3 comprises SEQ ID NO: 35, LCDR1 comprises SEQ ID NO: 36, LCDR2 comprises SEQ ID NO: 37, and LCDR3 comprises SEQ ID NO: 38, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 41, HCDR2 comprises SEQ ID NO: 42, HCDR3 comprises SEQ ID NO: 43, LCDR1 comprises SEQ ID NO: 44, LCDR2 comprises SEQ ID NO: 45, and LCDR3 comprises SEQ ID NO: 46, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 49, HCDR2 comprises SEQ ID NO: 50, HCDR3 comprises SEQ ID NO: 51, LCDR1 comprises SEQ ID NO: 52, LCDR2 comprises SEQ ID NO: 53, and LCDR3 comprises SEQ ID NO: 54, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 65, HCDR2 comprises SEQ ID NO: 66, HCDR3 comprises SEQ ID NO: 67, LCDR1 comprises SEQ ID NO: 68, LCDR2 comprises SEQ ID NO: 69, and LCDR3 comprises SEQ ID NO: 70, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 73, HCDR2 comprises SEQ ID NO: 74, HCDR3 comprises SEQ ID NO: 75, LCDR1 comprises SEQ ID NO: 76, LCDR2 comprises SEQ ID NO: 77, and LCDR3 comprises SEQ ID NO: 79, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 81, HCDR2 comprises SEQ ID NO: 82, HCDR3 comprises SEQ ID NO: 83, LCDR1 comprises SEQ ID NO: 84, LCDR2 comprises SEQ ID NO: 85, and LCDR3 comprises SEQ ID NO: 86, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 89, HCDR2 comprises SEQ ID NO: 90, HCDR3 comprises SEQ ID NO: 91, LCDR1 comprises SEQ ID NO: 92, LCDR2 comprises SEQ ID NO: 93, and LCDR3 comprises SEQ ID NO: 94, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 97, HCDR2 comprises SEQ ID NO: 98, HCDR3 comprises SEQ ID NO: 99, LCDR1 comprises SEQ ID NO: 100, LCDR2 comprises SEQ ID NO: 101, and LCDR3 comprises SEQ ID NO: 102, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 105, HCDR2 comprises SEQ ID NO: 106, HCDR3 comprises SEQ ID NO: 107, LCDR1 comprises SEQ ID NO: 108, LCDR2 comprises SEQ ID NO: 109, and LCDR3 comprises SEQ ID NO: 110, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 113, HCDR2 comprises SEQ ID NO: 114, HCDR3 comprises SEQ ID NO: 115, LCDR1 comprises SEQ ID NO: 116, LCDR2 comprises SEQ ID NO: 117, and LCDR3 comprises SEQ ID NO: 118, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 121, HCDR2 comprises SEQ ID NO: 122, HCDR3 comprises SEQ ID NO: 123, LCDR1 comprises SEQ ID NO: 124, LCDR2 comprises SEQ ID NO: 125, and LCDR3 comprises SEQ ID NO: 126, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 129, HCDR2 comprises SEQ ID NO: 130, HCDR3 comprises SEQ ID NO: 131, LCDR1 comprises SEQ ID NO: 132, LCDR2 comprises SEQ ID NO: 133, and LCDR3 comprises SEQ ID NO: 134, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 137, HCDR2 comprises SEQ ID NO: 138, HCDR3 comprises SEQ ID NO: 139, LCDR1 comprises SEQ ID NO: 140, LCDR2 comprises SEQ ID NO: 141, and LCDR3 comprises SEQ ID NO: 142, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 145, HCDR2 comprises SEQ ID NO: 146, HCDR3 comprises SEQ ID NO: 147, LCDR1 comprises SEQ ID NO: 148, LCDR2 comprises SEQ ID NO: 149, and LCDR3 comprises SEQ ID NO: 150, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 153, HCDR2 comprises SEQ ID NO: 154, HCDR3 comprises SEQ ID NO: 155, LCDR1 comprises SEQ ID NO: 156, LCDR2 comprises SEQ ID NO: 157, and LCDR3 comprises SEQ ID NO: 158, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 161, HCDR2 comprises SEQ ID NO: 162, HCDR3 comprises SEQ ID NO: 163, LCDR1 comprises SEQ ID NO: 164, LCDR2 comprises SEQ ID NO: 165, and LCDR3 comprises SEQ ID NO: 166, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 169, HCDR2 comprises SEQ ID NO: 170, HCDR3 comprises SEQ ID NO: 171, LCDR1 comprises SEQ ID NO: 172, LCDR2 comprises SEQ ID NO: 173, and LCDR3 comprises SEQ ID NO: 174, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, HCDR1 comprises SEQ ID NO: 177, HCDR2 comprises SEQ ID NO: 178, HCDR3 comprises SEQ ID NO: 179, LCDR1 comprises SEQ ID NO: 180, LCDR2 comprises SEQ ID NO: 181, and LCDR3 comprises SEQ ID NO: 182, or an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

The present disclosure provides, in some aspects, antibodies or antigen-binding fragments thereof, comprising a heavy chain variable region (VH) and a light chain variable region (VL). In some embodiments, VH comprises at least 90% sequence identity to any one of SEQ ID NO: 7, 15, 23, 31, 39, 47, 55, 63, 71, 79, 87, 95, 103, 111, 119, 127, 135, 143, 151, 159, 167, 175, or 183; and VL comprises at least 90% sequence identity to any one of SEQ ID NO: 8, 16, 24, 32, 40, 48, 56, 64, 72, 80, 88, 96, 104, 112, 120, 128, 136, 144, 152, 160, 168, 176, or 184. In some embodiments, VH comprises SEQ ID NO: 7, and VL comprises SEQ ID NO: 8.

In some embodiments, VH comprises SEQ ID NO: 15, and VL comprises SEQ ID NO: 16. In some embodiments, VH comprises SEQ ID NO: 31, and VL comprises SEQ ID NO: 32. In some embodiments, VH comprises SEQ ID NO: 39, and VL comprises SEQ ID NO: 40. In some embodiments, VH comprises SEQ ID NO: 47, and VL comprises SEQ ID NO: 48. In some embodiments, VH comprises SEQ ID NO: 55, and VL comprises SEQ ID NO: 56. In some embodiments, VH comprises SEQ ID NO: 63, and VL comprises SEQ ID NO: 64. In some embodiments, VH comprises SEQ ID NO: 71, and VL comprises SEQ ID NO: 72. In some embodiments, VH comprises SEQ ID NO: 79, and VL comprises SEQ ID NO: 80. In some embodiments, VH comprises SEQ ID NO: 87, and VL comprises SEQ ID NO: 88. In some embodiments, VH comprises SEQ ID NO: 95, and VL comprises SEQ ID NO: 96. In some embodiments, VH comprises SEQ ID NO: 103, and VL comprises SEQ ID NO: 104. In some embodiments, VH comprises SEQ ID NO: 111, and VL comprises SEQ ID NO: 112. In some embodiments, VH comprises SEQ ID NO: 119, and VL comprises SEQ ID NO: 120. In some embodiments, VH comprises SEQ ID NO: 127, and VL comprises SEQ ID NO: 128. In some embodiments, VH comprises SEQ ID NO:

135, and VL comprises SEQ ID NO: 136. In some embodiments, VH comprises SEQ ID NO: 143, and VL comprises SEQ ID NO: 144. In some embodiments, VH comprises SEQ ID NO: 151, and VL comprises SEQ ID NO: 152. In some embodiments, VH comprises SEQ ID NO: 159, and VL comprises SEQ ID NO: 160. In some embodiments, VH comprises SEQ ID NO: 167, and VL comprises SEQ ID NO: 168. In some embodiments, VH comprises SEQ ID NO: 175, and VL comprises SEQ ID NO: 176. In some embodiments, VH comprises SEQ ID NO: 183, and VL comprises SEQ ID NO: 184. In other embodiments, the VH or VL may have an amino acid sequence having at least 80%, at least 85%, at least 90%, at least 91%, at least 92%, at least 93%, at least 94%, at least 95%, at least 96%, at least 97%, at least 98%, or at least 99% sequence identity to any of the aforementioned sequences.

In some embodiments, an antibody or antigen-binding fragment thereof comprises heavy chain framework regions and/or light chain framework regions. Framework regions are amino acid sequences present in VH or VL domains that are distinct from the CDRs and support the formation of the VH or VL domains. In some embodiments, the antibody or antigen-binding fragment comprises heavy chain framework regions HFR1, HFR2, HFR3, and HFR4, and light chain framework regions LFR1, LFR2, LFR3, and LFR4. Representative amino acid sequences of framework regions of antibodies provided herein are shown in Table 2. In some embodiments, the HFR1 region comprises the amino acid sequence of any one of SEQ ID NOs: 185, 193, 197, 205, 213, 226, 234, 241, 250, or 269, the HFR2 region comprises the amino acid sequence of any one of SEQ ID NOs: 186, 194, 198, 206, 214, 223, 227, 232, 242, or 253, the HFR3 region comprises the amino acid sequence of any one of SEQ ID NOs: 187, 195, 199, 207, 215, 219, 224, 228, 233, 235, 243, 251, 254, 258, 259, 262, 265, 267, or 270, the HFR4 region comprises the amino acid sequence of any one of SEQ ID NOs: 188, 200, 208, 220, 229, 236, 244, or 271, the LFR1 region comprises the amino acid sequence of any one of SEQ ID NOs: 189, 201, 209, 237, 245, 255, or 260, the LFR2 region comprises the amino acid sequence of any one of SEQ ID NOs: 190, 202, 210, 216, 221, 225, 230, 238, 246, 261, 263, or 272, the LFR3 region comprises SEQ ID NOs: 191, 196, 203, 211, 217, 222, 230, 239, 247, 249, 252, 256, 264, 266, 268, or 273, and the LFR4 region comprises the amino acid sequence of any one of SEQ ID NOs: 192, 204, 212, 218, 240, 248, or 257.

In some embodiments, an antibody or antigen-binding fragment thereof comprises one or more heavy CH domains and/or one or more CL domains. CH and CL domains are members of the immunoglobulin superfamily, each comprising multiple β-strands. In some embodiments, an antibody or antigen-binding fragment thereof comprises three, four, five, six, seven, or eight CH domains. In some embodiments, one or more CH domains are selected from the group consisting of IgG, IgG1, IgG2, IgG2a, IgG2b, IgG2c, IgG3, IgG4, IgA, IgA1, IgA2, IgD, IgM, and IgE constant domains. Representative amino acid sequences of the heavy chain CH domains are provided in Table 3. Two antibodies may have identical VH and VL domains, and therefore bind to the same epitope or antigen, but comprise different CH domains, and thus differ in structure. When a B cell first becomes activated after the B cell receptor or antibody on its surface binds to an epitope or antigen, expression of a soluble antibody begins with the step of transcribing a pre-mRNA, in which nucleic acid sequence encoding the IgM CH domain and a nucleic acid sequence encoding the IgD CH domain are located downstream from the nucleic acid sequence encoding the VH domain. During pre-mRNA processing, the pre-mRNA is spliced such that the nucleic acid sequence encoding the IgM CH domain, or the nucleic acid sequence encoding the IgD CH domain, is adjacent to the nucleic acid sequence encoding the VH domain, such that translation of the mRNA produces an IgM or IgD heavy chain. The isotype of an antibody refers to the CH domain chain. The isotype of an antibody refers to the CH domain of the antibody (e.g., an antibody with an IgG CH domain has an IgG isotype). A B cell genome comprising a nucleic acid sequence encoding an antibody may undergo recombination, that results in the excision of a nucleic acid sequence encoding one or more CH domains, such that a nucleic acid sequence encoding a different CH domain becomes the first CH domain-encoding nucleic acid that downstream of the VDJ-encoding nucleic acid. The antibody produced by a B cell with a genome that has been recombined in this manner is then of a different isotype than IgM or IgD, such as IgG, IgG1, IgG2, IgG2a, IgG2b, IgG2c, IgG3, IgG4, IgA, IgA1, IgA2, or IgE.

In some embodiments, one or more CL domains are selected from the group consisting of Ig kappa and Ig lambda constant domains. Representative amino acid sequences of the heavy chain CH domains are provided in Table 4. In some animals, including mice and humans, the genome comprises two loci, referred to as the Ig kappa locus and the Ig lambda locus, that are capable of recombination to form a nucleic acid sequence encoding a VL domain. In developing B cells, recombination occurs at the Ig kappa locus or the Ig lambda locus, to place a light chain V segment adjacent to a light chain J segment, and if recombination is successful in generating a VL domain, then the light chain that is expressed comprises the Ig kappa or Ig lambda CL domain, respectively.

In some embodiments, one or more CH domains comprise an amino acid sequence with at least 90% sequence identity to one of SEQ ID NOs: 274-290. In some embodiments, an antibody or antigen-binding fragment thereof comprises one or two CL domains. In some embodiments, one or more CL domains comprise an amino acid sequence with at least 90% sequence identity to one of SEQ ID NOs: 291-301.

The present disclosure provides, in some aspects, an isolated antibody or antigen-binding fragment thereof, wherein, when bound to BK virus VP1 protein, the antibody binds to at least one of the following residues: S80, D82, R83, or R170 of SEQ ID NO: 529, and wherein the antibody blocks binding of BK virus VP1 to sialic acid. An example sequence of BK virus VP1 protein is given by Accession No. P03088, which is reproduced as SEQ ID NO: 529. Whether an antibody binds to a given residue of a protein may be determined by many methods of epitope mapping known in the art, such as X-ray co-crystallography or mutagenesis mapping (see, e.g., King et al. Methods Mol Biol. 2018. 1785:13-27 and Davidson et al. Immunology. 2014. 143(1): 13-20). X-ray co-crystallography is the process of crystallizing an antibody that is bound to an antigen and using X-ray analysis to visualize the interaction between the antibody and antigen. The location at which an antibody binds to the antigen can then be observed from this visualization. Mutagenesis mapping refers to the process of generating modified forms of a protein, such as VP1, and determining how well an antibody binds to the modified forms of the protein relative to the unmodified protein. For example, if an antibody binds to a protein with the amino acid sequence set forth in SEQ ID NO: 529, but does not bind to a protein with the same amino acid sequence in which the seine at position 80 (S80) is substituted for an alanine, then the antibody is said to bind to residue S80.

The present disclosure provides, in some aspects, an isolated antibody or antigen-binding fragment thereof, wherein (a) the antibody is capable of inhibiting infection by a virus comprising VP1 of BK virus serotype 1, a virus comprising VP1 of BK virus serotype 2, a virus comprising VP1 of BK virus serotype 3, and a virus comprising VP1 of BK virus serotype 4, wherein an antibody capable of inhibiting infection by a virus is an antibody that inhibits infection of a target cell by a virus, as determined by a method comprising the steps of:

(i) contacting the virus with the antibody or a control protein;

(ii) incubating the virus with target cells;

(iii) determining the proportion of the target cells infected by the virus, or the amount of viral RNA or DNA present in the target cells, at the end of step (ii);

wherein determination of a lesser proportion of target cells infected by the virus, or a lesser amount of pseudoviral RNA or DNA present in the target cells, in the presence of the antibody, relative to the amount of target cells infected or amount of viral RNA or DNA in the absence of the antibody, is indicative of inhibition of infection by the virus; and (b) the antibody is capable of binding to an epitope that is present on VP1 of BK virus serotype 1, VP1 of BK virus serotype 2, VP1 of BK virus serotype 3, and VP1 of BK virus serotype 4.

Infection of a cell by BK virus begins with binding of BK virus VP1 to a sialic residue (e.g., $\alpha$2,8-linked sialic acid) on the surface of the cell. Following sialic binding, endocytosis forms an endosome containing the virus particle, after which the VP1-containing capsid uncoats to facilitate viral entry into the cytoplasm. Binding of an antibody to an epitope on the viral VP1 protein can interfere with the function of VP1. For example, if amino acids of the epitope to which the antibody is bound are required for adherence to sialic acid, then steric hindrance by the bound antibody can prevent antibody-bound VP1 from binding to the host cell surface. Alternatively, antibody binding may inhibit the uncoating process, such that endocytosed virus particles are unable to enter the cytoplasm.

Determining whether an antibody inhibits infection by a virus comprising a given VP1 protein, or a VP1 protein of a given serotype, may be achieved by one of multiple methods known in the art, such as a virus or pseudovirus neutralization assay. A pseudovirus is a virus that is capable of infecting a cell, but not replicating or producing new virus particles in that cell, often because it lacks at least one nucleic acid required for the production of new virus particles.

Pseduoviruses may comprise the same viral proteins as a virus of interest, and optionally a reporter protein, such as green fluorescent protein, which allows one of ordinary skill in the art to measure the ability of the pseudovirus to infect target cells. For example, the pseudovirus may be incubated with a population of target cells for a defined period of time. Following that period of time, the number or proportion of cells infected may be measured by one of multiple methods known in the art. For example, if the pseudovirus comprises a reporter protein, such as green fluorescent protein, the number of cells in which GFP is present may be measured by flow cytometry, and used to calculate the proportion of cells infected. A similar approach may be used to measure the infectivity of the virus of interest, provided the virus comprises a reporter protein. Alternatively, after the virus is incubated with target cells and residual, non-infecting virus particles are removed from the surfaces of target cells, the amount of viral DNA or viral RNA present in the target cells may be quantified by PCR or RT-qPCR.

Determining whether an antibody of interest or antigen-binding fragment inhibits infection by a virus comprising a given protein, such as a VP1 protein of a given serotype, may be accomplished by similar approaches to those described in the preceding paragraph, with the addition of a first step, in which the virus or pseudovirus is contacted with the antibody or a control protein before the step of incubating the virus or pseudovirus with target cells. A control protein refers to a protein that is not known to bind to the virus or pseudovirus. Non-limiting examples of control proteins include bovine serum albumin and antibodies of the same isotype as the antibody of interest that binds to an epitope or antigen that is not present on the virus or pseudovirus.

To determine whether the antibody inhibits infection, the proportion of target cells infected when the virus or pseudovirus was contacted with the antibody is compared to the proportion of target cells infected when the virus or pseudovirus was contacted with the control protein. Alternatively, the total amount of viral RNA or DNA present in the target cells following incubation with the virus or pseudovirus may be measured in both cases. If the proportion of cells infected, or total amount of viral RNA or DNA, is lower when the virus or pseudovirus is contacted with the antibody, compared to the control protein, then the antibody is said to inhibit infection by the virus or pseudovirus.

The present disclosure provides, in some aspects, an isolated antibody or antigen-binding fragment thereof that competes for binding to BK virus VP1 protein with an antibody produced by a hybridoma. Methods for generating hybridomas, and generating monoclonal antibodies using hybridoma technology, are known in the art (Antibody Methods and Protocols, Methods in Molecular Biology vol. 901, 2012, Chapter 7: 117). Briefly, B cells from an animal, such as a mouse or human, are mixed with immortalized myeloma cells, and exposed to electricity so that a B cell may fuse with a myeloma cell, producing a hybridoma, an immortal cell capable of producing the antibody encoded by the B cell. Individual hybridoma clones may be isolated, proliferated, and preserved. Culturing a clonal lineage derived from a single hybridoma cell results in the production of a monoclonal antibody, where each antibody in the culture comprises a substantially identical amino acid sequence.

In some embodiments, the antibody or antigen-binding fragment thereof has a dissociation constant ($K_D$) from BK virus VP1 protein selected from the group consisting of at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M. The dissociation constant $K_D$ of an antibody from an epitope or antigen refers to the rate is a measure of the affinity of the antibody for the epitope or antigen, with a lower $K_D$ representing a higher affinity for the epitope or antigen. In reference to an antibody and a given epitope or antigen, $K_D$ is defined as the concentration of an antibody at which half of the antibody molecules in a solution are associated with the epitope or antigen. Methods of measuring the $K_D$ of an antibody with respect to an epitope or antigen are well known in the art (see, e.g., Pichler et al. *J Immunol. Methods.* 1997; 201(2): 189-206).

In some embodiments, the antibody is a monoclonal antibody or antigen-binding fragment thereof. The term "monoclonal antibody" refers to proteins or polypeptides derived from the same genetic source, and thus having substantially identical amino acid sequences.

In some embodiments, the antibody is a chimeric antibody or antigen-binding fragment thereof. A chimeric antibody is an antibody comprising amino acid sequences from different genetic sources. In some embodiments, the chimeric antibody comprises amino acid sequences from a mouse and amino acid sequences from a human. In some embodiments a chimeric antibody comprises a variable domain derived from a mouse and constant domains derived from a human.

In some embodiments, the antibody is a humanized antibody or antigen-binding fragment thereof. A humanized antibody is an antibody comprising constant domains and framework regions derived from a human. In some embodiments, a humanized antibody comprises one or more CDRs derived from a non-human animal. Non-limiting examples of non-human animals from which CDRs may be derived include mice, rats, hamsters, rabbits, goats, sheep, and non-human primates.

In some embodiments, the antibody is a human engineered antibody. A human engineered antibody refers to an antibody derived from a non-human source, such as mouse, in which one or more substitutions have been made to improve a desired characteristic of the antibody, such as to increase stability or reduce immunogenicity when the antibody is administered to a subject. In some embodiments, the substitutions are made at low-risk positions (e.g., exposed to solvent but not contributing to antigen binding or antibody structure). Such substitutions mitigate the risk that a subject will generate an immune response against the antibody following its administration, without affecting the ability of the antibody to bind to a desired epitope or antigen (see, e.g., Studnicka et al. Protein Eng. 1994. 7(6):805-814).

In some embodiments, the antibody is a single chain antibody or antigen-binding fragment. A single chain antibody, or single chain variable fragment (scFV) is a protein or polypeptide comprising a VH domain and a VL domain joined together, such as by a synthetic linker, to form a single protein or polypeptide (see, e.g., Bird et al., Science. 242: 423-426, 1988; and Huston et al., *Proc. Natl. Acad. Sci.* 85:5879-5883, 1988).

In some embodiments, the antibody is an antibody fragment or antigen-binding fragment. An antibody fragment is protein or polypeptide derived from an antibody. An antigen-binding fragment is a protein or polypeptide derived from an antibody that is capable of binding to the same epitope or antigen as the antibody from which it was derived.

In some embodiments, the antibody has reduced glycosylation, no glycosylation, or is hypofucosylated. Glycosylation refers to the covalent attachment of sugar, monosaccharide, disaccharide, oligosaccharide, polysaccharide, or glycan moieties to a molecule, such as a polypeptide or protein. These sugar or glycan moieties are generally attached to an antibody in a post-translational matter, prior to secretion by a B cell. An antibody with reduced glycosylation has fewer of these attached sugar or glycan moieties than the number that are typically attached to an antibody with a substantially identical amino acid sequence, such as when the antibody is produced by a B cell in vitro or in vivo in a mouse or human. An antibody with no glycosylation has no attached sugar or glycan moieties. An antibody that is hypofucosylated has fewer fucosyl residues than the number that are typically attached to an antibody with a substantially identical amino acid sequence, such as when the antibody is produced by a B cell in vitro or in vivo in a mouse or human.

Compositions Comprising Antibodies and Uses Thereof

The present disclosure provides, in some aspects, compositions comprising two or more of the antibodies and/or antigen-binding fragments described herein. In some embodiments, a second antibody comprises at least one CDR sequence which is distinct from at least one CDR sequence of a first CDR sequence. The structure of an antibody, and whether the antibody is capable of binding to a given epitope or antigen is determined in part by the combination of six CDRs (HCDR1, HCDR2, HCDR3, LCDR1, LCDR2, and LCDR3). Thus, two antibodies that differ by at least one CDR are structurally distinct, and may be capable of binding to different epitopes or antigens.

In some embodiments, a second antibody comprises at least one VH sequence which is distinct from at least one VH sequence of a first antibody. In some embodiments, a second antibody comprises at least one VL sequence which is distinct from at least one VL sequence of a first antibody. The structure of an antibody, and whether the antibody is capable of binding to a given epitope or antigen, is determined by the combination of the VH and VL amino acid sequences. Thus, two antibodies that differ by a VH sequence, a VL sequence, or both are structurally distinct, and may be capable of binding to different epitopes or antigens.

The antibodies and/or antigen-binding fragments provided herein may be formulated in a pharmaceutical composition comprising an antibody or antigen-binding fragment, and a pharmaceutically acceptable excipient. A pharmaceutically acceptable excipient can also be incorporated in a formulation and can be any excipient (e.g., carrier) known in the art. Non-limiting examples include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such excipients. In some embodiments, the pharmaceutically acceptable excipient contains histidine or a sugar. In some embodiments, the pharmaceutically acceptable excipient contains sugar. In some embodiments, the pharmaceutically acceptable excipient contains sucrose.

Pharmaceutically acceptable excipients are known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, and silicylate. Each pharmaceutically acceptable excipients used in a pharmaceutical composition of the invention must be "acceptable" in the sense of being compatible with the other ingredients of the formulation and not injurious to the subject. Excipients suitable for a selected dosage form and intended route of administration are well known in the art, and acceptable diluents or carriers for a chosen dosage form and method of administration can be determined using ordinary skill in the art.

In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with DNA or RNA (e.g., for transplantation into a subject), hyaluronidase, nanoparticle mimics and combinations thereof.

Routes of administration of the antibodies or antigen-binding fragments provided herein include, for example, intravenous, intramuscular, intraperitoneal, subcutaneous, or intranasal. Thus, in some embodiments, a composition comprising an antibody or antigen-binding fragment may be formulated for intravenous, intramuscular, intraperitoneal, subcutaneous, or intranasal delivery.

In some embodiments of the pharmaceutical compositions provided herein, at least 0.05%, at least 0.1%, at least 0.1%, at least 0.5%, at least 1%, at least 2%, at least 3%, at least 4%, or at least 5% of the antibodies in the composition have an α2,3-linked sialic acid residue. Antibodies may be glycosylated, in which sugars or glyans, such as sialic acid, may be covalently attached to amino acid residues of the antibody. Glycosylation of antibodies, including attachment of sialic acid residues such as by α2,3-linkage, may affect the function of the antibodies (see, e.g., Thomann et al. *Bioanalysis*. 2019. 11(15):1437-1449).

In some embodiments of the pharmaceutical compositions provided herein, none of the antibodies comprise a bisecting N-acetylglucosamine (GlcNAc). A bisecting N-acetylglucosamine is N-glycosylation in which a β1,4-linked GlcNAc is attached to a core 0-mannose residue. Glycosylation of proteins with a bisecting GlcNAc has been shown to affect numerous biological processes, including cell adhesion and tumor development, and the presence of a bisecting GlcNAc may affect the ability of an antibody to bind to an epitope or antigen or neutralize a virus (see, e.g., Thomann et al. *Bioanalysis*. 2019. 11(15):1437-1449).

In some embodiments of the pharmaceutical compositions provided herein, the composition is prepared as a lyophilisate. Lyophilization, or freeze-drying, is the process of removing water from a composition by freezing the composition, then drying the frozen composition at low temperature and pressure to allow ice to sublimate away from the frozen composition. The dried form of the composition that remains after sublimation is the lyophilisate.

Vectors and Cells Comprising Nucleic Acids Encoding Antibodies

The present disclosure provides, in some aspects, nucleic acids encoding an antibody or antigen-binding fragment provided herein. In some embodiments, the nucleic acid comprises a sequence encoding a CDR, VH domain, VL domain, CH domain, CL domain, heavy chain, or light chain provided herein. In some embodiments, the nucleic acid comprises a sequence with at least 90% sequence identity to any one of the CDRs, VH domains, VL domains, CH domains, CL domains, heavy chains, or light chains provided herein. In some embodiments, the nucleic acid sequence is codon-optimized for expression in a cell. A codon-optimized nucleic acid is one that has been modified to encode the same amino acid sequence as an unmodified form of the nucleic acid, but using codons that are preferred in a host cell or organism that is used to produce a protein with the amino acid sequence. The host cell or organism may be, for example, a prokaryotic or eukaryotic cell, such as a yeast cell, Chinese hamster ovary (CHO) cell, a human embryonic kidney 293 (HEK-293) cell, or *E. coli* cell.

In some aspects, the disclosure provides a vector comprising a nucleic acid encoding an antibody provided herein or an antigen-binding fragment thereof. In some embodiments, the vector comprises a nucleic acid sequence encoding a CDR, VH domain, VL domain, CH domain, CL domain, heavy chain, or light chain provided herein. In some embodiments, the vector comprises a nucleic acid sequence with at least 90% sequence identity to any one of the CDRs, VH domains, VL domains, CH domains, CL domains, heavy chains, or light chains provided herein. Various vectors can be used to express nucleic acids encoding the antibodies or fragments thereof provided herein. A vector may be a DNA or RNA vector, such as a plasmid, bacterial artificial chromosome, human artificial chromosome, or mRNA, comprising the nucleic acid sequence encoding an antibody or fragment thereof. In some embodiments, the vector is a viral vector. Non-limiting examples of viral vectors include retroviral vectors, lentiviral vectors, adeno-associated viral vectors, adenoviral vectors, baculoviral vectors, foamy virus vectors, SV40 viral vectors, MPSV vectors, Epstein-Barr viral vectors, and bacteriophage vectors. Methods of cloning nucleic acid sequences encoding antibodies or fragments thereof into expression vectors are well known in the art, as are methods of producing antibodies or fragments thereof using said vectors (see, e.g., Spidel et al. *J Immunol Methods*. 2016. 439:50-58).

Vectors for the expression of antibodies or fragments thereof provided herein may also comprise one or more regulatory elements, such as a promoter operably linked to the nucleic acid encoding the antibody or fragment. The promoter may be a constitutive promoter, which continuously drives expression of the nucleic acid sequence to which it is linked. The promoter may be an inducible promoter, which regulates expression of the operably linked nucleic acid sequence such that the sequence is expressed only under certain conditions, such as the presence, absence, or concentration of a specific nucleotide, protein, peptide, or other molecule in the cell.

In some aspects, the disclosure provides an isolated host cell comprising a vector encoding an antibody provided herein or antigen-binding fragment thereof. The host cell may be a prokaryotic cell, such as *E. coli*. The host cell may be a eukaryotic cell, such as a yeast (e.g., *Saccharomyces cerevisiae*) cell, Chinese hamster ovary (CHO) cell, human embryonic kidney 293 (e.g., HEK-293, HEK-293A, HEK-293T) cell, hybridoma cell, or insect cell. The choice of host cell will depend on multiple factors, including the particular vector to be used, desired characteristics of the antibody, and aspects of the protein expression process. For example, human cells are more permissive to certain viral vectors, such as lentiviral and adeno-associated viral vectors, while insect cells are more permissive to baculoviral vectors. Additionally, fewer post-translational modifications occur in proteins expressed by prokaryotic cells, in contrast to eukaryotic cells, so expression of the same nucleic acid sequence in from an *E. coli* cell may result in the production of an antibody with less glycosylation than the same antibody expressed from a human or yeast cell.

In one aspect, the present disclosure provides a process of producing an antibody or antigen-binding fragment thereof provided herein, using a host cell comprising a vector or nucleic acid sequence encoding the antibody or antigen-binding fragment. Methods of producing an antibody using a host cell are well known in the art (see, e.g., Frenzel et al.

*Front Immunol.* 2013. 4:217). Briefly, the host cell is cultivated in a medium that allows for a.) suitable for survival and/or proliferation of the host cell, and b.) expression of the nucleic acid sequence encoding the antibody or antigen-binding fragment. For example, if the nucleic acid sequence is operably linked to an inducible promoter, a reagent may be added to the medium to induce the promoter and drive expression of the nucleic acid sequence encoding the antibody or antigen-binding fragment. If nucleic acid or vector comprising the sequence encoding the antibody or antigen-binding fragment also comprises a selectable marker, such as a sequence encoding resistance to an antibiotic or a selective agent, adding the antibiotic or selective agent promotes the survival of cells that are capable of producing the antibody or antigen-binding fragment. As host cells are cultivated, they express the antibody or antigen-binding fragment, which is secreted into the extracellular medium. Following a desired period of cultivation, the medium may be separated from the cells, and the desired protein may be purified from the medium using methods known in the art, such as column-based purification.

Therapeutic and Diagnostic Uses

The present disclosure provides, in some aspects, methods of neutralizing a BK virus infection by administering an antibody or antigen-binding fragment provided herein, and optionally a therapeutic agent, to a subject in need thereof. An effective amount, which may also be referred to as a therapeutically effective amount, refers to the amount (e.g., dose) at which a desired clinical result (e.g., reduction in viral load) is achieved in a subject. An effective amount is based, at least in part, on the target tissue, target cell type, means of administration, physical characteristics of the inhibitor, other components of the composition, and other determinants, such as age, body weight, height, sex and general health of the subject. A subject may be a mammal, such as a human, a non-human primate (e.g., Rhesus monkey, chimpanzee), or a rodent (e.g., a mouse or a rat). In some embodiments, the subject is a human subject.

In some embodiments, the subject is diagnosed with a BK virus infection or BK viremia. BK virus infection refers to the presence of BK virus particles in one or more organs or anatomical locations of the subject, such as the kidney, liver, or blood. BK viremia refers to the presence of BK virus particles in the blood of the subject.

In some aspects, the present disclosure provides a method of reducing the risk of transplant rejection in a transplant recipient receiving a donor organ, comprising (i) determining serotype of BK virus present in the donor organ, (ii) selecting an antibody, antigen-binding fragment thereof, or composition comprising an antibody or antigen-binding fragment thereof that neutralizes the serotype of BK virus present in the donor organ, and (iii) administering the selected antibody to the transplant recipient via injection or infusion. Methods of determining are the serotype of a virus are known in the art (Pastrana et al. *Plos Pathog.* 2012. 8(4):e1002650). Multiple preparations of the virus are prepared, each preparation is contacted with an antibody that binds to viruses of a specific serotype, and it is determined whether each antibody binds to the virus. If an antibody that binds to viruses of a serotype and to the virus in question, the virus is said to belong to the serotype. To determine the serotype of BK virus present in a donor organ, a portion of the donor organ is sampled to isolate BK virus, which may then be prepared for serotyping immediately or replicated in vitro before determining the serotype of the virus present in the donor organ.

In some embodiments, the method further comprises administering a therapeutic agent to the subject. In some embodiments, the therapeutic agent is an immunosuppressive agent. In some embodiments, the immunosuppressive agent is a monophosphate dehydrogenase inhibitor, a purine synthesis inhibitor, a calcineurin inhibitor, or an mTOR inhibitor. In some embodiments, the immunosuppressive agent is mycophenolate mofetil (MMF), mycophenolate sodium, azathioprine, tacrolimus, sirolimus, or cyclosporine. In some embodiments, the therapeutic agent is an additional anti-VP1 antibody.

In some aspects, the present disclosure provides a method of treating or reducing the likelihood of a BK virus or JC virus associated disorder, comprising administering one or more of the antibodies provided herein to a subject. In some embodiments, the disorder is transplant rejection, graft-versus-host disease (GvHD), nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, or immune reconstitution inflammatory syndrome (IRIS). In some embodiments, the method further comprises administering a therapeutic agent. In some embodiments, the therapeutic agent is an immunosuppressive agent. In some embodiments, the immunosuppressive agent is a monophosphate dehydrogenase inhibitor, a purine synthesis inhibitor, a calcineurin inhibitor, or an mTOR inhibitor. In some embodiments, the immunosuppressive agent is mycophenolate mofetil (MMF), mycophenolate sodium, azathioprine, tacrolimus, sirolimus, or cyclosporine. In some embodiments, the therapeutic agent is an additional anti-VP1 antibody.

In some embodiments of the methods provided herein, the antibody is administered via injection or infusion. Administration by injection is a process in which an antibody or antigen-binding fragment is delivered to a subject through an apparatus. Injection may deliver a composition to a muscle (intramuscular), into the peritoneal cavity (intraperitoneal), or under the skin (subcutaneous) Administration by infusion is a process in which an antibody or antigen-binding fragment is delivered to a subject in a controlled manner over a period of time, such as by a needle or catheter. Infusion may deliver a composition directly to the bloodstream (intravenous) or under the skin (subcutaneous).

In some embodiments, the antibody or antigen-binding fragment is reconstituted prior to injection. Reconstitution involves preparing a liquid suitable for administration by injection or infusion by adding a liquid, gel, or other excipient to a powder formulation of the antibody.

In some aspects, the present disclosure provides diagnostic reagents comprising an antibody or antigen-binding fragment thereof, which is labeled. A labeled antibody is an antibody to which a label, such as an atom, ion, or molecule is attached by a covalent or ionic bond. In some embodiments, the label is a radiolabel. A radiolabel is an atom, ion, or molecule that is radioactive, such that its presence may be detected by exposure to a radiation-sensitive material (e.g., radiographic film). In some embodiments, the label is a fluorophore. A fluorophore is a molecule that is capable of being excited by light, and, following excitation by light of a first wavelength, is capable of emitting light of a second wavelength. A chromophore is also a molecule that emits light of a second wavelength after excitation by light of a first wavelength, wherein the light emitted is in the visible spectrum. In some embodiments, the label is an imaging agent. An imaging agent, also referred to as a contrast agent, that emits energy in the form of X-rays, gamma rays, radio waves, or radioactive particles, such that its presence and location in a subject in a subject can be detected. In some embodiments, the label is a metal ion.

TABLE 1

Amino acid sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 1E2 | GFTFSDYY - SEQ ID NO: 1<br>IDSSAGAI - SEQ ID NO: 2<br>ARERRDGHKIFDC - SEQ ID NO: 3<br>QNILYSSNNKNY - SEQ ID NO: 4<br>WSS - SEQ ID NO: 5<br>QQYYSSPYN - SEQ ID NO: 6 | QVQLVESGGDLVKPG<br>GSLRLSCVASGFTFS<br>DYYMNWIRLPPGKGL<br>EWVSYIDSSAGAIYY<br>ADSVRGRFTVSRDDA<br>KNSLFLHMNSLRADD<br>TAVYYCARERRDGHK<br>IFDCWGPGTLVTVSS - SEQ ID NO: 7 | DIVMTQSPDSLAVSL<br>GERATINCKSSQNIL<br>YSSNNKNYLAWYQQK<br>AGQPPKLLIFWSSTR<br>ESGVPDRFSGSGSGT<br>DFTLTINSLQAEDVA<br>VYYCQQYYSSPYNFG<br>RGTTLEIK - SEQ ID NO: 8 |
| 1H10 | GFTFSDYY - SEQ ID NO: 9<br>IDSSAGAI - SEQ ID NO: 10<br>ARERRDGHKIFDC - SEQ ID NO: 11<br>QNILYSSNNKNY - SEQ ID NO: 12<br>WSS - SEQ ID NO: 13<br>QQYYSSPYN - SEQ ID NO: 14 | QVHLVESGGDLVKPG<br>GSLRLSCVASGFTFS<br>DYYMNWIRMPPGKGL<br>EWISYIDSSAGAIYY<br>ADSVKGRFTVSRDDA<br>KNSLFLHMNNLRADD<br>TAVYYCARERRDGHK<br>IFDCWGPGTLVTVSS - SEQ ID NO: 15 | DIVMTQSPDSLAVSL<br>GERATINCKSSQNIL<br>YSSNNKNYLAWYQQK<br>AGQPPKLLIFWSSTR<br>ESGVPDRFSGSGSGT<br>DFTLTISSLQAEDVA<br>VYYCQQYYSSPYNFG<br>RGTTLEIK - SEQ ID NO: 16 |
| 2A10 | GYSFTYYW - SEQ ID NO: 17<br>IYPGDSDT - SEQ ID NO: 18<br>TTHARNWNNVAY - SEQ ID NO: 19<br>QNINTE - SEQ ID NO: 20<br>AAS - SEQ ID NO: 21<br>QQSSSTPWT - SEQ ID NO: 22 | EVQLVQSGAEVKKPG<br>ESLKISCKGSGYSFT<br>YYWIGWVRQMPGKGL<br>EWMGIIYPGDSDTRY<br>SPSFQGQVTISADKS<br>ISTAYLQWSSLKASD<br>TAMYYCTTHARNWNN<br>VAYWGQGTLVTVSS - SEQ ID NO: 23 | DIQMTQSPSSLSASV<br>GDRLTITCRASQNIN<br>TFLNWYQQNPGKAPK<br>VLIYAASSLESGVPS<br>RFSGSGSGTDFTLTI<br>SSLQPEDFATYYCQQ<br>SSSTPWTFGQGTKVE<br>IK - SEQ ID NO: 24 |
| 2B9 | GFTFSGFA - SEQ ID NO: 25<br>ISGSGDIT - SEQ ID NO: 26<br>AKDPYNWNHGVYGMDV - SEQ ID NO: 27<br>QSISSY - SEQ ID NO: 28<br>GAS - SEQ ID NO: 29<br>QQSFNAPLT - SEQ ID NO: 30 | EVQLLESGGGLAQPG<br>KSLRLSCAASGFTFS<br>GFAMSWVRQAPGKGL<br>EWVSGISGSGDITYY<br>ADSVKGRFTISRDNS<br>KSTLYLQMNSLGAED<br>TAVYYCAKDPYNWNH<br>GVYGMDVWGQGTTVT<br>VSS - SEQ ID NO: 31 | DIQMTQSPSSLSASV<br>GDRVTITCRASQSIS<br>SYLNWYQQKPGKAPK<br>FLIYGASSLQSGVPS<br>RFSGSGSGTDETLTI<br>SSLQPEDFAAYYCQQ<br>SFNAPLTFGGGTKVE<br>IK - SEQ ID NO: 32 |
| 2F7 | GFTFSDYY - SEQ ID NO: 33<br>IDSSAGAI - SEQ ID NO: 34<br>ARERRDGHKIFDW - SEQ ID NO: 35<br>QNILYTSNNKNY - SEQ ID NO: 36<br>WSS - SEQ ID NO: 37<br>HQYYSSPYT - SEQ ID NO: 38 | QVQLVESGGGLVKPG<br>GSLRLSCVASGFTFS<br>DYYMNWIRLPPGRGL<br>QWISYIDSSAGAIYY<br>ADSVKGRFTVSRDDA<br>KNSLYLQMNSLRADD<br>TAVYYCARERRDGHK<br>IFDWWGQGTLVTVSS - SEQ ID NO: 39 | DIVMTQSPDSLAVSL<br>GERATINCKSSQNIL<br>YTSNNKNYLGWYQQK<br>AGQPPKLLIYWSSTR<br>NSGVPDRFSGSGSGT<br>DETLTISSLQAEDVA<br>VYYCHQYYSSPYTFG<br>QGTNLEIK - SEQ ID NO: 40 |
| 2F11 | GYSFTNYW - SEQ ID NO: 41<br>IYPGDSDT - SEQ ID NO: 42<br>ATHARSWNYVAY - SEQ ID NO: 43<br>QSVNNF - SEQ ID NO: 44<br>AAS - SEQ ID NO: 45<br>QQSNTTPWT - SEQ ID NO: 46 | EVQLVQSGAEVKKPG<br>ESLKISCKGSGYSFT<br>NYWIGWVRQMPGKGL<br>EWMGIIYPGDSDTRY<br>SPSFQGQVTLSADKS<br>ISTAYLQWNSLKASD<br>TAMYYCATHARSWNY<br>VAYWGQGTLVTVAS - SEQ ID NO: 47 | DIQMTQSPSSLSASV<br>GDRVTITCRASQSVN<br>NFLNWYQQKPGTAPK<br>LLIYAASSLQGGVPS<br>RFSGSGSGTDFTLTI<br>SSLQPEDFATYYCQQ<br>SNTTPWTFGQGTKVE<br>IK - SEQ ID NO: 48 |
| 2H1 | GFTFSDYY - SEQ ID NO: 49<br>IDSSAGAI - SEQ ID NO: 50<br>ARERRDGHKIFDC - SEQ ID NO: 51<br>QNILYSSNNKNY - SEQ ID NO: 52<br>WSS - SEQ ID NO: 53<br>QQYYSSPYN - SEQ ID NO: 54 | QVQLVESGGDLVKPG<br>GSLRLSCVASGFTFS<br>DYYMNWIRLPPGKGL<br>EWISYIDSSAGAIYY<br>ADSVKGRFTVSRDDA<br>KNSLFLHMNSLRADD<br>TAVYYCARERRDGHK<br>IFDCWGPGTLVTVSS - SEQ ID NO: 55 | DIVMTQSPDSLAVSL<br>GERATINCKSSQNIL<br>YSSNNKNYLAWYQQK<br>TGQPPKLLIFWSSTR<br>ESGVPDRFSGSGSGT<br>DFTLTISSLQAEDVA<br>VYYCQQYYSSPYNFG<br>RGTTLEIK - SEQ ID NO: 56 |

TABLE 1-continued

Amino acid sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 4E6 | GFTFDDYA - SEQ ID NO: 57 ISWSGVTM - SEQ ID NO: 58 ARGDGTNAFDI - SEQ ID NO: 59 QSVLYKSNNKNY - SEQ ID NO: 60 WAS - SEQ ID NO: 61 QQYYSVPLT - SEQ ID NO: 62 | EVQLVESGGDLVQPG RSLRLSCAASGFTFD DYAMHWVRQGPGKGL EWVSGISWSGVTMGY ADSVKGRFTISRDNA KNSLYLRMNSLRADD TAFYYCARGDGTNAF DIWGHGTMVTVSS - SEQ ID NO: 63 | DIVMTQSPDSLAVSL GERATINCKSSQSVL YKSNNKNYLDWYQQK PGQPPKLLIYWASSR ESGVPDRESGSGSGT DFTLTISSLQAEDVA VYYCQQYYSVPLTFG GGTKVEIK - SEQ ID NO: 6 |
| 4F7 | GFTFSDYY - SEQ ID NO: 65 IDSSAGAI - SEQ ID NO: 66 ARERRDGHKIFDC - SEQ ID NO: 67 QNILYSSNNKNY - SEQ ID NO: 68 WSS - SEQ ID NO: 69 QQYYSSPYN - SEQ ID NO: 70 | QVQLVESGGDLVKPG GSLRLSCVASGFTFS DYYMNWIRLPPGKGL EWISYIDSSAGAIYY ADSVKGRFTVSRDDA KNSLFLHMNNLRADD TAVYYCARERRDGHK IFDCWGPGTLVTVSS - SEQ ID NO: 71 | DIVMTQSPDSLAVSL GERATINCKSSQNIL YSSNNKNYLAWYQQK AGQPPKLLIFWSSTR ESGVPDRESGSGSGT DFTLTISSLQAEDVA VYYCQQYYSSPYNFG RGTTLEIK - SEQ ID NO: 72 |
| 5A8 | GFTFSDYY - SEQ ID NO: 73 IDSSAGAI - SEQ ID NO: 74 ARERRDGHKIFDY - SEQ ID NO: 75 QNILYSSNNKNY - SEQ ID NO: 76 WSS - SEQ ID NO: 77 HQYYSSPYN - SEQ ID NO: 78 | QVQLVESGGDLVKPG GSLRLSCVASGFTFS DYYMNWIRLPPGRGL EWISYIDSSAGAIYY ADSVKGRFTVSRDDA KKSLFLYMNSLRADD TAVYYCARERRDGHK IFDYWGPGTLVTVSS - SEQ ID NO: 79 | DIVMTQSPDSLAVSL GERATINCKSSQNIL YSSNNKNYLAWYQQK AGQPPKLLIFWSSTR ESGVPDRFSGSGSGT DFTLTISSLQAEDVA VYYCHQYYSSPYNFG RGTTLEIK - SEQ ID NO: 80 |
| 6E1 | GFTFSSFA - SEQ ID NO: 81 ISGSGGST - SEQ ID NO: 82 AKDKRNWNYGIDSFDF - SEQ ID NO: 83 QSISGY - SEQ ID NO: 84 ATS - SEQ ID NO: 85 HQSHSPPFT - SEQ ID NO: 86 | EVQLLESGGGLVQPG GSLRLSCAASGFTFS SFAMSWVRQAPGKGL EWVSGISGSGGSTYY ADSVKGRFTISRDNS KNTLYLQMNSLRAED TAIYYCAKDKRNWNY GIDSFDFWGQGTMVT VSS - SEQ ID NO: 87 | DIQMTQSPSSLSASV GGRVTITCRTSQSIS GYLNWYQQKAGKAPK LLIYATSNLQSGVPS RFTGSGSGTDFTLTI SSLQPEDFAAYYCHQ SHSPPFTFGPGTKVA FK - SEQ ID NO: 88 |
| 6H12 | GFTFSSYE - SEQ ID NO: 89 ISSGGSSI - SEQ ID NO: 90 ARVGGSYYYSYAMDV - SEQ ID NO: 91 QDISSY - SEQ ID NO: 92 AAS - SEQ ID NO: 93 QQPHNSPFS - SEQ ID NO: 94 | EVQLVESGGGLVQPG GSLRLSCAASGFTFS SYEMNWVRQAPGKGL EWVSYISSGGSSIKY ADSVRGRFAFSRDNA ENSVHLQMNSLRAED TAVYYCARVGGSYYY SYAMDVWGQGTAVTV SS - SEQ ID NO: 95 | DIQLTQSPSFLSASV GDRVTITCWASQDIS SYLAWYQQKPGKAPK LLIYAASTLQSGVPS RFTGSGSGTEFTLTI SSLQPEDFATYYCQQ PHNSPFSFGPGTKVD VK - SEQ ID NO: 96 |
| 7A4 | GFTFSDYY - SEQ ID NO: 97 IDSSAGAI - SEQ ID NO: 98 VRERRDGHKIFDY - SEQ ID NO: 99 QNILYSSNNKNY - SEQ ID NO: 100 WSS - SEQ ID NO: 101 QQYYSSPYN - SEQ ID NO: 102 | QVQLVESGGDLVKPG GSLRLSCVASGFTFS DYYMNWIRLPPGKGL EWISYIDSSAGAIYY ADSVKGRFTVSRDDA KNSLFLHMNSLRADD TAVYYCVRERRDGHK IFDYWGPGTLVTVSS - SEQ ID NO: 103 | DIVMTQSPDSLAVSL GERATINCKSSQNIL YSSNNKNYLAWYQQK AGQPPKLLIFWSSIR ESGVPDRFSGSGSGT DFTLTISSLQAEDVA VYYCQQYYSSPYNFG RGTTLEIK - SEQ ID NO: 104 |

TABLE 1-continued

Amino acid sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 7E5 | GFTFSGFA - SEQ ID NO: 105<br>ISGSGDIT - SEQ ID NO: 106<br>GKDPYNWNHGVYGMDV - SEQ ID NO: 107<br>QSISTY - SEQ ID NO: 108<br>GAS - SEQ ID NO: 109<br>QQSYNIPLT - SEQ ID NO: 110 | EVQLLESGGGLIQPG GSLRLSCAASGFTES GFAMSWVRQAPGKGL EWVSGISGSGDITYY GDSVKGRFTISRDNS KSTLYLQMNSLRDAD TAVYYCGKDPYNWNH GVYGMDVWGQGTTVT VSS - SEQ ID NO: 111 | DIQMTQSPSSLSASV GDRVTITCRASQSIS TYLNWYQQKPGKAPK FLIYGASSLQSGVPS RFSGSGSGTDFSLTI SSLHPGDFATYYCQQ SYNIPLTFGGGTKVE IK - SEQ ID NO: 112 |
| 7H8 | GFAFHTYD - SEQ ID NO: 113<br>VVGSGINT - SEQ ID NO: 114<br>AKDSSSWFSLHY - SEQ ID NO: 115<br>QSISNW - SEQ ID NO: 116<br>KAS - SEQ ID NO: 117<br>QQYRSYAYT - SEQ ID NO: 118 | EVQLLESGGGLVQPG GSLRLSCAASGFAFH TYDMTWVRQAPGKGL EWVSGVVGSGINTYY ADSVKGRFTISRDNS KSTLYLQMNSLRAED TAVYYCAKDSSSWFS LHYWGQGTLVTVSS - SEQ ID NO: 119 | DIQMTQSPSTLSASV GDRVTITCRASQSIS NWLAWYQQKPGKAPK LLIYKASSLESGVPS RFSGSGSGTDFTLTI SSLQPDDFASYYCQQ YRSYAYTFGQGTKLE IT - SEQ ID NO: 120 |
| 8A11 | GFTFSDYY - SEQ ID NO: 121<br>IDSSAGAT - SEQ ID NO: 122<br>ARERRSGHKIFDC - SEQ ID NO: 123<br>QNILYSSNNKNY - SEQ ID NO: 124<br>WSS - SEQ ID NO: 125<br>QQYYSSPYN - SEQ ID NO: 126 | QVQLVESGGDLVKPG GSLRLSCVASGFTFS DYYMNWIRLPPGKGL EWISYIDSSAGATYY ADSVKGRFTVSRDDA KNSLFLHMNSLRAED TAVYYCARERRSGHK IFDCWGPGTLVTVSS - SEQ ID NO: 127 | DIVMTQSPDSLAVSL GERATINCKSSQNIL YSSNNKNYLAWYQQK AGQPPKLLIFWSSTR ESGVPDRFSGSGSGT DFTLTISSLQAEDVA VYYCQQYYSSPYNFG RGTTLEIK - SEQ ID NO: 128 |
| 8D10 | GFTFSDYY - SEQ ID NO: 129<br>IDSSAGAI - SEQ ID NO: 130<br>ARERRDGHKIFDY - SEQ ID NO: 131<br>QNILYSSNNKNY - SEQ ID NO: 132<br>WSS - SEQ ID NO: 133<br>QQYYSSPYN - SEQ ID NO: 134 | QVHLVESGGDLVKPG GSLRLSCVASGFTFS DYYMNWIRLPPGKGL EWISYIDSSAGAIYY ADSVKGRFTVSRDDA KNSMFLHMNSLRADD TAVYYCARERRDGHK IFDYWGPGTLVTVSS - SEQ ID NO: 135 | DIVMTQSPDSLAVSL GERATINCKSSQNIL YSSNNKNYLAWYQQK AGQPPKLLIFWSSTR ESGVPDRFSGSGSGT DFTLTISSLQAEDVA VYYCQQYYSSPYNFG RGTTLEIK - SEQ ID NO: 136 |
| 9B4 | GFTFSDYY - SEQ ID NO: 137<br>IDSSAGAI - SEQ ID NO: 138<br>ARERREGHKIFDF - SEQ ID NO: 139<br>QNILYSSNNKNY - SEQ ID NO: 140<br>WSS - SEQ ID NO: 141<br>QQYYSSPYN - SEQ ID NO: 142 | QVQLVESGGDLVKPG GSLRLSCVASGFTFS DYYMNWIRLPPGKGL EWISYIDSSAGAIYY ADSVKGRFTVSRDDA KNSLFLHMNSLRADD TAVYYCARERREGHK IFDFWGPGTLVTVSS - SEQ ID NO: 143 | DIVMTQSPDSLALSL GERATINCKSSQNIL YSSNNKNYLACYQQK AGQPPKLLIFWSSTR ESGVPDRFSGSGSGT DFTLTISSLQAEDVA VYYCQQYYSSPYNFG RGTTLEIK - SEQ ID NO: 144 |
| 9G9 | GFTFHNYA - SEQ ID NO: 145<br>ISGSGGTA - SEQ ID NO: 146<br>AKDRFLEWVEGFDS - SEQ ID NO: 147<br>QSIGSF - SEQ ID NO: 148<br>AAS - SEQ ID NO: 149<br>QQSYNTPLT - SEQ ID NO: 150 | EVQLLESGGGLVQPG GSLRLSCAASGFTFH NYAMSWVRQAPGKGL EWVSGISGSGGTAYY ADSVKGRFTISRDNS KNTLYLQMNSLRADD TALYYCAKDRFLEWV EGFDSWGQGTLVTVS S - SEQ ID NO: 151 | DIQMTQSPSSLSASV GDRVTITCRASQSIG SFLIWYQQKPGKAPK LLIYAASSLQSGVPS RFSGSGSGTDFTLII SSLQPEDFATYYCQQ SYNTPLTFGGGTKVE IK - SEQ ID NO: 152 |

TABLE 1-continued

Amino acid sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 9H9 | GFTFSSYE - SEQ ID NO: 153<br>ISSGGSSI - SEQ ID NO: 154<br>ARVGGSYYYSYAMDV - SEQ ID NO: 155<br>QDISSY - SEQ ID NO: 156<br>AAS - SEQ ID NO: 157<br>QQPNNYPFS - SEQ ID NO: 158 | EVQLVESGGGLVQPG GSLRLSCAASGFTES SYEMNWVRQAPGKGL EWVSYISSGGSSIKY ADSVRGRFTFSRDNA ENSVHLQMNSLRGED TAVYYCARVGGSYYY SYAMDVWGQGTAVTV SS - SEQ ID NO: 159 | DIQLTQSPSFLSASV GDRVTITCWASQDIS SYLAWYQQKPGKAPK LLIYAASTLQSGVPS RFSGSGSGTEFTLTI SSLQPEDFATYYCQQ PNNYPFSFGPGTKVD VK - SEQ ID NO: 160 |
| 11D12 | GFTFSSYE - SEQ ID NO: 161<br>ISSGGSSI - SEQ ID NO: 162<br>ARVGGSYYYSYAMDV - SEQ ID NO: 163<br>QDISSY - SEQ ID NO: 164<br>AAS - SEQ ID NO: 165<br>QQPNNYPES - SEQ ID NO: 166 | EVQLVESGGGLVQPG GSLRLSCAASGFTFS SYEMNWVRQAPGKGL EWVSYISSGGSSIKY ADSVRGRFTFSRDNA ENSVFLQMNSLRGED TAVYYCARVGGSYYY SYAMDVWGQGTAVTV SS - SEQ ID NO: 167 | DIQLTQSPSFLSASV GDRVTITCWASQDIS SYLAWYQQKPGKAPK LLIYAASTLQSGVPS RFSGSGSGTEFTLTI SSLQPEDFATYYCQQ PNNYPFSFGPGTKVD VK - SEQ ID NO: 168 |
| 14F5 | GFTFSSFA - SEQ ID NO: 169<br>ISASGGTT - SEQ ID NO: 170<br>AKDRFLEWVEGFDP - SEQ ID NO: 171<br>QSIGRF - SEQ ID NO: 172<br>ATS - SEQ ID NO: 173<br>QQSYITPLT - SEQ ID NO: 174 | EVQLLESGGGLVQPG GSLRLSCAVSGFTFS SFAMSWVRQAPGKGL EWVSGISASGGTTNY ADSVKGRFTISRDNS KNTLYLQMSSLRAED TAEYYCAKDRFLEWV EGFDPWGQGILVTVS P - SEQ ID NO: 175 | DIQMTQSPSSLSASV GDRVTITCRASQSIG RFLIWYQQKPGKAPK LLLYATSSLQSGVPA RFTGSGSGTDFTLTI GSLQPEDFATYYCQQ SYITPLTFGGGTKVE IK - SEQ ID NO: 176 |
| 15C10 | GFTFSSFA - SEQ ID NO: 177<br>ISASGGTT - SEQ ID NO: 178<br>AKDRFLEWVEGFDP - SEQ ID NO: 179<br>QSIGRF - SEQ ID NO: 180<br>ATS - SEQ ID NO: 181<br>QQSYITPLT - SEQ ID NO: 182 | EVQLLESGGGLVQPG GSLRLSCAASGFTFS SFAMSWVRQAPGKGL EWVSGISASGGTTNY ADSVKGRFTISRDNS KNTLYLQMSSLRAED TAEYYCAKDRFLEWV EGFDPWGQGILVTVS P - SEQ ID NO: 183 | DIQMTQSPSSLSASV GDRVTITCRASQSIG RFLIWYQQKPGKAPK LLLYATSSLQSGVPA RFTGSGSGTDFTLTI GSLQPEDFATYYCQQ SYITPLTFGGGTKVE IK - SEQ ID NO: 184 |

TABLE 2

Amino acid sequences of antibody framework regions.

| Antibody Clone | Sequence |
|---|---|
| 1E2 | HFR1 - QVQLVESGGDLVKPGGSLRLSCVAS - SEQ ID NO: 185<br>HFR2 - MNWIRLPPGKGLEWVSY - SEQ ID NO: 186<br>HFR3 - YYADSVRGRFTVSRDDAKNSLFLHMNSLRADDTAVYC - SEQ ID NO: 187<br>HFR4 - WGPGTLVTVSS - SEQ ID NO: 188<br>LFR1 - DIVMTQSPDSLAVSLGERATINCKSS - SEQ ID NO: 189<br>LFR2 - LAWYQQKAGQPPKLLIF - SEQ ID NO: 190<br>LFR3 - TRESGVPDRFSGSGSGTDFTLTINSLQAEDVAVYYC - SEQ ID NO: 191<br>LFR4 - FGRGTTLEIK - SEQ ID NO: 192 |

TABLE 2-continued

| Amino acid sequences of antibody framework regions. |
| --- |

| Antibody Clone | Sequence |
| --- | --- |

1H10　　HFR1 - QVHLVESGGDLVKPGGSLRLSCVAS - SEQ ID NO: 193
HFR2 - MNWIRMPPGKGLEWISY - SEQ ID NO: 194
HFR3 - YYADSVKGRFTVSRDDAKNSLFLHMNNLRADDTAVYYC - SEQ ID
NO: 195
HFR4 - WGPGTLVTVSS - SEQ ID NO: 188
LFR1 - DIVMTQSPDSLAVSLGERATINCKSS - SEQ ID NO: 189
LFR2 - LAWYQQKAGQPPKLLIF - SEQ ID NO: 190
LFR3 - TRESGVPDRESGSGSGTDFTLTISSLQAEDVAVYYC - SEQ ID NO:
196
LFR4 - FGRGTTLEIK - SEQ ID NO: 192

2A10　　HFR1 - EVQLVQSGAEVKKPGESLKISCKGS - SEQ ID NO: 197
HFR2 - IGWVRQMPGKGLEWMGI - SEQ ID NO: 198
HFR3 - RYSPSFQGQVTISADKSISTAYLQWSSLKASDTAMYYC - SEQ ID
NO: 199
HFR4 - WGQGTLVTVSS - SEQ ID NO: 200
LFR1 - DIQMTQSPSSLSASVGDRLTITCRAS - SEQ ID NO: 201
LFR2 - LNWYQQNPGKAPKVLIY - SEQ ID NO: 202
LFR3 - SLESGVPSRFSGSGSGTDFTLTISSLQPEDFATYYC - SEQ ID NO:
203
LFR4 - FGQGTKVEIK - SEQ ID NO: 204

2B9　　HFR1 - EVQLLESGGGLAQPGKSLRLSCAAS - SEQ ID NO: 205
HFR2 - MSWVRQAPGKGLEWVSG - SEQ ID NO: 206
HFR3 - YYADSVKGRFTISRDNSKSTLYLQMNSLGAEDTAVYYC - SEQ ID
NO: 207
HFR4 - WGQGTTVTVSS - SEQ ID NO: 208
LFR1 - DIQMTQSPSSLSASVGDRVTITCRAS - SEQ ID NO: 209
LFR2 - LNWYQQKPGKAPKFLIY - SEQ ID NO: 210
LFR3 - SLQSGVPSRFSGSGCGXDFTLTISSLQREDFAAYYC - SEQ ID NO:
211
LFR4 - FGGGTKVEIK - SEQ ID NO: 212

2F7　　HFR1 - QVQLVESGGGLVKPGGSLRLSCVAS - SEQ ID NO: 213
HFR2 - MNWIRLPPGRGLQWISY - SEQ ID NO: 214
HFR3 - YYADSVKGRFTVSRDDAKNSLYLQMNSLRADDTAVYYC - SEQ ID
NO: 215
HFR4 - WGQGTLVTVSS - SEQ ID NO: 200
LFR1 - DIVMTQSPDSLAVSLGERATINCKSS - SEQ ID NO: 189
LFR2 - LGWYQQKAGQPPKLLIY - SEQ ID NO: 216
LFR3 - TRNSGVPDRFSGSGSGTDFTLTISSLQAEDVAVYYC - SEQ ID NO:
217
LFR4 - FGQGTNLEIK - SEQ ID NO: 218

2F11　　HFR1 - EVQLVQSGAEVKKPGESLKISCKGS - SEQ ID NO: 197
HFR2 - IGWVRQMPGKGLEWMGI - SEQ ID NO: 198
HFR3 - RYSPSFQGQVTLSADKSISTAYLQWNSLKASDTAMYYC - SEQ ID
NO: 219
HFR4 - WGQGTLVTVAS - SEQ ID NO: 220
LFR1 - DIQMTQSPSSLSASVGDRVTITCRAS - SEQ ID NO: 209
LFR2 - LNWYQQKPGTAPKLLIY - SEQ ID NO: 221
LFR3 - SLQGGVPSRFSGSGSGTDFTLTISSLQPEDFATYYC - SEQ ID NO:
222
LFR4 - FGQGTKVEIK - SEQ ID NO: 204

2H1　　HFR1 - QVQLVESGGDLVKPGGSLRLSCVAS - SEQ ID NO: 185
HFR2 - MNWIRLPPGKGLEWISY - SEQ ID NO: 223
HFR3 - YYADSVKGRFTVSRDDAKNSLFLHMNSLRADDTAVYYC - SEQ ID
NO: 224
HFR4 - WGPGTLVTVSS - SEQ ID NO: 188
LFR1 - DIVMTQSPDSLAVSLGERATINCKSS - SEQ ID NO: 189
LFR2 - LAWYQQKTGQPPKLLIF - SEQ ID NO: 225
LFR3 - TRESGVPDRFSGSGSGTDFTLTISSLQAEDVAVYYC - SEQ ID NO:
196
LFR4 - FGRGTTLEIK - SEQ ID NO: 192

TABLE 2-continued

Amino acid sequences of antibody framework regions.

Antibody
Clone    Sequence

4E6      HFR1 - EVQLVESGGDLVQPGRSLRLSCAAS - SEQ ID NO: 226
         HFR2 - MHWVRQGPGKGLEWVSG - SEQ ID NO: 227
         HFR3 - GYADSVKGRFTISRDNAKNSLYLRMNSLRADDTAFYYC - SEQ ID
         NO: 228
         HFR4 - WGHGTMVTVSS - SEQ ID NO: 229
         LFR1 - DIVMTQSPDSLAVSLGERATINCKSS - SEQ ID NO: 189
         LFR2 - LDWYQQKPGQPPKLLIY - SEQ ID NO: 230
         LFR3 - SRESGVPDRFSGSGSGTDFTLTISSLQAEDVAVYYC - SEQ ID NO:
         231
         LFR4 - FGGGTKVEIK - SEQ ID NO: 212

4F7      HFR1 - QVQLVESGGDLVKPGGSLRLSCVAS - SEQ ID NO: 185
         HFR2 - MNWIRLPPGKGLEWISY - SEQ ID NO: 223
         HFR3 - YYADSVKGRFTVSRDDAKNSLFLHMNNLRADDTAVYYC - SEQ ID
         NO: 195
         HFR4 - WGPGTLVTVSS - SEQ ID NO: 188
         LFR1 - DIVMTQSPDSLAVSLGERATINCKSS - SEQ ID NO: 189
         LFR2 - LAWYQQKAGQPPKLLIF - SEQ ID NO: 190
         LFR3 - TRESGVPDRESGSGSGTDETLTISSLQAEDVAVYYC - SEQ ID NO:
         196
         LFR4 - FGRGTTLEIK - SEQ ID NO: 192

5A8      HFR1 - QVQLVESGGDLVKPGGSLRLSCVAS - SEQ ID NO: 185
         HFR2 - MNWIRLPPGRGLEWISY - SEQ ID NO: 232
         HFR3 - YYADSVKGRFTVSRDDAKKSLFLYMNSLRADDTAVYYC - SEQ ID
         NO: 233
         HFR4 - WGPGTLVTVSS - SEQ ID NO: 188
         LFR1 - DIVMTQSPDSLAVSLGERATINCKSS - SEQ ID NO: 189
         LFR2 - LAWYQQKAGQPPKLLIF - SEQ ID NO: 190
         LFR3 - TRESGVPDRFSGSGSGTDFTLTISSLQAEDVAVYYC - SEQ ID NO:
         196
         LFR4 - FGRGTTLEIK - SEQ ID NO: 192

6E1      HFR1 - EVQLLESGGGLVQPGGSLRLSCAAS - SEQ ID NO: 234
         HFR2 - MSWVRQAPGKGLEWVSG - SEQ ID NO: 206
         HFR3 - YYADSVKGRFTISRDNSKNTLYLQMNSLRAEDTAIYYC - SEQ ID
         NO: 235
         HFR4 - WGQGTMVTVSS - SEQ ID NO: 236
         LFR1 - DIQMTQSPSSLSASVGGRVTITCRTS - SEQ ID NO: 237
         LFR2 - LNWYQQKAGKAPKLLIY - SEQ ID NO: 238
         LFR3 - NLQSGVPSRFTGSGSGTDFTLTISSLQPEDFAAYYC - SEQ ID NO:
         239
         LFR4 - FGPGTKVAFK - SEQ ID NO: 240

6H12     HFR1 - EVQLVESGGGLVQPGGSLRLSCAAS - SEQ ID NO: 241
         HFR2 - MNWVRQAPGKGLEWVSY - SEQ ID NO: 242
         HFR3 - KYADSVRGRFAFSRDNAENSVHLQMNSLRAEDTAVYYC - SEQ ID
         NO: 243
         HFR4 - WGQGTAVTVSS - SEQ ID NO: 244
         LFR1 - DIQLTQSPSFLSASVGDRVTITCWAS - SEQ ID NO: 245
         LFR2 - LAWYQQKPGKAPKLLIY - SEQ ID NO: 246
         LFR3 - TLQSGVPSRFTGSGSGTEFTLTISSLQPEDFATYYC - SEQ ID NO:
         247
         LFR4 - FGPGTKVDVK - SEQ ID NO: 248

7A4      HFR1 - QVQLVESGGDLVKPGGSLRLSCVAS - SEQ ID NO: 185
         HFR2 - MNWIRLPPGKGLEWISY - SEQ ID NO: 223
         HFR3 - YYADSVKGRFTVSRDDAKNSLFLHMNSLRADDTAVYYC - SEQ ID
         NO: 224
         HFR4 - WGPGTLVTVSS - SEQ ID NO: 188
         LFR1 - DIVMTQSPDSLAVSLGERATINCKSS - SEQ ID NO: 189
         LFR2 - LAWYQQKAGQPPKLLIF - SEQ ID NO: 190
         LFR3 - IRESGVPDRFSGSGSGTDFTLTISSLQAEDVAVYYC - SEQ ID NO:
         249
         LFR4 - FGRGTTLEIK - SEQ ID NO: 192

TABLE 2-continued

Amino acid sequences of antibody framework regions.

Antibody
Clone     Sequence

7E5       HFR1 - EVQLLESGGGLIQPGGSLRLSCAAS - SEQ ID NO: 250
          HFR2 - MSWVRQAPGKGLEWVSG - SEQ ID NO: 206
          HFR3 - YYGDSVKGRFTISRDNSKSTLYLQMNSLRDADTAVYYC - SEQ ID
          NO: 251
          HFR4 - WGQGTTVTVSS - SEQ ID NO: 208
          LFR1 - DIQMTQSPSSLSASVGDRVTITCRAS - SEQ ID NO: 209
          LFR2 - LNWYQQKPGKAPKFLIY - SEQ ID NO: 210
          LFR3 - SLQSGVPSRFSGSGCGTDESLTISSXHPGDFATYYC - SEQ ID NO:
          252
          LFR4 - FGGGTKVEIK - SEQ ID NO: 212

7H8       HFR1 - EVQLLESGGGLVQPGGSLRLSCAAS - SEQ ID NO: 234
          HFR2 - MTWVRQAPGKGLEWVSG - SEQ ID NO: 253
          HFR3 - YYADSVKGRFTISRDNSKSTLYLQMNSLRAEDTAVYYC - SEQ ID
          NO: 254
          HFR4 - WGQGTLVTVSS - SEQ ID NO: 200
          LFR1 - DIQMTQSPSTLSASVGDRVTITCRAS - SEQ ID NO: 255
          LFR2 - LAWYQQKPGKAPKLLIY - SEQ ID NO: 246
          LFR3 - SLESGVPSRFSGSGSGTDFTLTISSLQPDDFASYYC - SEQ ID NO:
          256
          LFR4 - FGQGTKLEIT - SEQ ID NO: 257

8A11      HFR1 - QVQLVESGGDLVKPGGSLRLSCVAS - SEQ ID NO: 185
          HFR2 - MNWIRLPPGKGLEWISY - SEQ ID NO: 223
          HFR3 - YYADSVKGRFTVSRDDAKNSLFLHMNSLRAEDTAVYYC - SEQ ID
          NO: 258
          HFR4 - WGPGTLVTVSS - SEQ ID NO: 188
          LFR1 - DIVMTQSPDSLAVSLGERATINCKSS - SEQ ID NO: 189
          LFR2 - LAWYQQKAGQPPKLLIF - SEQ ID NO: 190
          LFR3 - TRESGVPDRESGSGSGTDFTLTISSLQAEDVAVYYC - SEQ ID NO:
          196
          LFR4 - FGRGTTLEIK - SEQ ID NO: 192

8D10      HFR1 - QVHLVESGGDLVKPGGSLRLSCVAS - SEQ ID NO: 193
          HFR2 - MNWIRLPPGKGLEWISY - SEQ ID NO: 223
          HFR3 - YYADSVKGRFTVSRDDAKNSMFLHMNSLRADDTAVYYC - SEQ ID
          NO: 259
          HFR4 - WGPGTLVTVSS - SEQ ID NO: 188
          LFR1 - DIVMTQSPDSLAVSLGERATINCKSS - SEQ ID NO: 189
          LFR2 - LAWYQQKAGQPPKLLIF - SEQ ID NO: 190
          LFR3 - TRESGVPDRFSGSGSGTDFTLTISSLQAEDVAVYYC - SEQ ID NO:
          196
          LFR4 - FGRGTTLEIK - SEQ ID NO: 192

9B4       HFR1 - QVQLVESGGDLVKPGGSLRLSCVAS - SEQ ID NO: 185
          HFR2 - MNWIRLPPGKGLEWISY - SEQ ID NO: 223
          HFR3 - YYADSVKGRFTVSRDDAKNSLFLHMNSLRADDTAVYYC - SEQ ID
          NO: 224
          HER4 - WGPGTLVTVSS - SEQ ID NO: 188
          LFR1 - DIVMTQSPDSLALSLGERATINCKSS - SEQ ID NO: 260
          LFR2 - LACYQQKAGQPPKLLIF - SEQ ID NO: 261
          LFR3 - TRESGVPDRESGSGSGTDFTLTISSLQAEDVAVYYC - SEQ ID NO:
          196
          LFR4 - FGRGTTLEIK - SEQ ID NO: 192

9G9       HFR1 - EVQLLESGGGLVQPGGSLRLSCAAS - SEQ ID NO: 234
          HFR2 - MSWVRQAPGKGLEWVSG - SEQ ID NO: 206
          HFR3 - YYADSVKGRFTISRDNSKNTLYLQMNSLRADDTALYYC - SEQ ID
          NO: 262
          HFR4 - WGQGTLVTVSS - SEQ ID NO: 200
          LFR1 - DIQMTQSPSSLSASVGDRVTITCRAS - SEQ ID NO: 209
          LFR2 - LIWYQQKPGKAPKLLIY - SEQ ID NO: 263
          LFR3 - SLQSGVPSRFSGSGSGTDFTLIISSLQPEDFATYYC - SEQ ID NO:
          264
          LFR4 - FGGGTKVEIK - SEQ ID NO: 212

TABLE 2-continued

Amino acid sequences of antibody framework regions.

| Antibody Clone | Sequence |
|---|---|
| 9H9 | HFR1 - EVQLVESGGGLVQPGGSLRLSCAAS - SEQ ID NO: 241<br>HFR2 - MNWVRQAPGKGLEWVSY - SEQ ID NO: 242<br>HFR3 - KYADSVRGRFTFSRDNAENSVHLQMNSLRGEDTAVYYC - SEQ ID NO: 265<br>HFR4 - WGQGTAVTVSS - SEQ ID NO: 244<br>LFR1 - DIQLTQSPSFLSASVGDRVTITCWAS - SEQ ID NO: 245<br>LFR2 - LAWYQQKPGKAPKLLIY - SEQ ID NO: 246<br>LFR3 - TLQSGVPSRFSGSGXGTEFTLTISSLQREDFATYYC - SEQ ID NO: 266<br>LFR4 - FGPGTKVDVK - SEQ ID NO: 248 |
| 11D12 | HFR1 - EVQLVESGGGLVQPGGSLRLSCAAS - SEQ ID NO: 241<br>HFR2 - MNWVRQAPGKGLEWVSY - SEQ ID NO: 242<br>HFR3 - KYADSVRGRFTFSRDNAENSVFLQMNSLRGEDTAVYYC - SEQ ID NO: 267<br>HFR4 - WGQGTAVTVSS - SEQ ID NO: 244<br>LFR1 - DIQLTQSPSFLSASVGDRVTITCWAS - SEQ ID NO: 245<br>LFR2 - LAWYQQKPGKAPKLLIY - SEQ ID NO: 246<br>LFR3 - TLQSGVPSRFSGSGSGTEFTLTISSLQPEDFATYYC - SEQ ID NO: 268<br>LFR4 - FGPGTKVDVK - SEQ ID NO: 248 |
| 14F5 | HFR1 - EVQLLESGGGLVQPGGSLRLSCAVS - SEQ ID NO: 269<br>HFR2 - MSWVRQAPGKGLEWVSG - SEQ ID NO: 206<br>HFR3 - NYADSVKGRFTISRDNSKNTLYLQMSSLRAEDTAEYYC - SEQ ID NO: 270<br>HFR4 - WGQGILVTVSP - SEQ ID NO: 271<br>LFR1 - DIQMTQSPSSLSASVGDRVTITCRAS - SEQ ID NO: 209<br>LFR2 - LIWYQQKPGKAPKLLLY - SEQ ID NO: 272<br>LFR3 - SLQSGVPARFTGSGSGTDFTLTIGSLQPEDFATYYC - SEQ ID NO: 273<br>LFR4 - FGGGTKVEIK - SEQ ID NO: 212 |
| 15C10 | HFR1 - EVQLLESGGGLVQPGGSLRLSCAAS - SEQ ID NO: 234<br>HFR2 - MSWVRQAPGKGLEWVSG - SEQ ID NO: 206<br>HFR3 - NYADSVKGRFTISRDNSKNTLYLQMSSLRAEDTAEYYC - SEQ ID NO: 270<br>HER4 - WGQGILVTVSP - SEQ ID NO: 271LFR1 - DIQMTQSPSSLSASVGDRVTITCRAS - SEQ ID NO: 209<br>LFR2 - LIWYQQKPGKAPKLLLY - SEQ ID NO: 272<br>LFR3 - SLQSGVPARFTGSGSGTDFTLTIGSLQPEDFATYYC - SEQ ID NO: 273<br>LFR4 - FGGGTKVEIK - SEQ ID NO: 212 |

TABLE 3

Sequences of antibody heavy chain constant regions by isotype.

| Heavy Chain Isotype | Accession No. | Sequence |
|---|---|---|
| Human IgG1 | P01857 | ASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPQVYTLPPSRDELTKNQVSLTCLVKGFYPSDI<br>AVEWESNGQPENNYKTTPPVLDSDGSFFLYSKLTVDKSRWQQGNVFSCSVMH<br>EALHNHYTQKSLSLSPGK (SEQ ID NO: 274) |
| Human IgG2 | P01859 | ASTKGPSVFPLAPCSRSTSESTAALGCLVKDYFPEPVTVSWNSGALTSGVHT<br>FPAVLQSSGLYSLSSVVTVPSSNFGTQTYTCNVDHKPSNTKVDKTVERKCCV<br>ECPPCPAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVSNKGLP<br>APIEKTISKTKGQPREPQVYTLPPSREEMTKNQVSLTCLVKGFYPSDISVEW<br>ESNGQPENNYKTTPPMLDSDGSFFLYSKLTVDKSRWQQGNVFSCSVMHEALH<br>NHYTQKSLSLSPGK (SEQ ID NO: 275) |

TABLE 3-continued

Sequences of antibody heavy chain constant regions by isotype.

| Heavy Chain Isotype | Accession No. | Sequence |
|---|---|---|
| Human IgG3 | P01860 | ASTKGPSVFPLAPCSRSTSGGTAALGCLVKDYFPEPVTVSWNSGALTSGVHT FPAVLQSSGLYSLSSVVTVPSSSLGTQTYTCNVNHKPSNTKVDKRVELKTPL GDTTHTCPRCPEPKSCDTPPPCPRCPEPKSCDTPPPCPRCPEPKSCDTPPPC PRCPAPELLGGPSVFLFPPKPKDTLMISRTPEVTCVVVDVSHEDPEVQFKWY VDGVEVHNAKTKPREEQYNSTFRVVSVLTVLHQDWLNGKEYKCKVSNKALPA PIEKTISKTKGQPREPQVYTLPPSREEMTKNQVSLTCLVKGFYPSDIAVEWE SSGQPENNYNTTPPMLDSDGSFFLYSKLTVDKSRWQQGNIFSCSVMHEALHN RFTQKSLSLSPGK (SEQ ID NO: 276) |
| Human IgG4 | P01861 | ASTKGPSVFPLAPCSRSTSESTAALGCLVKDYFPEPVTVSWNSGALTSGVHT FPAVLQSSGLYSLSSVVTVPSSSLGTKTYTCNVDHKPSNTKVDKRVESKYGP PCPSCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEAL HNHYTQKSLSLSLGK (SEQ ID NO: 277) |
| Human IgA1 | P01876 | ASPTSPKVFPLSLCSTQPDGNVVIACLVQGFFPQEPLSVTWSESGQGVTARN FPPSQDASGDLYTTSSQLTLPATQCLAGKSVTCHVKHYTNPSQDVTVPCPVP STPPTPSPSTPPTPSPSCCHPRLSLHRPALEDLLLGSEANLTCTLTGLRDAS GVTFTWTPSSGKSAVQGPPERDLCGCYSVSSVLPGCAEPWNHGKTFTCTAAY PESKTPLTATLSKSGNTFRPEVHLLPPPSEELALNELVTLTCLARGFSPKDV LVRWLQGSQELPREKYLTWASRQEPSQGTTTFAVTSILRVAAEDWKKGDTFS CMVGHEALPLAFTQKTIDRLAGKPTHVNVSVVMAEVDGTCY (SEQ ID NO: 278) |
| Human IgA2 | P01877 | ASPTSPKVFPLSLDSTPQDGNVVVACLVQGFFPQEPLSVTWSESGQNVTARN FPPSQDASGDLYTTSSQLTLPATQCPDGKSVTCHVKHYTNSSQDVTVPCRVP PPPPCCHPRLSLHRPALEDLLLGSEANLTCTLTGLRDASGATFTWTPSSGKS AVQGPPERDLCGCYSVSSVLPGCAQPWNHGETFTCTAAHPELKTPLTANITK SGNTFRPEVHLLPPPSEELALNELVTLTCLARGFSPKDVLVRWLQGSQELPR EKYLTWASRQEPSQGTTTYAVTSILRVAAEDWKKGETFSCMVGHEALPLAFT QKTIDRMAGKPTHINVSVVMAEADGTCY (SEQ ID NO: 279) |
| Human IgD | P01880 | APTKAPDVFPIISGCRHPKDNSPVVLACLITGYHPTSVTVTWYMGTQSQPQR TFPEIQRRDSYYMTSSQLSTPLQQWRQGEYKCVVQHTASKSKKEIFRWPESP KAQASSVPTAQPQAEGSLAKATTAPATTRNTGRGGEEKKKEKEKEEQEERET KTPECPSHTQPLGVYLLTPAVQDLWLRDKATFTCFVVGSDLKDAHLTWEVAG KVPTGGVEEGLLERHSNGSQSQHSRLTLPRSLWNAGTSVTCTLNHPSLPPQR LMALREPAAQAPVKLSLNLLASSDPPEAASWLLCEVSGESPPNILLMWLEDQ REVNTSGFAPARPPPQPRSTTFWAWSVLRVPAPPSPQPATYTCVVSHEDSRT LLNASRSLEVSYVTDHGPMK (SEQ ID NO: 280) |
| Human IgM | P01871 | GSASAPTLFPLVSCENSPSDTSSVAVGCLAQDELPDSITESWKYKNNSDISS TRGFPSVLRGGKYAATSQVLLPSKDVMQGTDEHVVCKVQHPNGNKEKNVPLP VIAELPPKVSVFVPPRDGFFGNPRKSKLICQATGFSPRQIQVSWLREGKQVG SGVTTDQVQAEAKESGPTTYKVTSTLTIKESDWLGQSMFTCRVDHRGLTFQQ NASSMCVPDQDTAIRVFAIPPSFASIFLTKSTKLTCLVTDLTTYDSVTISWT RQNGEAVKTHTNISESHPNATFSAVGEASICEDDWNSGERFTCTVTHTDLPS PLKQTISRPKGVALHRPDVYLLPPAREQLNLRESATITCLVTGFSPADVFVQ WMQRGQPLSPEKYVTSAPMPEPQAPGRYFAHSILTVSEEEWNTGETYTCVVA HEALPNRVTERTVDKSTGKPTLYNVSLVMSDTAGTCY (SEQ ID NO: 281) |
| Human IgE | P01854 | ASTQSPSVFPLTRCCKNIPSNATSVTLGCLATGYFPEPVMVTWDTGSLNGTT MTLPATTLTLSGHYATISLLTVSGAWAKQMFTCRVAHTPSSTDWVDNKTFSV CSRDFTPPTVKILQSSCDGGGHFPPTIQLLCLVSGYTPGTINITWLEDGQVM DVDLSTASTTQEGELASTQSELTLSQKHWLSDRTYTCQVTYQGHTFEDSTKK CADSNPRGVSAYLSRPSPFDLFIRKSPTITCLVVDLAPSKGTVNLTWSRASG KPVNHSTRKEEKQRNGTLVTSTLPVGTRDWIEGETYQCRVTHPHLPRALMR STTKTSGPRAAPEVYAFATPEWPGSRDKRTLACLIQNFMPEDISVQWLHNEV QLPDARHSTTQPRKTKGSGFFVFSRLEVTRAEWEQKDEFICRAVHEAASPSQ TVQRAVSVNPGK (SEQ ID NO: 282) |
| Mouse IgG1 | P01868 | AKTTPPSVYPLAPGSAAQTNSMVTLGCLVKGYFPEPVTVTWNSGSLSSGVHT FPAVLQSDLYTLSSSVTVPSSPRPSETVTCNVAHPASSTKVDKKIVPRDCGC KPCICTVPEVSSVFIFPPKPKDVLTITLTPKVTCVVVDISKDDPEVQFSWFV DDVEVHTAQTQPREEQFNSTFRSVSELPIMHQDWLNGKEFKCRVNSAAFPAP IEKTISKTKGRPKAPQVYTIPPPKEQMAKDKVSLTCMITDFFPEDITVEWQW NGQPAENYKNTQPIMNTNGSYFVYSKLNVQKSNWEAGNTFTCSVLHEGLHNH HTEKSLSHSPGK (SEQ ID NO: 283) |

TABLE 3-continued

Sequences of antibody heavy chain constant regions by isotype.

| Heavy Chain Isotype | Accession No. | Sequence |
|---|---|---|
| Mouse IgG2a | P01863 | AKTTAPSVYPLAPVCGDTTGSSVTLGCLVKGYFPEPVTLTWNSGSLSSGVHT FPAVLQSDLYTLSSSVTVTSSTWPSQSITCNVAHPASSTKVDKKIEPRGPTI KPCPPCKCPAPNLLGGPSVFIFPPKIKDVLMISLSPIVTCVVVDVSEDDPDV QISWFVNNVEVHTAQTQTHREDYNSTLRVVSALPIQHQDWMSGKEFKCKVNN KDLPAPIERTISKPKGSVRAPQVYVLPPPEEEMTKKQVTLTCMVTDEMPEDI YVEWTNNGKTELNYKNTEPVLDSDGSYFMYSKLRVEKKNWVERNSYSCSVVH EGLHNHHTTKSFSRTPGK (SEQ ID NO: 284) |
| Mouse IgG2b | P01867 | KTTPPSVYPLAPGCGDTTGSSVTLGCLVKGYFPESVTVTWNSGSLSSSVHTF PALLQSGLYTMSSSVTVPSSTWPSQTVTCSVAHPASSTTVDKKLEPSGPIST INPCPPCKECHKCPAPNLEGGPSVFIFPPNIKDVLMISLTPKVTCVVVDVSE DDPDVQISWFVNNVEVHTAQTQTHREDYNSTIRVVSTLPIQHQDWMSGKEFK CKVNNKDLPSPIERTISKIKGLVRAPQVYILPPPAEQLSRKDVSLTCLVVGF NPGDISVEWTSNGHTEENYKDTAPVLDSDGSYFIYSKLNMKTSKWEKTDSFS CNVRHEGLKNYYLKKTISRSPGK (SEQ ID NO: 285) |
| Mouse IgG2c | P01864 | AKTTAPSVYPLVPVCGGTTGSSVTLGCLVKGYFPEPVTLTWNSGSLSSGVHT FPALLQSGLYTLSSSVTVTSNTWPSQTITCNVAHPASSTKVDKKIEPRVPIT QNPCPPHQRVPPCAAPDLLGGPSVFIFPPKIKDVLMISLSPMVTCVVVDVSE DDPDVQISWFVNNVEVHTAQTQTHREDYNSTLRVVSALPIQHQDWMSGKEFK CKVNNRALPSPIEKTISKPRGPVRAPQVYVLPPPAEEMTKKEFSLTCMITGE LPAEIAVDWTSNGRTEQNYKNTATVLDSDGSYFMYSKLRVQKSTWERGSLFA CSVVHEVLHNHLTTKTISRSLGK (SEQ ID NO: 286) |
| Mouse IgA | P01878 | ESARNPTIYPLTLPPALSSDPVIIGCLIHDYFPSGTMNVTWGKSGKDITTVN FPPALASGGRYTMSNQLTLPAVECPEGESVKCSVQHDSNPVQELDVNCSGPT PPPPITIPSCQPSLSLQRPALEDLLLGSDASITCTLNGLRNPEGAVFTWEPS TGKDAVQKKAVQNSCGCYSVSSVLPGCAERWNSGASFKCTVTHPESGTLTGT IAKVTVNTFPPQVHLLPPPSEELALNELLSLTCLVRAFNPKEVLVRWLHGNE ELSPESYLVFEPLKEPGEGATTYLVTSVLRVSAETWKQGDQYSCMVGHEALP MNFTQKTIDRLSGKPTNVSVSVIMSEGDGICY (SEQ ID NO: 287) |
| Mouse IgM | P01872 | SQSFPNVFPLVSCESPLSDKNLVAMGCLARDFLPSTISFTWNYQNNTEVIQG IRTFPTLRTGGKYLATSQVLLSPKSILEGSDEYLVCKIHYGGKNRDLHVPIP AVAEMNPNVNVFVPPRDGFSGPAPRKSKLICEATNFTPKPITVSWLKDGKLV ESGFTTDPVTIENKGSTPQTYKVISTLTISEIDWLNLNVYTCRVDHRGLTFL KNVSSTCAASPSTDILTFTIPPSFADIFLSKSANLTCLVSNLATYETLNISW ASQSGEPLETKIKIMESHPNGTFSAKGVASVCEDWNNRKEFVCTVTHRDLP SPQKKFISKPNEVHKHPPAVYLLPPAREQLNLRESATVTCLVKGFSPADISV QWLQRGQLLPQEKYVTSAPMPEPGAPGFYFTHSILTVTEEEWNSGETYTCVV GHEALPHLVTERTVDKSTGKPTLYNVSLIMSDTGGTCY (SEQ ID NO: 288) |
| Mouse IgD | P01881 | DKKEPDMFLLSECKAPEENEKINLGCLVIGSQPLKISWEPKKSSIVEHVFPS EMRNGNYTMVLQVTVLASELNLNHTCTINKPKRKEKPFKFPESWDSQSSKRV TPTLQAKNHSTEATKAITTKKDIEGAMAPSNLTVNILTTSTHPEMSSWLLCE VSGFFPENIHLMWLGVHSKMKSTNFVTANPTAQPGGTFQTWSVLRLPVALSS SLDTYTCVVEHEASKTKLNASKSLAISGCYHLLPESDGPSRRPDGPALA (SEQ ID NO: 289) |
| Mouse IgE | P06336 | SIRNPQLYPLKPCKGTASMTLGCLVKDYFPNPVTVTWYSDSLNMSTVNFPAL GSELKVTTSQVTSWGKSAKNFTCHVTHPPSFNESRTILVRPVNITEPTLELL HSSCDPNAFHSTIQLYCFIYGHILNDVSVSWLMDDREITDTLAQTVLIKEEG KLASTCSKLNITEQQWMSESTFTCKVTSQGVDYLAHTRRCPDHEPRGVITYL IPPSPLDLYQNGAPKLTCLVVDLESEKNVNVTWNQEKKTSVSASQWYTKHHN NATTSITSILPVVAKDWIEGYGYQCIVDHPDFPKPIVRSITKTPGQRSAPEV YVFPPPEEESEDKRTLTCLIQNFFPEDISVQWLGDGKLISNSQHSTTTPLKS NGSNQGFFIFSRLEVAKTLWTQRKQFTCQVIHEALQKPRKLEKTISTSLGNT SLRPS (SEQ ID NO: 290) |

TABLE 4

Sequences of antibody light chain constant regions by isotype.

| Light Chain Isotype | Accession No. | Sequence |
|---|---|---|
| Human Ig kappa | P01834 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSENRGEC (SEQ ID NO: 291) |
| Human Ig lambda 1 | P0CG04 | GQPKANPTVTLFPPSSEELQANKATLVCLISDFYPGAVTVAWKA DGSPVKAGVETTKPSKQSNNKYAASSYLSLTPEQWKSHRSYSCQ VTHEGSTVEKTVAPTECS (SEQ ID NO: 292) |
| Human Ig lambda 2 | P0DOY2 | GQPKAAPSVTLFPPSSEELQANKATLVCLISDFYPGAVTVAWKA DSSPVKAGVETTTPSKQSNNKYAASSYLSLTPEQWKSHRSYSCQ VTHEGSTVEKTVAPTECS (SEQ ID NO: 293) |
| Human Ig lambda 3 | P0DOY3 | GQPKAAPSVTLFPPSSEELQANKATLVCLISDFYPGAVTVAWKA DSSPVKAGVETTTPSKQSNNKYAASSYLSLTPEQWKSHKSYSCQ VTHEGSTVEKTVAPTECS (SEQ ID NO: 294) |
| Human Ig lambda 6 | P0CF74 | GQPKAAPSVTLFPPSSEELQANKATLVCLISDFYPGAVKVAWKA DGSPVNTGVETTTPSKQSNNKYAASSYLSLTPEQWKSHRSYSCQ VTHEGSTVEKTVAPAECS (SEQ ID NO: 295) |
| Human Ig lambda 7 | A0M8Q6 | GQPKAAPSVTLFPPSSEELQANKATLVCLVSDENPGAVTVAWKA DGSPVKVGVETTKPSKQSNNKYAASSYLSLTPEQWKSHRSYSCR VTHEGSTVEKTVAPAECS (SEQ ID NO: 296) |
| Mouse Ig kappa | P01837 | RADAAPTVSIFPPSSEQLTSGGASVVCFLNNFYPKDINVKWKID GSERQNGVLNSWTDQDSKDSTYSMSSTLTLTKDEYERHNSYTCE ATHKTSTSPIVKSENRNEC (SEQ ID NO: 297) |
| Mouse Ig lambda 1 | A0A0G2JE99 | XQPKSSPSVTLFPPSSEELETNKATLVCTITDFYPGVVTVDWKV DGTPVTQGMETTQPSKQSNNKYMASSYLTLTARAWERHSSYSCQ VTHEGHTVEKSLSRADCS (SEQ ID NO: 298) |
| Mouse Ig lambda 2 | Q99JC1 | GQPKSTPTLTVFPPSSEELKENKATLVCLISNFSPSGVTVAWKA NGTPITQGVDTSNPTKEGNKFMASSFLHLTSDQWRSHNSFTCQV THEGDTVEKSLSPAECL (SEQ ID NO: 299) |
| Mouse Ig lambda 3 | P01845 | QPKSTPTLTMFPPSPEELQENKATLVCLISNFSPSGVTVAWKAN GTPITQGVDTSNPTKEDNKYMASSFLHLTSDQWRSHNSFTCQVT HEGDTVEKSLSPAECL (SEQ ID NO: 300) |
| Mouse Ig lambda 4 | A0A0G2JEK5 | XQPKATPSVNLFPPSSEELKTKKATLVCMITEFYAAAVRVAWKA DGTPFTQGVETTQPPKQRDNMASSYLLFTAEAWESHSSYSCHVT HEGNTVEKSLSRAECS (SEQ ID NO: 301) |

TABLE 5

Nucleotide sequences of antibody complementary determining regions, variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 1E2 | ggattcaccttcagtgac tactac - SEQ ID NO: 302 attgatagtagtgctggt gccatt - SEQ ID NO: 303 gcgagagagcgtagagat ggccacaaaatctttgac tgt - SEQ ID NO: 304 cagaatattttgtacagt tccaacaataagaactac - SEQ ID NO: 305 tggtcatct - SEQ ID NO: 306 | caggtgcagctggtggagt ctggggggagacttggtcaa gcctggagggtccctgaga ctctcctgtgtagcctcgg gattcaccttcagtgacta ctacatgaactggatccgc ctgcctccagggaagggcc tggagtgggtttcatacat tgatagtagtgctggtgcc atttactatgcagactctg tgaggggccgattcaccgt ctccagggacgacgccaag aattcactatttctgcaca tgaacagcctgagagccga tgacacggccgtttattac | gacatcgtgatgacccagt ctccagactccctggctgt gtctctgggcgagagggcc accatcaactgcaagtcca gccagaatattttgtacag ttccaacaataagaactac ttagcttggtaccagcaga aagcaggacagcctcctaa gttgctcattttctggtca tctacccgggaatccgggg tccctgaccgattcagtgg cagcgggtctgggacagat ttcactctcaccatcaaca gcctgcaggctgaagatgt ggcagtttattactgtcag |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| | cagcaatattacagtagt ccgtataat - SEQ ID NO: 307 | tgtgcgagagagcgtagag atggccacaaaatctttga ctgttggggcccgggaacc ctggtcaccgtctcttca - SEQ ID NO: 308 | caatattacagtagtccgt ataattttggccgggggac cacactggagatcaaa - SEQ ID NO: 309 |
| 1H10 | ggattcaccttcagtgac tactac - SEQ ID NO: 302 attgatagtagtgctggt gccatt - SEQ ID NO: 303 gcgagagagcgtagagat ggccacaaaatctttgac tgt - SEQ ID NO: 304 cagaatattttatacagt tccaacaataagaactat - SEQ ID NO: 310 tggtcatct - SEQ ID NO: 306 cagcaatattacagtagt ccgtataat - SEQ ID NO: 307 | caggtgcacctggtggagt ctggggggagacttggtcaa gcctggagggtccctgaga ctctcctgtgtagcctctg gattcaccttcagtgacta ctacatgaactggatccgt atgcctccagggaagggcc tggagtggattcatacat tgatagtagtgctggtgcc atttactatgcagactctg tgaagggccgattcaccgt ctccagggacgacgccaag aactcactgtttctacaca tgaacaacctgagagccga tgacacggccgtttattac tgtgcgagagagcgtagag atggccacaaaatctttga ctgttggggcccgggaacc ctggtcaccgtctcctca - SEQ ID NO: 311 | gacatcgtgatgacccagt ctccagactccctggctgt gtctctgggcgagagggcc accatcaactgcaagtcca gccagaatattttatacag ttccaacaataagaactat ttagcttggtaccagcaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcag caatattacagtagtccgt ataattttggccgggggac cacactggagatcaaa - SEQ ID NO: 312 |
| 2A10 | ggatacagttttacatac tactgg - SEQ ID NO: 313 atctatcctggtgactct gatacc - SEQ ID NO: 314 actacacatgcgcgcaac tggaacaacgtggcctac - SEQ ID NO: 315 cagaacattaacacctttt - SEQ ID NO: 316 gctgcatcc - SEQ ID NO: 317 caacagagttctagtacc ccgtggacg - SEQ ID NO: 318 | gaggtgcagctggtgcagt ctggagcagaggtgaaaaa gcccggggagtctctgaag atctcctgtaagggttctg gatacagttttacatacta ctggatcggctgggtgcgc cagatgcccgggaaaggcc tggagtggatgggatcat ctatcctggtgactctgat accagatacagcccgtcct tccaaggccaggtcaccat ctcagccgacaagtccatc agtaccgcctatttgcagt ggagcagcctgaaggcctc ggacaccgccatgtattac tgtactacacatgcgcgca actggaacaacgtggccta ctggggccagggaaccctg gtcaccgtctcctca - SEQ ID NO: 319 | gacatccagatgacccagt ctccatcctccctgtctgc atctgtcggagacagactc accatcacttgccgggcaa gtcagaacattaacacctt tttaaattggtatcaacag aacccagggaaagcccta aggtcctgatctatgctgca aggtcctgatctatgctgca atccagtttggaaagtggg gtcccatcaaggttcagtg gcagtggatctgggacaga tttcactctcaccatcagc agtctgcaacctgaagatt ttgcaacttactactgtca acagagttctagtacccog tggacgttcggccaaggga ccaaggtggaaatcaaac - SEQ ID NO: 320 |
| 2B9 | ggattcacctttagtggc ttcgcc - SEQ ID NO: 321 attagtgggagtggtgat atcaca - SEQ ID NO: 322 gcgaaagacccatataac tggaaccacggggtctac ggcatggacgtc - SEQ ID NO: 323 cagagcattagcagctat - SEQ ID NO: 3244 ggtgcatcc - SEQ ID NO: 325 caacagagtttcaatgcc cctctcact - SEQ ID NO: 326 | gaggtgcagcttttggagt cggggggaggcttggcaca gccgggggaagtccctgaga ctctcctgtgcagcctctg gattcacctttagtggctt cgccatgagctgggtccgc caggctcctgggaaggggc tggagtgggtctcaggtat tagtgggagtggtgatatc acatactatgcagactccg tgaagggccggttcaccat ttccagagacaattccaag agtacgctgtatcttcaaa tgaacagcctgggagccga ggacacggccgtgtattac tgtgcgaaagacccatata actggaaccacggggtcta cggcatggacgtctggggc caaggaccacggtcaccg tctcctca - SEQ ID NO: 327 | gacatccagatgacccagt ctccatcctccctgtctgc atctgtaggagacagagtc accatcacttgccgggcaa gtcagagcattagcagcta tttaaattggtatcagcag aaaccagggaaagcccta aattcctgatctatgctgac atccagtttgcaaagtggg gtcccatcaaggttcagtg gcagtggatctgggactga tttcactctcaccatcagc agtctgcaacctgaagatt tcgcagcttactactgtca acagagtttcaatgcccct ctcacttcggcggcggga ccaaggtggagatcaaa - SEQ ID NO: 328 |
| 2F7 | ggattcaccttcagtgac tactac - SEQ ID NO: 302 | caggtgcagctggtggagt ctggggggaggcttggtcaa gcctggagggtccctgaga | gacatcgtgatgacccagt ctccagactccctggctgt gtctctgggcgagagggcc |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| | attgatagtagtgctggt gccatt - SEQ ID NO: 303 gcgagagaacgtagagat ggccacaaaatctttgac tgg - SEQ ID NO: 329 cagaatattttatacact tccaacaataagaactac - SEQ ID NO: 330 tggtcatct - SEQ ID NO: 306 catcagtattacagtagt ccgtacact - SEQ ID NO: 331 | ctctcctgcgtagcctctg gattcaccttcagtgacta ctacatgaactggatccgc ctgcctccagggagggggc tgcagtggatttcatacat tgatagtagtgctggtgcc atttactacgcagactctg tgaagggccgattcaccgt ctccagggacgacgccaag aattcactttatctgcaaa tgaacagcctgagagccga tgacacggccgtttattac tgtgcgagagaacgtagag atggccacaaaatctttga ctggtgggggccagggaacc ctggtcaccgtctcctca - SEQ ID NO: 332 | accatcaactgcaagtcca gccagaatattttatacac ttccaacaataagaactac ttaggttggtaccagcaga aagcaggacagcctcctaa actgctcatttactggtca tctacccggaattccgggg tccctgaccgcttcagtgg cagcgggtctgggacagat ttcactctcaccatcagca gcctgcaggctgaggatgt ggcagtttattactgtcat cagtattacagtagtccgt acacttttggccagggggac caacctggagatcaaa - SEQ ID NO: 3333 |
| 2F11 | ggatacagttttaccaac tactgg - SEQ ID NO: 334 atctatcctggtgactct gatacc - SEQ ID NO: 314 gcgacacatgcgcgcagc tggaactacgtggcctac - SEQ ID NO: 335 cagagcgtcaacaacttt - SEQ ID NO: 336 gctgcatcc - SEQ ID NO: 317 caacagagtaacactacc ccgtggacg - SEQ ID NO: 337 | gaggtgcagctggtgcagt ctggagcagaggtgaaaaa gcccggggagtctctgaag atctcctgtaagggttctg gatacagttttaccaacta ctggatcggctgggtgcgc cagatgcccgggaaaggcc tggagtggatggggatcat ctatcctggtgactctgat accagatacagcccgtcct tccaaggccaggtcaccct ctcagccgacaagtccatc agtaccgcctacctacagt ggaacagcctgaaggcctc ggacaccgccatgtattac tgtgcgacacatgcgcgca gctggaactacgtggccta ctggggccagggaaccctg gtcaccgtcgcctcat SEQ ID NO: 338 | gacatccagatgacccagt ctccatcctccctgtctgc atctgtaggagacagagtc accatcacttgccgggcaa gtcagagcgtcaacaactt tttaaattggtatcagcag aaaccagggacagccccta aactcctgatctatgctgc atccagtttgcaaggtgg gtcccatcaaggttcagtg gcagtggctctgggacaga tttcactctcaccatcagc agtctgcaacctgaagatt ttgcaacttactactgtca acagagtaacactacccccg tggacgttcggccaaggga ccaaggtggaaatcaaa - SEQ ID NO: 339 |
| 2H1 | ggattcaccttcagtgac tactac - SEQ ID NO: 302 attgatagtagtgctggt gccatt - SEQ ID NO: 303 gcgagagagcgtagagat ggccacaaaatctttgac tgt - SEQ ID NO: 304 cagaatattttatacagt tccaacaataagaactac - SEQ ID NO: 340 tggtcatct - SEQ ID NO: 306 cagcaatattacagtagt ccgtataat - SEQ ID NO: 307 | caggtgcagctggtggagt ctggggggagacttggtcaa gcctggagggtccctgaga ctctcctgtgtagcctctg gattcaccttcagtgacta ctacatgaactggatccgc ctgcctccagggaagggcc tggagtggatttcctacat tgatagtagtgctggtgcc atttactatgcagactctg tgaagggccgattcaccgt ctccagggacgacgccaag aactcactatttctgcaca tgaacagcctgagagccga tgacacggccgtttattac tgtgcgagagagcgtagag atggccacaaaatctttga ctgttgggggcccgggaacc ctggtcaccgtctcctca - SEQ ID NO: 341 | gacatcgtgatgacccagt ctccagactccctggctgt gtctctgggcgagagggcc accatcaactgcaagtcca gccagaatattttatacag ttccaacaataagaactac ttagcttggtaccagcaga aaacaggacagcctcctaa gttgctcattttctggtca tctacccgggaatccgggg tccctgaccgattcagtgg cagcgggtctgggacagat ttcactctcaccatcagca gcctgcaggctgaggatgt ggcagtttattactgtcag caatattacagtagtccgt ataattttggccgggggac cacactggagatcaaa - SEQ ID NO: 342 |
| 4E6 | ggattcacctttgatgat tatgcc - SEQ ID NO: 343 attagttggagtggtgtt accatg - SEQ ID NO: 344 gcaagagggatggaacc aatgcttttgatatc - SEQ ID NO: 345 cagagtgttttgtacaag tccaacaataagaactac - SEQ ID NO: 346 | gaagtgcagttggtggagt ctggggggagacttggtaca gcctggcaggtccctgaga ctctcctgtgcagcctctg gattcacctttgatgatta tgccatgcactgggtccgg caaggtccagggaagggc tggagtgggtctcaggcat tagttggagtggtgttacc atgggctatgcggactctg tgaagggccgattcaccat ttccagagacaacgccaag | gacatcgtgatgacccagt ctccagactccctggctgt gtctctgggcgagagggcc accatcaactgcaagtcca gccagagtgttttgtacaa gtccaacaataagaactac ttggattggtatcagcaga aaccaggacagcctcctaa gctgctcatttattgggca tcttcccgggaatccgggg tccctgaccgattcagtgg cagcgggtctgggacagat |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| | tgggcatct - SEQ ID NO: 347 cagcaatattatagtgtt ccgctcact - SEQ ID NO: 348 | aactccctgtacctgcgaa tgaacagtctgagagctga cgacacggccttctattac tgtgcaagaggggatggaa ccaatgcttttgatatctg gggccacgggacaatggtc accgtctcttca - SEQ ID NO: 349 | ttcactctgaccatcagca gcctgcaggctgaagatgt ggcagtttattactgtcag caatattatagtgttccgc tcactttcggcggagggac caaggtggagatcaaa SEQ ID NO: 350 |
| 4F7 | ggattcaccttcagtgac tactac - SEQ ID NO: 302 attgatagtagtgctggt gccatt - SEQ ID NO: 303 gcgagagagcgtagagat ggccacaaaatctttgac tgt - SEQ ID NO: 304 cagaatattttatacagt tccaacaataagaactac - SEQ ID NO: 340 tggtcatct - SEQ ID NO: 306 cagcaatattacagtagt ccgtataat - SEQ ID NO: 307 | caggtgcagctggtggagt ctgggggagacttggtcaa gcctggagggtccctgaga ctctcctgtgtagcctctg gattcaccttcagtgacta ctacatgaactggatccgc ctgcctccagggaagggcc tggagtggatttcatacat tgatagtagtgctggtgcc atttactatgcagactctg tgaagggccgattcaccgt ctccagggacgacgccaag aactcactatttctacaca tgaacaacctgagagccga tgacacggccgtttattac tgtgcgagagagcgtagag atggccacaaaatctttga ctgttggggcccgggaacc ctggtcaccgtctcctca - SEQ ID NO: 351 | gacatcgtgatgacccagt ctccagactccctggctgt gtctctgggcgagagggcc accatcaactgcaagtcca gccagaatattttatacag ttccaacaataagaactac ttagcttggtaccagcaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcag caatattacagtagtccgt ataattttggccggggggac cacactggagatcaaa - SEQ ID NO: 352 |
| 5A8 | ggattcaccttcagtgac tactac - SEQ ID NO: 302 attgatagtagtgctggt gccatt - SEQ ID NO: 303 gcgagagagcgtagagat ggccacaaaatctttgac tat - SEQ ID NO: 353 cagaatattttatacagt tccaacaataagaactac - SEQ ID NO: 340 tggtcatct - SEQ ID NO: 306 caccaatattacagtagt ccgtataat - SEQ ID NO: 354 | caggtgcagctggtggagt ctgggggagacttggtcaa gcctggagggtccctgaga ctctcctgtgtagcctctg gattcaccttcagtgacta ctacatgaactggatccgc ctgcctccagggaggggcc tggagtggatttcatacat tgatagtagtgctggtgcc atttactatgcagactctg tgaagggccgattcaccgt ctccagggacgacgccaag aagtcactatttctgtaca tgaacagcctgagagccga tgacacggccgtttattac tgtgcgagagagcgtagag atggccacaaaatctttga ctattgggcccgggaacc ctggtcaccgtctcctca - SEQ ID NO: 355 | gacatcgtgatgacccagt ctccagactccctggctgt gtctctgggcgagagggcc accatcaactgcaagtcca gccagaatattttatacag ttccaacaataagaactac ttagcttggtaccagcaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcac caatattacagtagtccgt ataattttggccggggggac cacactggagatcaaa - SEQ ID NO: 356 |
| 6E1 | ggattcacctttagcagc tttgcc - SEQ ID NO: 357 attagtggtagtggtggt agcaca - SEQ ID NO: 358 gcgaaagataaaaggaac tggaactacgggattgat tctttgatttc - SEQ ID NO: 359 cagagcattagcggctat - SEQ ID NO: 360 gctacatcc - SEQ ID NO: 361 catcagagtcacagtccc ccattcact - SEQ ID NO: 362 | gaggtgcagttgttggagt ctgggggaggcttggtaca gcctgggggggtccctgaga ctctcctgtgcagcctctg gattcacctttagcagctt tgccatgagctgggtccgc caggctccagggaaggggc tggagtgggtctcaggtat tagtggtagtggtggtagc acatactacgcagactccg tgaagggccggttcaccat ctccagagacaattccaag aacacgctgtatctgcaaa tgaacagcctgagagccga ggacacggccatatattac tgtgcgaaagataaaagga actggaactacgggattga ttcttttgatttctggggc caaggggacgatggtcaccg tctcttca - SEQ ID NO: 363 | gacatccagatgacccagt ctccgtcctccctgtctgc atctgtaggaggcagagtc accatcacttgccggacaa gtcagagcattagcggcta tttaaattggtatcagcag aaagcagggaaagccccta aactcctgatctatgctac atccaatttgcaaagtgg gtcccatcaaggttcactg gcagtggctctgggacaga tttcactctcaccatcagc agtctgcaacctgaagatt ttgcagcttactactgtca tcagagtcacagtcccccaa ttcacttcggccctggga ccaaagtggctttcaaa - SEQ ID NO: 364 |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 6H12 | ggattcaccttcagtagt tatgaa - SEQ ID NO: 365 attagtagtggtggtagt tctata - SEQ ID NO: 366 gcgagagtgggtggaagc tactactactcctacgct atggacgtc - SEQ ID NO: 367 caggacattagcagttat - SEQ ID NO: 368 gctgcatcc - SEQ ID NO: 317 caacagcctcataattcc ccattcagt - SEQ ID NO: 369 | gaggtgcagttggtggagt ctggggggaggcttggtcca gcctggagggtccctgaga ctctcctgtgcagcctctg gattcaccttcagtagtta tgaaatgaactgggtccgc caggctccagggaagggac tggagtgggtttcatacat tagtagtggtggtagttct ataaaatacgcagactctg tgaggggccgattcgcctt ctccagagacaacgccgag aactcagtgcatctgcaaa tgaacagcctgagagccga ggacacggctgtttattac tgtgcgagagtgggtggaa gctactactactcctacgc tatggacgtctggggccaa gggaccgcggtcaccgtct cctca - SEQ ID NO: 370 | gacatccagttgacccagt ctccatccttcctgtctgc atctgtaggagacagagtc accatcacttgctgggcca gtcaggacattagcagtta tttagcctggtatcagcaa aaaccagggaaagccccta agctcctgatctatgctgc atccactttgcaaagtggg gtcccatcaaggttcaccg gcagtggatctgggacaga attcactctcacaatcagc agcctgcagcctgaagatt ttgcaacttattactgtca acagcctcataattcccca ttcagtttcggccctggga ccaaagtggatgtcaaa - SEQ ID NO: 371 |
| 7A4 | ggattcaccttcagtgac tactac - SEQ ID NO: 302 attgatagtagtgctggt gccatt - SEQ ID NO: 303 gtgagagagcgtagagat ggccacaaaatctttgac tat - SEQ ID NO: 372 cagaatattttatacagt tccaacaataagaactac - SEQ ID NO: 340 tggtcatct - SEQ ID NO: 306 cagcaatattacagtagt ccgtataat - SEQ ID NO: 307 | caggtgcagctggtggagt ctggggggagacttggtcaa gcctggagggtccctgaga ctctcctgtgtagcctctg gattcaccttcagtgacta ctacatgaactggatccgc ctgcctccagggaagggcc tggagtggattttcatacat tgatagtagtgctggtgcc atttactatgcagactctg tgaagggccgattcaccgt ctccagggacgacgccaag aactcactatttctgcaca tgaacagcctgagagccga tgacacggccgtttattac tgtgtgagagagcgtagag atggccacaaaatctttga ctattggggcccgggaacc ctggtcaccgtctcctcc - SEQ ID NO: 373 | gacatcgtgatgacccagt ctccagactccctggctgt gtctctgggcgagagggcc accatcaactgcaagtcca gccagaatattttatacag ttccaacaataagaactac ttagcttggtaccagcaga aagcaggacagcctcctaa gttgctcattttctggtca tctattcgggaatccgggg tccctgaccgattcagtgg cagcgggtctgggacagat ttcactctcaccatcagca gcctgcaggctgaagatgt ggcagtttattattgtcag caatattacagtagtccgt ataattttggccggggggac cacactggagatcaaa - SEQ ID NO: 374 |
| 7E5 | ggattcacctttagtggc ttcgcc - SEQ ID NO: 321 attagtgggagtggtgat atcaca - SEQ ID NO: 322 gggaaagatccatataac tggaatcacggggtctac ggcatggacgtc - SEQ ID NO: 375 cagagcattagcacctat - SEQ ID NO: 376 ggtgcttcc - SEQ ID NO: 377 caacagagttacaatatc cctctcact - SEQ ID NO: 378 | gaggtgcagctgttggaat ctggggggaggcctgataca accggggggggtccctgaga ctctcctgtgcagcctctg gattcacctttagtggctt cgccatgagctgggtccgc caggctcctgggaaggggc tggagtgggtctcaggtat tagtgggagtggtgatatc acatactatggagactccg tgaagggccggttcaccat ttccagagacaattccaag agtacgctgtatctgcaaa tgaacagcctgagagacgc ggacacggccgtatattat tgtgggaaagatccatata actggaatcacggggtcta cggcatggacgtctggggc caagggaccacggtcaccg tctcctca - SEQ ID NO: 379 | gacatccagatgacccagt ctccatcctccctgtctgc atccgtaggagacagagtc accatcacttgccgggcaa gtcagagcattagcaccta tttaaattggtatcagcag aagccagggaaagcccccta agttcctgatctatggtgc ttccagtttgcaaagtggg gtcccatcaaggttcagtg gcagtggatctgggacaga tttctctctcaccatcagc agtctgcaccctggagact cgcaacttactactgtca acagagttacaatatccct ctcactttcggcggaggga ccaaggtggagatcaaa - SEQ ID NO: 380 |
| 7H8 | ggattcgcctttcacacc tatgac - SEQ ID NO: 381 gttgttggtagtggtatt aacaca - SEQ ID NO: 382 | gaggtgcagttgttggagt ctggggggaggcttggtaca gcctggggggtccctgaga ctctcctgtgcagcctctg gattcgcctttcacaccta tgacatgacctgggtccgc | gacatccagatgacccagt ctccttccaccctgtctgc atctgtaggagacagagtc accatcacttgccgggcca gtcagagcataagtaactg gttggcctggtatcagcag |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| | gcgaaagatagcagcagt tggttttccctccactac - SEQ ID NO: 383 cagagcataagtaactgg - SEQ ID NO: 384 aaggcgtct - SEQ ID NO: 385 caacagtatagaagttat gcgtacact - SEQ ID NO: 386 | caggctccagggaagggac tggagtgggtctcaggtgt tgttggtagtggtattaac acatactacgcagactccg tgaagggccggttcaccat ttccagagacaattccaag agcacgctctatctgcaaa tgaacagtctgagagccga ggacacggccgtatattac tgtgcgaaagatagcagca gttggttttccctccacta ctggggccagggaaccctg gtcaccgtctcctca - SEQ ID NO: 387 | aaaccagggaaagccccta aactcctgatctataaggc gtctagtttagaaagtggg gtcccatcaaggttcagcg gcagtggatctgggacaga tttcactctcaccatcagc agcctgcagcctgatgatt ttgcaagttattactgcca acagtatagaagttatgcg tacactttggccaggggga ccaagctggagatcaca - SEQ ID NO: 388 |
| 8A11 | ggattcaccttcagtgac tattac - SEQ ID NO: 389 attgatagtagtgctggt gccact - SEQ ID NO: 390 gcgagagagcgtagaagt ggccacaaaatctttgac tgt - SEQ ID NO: 391 cagaatatttttatacagt tccaacaataagaactac SEQ ID NO: 340 tggtcatct - SEQ ID NO: 306 cagcaatattacagtagt ccgtataat - SEQ ID NO: 307 | caggtgcagttggtggagt ctgggggagacttggtcaa gcctggagggtccctgaga ctctcctgtgtagcctctg gattcaccttcagtgacta ttacatgaactggatccgc ctgcctccagggaagggcc tggagtggatttcatacat tgatagtagtgctggtgcc acttactatgcagactctg tgaagggccgattcaccgt ctccagggacgacgccaag aattcactatttctgcaca tgaacagtctgagagccga ggacacggccgtttattac tgtgcgagagagcgtagaa gtggccacaaaatctttga ctgttggggcccgggaacc ctggtcaccgtctcctca - SEQ ID NO: 392 | gacatcgtgatgacccagt ctccagactccctggctgt gtctctgggcgagagggcc accatcaactgcaagtcca gccagaatatttttatacag ttccaacaataagaactac ttagcttggtaccagcaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcag caatattacagtagtccgt ataattttggccggggggac cacactggagatcaaa - SEQ ID NO: 352 |
| 8D10 | ggattcaccttcagtgac tactac - SEQ ID NO: 302 attgatagtagcgctggt gccatt - SEQ ID NO: 393 gcgagagagcgtagagat ggccacaaaatctttgac tat - SEQ ID NO: 353 cagaatatttttatacagt tccaacaataagaactac - SEQ ID NO: 340 tggtcatct - SEQ ID NO: 306 cagcaatattacagtagt ccgtataat - SEQ ID NO: 307 | caggtgcacctggtggagt ctgggggagacttggtcaa gcctggagggtccctgaga ctctcctgtgtagcctctg gattcaccttcagtgacta ctacatgaactggatccgc ctgcctccagggaagggcc tggagtggatttcatacat tgatagtagcgctggtgcc atttactatgcagactctg tgaagggccgattcaccgt ctccaggacgacgccaag aactcaatgtttctgcaca tgaacagcctgagagccga tgacacggccgtttattac tgtgcgagagagcgtagag atggccacaaaatctttga ctattggggcccgggaacc ctggtcaccgtctcctca - SEQ ID NO: 394 | gacatcgtgatgacccagt ctccagactccctggctgt gtctctgggcgagagggcc accatcaactgcaagtcca gccagaatatttttatacag ttccaacaataagaactac ttagcttggtaccagcaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcag caatattacagtagtccgt ataattttggccggggggac cacactggagatcaaa - SEQ ID NO: 352 |
| 9B4 | ggtttcaccttcagtgac tactac - SEQ ID NO: 395 attgatagtagtgctggt gccatt - SEQ ID NO: 303 gcgagagagcggagagaa ggccacaaaatctttgac ttt - SEQ ID NO: 396 cagaatatttttatacagt tccaacaataagaactac - SEQ ID NO: 340 tggtcatct - SEQ ID NO: 306 | caggtgcaactggtggagt ctgggggagacttggtcaa gcctggagggtccctgaga ctctcctgtgtagcctctg gtttcaccttcagtgacta ctacatgaactggatccgc ctgcctccagggaagggcc tggagtggatttcatacat tgatagtagtgctggtgcc atttactatgcagactctg tgaagggccgattcaccgt ctccagggacgacgccaag aactcattatttctgcaca tgaacagcctgagagccga tgacacggccgtttattac | gacatcgtgatgacccagt ctccagactccctggctct gtctctgggcgagagggcc accattaactgcaagtcca gccagaatatttttatacag ttccaacaataagaactac ttagcttgttaccaacaga aagcaggacagcctcctaa gttgctcattttctggtca tctacccgggaatccgggg tccctgaccgattcagtgg cagcgggtctgggacagat ttcactctcaccatcagca gcctgcaggctgaagatgt ggcagtttattactgtcag |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| | cagcaatattacagtagt ccgtataat - SEQ ID NO: 30 | tgtgcgagagagcggagag aaggccacaaaatctttga ctttttggggcccgggaacc ctggtcaccgtctcctca - SEQ ID NO: 397 | caatattacagtagtccgt ataatttcggccggggac cacactggagatcaaa - SEQ ID NO: 398 |
| 9G9 | ggcttcacctttcacaac tatgcc - SEQ ID NO: 399 attagtggtagtggtggt accgca - SEQ ID NO: 400 gcgaaagaccgattttg gagtgggtagagggttc gactcc - SEQ ID NO: 401 cagagcattggcagcttt - SEQ ID NO: 402 gctgcatcc - SEQ ID NO: 317 caacagagttacaatacc ccgctcact - SEQ ID NO: 403 | gaggtgcagctgttggagt ctggggggaggcttggtaca gcctggggggtccctgaga ctctcctgtgcagcctctg gcttcacctttcacaacta tgccatgagctgggtccgc caggctccagggaagggc tggagtgggtctcaggtat tagtggtagtggtggtacc gcatactacgcagactccg tgaagggccggttcaccat ttccagagacaattccaag aacacgctgtatctgcaaa tgaacagcctgagagccga cgacacggccttatattac tgtgcgaaagaccgatttt tggagtgggtagagggtt cgactcctggggccaggga accctggtcaccgtctcct ca - SEQ ID NO: 404 | gacatccagatgacccagt ctccatcctccctgtctgc atctgtaggagacagagtc accatcacttgccgggcaa gtcagagcattggcagctt tttaatttggtatcagcag aaaccagggaaagcccta agctcctgatttatgctgc atccagtttgcaaagtggg gtcccatcaaggttcagtg gcagtggatctgggacaga tttcactctcattatcagc agtctgcaacctgaagatt ttgcaacttattactgtca acagagttacaataccccg ctcactttcggcggaggga ccaaagtggagatcaaa - SEQ ID NO: 405 |
| 9H9 | ggattcaccttcagtagt tatgaa - SEQ ID NO: 365 attagtagtggtggtagt tccata - SEQ ID NO: 406 gcgagagtgggtggaagc tactactactcctacgct atggacgtc - SEQ ID NO: 367 caggacattagcagttat - SEQ ID NO: 368 gctgcatcc - SEQ ID NO: 317 caacagcctaataattac ccattcagt - SEQ ID NO: 407 | gaggtgcagttggtggagt ctggggggaggcttggtcca gcctggagggtccctgaga ctctcctgtgcagcctctg gattcaccttcagtagtta tgaaatgaactgggtccgc caggctccagggaagggac tggagtgggtttcatacat tagtagtggtggtagttcc ataaaatacgcagactctg tgaggggccgattcaccttt ctccagagacaacgccgag aactcagtgcatctgcaaa tgaacagcctgagaggcga ggacacggctgtttattac tgtgcgagagtgggtggaa gctactactactcctacgc tatggacgtctgggccaa gggaccgcggtcaccgtct cctca - SEQ ID NO: 408 | gacatccagttgacccagt ctccatccttcctgtctgc atctgtaggagacagagtc accatcacttgctgggcca gtcaggacattagcagtta tttagcctggtatcagcaa aaaccagggaaagcccta agctcctgatctatgctgc atccactttgcaaagtggg gtcccatcaaggttcagcg gcagtggatctgggacaga attcactctcacaatcagc agcctgcagcctgaagatt ttgcaacttattactgtca acagcctaataattaccca ttcagtttcggccctggga ccaaagtggatgtcaaa - SEQ ID NO: 409 |
| 11D12 | ggattcaccttcagtagt tatgaa - SEQ ID NO: 365 attagtagtggtggtagt tccata - SEQ ID NO: 406 gcgagagtgggtggaagc tactactactcctacgct atggacgtc - SEQ ID NO: 367 caggacattagcagttat - SEQ ID NO: 368 gctgcatcc - SEQ ID NO: 317 caacagcctaataattac ccattcagt - SEQ ID NO: 407 | gaggtgcagttggtggagt ctggggggaggcttggtcca gcctggagggtccctgaga ctctcctgtgcagcctctg gattcaccttcagtagtta tgaaatgaactgggtccgc caggctccagggaagggac tggagtgggtttcatacat tagtagtggtggtagttcc ataaaatacgcagactctg tgaggggccgattcaccttt ctccagagacaacgccgag aactcagtgtttctccaaa tgaacagcctgagaggcga ggacacggctgtttattac tgtgcgagagtggggaa gctactactactcctacgc tatggacgtctgggccaa gggaccgcggtcaccgtct cctca - SEQ ID NO: 410 | gacatccagttgacccagt ctccatccttcctgtctgc atctgtaggagacagagtc accatcacttgctgggcca gtcaggacattagcagtta tttagcctggtatcagcaa aaaccagggaaagcccta agctcctgatctatgctgc atccactttacaaagtggg gtcccatcaaggttcagcg gcagtggatctgggacaga attcactctcacaatcagc agcctgcagcctgaagatt ttgcaacttattactgtca acagcctaataattaccca ttcagtttcggccctggga ccaaagtggatgtcaaa - SEQ ID NO: 411 |

TABLE 5-continued

Nucleotide sequences of antibody complementary determining regions,
variable heavy chain domains, and variable light chain domains.

| Antibody Clone | Complementarity Determining Region (CDR) sequences | Variable Heavy Chain (VH) Sequence | Variable Light Chain (VL) Sequence |
|---|---|---|---|
| 14F5 | ggattcacctttagcagc tttgcc - SEQ ID NO: 357 attagtgctagtggcggt accaca - SEQ ID NO: 412 gcgaaagaccgattttg gagtgggtagagggttc gacccc - SEQ ID NO: 413 cagagcattggcaggttt - SEQ ID NO: 414 gctacatcc - SEQ ID NO: 361 caacagagttacattacc ccgctcact - SEQ ID NO: 415 | gaggtgcagttgttggagt ctggggggaggcttggtaca gcctggggggtccctgaga ctctcctgtgcagtctctg gattcacctttagcagctt tgccatgagctgggtccgc caggctccagggaagggcc tggagtgggtctcgggtat tagtgctagtggcggtacc acaaattacgcagactccg tgaaaggccggttccat ctccagagacaattccaag aacacgctctatctgcaaa tgagcagcctgagagccga ggacacggccgaatattac tgtgcgaaagaccgatttt tggagtgggtagaggggtt cgacccctgggggccaggga atcctggtcaccgtctccc ca - SEQ ID NO: 416 | gacatccagatgacccagt ctccatcctccctgtctgc atctgtaggagacagagtc accatcacttgccgggcaa gtcagagcattggcaggtt tttaatttggtatcagcag aaaccagggaaagccccta aactcctgctttatgctac atccagtttgcaaagtggg gtcccagcaaggttcactg gcagtgggtctgggacaga tttcactctcaccatcggc agtctgcaacctgaagatt ttgcaacttactactgtca acagagttacattacccccg ctcactttcggcggaggga ccaaggtggagatcaaa - SEQ ID NO: 417 |
| 15C10 | ggattcacctttagcagc tttgcc - SEQ ID NO: 357 attagtgctagtggcggt accaca - SEQ ID NO: 412 gcgaaagaccgattttg gagtgggtagagggttc gacccc - SEQ ID NO: 413 cagagcattggcaggttt - SEQ ID NO: 414 gctacatcc - SEQ ID NO: 361 caacagagttacattacc ccgctcact - SEQ ID NO: 415 | gaggtgcagttgttggagt ctggggggaggcttggtaca gcctggggggtccctgaga ctctcctgtgcagcctctg gattcacctttagcagctt tgccatgagctgggtccgc caggctccagggaagggcc tggagtgggtctcgggtat tagtgctagtggcggtacc acaaattacgcagactccg tgaaaggccggttccat ctccagagacaattccaag aacacgctctatctgcaaa tgagcagcctgagagccga ggacacggccgaatattac tgtgcgaaagaccgatttt tggagtgggtagaggggtt cgacccctgggggccaggga atcctggtcaccgtctccc ca - SEQ ID NO: 418 | gacatccagatgacccagt ctccatcctccctgtctgc atctgtaggagacagagtc accatcacttgccgggcaa gtcagagcattggcaggtt tttaatttggtatcagcag aaaccagggaaagccccta agctcctgctctatgctac atccagtttgcaaagtggg gtcccagcaaggttcactg gcagtgggtctgggacaga tttcactctcaccatcggc agtctgcaacctgaagatt ttgcaacttactactgtca acagagttacattacccccg ctcactttcggcggaggga ccaaggtggagatcaaa - SEQ ID NO: 419 |

TABLE 6

Nucleotide sequences of antibody framework regions.

| Antibody Clone | Sequence |
|---|---|
| 1E2 | HFR1 - caggtgcagctggtggagtctggggggagacttggtcaagcctggagggtccctgagact ctcctgtgtagcctcg - SEQ ID NO: 420 HFR2 - atgaactggatccgcctgcctccagggaagggcctggagtgggtttcatac - SEQ ID NO: 421 HFR3 - tactatgcagactctgtgaggggccgattcaccgtctccagggacgacgccaagaattc actatttctgcacatgaacagcctgagagccgatgacacggccgtttattactgt - SEQ ID NO: 422 HFR4 - tggggcccgggaaccctggtcaccgtctcttca - SEQ ID NO: 423 LFR1 - gacatcgtgatgacccagtctccagactccctggctgtgtctctgggcgagagggccac catcaactgcaagtccagc - SEQ ID NO: 424 LFR2 - ttagcttggtaccagcagaaagcaggacagcctcctaagttgctcattttc - SEQ ID NO: 425 LFR3 - acccgggaatccggggtccctgaccgattcagtggcagcgggtctgggacagatttcac tctcaccatcaacagcctgcaggctgaagatgtggcagtttattactgt - SEQ ID NO: 426 LFR4 - tttggccggggggaccacactggagatcaaa - SEQ ID NO: 427 |

TABLE 6-continued

Nucleotide sequences of antibody framework regions.

| Antibody Clone | Sequence |
|---|---|
| 1H10 | HFR1 - caggtgcacctggtggagtctggggggagacttggtcaagcctggagggtccctgagact ctcctgtgtagcctct - SEQ ID NO: 428 <br> HFR2 - atgaactggatccgtatgcctccagggaagggcctggagtggatttcatac - SEQ ID NO: 429 <br> HFR3 - tactatgcagactctgtgaagggccgattcaccgtctccagggacgacgccaagaactc actgtttctacacatgaacaacctgagagccgatgacacggccgtttattactgt - SEQ ID NO: 430 <br> HFR4 - tggggcccgggaaccctggtcaccgtctcctca - SEQ ID NO: 431 <br> LFR1 - gacatcgtgatgacccagtctccagactccctggctgtgtctctgggcgagagggccac catcaactgcaagtccagc - SEQ ID NO: 424 <br> LFR2 - ttagcttggtaccagcagaaagcaggacagcctcctaagttgctcattttc - SEQ ID NO: 425 <br> LFR3 - acccgggaatccggggtccctgaccgattcagtggcagcgggtctgggacagatttcac tctcaccatcagcagcctgcaggctgaagatgtggcagtttattactgt - SEQ ID NO: 432 <br> LFR4 - tttggccggggggaccacactggagatcaaa - SEQ ID NO: 427 |
| 2A10 | HFR1 - gaggtgcagctggtgcagtctggagcagaggtgaaaaagcccggggagtctctgaagat ctcctgtaagggttct - SEQ ID NO: 433 <br> HFR2 - atcggctgggtgcgccagatgcccgggaaaggcctggagtggatggggatc - SEQ ID NO: 434 <br> HFR3 - agatacagcccgtccttccaaggccaggtcaccatctctagccgacaagtccatcagtac cgcctatttgcagtggagcagcctgaaggcctcggacaccgccatgtattactgt - SEQ ID NO: 435 <br> HFR4 - tggggccagggaaccctggtcaccgtctcctca - SEQ ID NO: 436 <br> LFR1 - gacatccagatgacccagtctccatcctccctgtctgcatctgtcggagacagactcac catcacttgccgggcaagt - SEQ ID NO: 437 <br> LFR2 - ttaaattggtatcaacagaacccagggaaagcccctaaggtcctgatttat - SEQ ID NO: 438 <br> LFR3 - agtttggaaagtggggtcccatcaaggttcagtggcagtggatctgggacagatttcac tctcaccatcagcagtctgcaacctgaagattttgcaacttactactgt - SEQ ID NO: 439 <br> LFR4 - ttcggccaagggaccaaggtggaaatcaaa - SEQ ID NO: 440 |
| 2B9 | HFR1 - gaggtgcagcttttggagtcggggggaggcttggcacagccggggaagtccctgagact ctcctgtgcagcctct - SEQ ID NO: 441 <br> HFR2 - atgagctgggtccgccaggctcctgggaaggggctggagtgggtctcaggt - SEQ ID NO: 442 <br> HFR3 - tactatgcagactccgtgaagggccggttcaccatttccagagacaattccaagagtac gctgtatcttcaaatgaacagcctgggagccgaggacacggccgtgtattactgt - SEQ ID NO: 443 <br> HFR4 - tggggccaagggaccacggtcaccgtctcctca - SEQ ID NO: 444 <br> LFR1 - gacatccagatgacccagtctccatcctccctgtctgcatctgtaggagacagagtcac catcacttgccgggcaagt - SEQ ID NO: 445 <br> LFR2 - ttaaattggtatcagcagaaaccagggaaagcccctaaattcctgatttat - SEQ ID NO: 446 <br> LFR3 - agtttgcaaagtggggtcccatcaaggttcagtggcagtggatgtgggantgatttcac tctcaccatcagcagtctgcaacgtgaagatttcgcagcttactactgt - SEQ ID NO: 447 <br> LFR4 - ttcgggggggggaccaaggtggagatcaaac - SEQ ID NO: 448 |
| 2F7 | HFR1 - caggtgcagctggtggagtctggggggaggcttggtcaagcctggagggtccctgagact ctcctgcgtagcctct - SEQ ID NO: 449 <br> HFR2 - atgaactggatccgcctgcctccagggaggggggctgcagtggatttcatac - SEQ ID NO: 450 <br> HFR3 - tactacgcagactctgtgaagggccgattcaccgtctccagggacgacgccaagaattc actttatctgcaaatgaacagcctgagagccgatgacacggccgtttattactgt - SEQ ID NO: 451 <br> HFR4 - tggggccagggaaccctggtcaccgtctcctca - SEQ ID NO: 436 |

TABLE 6-continued

---

Nucleotide sequences of antibody framework regions.

| Antibody Clone | Sequence |
|---|---|
| | LFR1 - gacatcgtgatgacccagtctccagactccctggctgtgtctctgggcgagagggccac catcaactgcaagtccagc - SEQ ID NO: 424<br>LFR2 - ttaggttggtaccagcagaaagcaggacagcctcctaaactgctcatttac - SEQ ID NO: 452<br>LFR3 - acccggaattccggggtccctgaccgcttcagtggcagcgggtctgggacagatttcac tctcaccatcagcagcctgcaggctgaggatgtggcagtttattactgt - SEQ ID NO: 453<br>LFR4 - tttggccaggggaccaacctggagatcaaa - SEQ ID NO: 454 |
| 2F11 | HFR1 - gaggtgcagctggtgcagtctggagcagaggtgaaaaagcccggggagtctctgaagat ctcctgtaagggttct - SEQ ID NO: 433<br>HFR2 - atcggctgggtgcgccagatgcccgggaaaggcctggagtggatggggatc - SEQ ID NO: 434<br>HFR3 - agatacagcccgtccttccaaggccaggtcaccctctcagccgacaagtccatcagtac cgcctacctacagtggaacagcctgaaggcctcggacaccgccatgtattactgt - SEQ ID NO: 455<br>HFR4 - tggggccagggaaccctggtcaccgtcgcctcat - SEQ ID NO: 456<br>LFR1 - gacatccagatgacccagtctccatcctccctgtctgcatctgtaggagacagagtcac catcacttgccgggcaagt - SEQ ID NO: 445<br>LFR2 - ttaaattggtatcagcagaaaccagggacagcccctaaactcctgatttat - SEQ ID NO: 457<br>LFR3 - agtttgcaaggtggggtcccatcaaggttcagtggcagtggctctgggacagatttcac tctcaccatcagcagtctgcaacctgaagattttgcaacttactactgt - SEQ ID NO: 458<br>LFR4 - ttcggccaagggaccaaggtggaaatcaaa - SEQ ID NO: 440 |
| 2H1 | HFR1 - caggtgcagctggtggagtctgggggagacttggtcaagcctggagggtccctgagact ctcctgtgtagcctct - SEQ ID NO: 459<br>HFR2 - atgaactggatccgcctgcctccagggaagggcctggagtggatttcctac - SEQ ID NO: 460<br>HFR3 - tactatgcagactctgtgaagggccgattcaccgtctccagggacgacgccaagaactc actatttctgcacatgaacagcctgagagccgatgacacggccgtttattactgt - SEQ ID NO: 461<br>HFR4 - tggggcccgggaaccctggtcaccgtctcctca - SEQ ID NO: 431<br>LFR1 - gacatcgtgatgacccagtctccagactccctggctgtgtctctgggcgagagggccac catcaactgcaagtccagc - SEQ ID NO: 424<br>LFR2 - ttagcttggtaccagcagaaaacaggacagcctcctaagttgctcattttc - SEQ ID NO: 462<br>LFR3 - acccgggaatccggggtccctgaccgattcagtggcagcgggtctgggacagatttcac tctcaccatcagcagcctgcaggctgaggatgtggcagtttattactgt - SEQ ID NO: 463<br>LFR4 - tttggccggggggaccacactggagatcaaa - SEQ ID NO: 427 |
| 4E6 | HFR1 - gaagtgcagttggtggagtctgggggagacttggtacagcctggcaggtccctgagact ctcctgtgcagcctct - SEQ ID NO: 464<br>HFR2 - atgcactgggtccggcaaggtccagggaagggcctggagtgggtctcaggc - SEQ ID NO: 465<br>HFR3 - ggctatgcggactctgtgaagggccgattcaccatttccagagacaacgccaagaactc cctgtacctgcgaatgaacagtctgagagctgacgacacggccttctattactgt - SEQ ID NO: 466<br>HFR4 - tggggccacgggacaatggtcaccgtctcttca - SEQ ID NO: 467<br>LFR1 - gacatcgtgatgacccagtctccagactccctggctgtgtctctgggcgagagggccac catcaactgcaagtccagc - SEQ ID NO: 424<br>LFR2 - ttggattggtatcagcagaaaccaggacagcctcctaagctgctcatttat - SEQ ID NO: 468<br>LFR3 - tcccgggaatccggggtccctgaccgattcagtggcagcgggtctgggacagatttcac tctgaccatcagcagcctgcaggctgaagatgtggcagtttattactgt - SEQ ID NO: 469<br>LFR4 - ttcggcggagggaccaaggtggagatcaaa - SEQ ID NO: 470 |

TABLE 6-continued

Nucleotide sequences of antibody framework regions.

| Antibody Clone | Sequence |
| --- | --- |
| 4F7 | HFR1 - caggtgcagctggtggagtctggggggagacttggtcaagcctggagggtccctgagact ctcctgtgtagcctct - SEQ ID NO: 459<br>HFR2 - atgaactggatccgcctgcctccagggaagggcctggagtggatttcatac - SEQ ID NO: 471<br>HFR3 - tactatgcagactctgtgaagggccgattcaccgtctccagggacgacgccaagaactc actatttctacacatgaacaacctgagagccgatgacacggccgtttattactgt - SEQ ID NO: 472<br>HFR4 - tggggcccgggaaccctggtcaccgtctcctca - SEQ ID NO: 431<br>LFR1 - gacatcgtgatgacccagtctccagactccctggctgtgtctctgggcgagagggccac catcaactgcaagtccagc - SEQ ID NO: 424<br>LFR2 - ttagcttggtaccagcagaaagcaggacagcctcctaagttgctcattttc - SEQ ID NO: 425<br>LFR3 - acccgggaatccggggtccctgaccgattcagtggcagcgggtctgggacagatttcac tctcaccatcagcagcctgcaggctgaagatgtggcagtttattactgt - SEQ ID NO: 432<br>LFR4 - tttggccggggggaccacactggagatcaaa - SEQ ID NO: 427 |
| 5A8 | HFR1 - caggtgcagctggtggagtctggggggagacttggtcaagcctggagggtccctgagact ctcctgtgtagcctct - SEQ ID NO: 459<br>HFR2 - atgaactggatccgcctgcctccagggaggggcctggagtggatttcatac - SEQ ID NO: 473<br>HFR3 - tactatgcagactctgtgaagggccgattcaccgtctccagggacgacgccaagaagtc actatttctgtacatgaacagcctgagagccgatgacacggccgtttattactgt - SEQ ID NO: 474<br>HFR4 - tggggcccgggaaccctggtcaccgtctcctca - SEQ ID NO: 431<br>LFR1 - gacatcgtgatgacccagtctccagactccctggctgtgtctctgggcgagagggccac catcaactgcaagtccagc - SEQ ID NO: 424<br>LFR2 - ttagcttggtaccagcagaaagcaggacagcctcctaagttgctcattttc - SEQ ID NO: 425<br>LFR3 - acccgggaatccggggtccctgaccgattcagtggcagcgggtctgggacagatttcac tctcaccatcagcagcctgcaggctgaagatgtggcagtttattactgt - SEQ ID NO: 432<br>LFR4 - tttggccggggggaccacactggagatcaaa - SEQ ID NO: 427 |
| 6E1 | HFR1 - gaggtgcagttgttggagtctggggggaggcttggtacagcctggggggtccctgagact ctcctgtgcagcctct - SEQ ID NO: 475<br>HFR2 - atgagctgggtccgccaggctccagggaaggggctggagtgggtctcaggt - SEQ ID NO: 476<br>HFR3 - tactacgcagactccgtgaagggccggttcaccatctccagagacaattccaagaacac gctgtatctgcaaatgaacagcctgagagccgaggacacggccatatattactgt - SEQ ID NO: 477<br>HFR4 - tggggccaagggacgatggtcaccgtctcttca - SEQ ID NO: 478<br>LFR1 - gacatccagatgacccagtctccgtcctccctgtctgcatctgtaggaggcagagtcac catcacttgccggacaagt - SEQ ID NO: 479<br>LFR2 - ttaaattggtatcagcagaaagcagggaaagcccctaaactcctgatctat - SEQ ID NO: 480<br>LFR3 - aatttgcaaagtggggtcccatcaaggttcactggcagtggctctgggacagatttcac tctcaccatcagcagtctgcaacctgaagattttgcagcttactactgt - SEQ ID NO: 481<br>LFR4 - ttcggccctgggaccaaagtggctttcaaa - SEQ ID NO: 482 |
| 6H12 | HFR1 - gaggtgcagttggtggagtctggggggaggcttggtccagcctggagggtccctgagact ctcctgtgcagcctct - SEQ ID NO: 483<br>HFR2 - atgaactgggtccgccaggctccagggaagggactggagtgggtttcatac - SEQ ID NO: 484<br>HFR3 - aaatacgcagactctgtgaggggccgattcgccttctccagagacaacgccgagaactc agtgcatctgcaaatgaacagcctgagagccgaggacacggctgtttattactgt - SEQ ID NO: 485<br>HFR4 - tggggccaagggaccgcggtcaccgtctcctca - SEQ ID NO: 486 |

TABLE 6-continued

| Nucleotide sequences of antibody framework regions. |
| --- |

| Antibody Clone | Sequence |
| --- | --- |
|  | LFR1 - gacatccagttgacccagtctccatccttcctgtctgcatctgtaggagacagagtcac catcacttgctgggccagt - SEQ ID NO: 487<br>LFR2 - ttagcctggtatcagcaaaaaccagggaaagcccctaagctcctgatctat - SEQ ID NO: 488<br>LFR3 - actttgcaaagtggggtcccatcaaggttcaccggcagtggatctgggacagaattcac tctcacaatcagcagcctgcagcctgaagattttgcaacttattactgt - SEQ ID NO: 489<br>LFR4 - ttcggccctgggaccaaagtggatgtcaaa - SEQ ID NO: 490 |
| 7A4 | HFR1 - caggtgcagctggtggagtctgggggagacttggtcaagcctggagggtccctgagact ctcctgtgtagcctct - SEQ ID NO: 459<br>HFR2 - atgaactggatccgcctgcctccagggaagggcctggagtggatttcatac - SEQ ID NO: 471<br>HFR3 - tactatgcagactctgtgaagggccgattcaccgtctccagggacgacgccaagaactc actatttctgcacatgaacagcctgagagccgatgacacggccgtttattactgt - SEQ ID NO: 461<br>HFR4 - tggggcccgggaaccctggtcaccgtctcctcc - SEQ ID NO: 491<br>LFR1 - gacatcgtgatgacccagtctccagactccctggctgtgtctctgggcgagagggccac catcaactgcaagtccagc - SEQ ID NO: 424<br>LFR2 - ttagcttggtaccagcagaaagcaggacagcctcctaagttgctcattttc - SEQ ID NO: 425<br>LFR3 - attcgggaatccggggtccctgaccgattcagtggcagcgggtctgggacagatttcac tctcaccatcagcagcctgcaggctgaagatgtggcagtttattattgt - SEQ ID NO: 492<br>LFR4 - tttggccggggggaccacactggagatcaaa - SEQ ID NO: 427 |
| 7E5 | HFR1 - gaggtgcagctgttggaatctggggggaggcctgatacaaccggggggtccctgagact ctcctgtgcagcctct - SEQ ID NO: 493<br>HFR2 - atgagctgggtccgccaggctcctgggaaggggctggagtgggtctcaggt - SEQ ID NO: 442<br>HFR3 - tactatggagactccgtgaagggccggttcaccatttccagagacaattccaagagtac gctgtatctgcaaatgaacagcctgagagacgcggacacggccgtatattattgt - SEQ ID NO: 494<br>HFR4 - tggggccaagggaccacggtcaccgtctcctca - SEQ ID NO: 444<br>LFR1 - gacatccagatgacccagtctccatcctccctgtctgcatccgtaggagacagagtcac catcacttgccgggcaagt - SEQ ID NO: 495<br>LFR2 - ttaaattggtatcagcagaaagccagggaaagcccctaagttcctgatttat - SEQ ID NO: 496<br>LFR3 - agtttgcaaagtggggtcccatcaaggttcagtggcagtggatgtgggacagatttctc tctcaccatcagcagtntgcaccctggagacttcgcaacttactactgt - SEQ ID NO: 497<br>LFR4 - ttcggcggagggaccaaggtggagatcaaa - SEQ ID NO: 470 |
| 7H8 | HFR1 - gaggtgcagttgttggagtctggggggaggcttggtacagcctggggggtccctgagact ctcctgtgcagcctct - SEQ ID NO: 475<br>HFR2 - atgacctgggtccgccaggctccagggaagggactggagtgggtctcaggt - SEQ ID NO: 498<br>HFR3 - tactacgcagactccgtgaagggccggttcaccatttccagagacaattccaagagcac gctctatctgcaaatgaacagtctgagagccgaggacacggccgtatattactgt - SEQ ID NO: 499<br>HFR4 - tggggccagggaaccctggtcaccgtctcctca - SEQ ID NO: 436<br>LFR1 - gacatccagatgacccagtctccttccaccctgtctgcatctgtaggagacagagtcac catcacttgccgggccagt - SEQ ID NO: 500<br>LFR2 - ttggcctggtatcagcagaaaccagggaaagcccctaaactcctgatctat - SEQ ID NO: 501<br>LFR3 - agtttagaaagtggggtcccatcaaggttcagcggcagtggatctgggacagatttcac tctcaccatcagcagcctgcagcctgatgattttgcaagttattactgc - SEQ ID NO: 502<br>LFR4 - tttggccaggggaccaagctggagatcaca - SEQ ID NO: 503 |

TABLE 6-continued

| Antibody Clone | Sequence |
| --- | --- |

Nucleotide sequences of antibody framework regions.

8A11    HFR1 -
caggtgcagttggtggagtctggggggagacttggtcaagcctggagggtccctgagact
ctcctgtgtagcctct - SEQ ID NO: 504
HFR2 - atgaactggatccgcctgcctccagggaagggcctggagtggatttcatac -
SEQ ID NO: 471
HFR3 -
tactatgcagactctgtgaagggccgattcaccgtctccagggacgacgccaagaattc
actatttctgcacatgaacagtctgagagccgaggacacggccgtttattactgt -
SEQ ID NO: 505
HFR4 - tggggcccgggaaccctggtcaccgtctcctca - SEQ ID NO: 431
LFR1 -
gacatcgtgatgacccagtctccagactccctggctgtgtctctgggcgagagggccac
catcaactgcaagtccagc - SEQ ID NO: 424
LFR2 - ttagcttggtaccagcagaaagcaggacagcctcctaagttgctcattttc -
SEQ ID NO: 425
LFR3 -
acccgggaatccggggtccctgaccgattcagtggcagcgggtctgggacagatttcac
tctcaccatcagcagcctgcaggctgaagatgtggcagtttattactgt - SEQ ID
NO: 432
LFR4 - tttggccggggggaccacactggagatcaaa - SEQ ID NO: 427

8D10    HFR1 -
caggtgcacctggtggagtctggggggagacttggtcaagcctggagggtccctgagact
ctcctgtgtagcctct - SEQ ID NO: 428
HFR2 - atgaactggatccgcctgcctccagggaagggcctggagtggatttcatac -
SEQ ID NO: 471
HFR3 -
tactatgcagactctgtgaagggccgattcaccgtctccagggacgacgccaagaactc
aatgtttctgcacatgaacagcctgagagccgatgacacggccgtttattactgt -
SEQ ID NO: 506
HFR4 - tggggcccgggaaccctggtcaccgtctcctca - SEQ ID NO: 431
LFR1 -
gacatcgtgatgacccagtctccagactccctggctgtgtctctgggcgagagggccac
catcaactgcaagtccagc - SEQ ID NO: 424
LFR2 - ttagcttggtaccagcagaaagcaggacagcctcctaagttgctcattttc -
SEQ ID NO: 425
LFR3 -
acccgggaatccggggtccctgaccgattcagtggcagcgggtctgggacagatttcac
tctcaccatcagcagcctgcaggctgaagatgtggcagtttattactgt - SEQ ID
NO: 432
LFR4 - tttggccggggggaccacactggagatcaaa - SEQ ID NO: 427

9B4    HFR1 -
caggtgcaactggtggagtctggggggagacttggtcaagcctggagggtccctgagact
ctcctgtgtagcctct - SEQ ID NO: 507
HFR2 - atgaactggatccgcctgcctccagggaagggcctggagtggatttcatac -
SEQ ID NO: 471
HFR3 -
tactatgcagactctgtgaaggggcgattcaccgtctccagggacgacgccaagaactc
attatttctgcacatgaacagcctgagagccgatgacacggccgtttattactgt -
SEQ ID NO: 508
HFR4 - tggggcccgggaaccctggtcaccgtctcctca - SEQ ID NO: 431
LFR1 -
gacatcgtgatgacccagtctccagactccctggctctgtctctgggcgagagggccac
cattaactgcaagtccagc - SEQ ID NO: 509
LFR2 - ttagcttgttaccaacagaaagcaggacagcctcctaagttgctcattttc -
SEQ ID NO: 510
LFR3 -
acccgggaatccggggtccctgaccgattcagtggcagcgggtctgggacagatttcac
tctcaccatcagcagcctgcaggctgaagatgtggcagtttattactgt - SEQ ID
NO: 432
LFR4 - ttcggccggggggaccacactggagatcaaa - SEQ ID NO: 511

9G9    HFR1 -
gaggtgcagctgttggagtctggggggaggcttggtacagcctggggggtccctgagact
ctcctgtgcagcctct - SEQ ID NO: 512
HFR2 - atgagctgggtccgccaggctccagggaaggggctggagtgggtctcaggt -
SEQ ID NO: 476
HFR3 -
tactacgcagactccgtgaagggccggttcaccatttccagagacaattccaagaacac
gctgtatctgcaaatgaacagcctgagagccgacgacacggccttatattactgt -
SEQ ID NO: 513
HFR4 - tggggccagggaaccctggtcaccgtctcctca - SEQ ID NO: 436

TABLE 6-continued

Nucleotide sequences of antibody framework regions.

| Antibody Clone | Sequence |
|---|---|
| | LFR1 - gacatccagatgacccagtctccatcctccctgtctgcatctgtaggagacagagtcac catcacttgccgggcaagt - SEQ ID NO: 445<br>LFR2 - ttaatttggtatcagcagaaaccagggaaagcccctaagctcctgatttat - SEQ ID NO: 514<br>LFR3 - agtttgcaaagtgggggtcccatcaaggttcagtggcagtggatctgggacagatttcac tctcattatcagcagtctgcaacctgaagattttgcaacttattactgt - SEQ ID NO: 515<br>LFR4 - ttcggcggagggaccaaagtggagatcaaa - SEQ ID NO: 516 |
| 9H9 | HFR1 - gaggtgcagttggtggagtctggggggaggcttggtccagcctggagggtccctgagact ctcctgtgcagcctct - SEQ ID NO: 483<br>HFR2 - atgaactgggtccgccaggctccagggaagggactggagtgggtttcatac - SEQ ID NO: 484<br>HFR3 - aaatacgcagactctgtgaggggccgattcaccttctccagagacaacgccgagaactc agtgcatctgcaaatgaacagcctgagaggcgaggacacggctgtttattactgt - SEQ ID NO: 517<br>HFR4 - tggggccaagggaccgcggtcaccgtctcctca - SEQ ID NO: 486<br>LFR1 - gacatccagttgacccagtctccatccttcctgtctgcatctgtaggagacagagtcac catcacttgctgggccagt - SEQ ID NO: 487<br>LFR2 - ttagcctggtatcagcaaaaaccagggaaagcccctaagctcctgatttat - SEQ ID NO: 518<br>LFR3 - actttgcaaagtgggggtcccatcaaggttcagcggcagtggatntgggacagaattcac tctcacaatcagcagcttgcagcgtgaagattttgcaacttattactgt - SEQ ID NO: 519<br>LFR4 - ttcggccctgggaccaaagtggatgtcaaa - SEQ ID NO: 490 |
| 11D12 | HFR1 - gaggtgcagttggtggagtctggggggaggcttggtccagcctggagggtccctgagact ctcctgtgcagcctct - SEQ ID NO: 483<br>HFR2 - atgaactgggtccgccaggctccagggaagggactggagtgggtttcatac - SEQ ID NO: 484<br>HFR3 - aaatacgcagactctgtgaggggccgattcaccttctccagagacaacgccgagaactc agtgtttctccaaatgaacagcctgagaggcgaggacacggctgtttattactgt - SEQ ID NO: 520<br>HFR4 - tggggccaagggaccgcggtcaccgtctcctca - SEQ ID NO: 486<br>LFR1 - gacatccagttgacccagtctccatccttcctgtctgcatctgtaggagacagagtcac catcacttgctgggccagt - SEQ ID NO: 487<br>LFR2 - ttagcctggtatcagcaaaaaccagggaaagcccctaagctcctgatctat - SEQ ID NO: 488<br>LFR3 - actttacaaagtgggggtcccatcaaggttcagcggcagtggatctgggacagaattcac tctcacaatcagcagcctgcagcctgaagattttgcaacttattactgt - SEQ ID NO: 521<br>LFR4 - ttcggccctgggaccaaagtggatgtcaaa - SEQ ID NO: 490 |
| 14F5 | HFR1 - gaggtgcagttgttggagtctggggggaggcttggtacagcctgggggggtccctgagact ctcctgtgcagtctct - SEQ ID NO: 522<br>HFR2 - atgagctgggtccgccaggctccagggaagggcctggagtgggtctcgggt - SEQ ID NO: 523<br>HFR3 - aattacgcagactccgtgaaaggccggttcaccatctccagagacaattccaagaacac gctctatctgcaaatgagcagcctgagagccgaggacacggccgaatattactgt - SEQ ID NO: 524<br>HFR4 - tggggccagggaatcctggtcaccgtctccca - SEQ ID NO: 525<br>LFR1 - gacatccagatgacccagtctccatcctccctgtctgcatctgtaggagacagagtcac catcacttgccgggcaagt - SEQ ID NO: 445<br>LFR2 - ttaatttggtatcagcagaaaccagggaaagcccctaaactcctgctttat - SEQ ID NO: 526<br>LFR3 - agtttgcaaagtgggggtcccagcaaggttcactggcagtgggtctgggacagatttcac tctcaccatcggcagtctgcaacctgaagattttgcaacttactactgt - SEQ ID NO: 527<br>LFR4 - ttcggcggagggaccaaggtggagatcaaa - SEQ ID NO: 470 |

TABLE 6-continued

```
              Nucleotide sequences of antibody framework regions.

Antibody
Clone     Sequence

15C10     HFR1 -
          gaggtgcagttgttggagtctggggggaggcttggtacagcctggggggtccctgagact
          ctcctgtgcagcctct - SEQ ID NO: 475
          HFR2 - atgagctgggtccgccaggctccagggaagggcctggagtgggtctcgggt -
          SEQ ID NO: 523
          HFR3 -
          aattacgcagactccgtgaaaggccggttcaccatctccagagacaattccaagaacac
          gctctatctgcaaatgagcagcctgagagccgaggacacggccgaatattactgt -
          SEQ ID NO: 524
          HFR4 - tggggccagggaatcctggtcaccgtctcccca - SEQ ID NO: 525
          LFR1 -
          gacatccagatgacccagtctccatcctccctgtctgcatctgtaggagacagagtcac
          catcacttgccgggcaagt - SEQ ID NO: 445
          LFR2 - ttaatttggtatcagcagaaaccagggaaagcccctaagctcctgctctat -
          SEQ ID NO: 528
          LFR3 -
          agtttgcaaagtggggtcccagccaaggttcactggcagtgggtctgggacagatttcac
          tctcaccatcggcagtctgcaacctgaagattttgcaacttactactgt - SEQ ID
          NO: 527
          LFR4 - ttcggcggagggaccaaggtggagatcaaa - SEQ ID NO: 470
```

Sequences

```
BK virus VP1 protein Accession No. P03088
                                    SEQ ID NO: 529
MAPTKRKGECPGAAPKKPKEPVQVPKLLIKGGVEVLEVKTGVDAITEVE

CFLNPEMGDPDENLRGESLKLSAENDFSSDSPERKMLPCYSTARIPLPN

LNEDLTCGNLLMWEAVTVQTEVIGITSMLNLHAGSQKVHEHGGGKPIQG

SNFHFFAVGGEPLEMQGVLMNYRSKYPDGTITPKNPTAQSQVMNTDHKA

YLDKNNAYPVECWVPDPSRNENARYFGTFTGGENVPPVLHVTNTATTVL

LDEQGVGPLCKADSLYVSAADICGLFTNSSGTQQWRGLARYFKIRLRKR

SVKNPYPISFLLSDLINRRTQRVDGQPMYGMESQVEEVRVEDGTERLPG

DPDMIRYIDKQGQLQTKML
```

EXAMPLES

Example 1

INTRODUCTION

BK virus is a member of the polyoma virus family and is most closely related to JC virus, the causative agent of progressive multifocal leukoencephalopathy (PML). BK is a non-enveloped ds DNA virus with three functional regions: early viral gene region (EVGR) that encodes the large and small T cell antigens, the late viral gene region (LVGR) encoding the capsid proteins VP1, VP2 and VP3 and the non-structural agnoprotein and the non-coding control region (NCCR). The capsid protein, VP1, found in both viruses and virus like particles (VLP) is essential for target cell binding and is the target of neutralizing antibodies (2). BK virus infection occurs in approximately 80-90% of the population with most occurring early in life (2). Following primary infection, the virus is largely asymptomatic in individuals with intact immunity and resides in the renal urinary tract as a persistent or latent infection. The virus is not detectable in the blood but in some individuals, virus is excreted in the urine (viruria). In immune suppressed patients 30-60% secrete virus into urine, half of these at very high levels ($>7$ $\log_{10}$ c/ml). Half of the high viruria patients develop viremia (BK DNA in plasma). PyVAN following kidney transplantation and polyomavirus-associated hemorrhagic cystitis (PyVHC) following allogeneic hematopoietic stem cell transplantation represent unmet medical needs associated with reactivation of BK viruses. BK virus replication occurs in 30-50% of kidney transplant patients with 7-8% leading to graft dysfunction and/or loss (3). BKPyV in blood represents the primary method for diagnosis and levels of BKPyV-DNA greater than $10^3$ particles per ml suggests probable PyVAN while above $10^4$/ml it is presumed (2, 4, 5). When such levels of viral DNA are observed along with changes in kidney function the only treatment is lowering of immunosuppressive therapy (5). In hematopoietic stem cell transplantation patients, 10-25% develop PyVHC leading to pain, bleeding, obstruction and in some cases, renal failure (6, 7).

Several factors have been reported to predispose a recipient to develop PyVAN. High urine levels of virus or high serum antibody titers to the virus in the donor are risk factors for the development of PyVAN in the recipient (3, 8-10). There are four genotypes of the virus found in the population, I, II, III and IV with I the most prevalent (60-80%) and IV (10-20%) next most common. These genotypes/serotypes are serological distinct (11). The genotype of the donor is responsible for infection in most instances (2). The early appearance of BK replication/viremia increases the risk of acute graft rejection (12). Importantly, if the graft recipient lacks antibodies against the viral genotype found in the donor organ (8-10) or there is a mismatch in viral genotype between donor and recipient, the risk of developing viremia and PyVAN is increased (2, 3). The combination of high antibody titers in donor (indicating high viral load) and low or mismatched antibody titers in recipient is a significant risk factor (3, 8). In a prospective study of 168 transplant patients by Solis et al (3) the authors showed that high neutralizing antibody titer against the donor strain led to a very significant reduction in risk of viral BK viremia and each $\log_{10}$ rise in antibody titer reduced the risk by 50%. The observations that genotype mismatch increased the risk significantly support a primary role for antibodies in prevention of disease and argue that monoclonal antibodies may be utilized prophylactically/therapeutically to lessen the risk of PyVAN (2, 3, 8). The goal of this study was to produce mAbs capable of neutralizing all four genotypes of BK virus or find combinations that could achieve the same.

Results

Generation of BK Virus Neutralizing Monoclonal Antibodies

Figure 2:
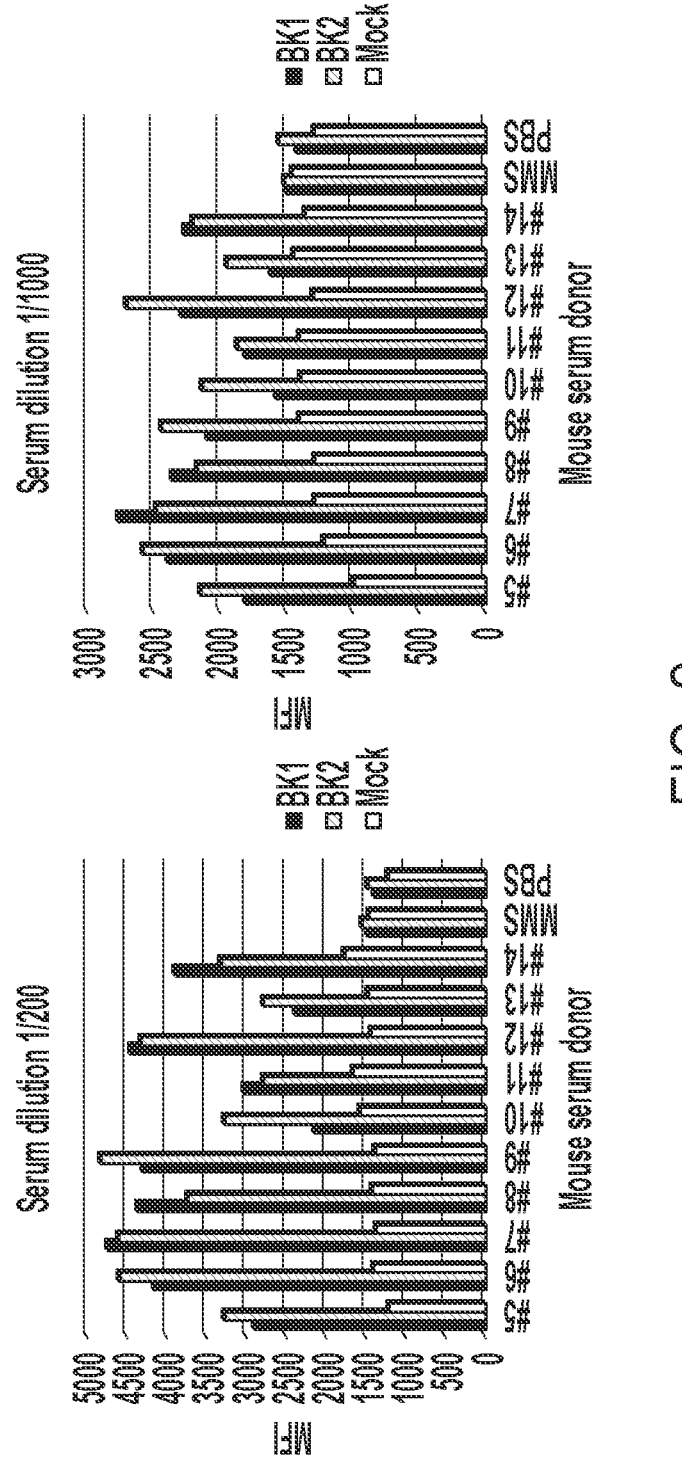
FIG. 2: Flow cytometry of serum from immunized animals showing binding to VP1-expressing cells. Sera analysis by flow cytometry: EXPI293F cells (Invitrogen) were transfected with BK genotype 1 or 4 VP1, along with VP2 and VP3 in the ratio of 3-1-1. Forty-eight hrs. later, cells were washed and stained with immunized mouse sera (1:200, 1:1000, 1:5000) after washing, and incubated with Allophycocyanin-conjugated goat anti-mouse gamma-chain specific secondary (Jackson Immunoresearch) for 30 mins. Cells were washed again and resuspended in 50 ul PBS to be analyzed on a high throughput flow cytometer (HTFC) (Intellicyt).
Figure 3:
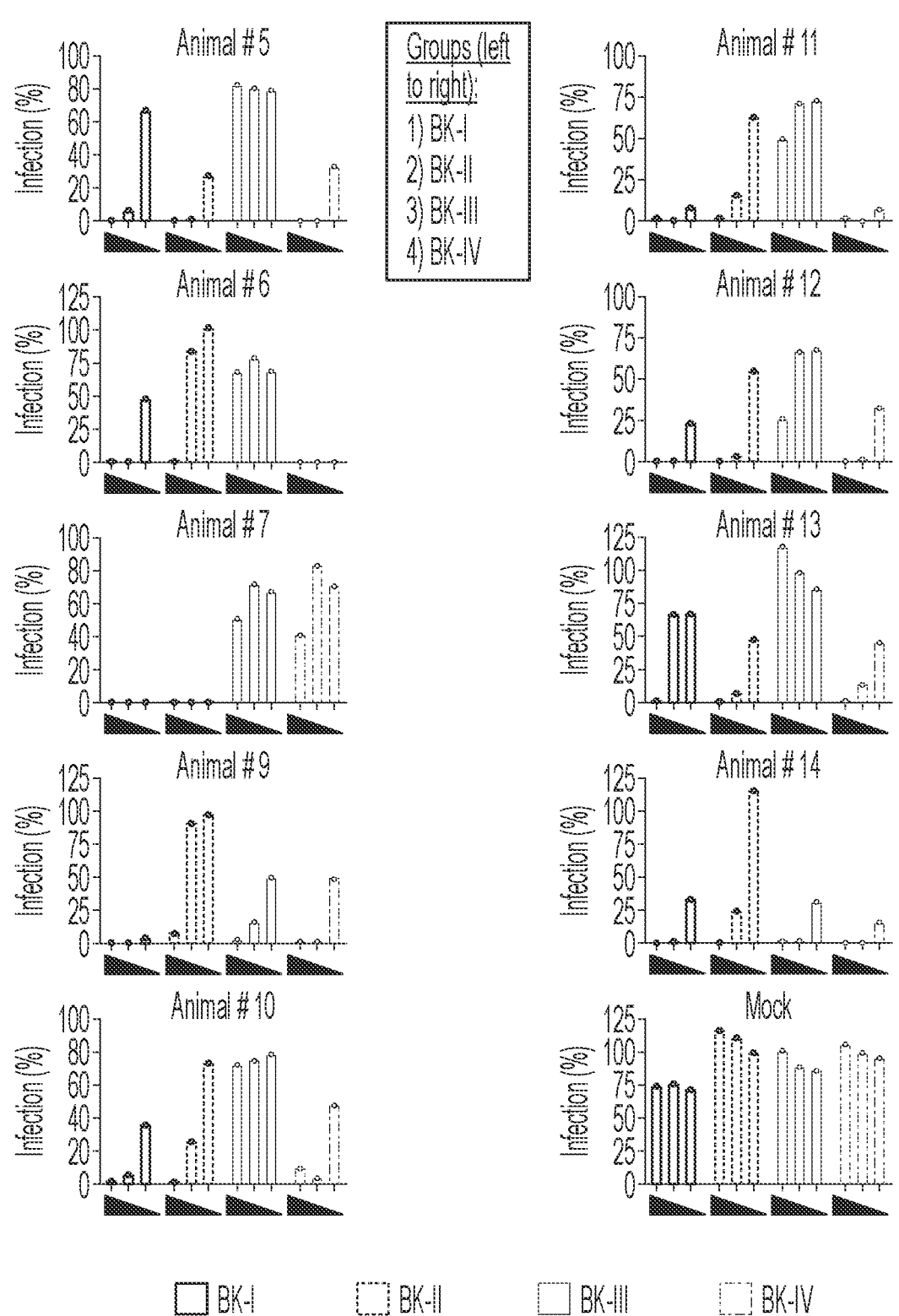
FIG. 3: Pseudovirus neutralization by serum from BK immunized Velocimmune mice. 293 TT cells were plated in 96 well plates and 24 hours later incubated with dilutions of mouse serum and pseudovirus-GFP and incubated at RT for 15 mins. Cells were cultured for 72 hrs and PsV infected cells visualized by flow cytometry using GFP as the readout for infection.

Immunization and serum testing: To generate mAb against BK virus, VelocImmune mice (13) were immunized with various combination of cDNAs encoding for the VP1 protein of the diverse BKV genotypes (Table 7). In general, three immunization regimens were utilized to develop antibodies to diverse BK serotypes. VelocImmune mice encode for chimeric immunoglobulins consisting of human Vh and Vl chains and a mouse Fc domain. They can be made fully human by a simple cloning step (13). The immunization strategy of utilizing different VP1 genotypes cDNA was to enrich for broadly neutralizing mAbs against different BKV genotypes. Following immunization, the sera from the respective animals were collected and analyzed by flow cytometry on EXPI293F cells transfected with the VP1. Serum binding to VP1 from BK1 and BK4 is shown in FIG. 2. Sera from the animals was subsequently tested for neutralization of pseudoviruses generated with the VP1 from genotypes I, II, III and IV (FIG. 3).

TABLE 7

Immunization strategy to generate BK virus neutralizing monoclonal antibodies

| | Primary-genotype DNA | Secondary-genotype DNA | Tertiary-DNA | Boost-pseudovirus preps | |
|---|---|---|---|---|---|
| Group 1 | BKI | BKIV | BKIV | PSV I, IV | Fusion 1, 2 |
| Group 2 | BKI, BKIV | BKI, BKIV | BKI, BKII, BKIII | PSV I, IV | Fusion 3 |
| Group 3 | BKII, BKIII | BKII, BIII | BKI, BKIV BKI alone | PSV I, II, III, IV | Fusion 4 |

Figure 4:
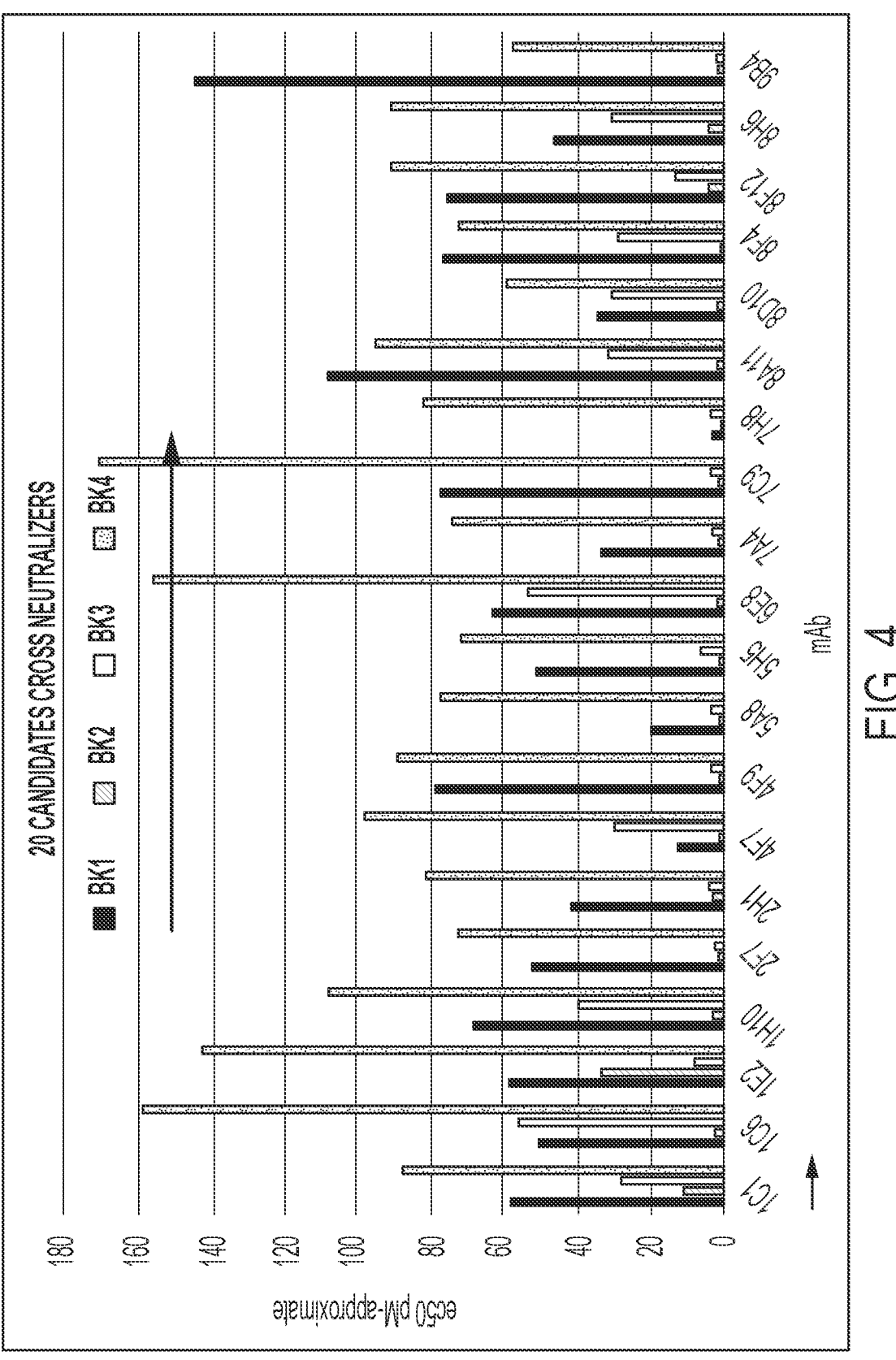
FIG. 4: Estimation of EC50 neutralization titers of select supernatants. The concentration of mAb in the supernatants was calculated using the Octet and the amount of protein needed to neutralize against each of the viral genotypes was determined and reported as pM. Infection was determined by expression of GFP in infected cells. The results are expressed as EC50 pM (concentration that inhibits 50% PsV infection). Along the x-axis from left to right, the arrow designates that the order of bars in each cluster of four bars corresponds to order of the legend in the left to right orientation.

Generation of hybridomas: The immunized mice whose serum demonstrated a robust cross-neutralizing activity against diverse BK pseudoviruses were selected for the generation of hybridomas. The spleens from animals 9, 12, and 14 were fused to Sp2/0 cells, plated in culture dishes with selective media and individual clones collected 12-14 days later using the Hamilton/Stem Cell EzPick. Two days later supernatants were screened by flow cytometry on BK-VP1 transfected 293TT cells transfected with each of the four VP1 and positive clones were further evaluated in a pseudovirus neutralization assay against BK I, II, III, and IV genotypes. Antibodies binding and neutralizing all four genotypes, 3, 2 or a single genotype were identified. Neutralization of pseudovirus was performed as follows: Upper portion of the table shows responses of selection of supernatants tested for both neutralizing and binding to the VP1 of each of the four genotypes. Numbers in tables for neutralization represent percent of infected cells with antibody treatment. Numbers in table for flow cytometry represent MFI of antibody binding to cells transfected with BK I-IV VP I or mock transfected (median). In the lower portion of the table, the supernatants are grouped by the similarities of their binding profiles. These results are performed with undiluted culture supernatant with unknown protein concentration. These results represent hybridoma supernatants of unknown concentration at a single dilution. Hybridomas producing antibodies shown to have activity in the preliminary screening were grown and the approximate concentration of antibody was measured using biolayer label-free protein interferometry on an Octet Red 96 compared to isotype matched standard controls. Based upon the predicted protein concentrations the supernatants were tested for pseudovirus neutralization (FIG. 4) and approximate EC50 determined.

Figure 5:
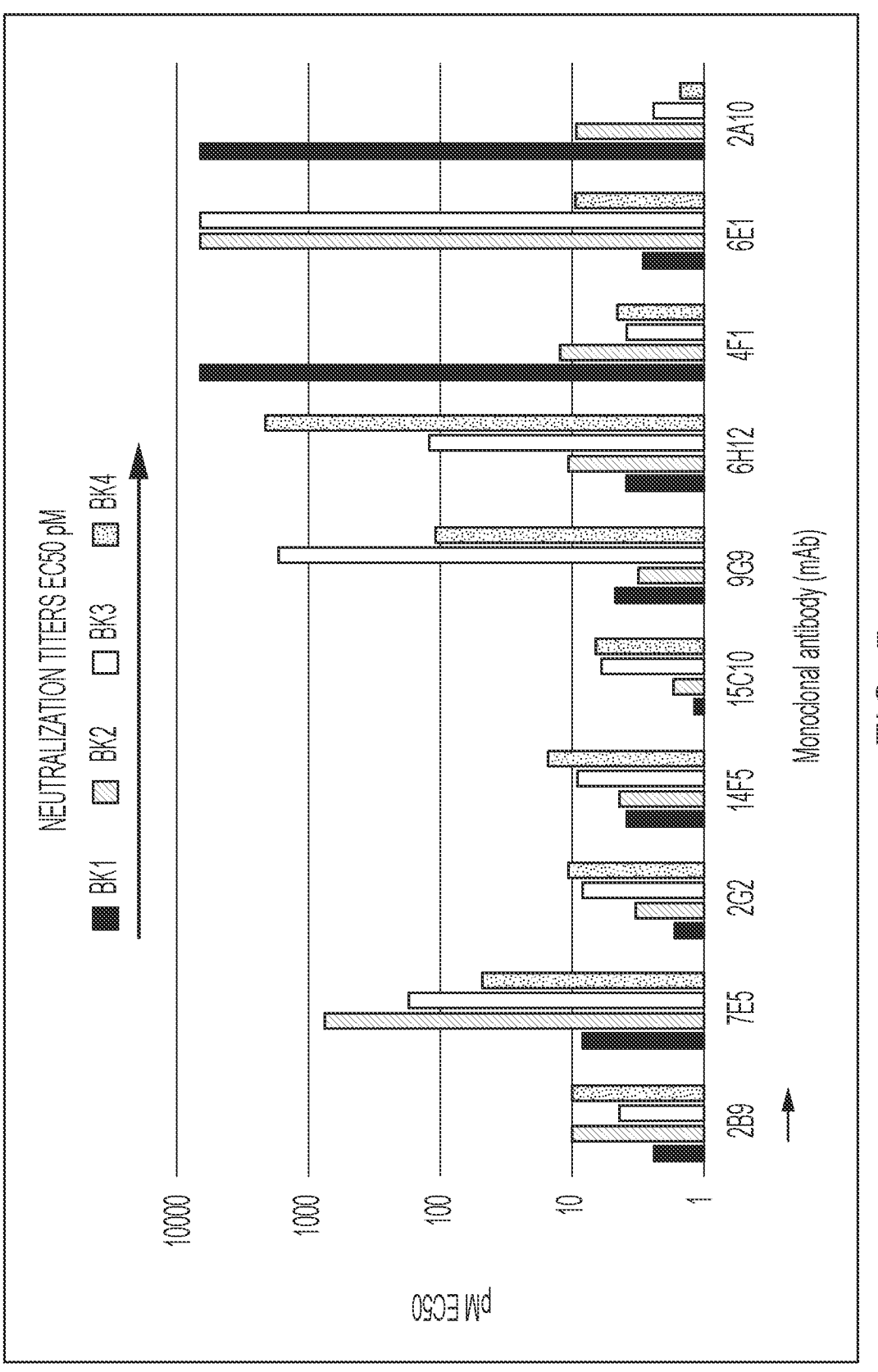
FIG. 5: EC50 neutralization using purified monoclonal antibodies. Antibodies from supernatants shown to have neutralizing activity were purified on Protein A columns, resuspended in PBS and tested for neutralization of BK genotype 1, 2, 3 or 4 pseudovirus infection of 293TT cells. The results are expressed as EC50 pM (concentration that inhibits 50% PsV infection). Infection was determined by expression of GFP in infected cells. Along the x-axis from left to right, the arrow designates that the order of bars in each cluster of four bars corresponds to order of the legend in the left to right orientation.

Selection of Broadly Cross Neutralizing Antibodies:

While many of the supernatants inhibited infection of BK I, II, III, and IV genotype pseudoviruses, in subsequent experiments using purified immunoglobulin many were unable to effectively neutralize all four genotypes efficiently when tested at concentrations below 200 ng/ml. The isotypes of all the positive clones were determined and antibodies of the IgG class were purified and tested for neutralization of all four genotypes and EC50 values calculated for each. FIG. 5 shows the EC50 values of a panel of purified cross neutralizing antibodies from three separate fusions. Several mAbs show broad cross neutralization at low pM concentrations while others neutralize two or three of the genotypes. An EC50 above 1000 is considered non-neutralizing.

Comparison of Neutralization with a Known Therapeutic Candidate Antibody

Figure 6:
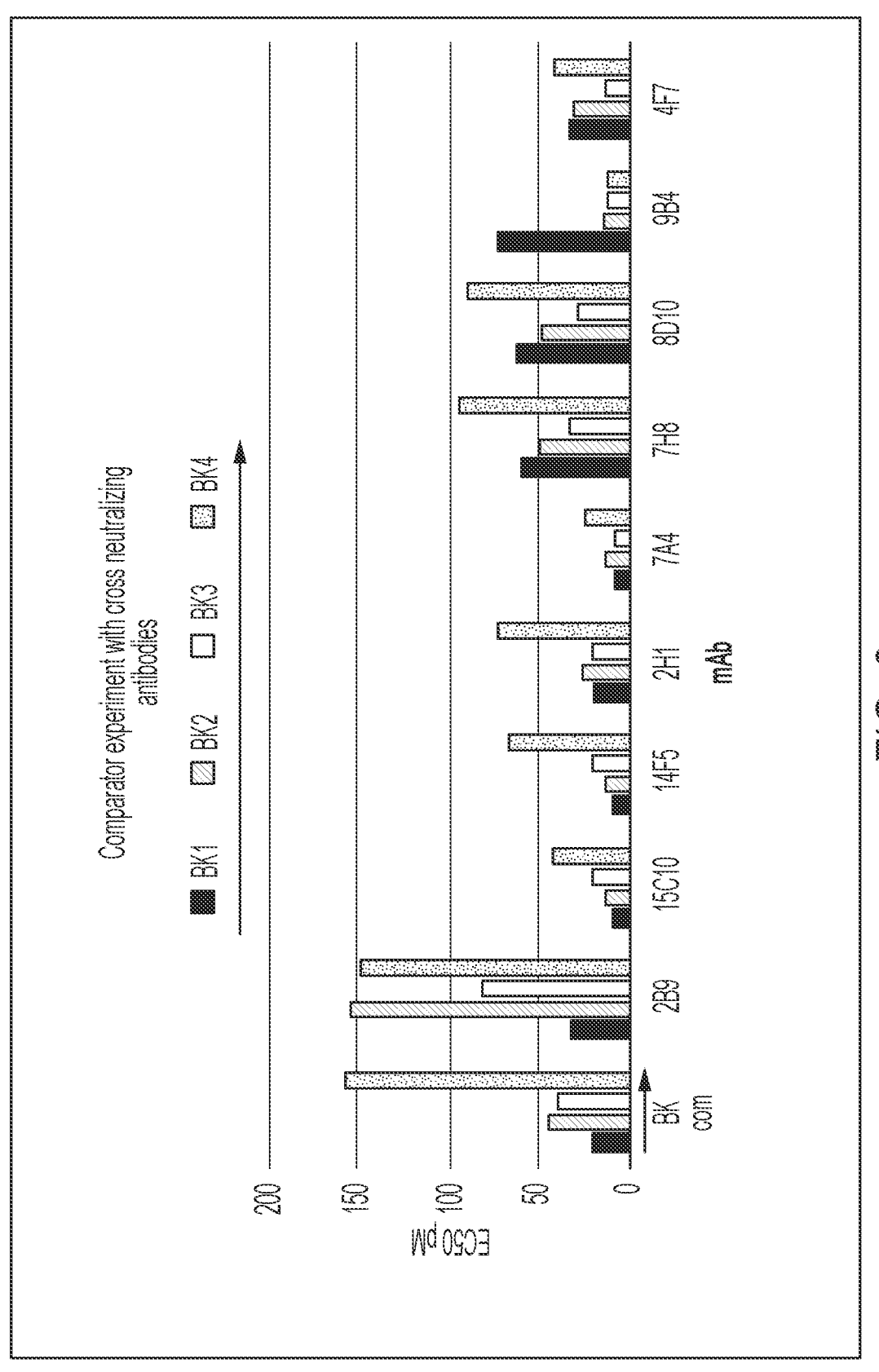
FIG. 6: Neutralization titers of mAb against all four genotypes relative to the comparator antibody. Purified cross neutralizing mAb were tested for neutralization of each genotype PsV in the PsV infection assays using 293TT cells. Infection was determined by expression of GFP in infected cells. Along the x-axis from left to right, the arrow designates that the order of bars in each cluster of four bars corresponds to order of the legend in the left to right orientation.

Purified monoclonal antibodies that neutralized all four genotypes were compared in pseudoviral neutralization assays to a control mAb known to be a therapeutic candidate (BK comparator) (FIG. 6). Most of the mAb neutralize as well or belier than the comparator mAb.

List of Candidate mAbs that Neutralize BK Virus

Figure 7:
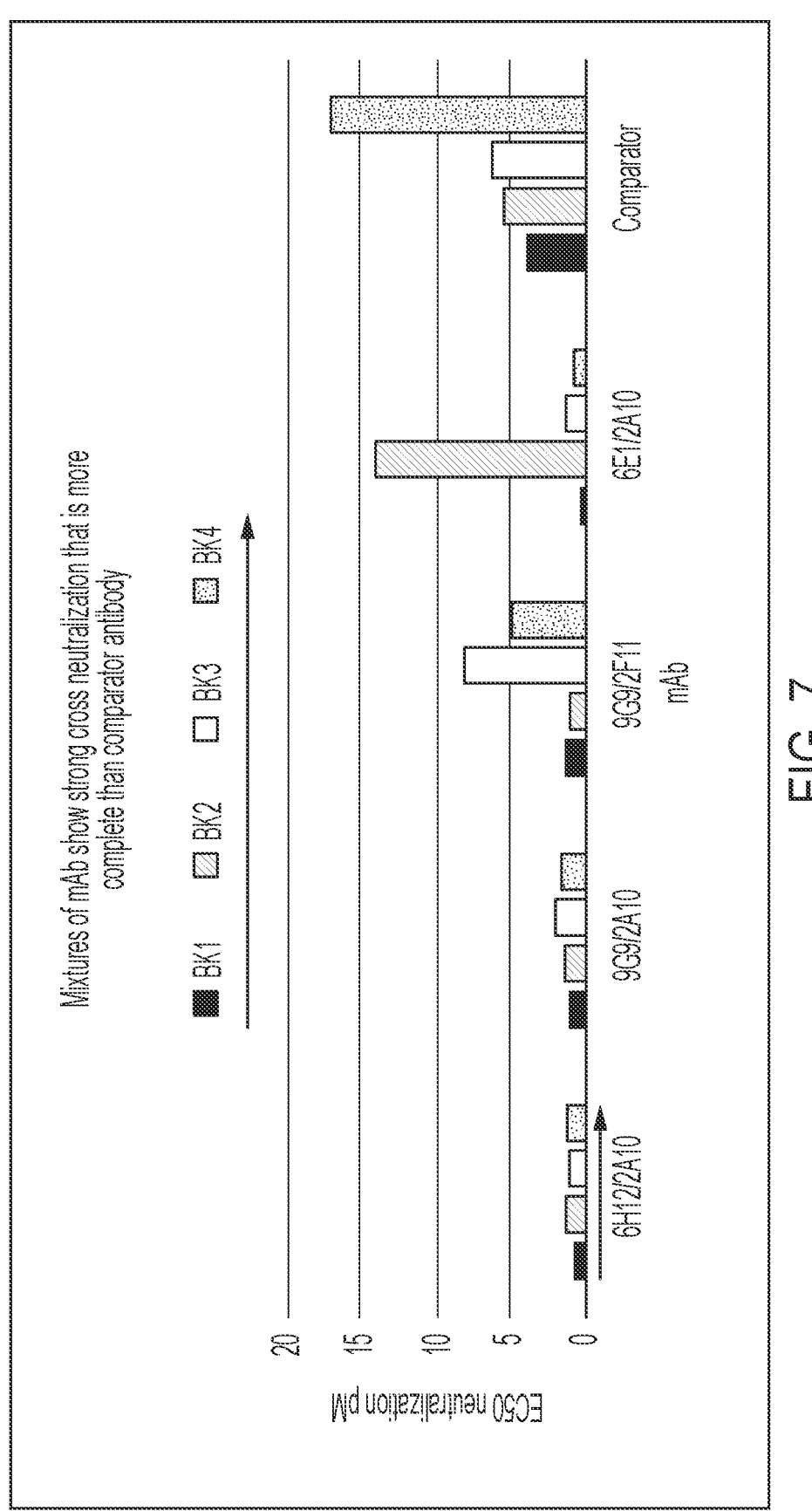
FIG. 7: Combinations of partial neutralizing antibodies can provide protection against all four genotypes of BK. Mixtures containing pairs of mAbs, and each mixture was tested for neutralization of BK genotype 1, 2, 3 or 4 pseudovirus infection of 293TT cells. The results are expressed as EC50 pM (concentration that inhibits 50% PsV infection). Infection was determined by expression of GFP in infected cells. These results are reproduced in Table 9. Along the x-axis from left to right, the arrow designates that the order of bars in each cluster of four bars corresponds to order of the legend in the left to right orientation.

Table 8 shows a summary of mAb collected from four different fusions that neutralize some or all the BK genotypes as measured by pseudovirus assays (also see FIG. 7). The antibodies are all primarily IgG2a and IgG2b with a single IgG1. They represent 9 unique sequence families. All listed antibodies are unique within their sequence family. The EC50 of the comparator antibody is included for comparison.

TABLE 8

Summary of the neutralizing antibodies generated against BK viruses

| | BK1 | BK2 | BK3 | BK4 | Sequence Group | ISOTYPE | Fusion number |
|---|---|---|---|---|---|---|---|
| CROSS NEUTRALIZERS | | | | | | | |
| 2B9 | 32.2 | 154 | 80.8 | 148.2 | C | IgG2b | 1 |
| 7E5 | 24.9 | 1162 | 414.9 | 133 | C | IgG2a | 1 |
| 14F5 | 10.1 | 13.1 | 21.5 | 67.1 | H | IgG2b | 3 |
| 15C10 | 9.4 | 13.1 | 21.1 | 42.3 | H | IgG2b | 3 |

TABLE 8-continued

| | BK1 | BK2 | BK3 | BK4 | Sequence Group | ISOTYPE | Fusion number |
|---|---|---|---|---|---|---|---|
| | | Summary of the neutralizing antibodies generated against BK viruses | | | | | |
| 7A4 | 9.1 | 13.2 | 8.1 | 25.1 | J | IgG2a | 4 |
| 2H1 | 20.2 | 26.1 | 21.9 | 72.8 | J | IgG2a | 4 |
| 7H8 | 59.6 | 50 | 33.4 | 94.3 | K | IgG2a | 4 |
| 8D10 | 62.9 | 49.2 | 29 | 89.4 | J | IgG2a | 4 |
| 9B4 | 72.5 | 15.2 | 11.8 | 11.8 | J | IgG1 | 4 |
| 4F7 | 32.5 | 31.9 | 14.3 | 41.6 | J | IgG2a | 4 |
| 2F7 | 52.5 | 1.1 | 2.2 | 72.4 | J | IgG2a | 4 |
| 8A11 | 108 | 1.4 | 31.5 | 94.8 | J | IgG2a | 4 |
| 5A8 | 20.1 | 0.9 | 3.9 | 77.4 | J | IgG2a | 4 |
| 2H1 | 41.8 | 2.8 | 3.4 | 81.5 | J | IgG2a | 4 |
| 1E2 | 59 | 33.2 | 8.1 | 142.7 | J | IgG2a | 4 |
| 1H10 | 68.4 | 2.8 | 39.7 | 107.3 | J | IgG2a | 4 |
| Comparator | 20.2 | 45.1 | 40.2 | 156.3 | | | |
| | | PARTIAL NEUTRALIZERS-separate experiment | | | | | |
| 2F11 | >6667 | 83.8 | 10.5 | 6.1 | E | IgG2a | 2 |
| 6E1 | 2.95 | >6667 | >6667 | 9.5 | G | IgG2a | 2 |
| 2A10 | >6667 | 9.4 | 2.4 | 1.5 | D | IgG2a | 2 |
| 4E6 | >6667 | 2.1 | 29.6 | 19.7 | I | IgG2a | 3 |
| 6H12 | 3.9 | 10.9 | 126.6 | 2206.6 | L | IgG2b | 3 |
| 9H9 | 8.7 | 8.3 | 1144.9 | >6667 | (in progress) | IgG2b | 3 |
| 11D12 | 10.9 | 9.5 | 6385 | >6667 | L | IgG2b | 3 |
| 9G9 | 4.7 | 3.2 | 1698 | 110 | H | IgG2b | 3 |

Epitope Mapping with Mutated VP1

Figure 8A:
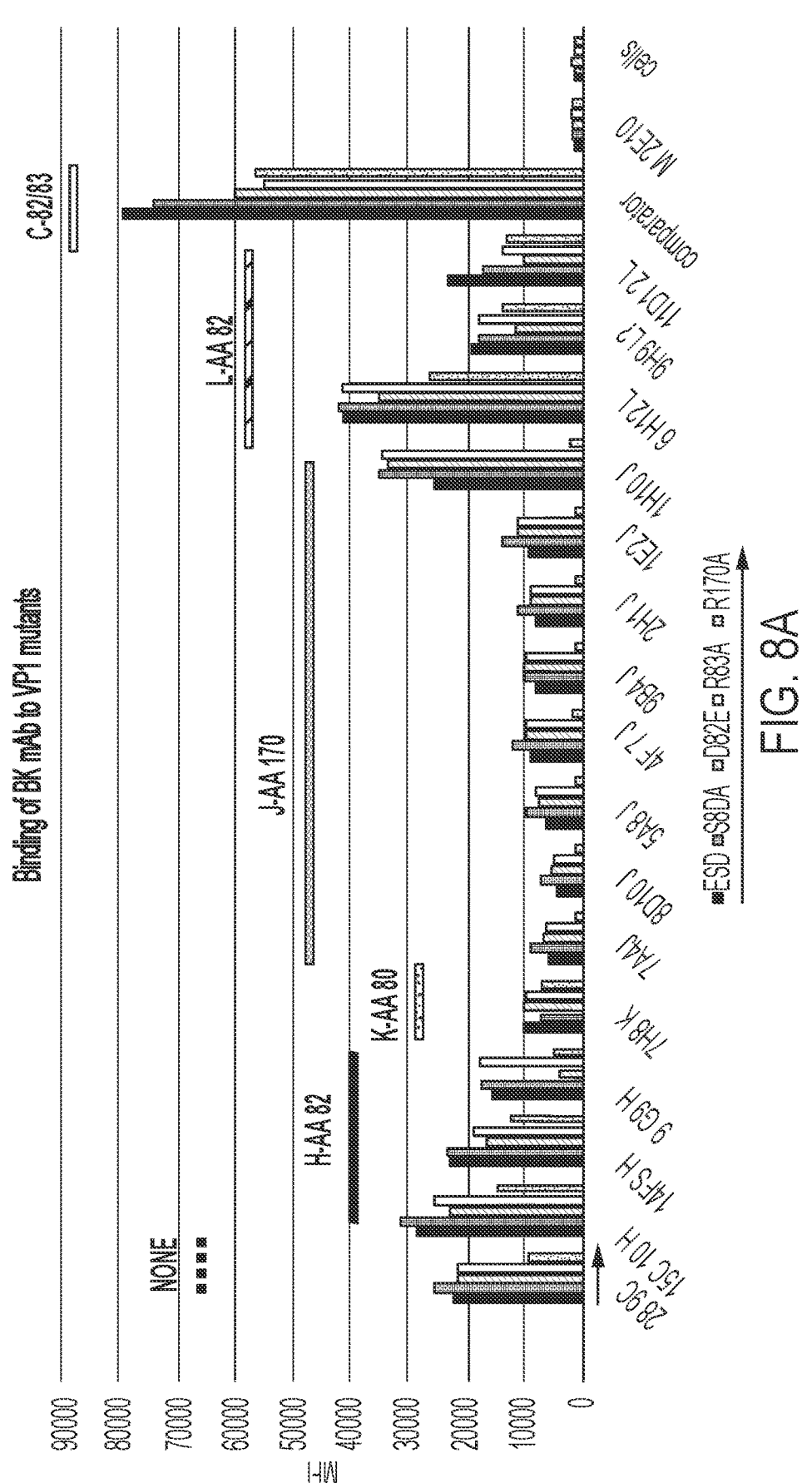
FIG. 8A: Binding of cross neutralizing mAb to genotype 1 VP1 with select mutations. VP1 with the indicated mutation or unmutated were used to transfect 293TT cells and changes in binding determined by flow cytometer. Colored lines indicate that the mutations affected the binding of the indicated family of antibodies. Families C, H, J, K, and L are shown. The comparator antibody is fully human, and binding is identified using a different secondary antibody. Along the x-axis from left to right, the arrow designates that the order of bars in each cluster of five bars corresponds to order of the legend in the left to right orientation.
Figure 8B:
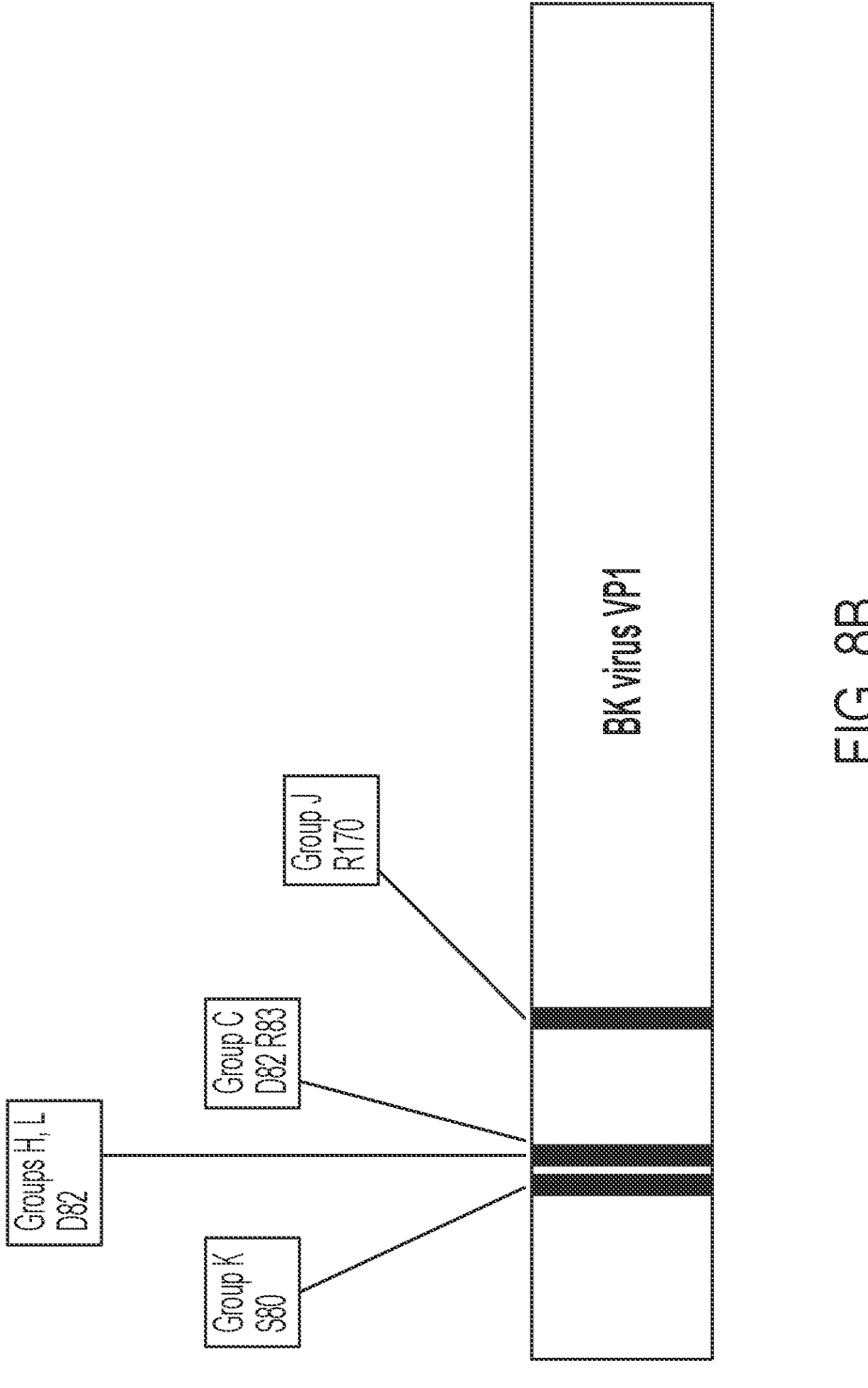
FIG. 8B: Location of epitopes on BK virus VP1 targeted by monoclonal antibodies of families C, H, J, K, and L.

The region of the VP1 believed to be utilized for binding to target cells is between AA 70-85. Some have reported an epitope that utilized aa in the 170 range as well (14). To evaluate epitope specificity, genotype 1 VP1 expression mutant plasmids were constructed. These VP1 expression plasmids has single mutations at positions 80, 82, 83 or 170 or were unmutated (ESD). Cells transfected with these vectors were used in flow cytometry to determine if the inserted mutations altered the binding of the mAb. As shown in FIG. 8A characteristic binding changes can be identified by flow cytometry on cells transfected with wild type VP1 relative to those transfected with the mutant plasmids. The reduction in binding can be observed by all members of the same genetic family but to a different degree indicating key amino acids involved in their binding. Family H is most affected by a change at AA 82 as is family L. Family K is most influenced by a change at position 80 while family J shows profound reduction in binding when R170 is converted to an A.

Complementation of a Cross Reactive Neutralizing Antibody (2B9) with Partial Cross Neutralizing Antibodies from Different Genetic Families.

Monoclonal antibody 2B9, an antibody from family C was not affected significantly by any of the mutational changes. Because of its seeming uniqueness, mixture experiments were set up to determine if its activity could be complemented by antibodies from different families (Table 9). As a baseline, each individual mAb was mixed with an irrelevant isotype matched monoclonal antibody (M2) and dilutions performed. The addition of a partial cross neutralizing antibody from family D (2A10, does not neutralize genotype I) did not improve neutralization with 2B9. However, if 6E1 (only neutralizes I and IV) is mixed with 2A10 (also a partial cross neutralizer) they complement each other to give strong neutralization of all 4 genotypes. 6E1 added to 2B9 improves neutralization against BK1 and BK4 over 2B9 alone showing that they can synergize with each other without interfering. More importantly perhaps is the fact that the combination of 6E1 and 2B9 will simultaneously cover two neutralizing epitopes on BK1 and 4, thus greatly reducing the risk of escape mutations arising from selective antibody pressure.

TABLE 9

| | | BK1 | BK2 | BK3 | BK4 |
|---|---|---|---|---|---|
| | Combination of neutralizing antibodies can complement to improve neutralization | | | | |
| Gene family | | BK1 | BK2 | BK3 | BK4 |
| C | 2B9/M2 | 2.77 | 44 | 5.4 | 10.8 |
| D | 2A10/M2 | >6667 | 55.7 | 6.4 | 5.9 |
| C and D | 2B9/2A10 | 5.5 | 41.4 | 5.1 | 5.8 |
| D | 2A10/M2 | >6667 | 55.7 | 6.4 | 5.9 |
| G | 6E1/M2 | 0.67 | >6667 | >6667 | 49.6 |
| D and G | 2A10/6E1 | 1.1 | 64.4 | 7.3 | 5.8 |
| C | 2B9/M2 | 2.77 | 44 | 5.4 | 10.8 |
| G | 6E1/M2 | 0.67 | >6667 | >6667 | 49.6 |
| C and G | 2B9/6E1 | 0.09 | 53.9 | 7 | 6.8 |

Complementation of Partial Neutralizing Antibodies from Different Genetic Families Mixtures of partial neutralizers from different families were tested for neutralization of pseudovirus particles from the VP1 of all four genotypes (Table 10). The family L mAb, 6H12, poorly neutralizes BK3 and BK4. However, when mixed with 2A10 from family D which neutralizes BK2, BK3 and BK4 but poorly neutralizes BK1, all four genotypes are strongly neutralized. When 9G9 (poorly neutralizes BK3 and BK4) from family H is mixed with either family D or family E, potent cross neutralization is achieved. Comparable results are observed when mAb from family G and D are mixed. These data argue that the families from which these antibodies derive bind to different but unique sites on the virus allowing them to work cooperatively. If one assumes that each of the individual families binds to a particular epitopic region than 9G9 from family H probably binds to the same site as the most potent cross neutralizing antibody of the family, 15C10. If true, a mixture of 15C10 with either 2A10 or 2F11 should constitute a very potent mixture and may work to block escape mutants from appearing in vivo.

TABLE 9

Combinations of partial neutralizing antibodies can
provide protection against all four genotypes of BK

| Family | Antibodies | BK1 | BK2 | BK3 | BK4 |
|---|---|---|---|---|---|
| L | 6H12/M2 | 0.96 | 2.4 | 172.3 | 944 |
| D | 2A10/M2 | >2000 | 11.2 | 0.654 | 0.72 |
| L & D | 6H12/2A10 | 0.95 | 1.4 | 1.2 | 1.3 |
| H | 9G9/M2 | 2.76 | 2.3 | 1292 | 196 |
| D | 2A10/M2 | >2000 | 11.2 | 0.654 | 0.72 |
| H & D | 9G9/2A10 | 1 | 1.5 | 2.2 | 1.6 |
| H | 9G9/M2 | 2.76 | 2.3 | 1292 | 196 |
| E | 2F11/M2 | >2000 | 148 | 6.1 | 1.85 |
| H & E | 9G9/2F11 | 1.3 | 1.2 | 8.1 | 5 |
| G | 6E1/M2 | 0.78 | >2000 | >2000 | 21 |
| D | 2A10/M2 | >2000 | 11.2 | 0.654 | 0.72 |
| G & D | 6E1/2A10 | 0.43 | 14 | 1.3 | 0.93 |
| Cross | 2B9 | 4.20 | 61.30 | 6.80 | 11.40 |
| neutralizing | 15C10 | 0.1 | 0.58 | 1.86 | 2.30 |
| antibodies | Comparator | 3.90 | 5.50 | 6.30 | 17.00 |

Discussion

There were 21,167 kidney transplant and 836 kidney-pancreas transplants performed in the US (United States) in 2018 according to the United Network for Organ Sharing. According to the World Health Organization, 70,000 transplants are performed yearly, worldwide. 23000 bone marrow transplants are performed yearly in the US and 50,000 are performed worldwide according to the WHO (World Health Organization). In hematopoietic stem cell transplantation patients, 10-25% develop PyVHC leading to pain, bleeding, obstruction and in some cases, renal failure (6, 7). According to NIDDK, Interstitial cystitis affects 3-8 million women and 1-4 million men every year. BK virus replication occurs in 30-50% of kidney transplant patients with 7-8% leading to graft dysfunction and/or loss (3). BKPyV in blood represents the primary method for diagnosis and levels of BKPyV-DNA (2, 4, 5). BK viremia precedes the development of PyVAN by 1-12 weeks. Blood samples with more than $10^4$ copies per ml indicate presumptive PyVAN. Patients with this level of viremia post transplantation are treated by reduction of immunosuppression and administration of drugs such as leflunomide but the risk of graft rejection escalates (46% loss).

Studies of patients given IVIG support an important role for antibodies in control of BK infection in transplant patients. In the study by Vu et al, patients that failed to respond (persistent viremia>$10^4$) were treated with intravenous immunoglobulin (IVIG) (15). Thirty transplant patients with persistent viremia and presumptive PyVAN after standard treatment received IVIG. 27 patients showed clearance of virus from blood and only one of the grafts (from a patient that failed to respond to the IVIG) was lost. Several other studies with IVIG supported the observations and demonstrated control of viremia (16-18). Additionally, animal models of polyoma virus have shown that IgG antibodies can control infection and prevent nephropathy (19).

Further support for the use of antibody therapy as a viable treatment for PyVAN comes from a prospective study of 168 transplant patients by Solis et al (3) the authors showed that high titers of endogenous neutralizing antibody against the strain of BK carried by the donor led to a very significant reduction in risk of viral BK viremia with each $log_{10}$ rise in antibody titer reducing the risk by 50%. As reported in this and other studies, viral genotype mismatch between the donor and recipient increases the risk of PyVAN significantly (2, 3, 8). These observations support a primary role for antibodies in prevention of disease and argue that monoclonal antibodies may be utilized prophylactically to lessen the risk of PyVAN. To respond to this unmet need CTAD has developed an extensive panel of antibodies that alone or in combination can neutralize all known BK virus genotypes. These antibodies could be utilized prophylactically or therapeutically to reduce virus titers and conceivably protect the donated tissue.

More than 100 mAb were identified and tested against all four BK genotypes. mAb deriving from 4 different genetic families were found that neutralized all four of the BK genotypes.

Recently, a phase II clinical trial to determine the value of BK neutralizing mAb to prevent kidney graft infection had been initiated. The sequence of the monoclonal antibody used in this study was available and it was made genetically. This antibody, referred to as the comparator, was used as a standard to determine the relative efficacy of the antibodies. While the comparator was very good, many of the antibodies showed superior neutralization across the board particularly against genotype IV. The clinical trial was eventually withdrawn due to a reorganization in the company (ClinicalTrials.gov Identifier: NCT03456999).

Clinical trials using antibodies against pathogens like HIV or Ebola utilized pairs of antibodies based upon the assumption that doing this reduced the risk of viral mutants escaping from neutralization of a single antibody. Such antibody "cocktails" are attempted using pairs of antibodies that bind to non-overlapping sites on the viral attachment protein. Since antibodies from a single family use the same genetic elements with slight changes in the CDR or elsewhere resulting from somatic mutation they are likely to bind to an overlapping site on the protein. In order to identify where on the VP1 the antibodies bound, mutants of the VP1 were made at various positions reported to be involved in viral binding. Members of each family were tested by flow cytometry for an effect of the mutations on binding to cells expressing the VP1 following transfection. Family H, which has some of the strongest neutralizers showed reduced binding with a D82E change in the VP1. This change was most apparent with the 9G9 family member which while only a partial cross neutralizer (BK1 and BK2 strongly and BK4 less strong) was profoundly affected by the change. The K family cross neutralizing antibody, 7H8, showed reduced binding when the S80A mutation was incorporated into VP1. Interestingly, the J family, that represents the largest family of neutralizers, was profoundly affected when the R170A mutation was put into the VP1. This mutation would seem to be far from the alleged binding site (AA 70-85), but it has been reported by others that this area of the VP1 is somehow involved in binding of the virus. Lastly, the L family also showed reduced binding with the D82E change in the VP1. The comparator antibody shows reduced binding with either the change at position 82 or 83. Based upon these and other observations studies of complementation were undertaken to determine if mixtures of mAb would show enhanced neutralization. 2B9 when mixed with a partial neutralizer, 2A10 didn't improve but neither did it lose potency. This argues that the two antibodies probably bind to different sites. 2B9 when mixed with 6E1 showed an improvement in neutralization against BK1 and BK4. 2A10 and 6E1, two partial neutralizers did not show enhancement but neither was there any negative impact of mixing the antibodies.

Since it was difficult to show complementation with the potent cross neutralizers, experiments were designed to mix partial cross neutralizers. 6H12(family L) was mixed with 2A10(family D) leading to exceptional cross neutralization not seen with either alone. 6E1 (family G) when mixed with 2A10 showed exceptional activity against all genotypes. 9G9, a member of the H family that includes the potent cross neutralizer, 15C10, when mixed with 2A10 (family D) or 2F11 (family E) showed profound cross neutralizing activity. This data argues that family H members such as 15C10 could be mixed with 2A10 or 2F11 to achieve even more potent neutralization and such a combination is likely to prevent the escape of mutants that may arise in some situations. Further experiments of this type are ongoing.

The primary use for these antibodies would be as a prophylactic treatment given to the recipient prior to kidney transplantation to decrease viral load by preventing dissemination within the host. They should also be effective therapeutically in cases with existing PyVAN. The ideal antibody(s) would be capable of neutralizing all the BK genotypes. Such antibodies would avoid the need to identify genotypes in donor and recipient prior to transplant. While genotype I and IV make up most of the cases, worldwide the hierarchy of the genotypes may vary (2). Moreover, in the kidney transplant study of Solis et al 27% of DNA virus positive patients and 19% of DNA negative patients had neutralizing antibodies to 2 or 3 genotypes that may indicate infections with multiple genotypes are more common than previously believed (3). Ideally, pairs of mAb that could complement one another might be the ideal solution.

Methods and Materials

Animals, Cells, Reagents

VelocImmune mice are provided by Regeneron Pharmaceuticals and express human variable light and heavy chains in their antibodies as described (13). HEK-293TT were a gift from Chris Buck, NIH EXPI293F and transfection system were purchased from Invitrogen.

Immunizations

Expression plasmids for VP1, VP2 and VP3 were used for immunizations with electroporation. Groups of mice were immunized with various protocols and the mice displaying the highest sera titer of neutralizing antibodies against BK I, II, III, and IV pseudoviruses were selected for fusion. The genotypes used for immunizations are shown in Table 7. Boosts with BK pseudovirus preparations were administered IP without adjuvant at 3-4 days prior to fusion (Table 7).

Flow Cytometry Analysis

EXPI293F cells were transfected with either BK genotype VP1-I, -II, -III, and -IV along with VP2 and VP3 in the ratio of 3:1:1. Forty-eight hrs. later cells were permeabilized, washed and stained with immunized mouse sera (1:200, 1:1000, 1:5000), supernatant from the hybridoma clone or purified mAb in PBS with 0.5% BSA for 1 hr. After 2 washes in PBS/BSA, cells were incubated with Allophycocyanin-conjugated goat anti-mouse IgG secondary (Jackson Immunoresearch) for 30 mins. Cells were washed 1×PBS and resuspended in 50 ul PBS to be analyzed on a HTFC (Intellicyt).

Pseudovirus Generation

BK pseudoviruses were produced from HEK-293TT cells transfected with plasmids that express VP1, VP2, VP3, and GFP reporter vector at ratio of 2:1:1:1 using Lipofectamine 2000 (Invitrogen). Forty-eight hours after transfection, the cells were harvested at ~100 million cells/ml in PBS, washed 1× with PBS and lysed by addition of 0.5% Triton X-100, and RNase A/Ti cocktail (Ambion). The lysate was incubated at 37° C. overnight and cell lysates centrifuge at 5,000×g. The pseudovirus particles were isolated by ultracentrifugation through a 27-33-39% iodixanol (Optiprep, Sigma) step gradient at 300,000×g for 3.4 hrs at 16° C. The fractions from the Optiprep column were analyzed for detection of VP1/VP2/VP3 using SDS-PAGE (11, 20)

Pseudovirus Neutralization Assay:

Neutralization of BK I, II, III, and IV pseudoviruses was performed as follows: 15,000 HEK-293 TT cells were plated in 96 well plates. The next day, hybridoma supernatant (or purified antibody, where indicated) and BK I, II, III, and IV pseudoviruses (titered to 30-60% infectivity) diluted in complete DMEM were pre-incubated at room temperature for 15 inns. 50 ul fresh complete media is added to the cells along with ab/PsV mixture and cultured for 72 hrs. PsV infected cells are visualized by fluorescent microscopy and, after incubation with trypsin and washing, analyzed by flow cytometry using GFP as the readout for infection using the HTFC (Intellicyt).

ELISA

For measuring antibody binding by ELISA, 96 well plates were coated with 2 ug/ml purified pseudovirus in PBS overnight at 4 degrees C. and blocked for 30 minutes with PBS-0.5% BSA prior to the addition of the antibody containing solutions. Following a 90-minute incubation at room temperature the plates were washed, HRP-linked goat anti-mouse IgG heavy chain specific was added for 60 minutes, washed and substrate added. Plates were read on a microplate reader (BioTek Synergy) at 405 nm 45 minutes later.

Hybridoma Generation

For the generation of hybridomas, spleens are removed from the boosted animals and fused to SP2/0 myeloma cells. The Sp2/0 cells are grown in Stem Cell media A for three days prior to fusion and mixed with the spleen cells both of which have been washed free of serum using DMEM without serum. The Sp2/0 cells are mixed with spleen cells at a 1:5 ratio and fused by the addition of 1 ml of a 50% solution of PEG 4000 (EMD, Germany). The cell mixture is incubated overnight in Stem Cell Recovery Media (media C), washed, and plated in semisolid selection media, Media D; Stem Cell Technology). Individual clones were isolated 10-12 days later from the plates using the Hamilton/Stem Cell EzPick robot and deposited in 96 well plates containing Stem Cell media E. 48 hours later the supernatants are collected by the robot and deposited in plates for ELISA, flow or neutralization assays.

Hybridoma Screening

Primary screening was performed using high-throughput flow cytometry on HEK-293 cells transfected with the VP1 from both BKI and BKIV, as detailed above. Briefly, supernatants were added to the cell mixture and following permeabilization antibody binding was identified by the addition of goat anti-mouse IgG (heavy chain specific) APC (Jackson). Positive supernatants were confirmed by a similar flow experiment using HEK-293 cells expressing only one of the four subtypes. In some instances, the supernatants were also transferred to ELISA plates coated with BKI, BKII, BKII or BKIV pseudoviruses at 2 ug/ml. The supernatants (undiluted) were screened for neutralization in a pseudovirus neutralization assay using all four genotypes of the BK virus. It should be noted that a strong but not perfect correlation exists between binding and neutralization.

Mutagenesis of VP1

Mutagenesis of VP1 was first performed by site directed mutagenesis at four sites located in the predicted neutralization domains of VP1 creating four separate mutants. The sites chosen for mutation were positions that showed some degree of variance among VP1s of all BKs with the specific residue chosen for the mutant representing the other reported residue at that position. These sites included position: 42 (L>Q), 60 (D>N), 73 (E>Q), and 82 (D>E). Site directed mutagenesis was performed following factory supplied protocol using the QuickChange II Site Directed Mutagenesis kit (Agilent Technologies). Briefly, site directed mutagenesis was carried out by designing a forward (5'-3') and complementary (3'-5') reverse primer around each site with a single base change that would correspond to the translation of the mutated residue. This changed base would be position roughly in the middle of each primer set. Forward and reverse PCRs initiated from the primers were performed on denatured expression plasmids containing the BK VP1 with conditions that allowed for the single base mismatch. Methylated template stands were digested by DPN1 leaving only newly synthesized plasmid strands containing the incorporated mutation. Newly synthesized plasmid strands were re-annealed and then transformed into competent *E. coli* for nick repair and amplification. Following experiments assessing binding changes of monoclonal antibodies compared to wildtype VP1, each mutant was ranked based on binding reduction by flow cytometry. Position 82 showed a prominent effect on most of the monoclonals and thus to further elucidate this potential epitope, two more mutants were created that straddled residue 82 by alanine substitution at position 80 (S>A) and 83 (R>A). Further, a sixth mutant at position 170 was also created by alanine substitution (R>A). This position had previously been reported as an important residue in a putative neutralizing epitope located outside the known binding domains of VP1. These last three mutants were generated by de novo DNA synthesis and cloned into pcDNA3.1 mammalian expression vectors (Genscript).

Isotyping

The isotypes of positive hybridomas were determined using a commercial isotyping kit (BD Pharmingen Cat. 550487). Only IgG antibodies were further tested.

Quantitation of Monoclonal Antibodies

Mabs were quantitated using label-free, biolayer interferometry (BLI) on an Octet Red96 (ForteBio, Sartorius). Briefly, optically capable biosensors conjugated with either protein A or G were dipped into supernatants containing mabs. Supernatants were measured undiluted and diluted 1:10 in conditioned media and compared to an isotype standard, diluted in conditioned media in a 1:2 dilution series ranging from 100 ug/ml to 1.56 ug/ml. Standard curves were analyzed in the ForteBio Data Analysis Software v.10 (ForteBio) using a 5-parameter logistics (5PL) dose response curve fitting model on the initial binding slopes. Mab concentrations are then calculated from the standard curve. Diluted samples were compared to undiluted samples after application of the respective dilution factors. Total concentrations were averaged together from the diluted and undiluted sample.

Purification of Monoclonal Antibodies

Hybridomas producing antibodies positive for BK virus VP1 were grown in media E from 2 days and transferred to Serum Free Hybridoma Media (Gibco, ThermoFisher). The serum free supernatants from the hybridomas are purified using FPLC on a Akta Chromatography System (GE) using Protein A or Protein G HiTrap columns (GE).

REFERENCES

1. Stolt A, Sasnauskas K, Koskela P, Lehtinen M, Dillner J. 2003. Seroepidemiology of the human polyomaviruses. J Gen Virol 84:1499-1504.

2. Hirsch H H, Randhawa P S, Practice ASTIDCo. 2019. BK polyomavirus in solid organ transplantation-Guidelines from the American Society of Transplantation Infectious Diseases Community of Practice. Clin Transplant 33:e13528.

3. Solis M, Velay A, Porcher R, Domingo-Calap P, Soulier E, Joly M, Meddeb M, Kack-Kack W, Moulin B, Bahram S, Stoll-Keller F, Barth H, Caillard S, Fafi-Kremer S. 2018. Neutralizing Antibody-Mediated Response and Risk of BK Virus-Associated Nephropathy. J Am Soc Nephrol 29:326-334.

4. Helantera I, Salmela K, Kyllonen L, Raisanen-Sokolowski A, Auvinen E, Mannonen L, Koskinen P, Lautenschlager I. 2012. BK virus viremia in a well-HLA-matched kidney transplant population mainly on low-dose cyclosporine-based immunosuppression. Clin Transplant 26:E596-601.

5. Schaub S, Hirsch H H, Dickenmann M, Steiger J, Mihatsch M J, Hopfer H, Mayr M. 2010. Reducing immunosuppression preserves allograft function in presumptive and definitive polyomavirus-associated nephropathy. Am J Transplant 10:2615-23.

6. Bennett S M, Broekema N M, Imperiale M J. 2012. BK polyomavirus: emerging pathogen. Microbes Infect 14:672-83.

7. Gander R, Asensio M, Guillen G, Royo G F, Bolanos A, Perez M, Diaz-De-Heredia C, Benitez M, Lopez M. 2018. Hemorrhagic cystitis after hematopoietic stem cell transplantation: A challenge for the pediatric urologist. J Pediatr Urol 14:366-373.

8. Abend J R, Changala M, Sathe A, Casey F, Kistler A, Chandran S, Howard A, Wojciechowski D. 2017. Correlation of BK Virus Neutralizing Serostatus With the Incidence of BK Viremia in Kidney Transplant Recipients. Transplantation 101:1495-1505.

9. Ali A M, Gibson I W, Birk P, Blydt-Hansen T D. 2011. Pretransplant serologic testing to identify the risk of polyoma BK viremia in pediatric kidney transplant recipients. Pediatr Transplant 15:827-34.

10. Sood P, Senanayake S, Sujeet K, Medipalli R, Van-Why S K, Cronin D C, Johnson C P, Hariharan S. 2013. Donor and recipient BKV-specific IgG antibody and posttransplantation BKV infection: a prospective single-center study. Transplantation 95:896-902.

11. Pastrana D V, Brennan D C, Cuburu N, Storch G A, Viscidi R P, Randhawa P S, Buck C B. 2012. Neutralization serotyping of BK polyomavirus infection in kidney transplant recipients. PLoS Pathog 8:e1002650.

12. Seifert M E, Gunasekaran M, Horwedel T A, Daloul R, Storch G A, Mohanakumar T, Brennan D C. 2017. Polyomavirus Reactivation and Immune Responses to Kidney-Specific Self-Antigens in Transplantation. J Am Soc Nephrol 28:1314-1325.

13. Murphy A J, Macdonald L E, Stevens S, Karow M, Dore A T, Pobursky K, Huang T T, Poueymirou W T, Esau L, Meola M, Mikulka W, Krueger P, Fairhurst J, Valenzuela D M, Papadopoulos N, Yancopoulos G D. 2014. Mice with megabase humanization of their immunoglobulin genes generate antibodies as efficiently as normal mice. Proc Natl Acad Sci USA 111:5153-8.

14. Abend J, Dragic Z, Feire A L, Knapp M, Kovacs S, Traggiai E, Wang L, Wang Y, Wu D, Xu F. 2017. Polyomavirus neutralizing antibodies WO 2017/046676 A1.

15. Vu D, Shah T, Ansari J, Naraghi R, Min D. 2015. Efficacy of intravenous immunoglobulin in the treatment of persistent BK viremia and BK virus nephropathy in renal transplant recipients. Transplant Proc 47:394-8.
16. Kable K, Davies C D, O'Connell P J, Chapman J R, Nankivell B J. 2017. Clearance of BK Virus Nephropathy by Combination Antiviral Therapy With Intravenous Immunoglobulin. Transplant Direct 3:e142.
17. Sener A, House A A, Jevnikar A M, Boudville N, McAlister V C, Muirhead N, Rehman F, Luke P P. 2006. Intravenous immunoglobulin as a treatment for BK virus associated nephropathy: one-year follow-up of renal allograft recipients. Transplantation 81:117-20.
18. Sharma A P, Moussa M, Casier S, Rehman F, Filler G, Grimmer J. 2009. Intravenous immunoglobulin as rescue therapy for BK virus nephropathy. Pediatr Transplant 13:123-9.
19. Nickeleit V, Singh H K, Rivier L H. 2018. Antibodies Can Extenuate Polyomavirus Infections. J Am Soc Nephrol 29:1577.
20. Buck C B, Thompson C D. 2007. Production of papillomavirus-based gene transfer vectors. Curr Protoc Cell Biol Chapter 26:Unit 26 1.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists (e.g., in Markush group format), each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included in such ranges unless otherwise specified. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the disclosure, as defined in the following claims.

What is claimed is:

1. An isolated anti-VP1 antibody or antigen binding fragment thereof comprising a heavy chain variable region (VH) having three complementarity determining regions (CDRs) of HCDR1, HCDR2, and HCDR3, and a light chain variable region (VL) having three CDRs of LCDR1, LCDR2, and LCDR3, wherein:

(a) HCDR1 comprises SEQ ID NO: 113,
    HCDR2 comprises SEQ ID NO: 114,
    HCDR3 comprises SEQ ID NO: 115,
    LCDR1 comprises SEQ ID NO: 116,
    LCDR2 comprises SEQ ID NO: 117, and
    LCDR3 comprises SEQ ID NO: 118;
(b) HCDR1 comprises SEQ ID NO: 97,
    HCDR2 comprises SEQ ID NO: 98,
    HCDR3 comprises SEQ ID NO: 99, 131, or 139,
    LCDR1 comprises SEQ ID NO: 100,
    LCDR2 comprises SEQ ID NO: 101, and
    LCDR3 comprises SEQ ID NO: 102;
(c) HCDR1 comprises SEQ ID NO: 1,
    HCDR2 comprises SEQ ID NO: 2,
    HCDR3 comprises SEQ ID NO: 3, LCDR1 comprises SEQ ID NO: 4,
    LCDR2 comprises SEQ ID NO: 5, and
    LCDR3 comprises SEQ ID NO: 6;
(d) HCDR1 comprises SEQ ID NO: 9,
    HCDR2 comprises SEQ ID NO: 10,
    HCDR3 comprises SEQ ID NO: 11,
    LCDR1 comprises SEQ ID NO: 12,
    LCDR2 comprises SEQ ID NO: 13, and
    LCDR3 comprises SEQ ID NO: 14;
(e) HCDR1 comprises SEQ ID NO: 17,
    HCDR2 comprises SEQ ID NO: 18,
    HCDR3 comprises SEQ ID NO: 19,
    LCDR1 comprises SEQ ID NO: 20,
    LCDR2 comprises SEQ ID NO: 21, and
    LCDR3 comprises SEQ ID NO: 22;
(f) HCDR1 comprises SEQ ID NO: 25,
    HCDR2 comprises SEQ ID NO: 26,
    HCDR3 comprises SEQ ID NO: 27,
    LCDR1 comprises SEQ ID NO: 28,
    LCDR2 comprises SEQ ID NO: 29, and
    LCDR3 comprises SEQ ID NO: 30;

(g) HCDR1 comprises SEQ ID NO: 33,
  HCDR2 comprises SEQ ID NO: 34,
  HCDR3 comprises SEQ ID NO: 35,
  LCDR1 comprises SEQ ID NO: 36,
  LCDR2 comprises SEQ ID NO: 37, and
  LCDR3 comprises SEQ ID NO: 38;

(h) HCDR1 comprises SEQ ID NO: 41,
  HCDR2 comprises SEQ ID NO: 42,
  HCDR3 comprises SEQ ID NO: 43,
  LCDR1 comprises SEQ ID NO: 44,
  LCDR2 comprises SEQ ID NO: 45, and
  LCDR3 comprises SEQ ID NO: 46;

(i) HCDR1 comprises SEQ ID NO: 49,
  HCDR2 comprises SEQ ID NO: 50,
  HCDR3 comprises SEQ ID NO: 51,
  LCDR1 comprises SEQ ID NO: 52,
  LCDR2 comprises SEQ ID NO: 53, and
  LCDR3 comprises SEQ ID NO: 54;

(j) HCDR1 comprises SEQ ID NO: 65,
  HCDR2 comprises SEQ ID NO: 66,
  HCDR3 comprises SEQ ID NO: 67,
  LCDR1 comprises SEQ ID NO: 68,
  LCDR2 comprises SEQ ID NO: 69, and
  LCDR3 comprises SEQ ID NO: 70;

(k) HCDR1 comprises SEQ ID NO: 73,
  HCDR2 comprises SEQ ID NO: 74,
  HCDR3 comprises SEQ ID NO: 75,
  LCDR1 comprises SEQ ID NO: 76,
  LCDR2 comprises SEQ ID NO: 77, and
  LCDR3 comprises SEQ ID NO: 78;

(l) HCDR1 comprises SEQ ID NO: 81,
  HCDR2 comprises SEQ ID NO: 82,
  HCDR3 comprises SEQ ID NO: 83,
  LCDR1 comprises SEQ ID NO: 84,
  LCDR2 comprises SEQ ID NO: 85, and
  LCDR3 comprises SEQ ID NO: 86;

(m) HCDR1 comprises SEQ ID NO: 89,
  HCDR2 comprises SEQ ID NO: 90,
  HCDR3 comprises SEQ ID NO: 91,
  LCDR1 comprises SEQ ID NO: 92,
  LCDR2 comprises SEQ ID NO: 93, and
  LCDR3 comprises SEQ ID NO: 94;

(n) HCDR1 comprises SEQ ID NO: 105,
  HCDR2 comprises SEQ ID NO: 106,
  HCDR3 comprises SEQ ID NO: 107,
  LCDR1 comprises SEQ ID NO: 108,
  LCDR2 comprises SEQ ID NO: 109, and
  LCDR3 comprises SEQ ID NO: 110;

(o) HCDR1 comprises SEQ ID NO: 121,
  HCDR2 comprises SEQ ID NO: 122,
  HCDR3 comprises SEQ ID NO: 123,
  LCDR1 comprises SEQ ID NO: 124,
  LCDR2 comprises SEQ ID NO: 125, and
  LCDR3 comprises SEQ ID NO: 126;

(p) HCDR1 comprises SEQ ID NO: 145,
  HCDR2 comprises SEQ ID NO: 146,
  HCDR3 comprises SEQ ID NO: 147,
  LCDR1 comprises SEQ ID NO: 148,
  LCDR2 comprises SEQ ID NO: 149, and
  LCDR3 comprises SEQ ID NO: 150;

(q) HCDR1 comprises SEQ ID NO: 153,
  HCDR2 comprises SEQ ID NO: 154,
  HCDR3 comprises SEQ ID NO: 155,
  LCDR1 comprises SEQ ID NO: 156,
  LCDR2 comprises SEQ ID NO: 157, and
  LCDR3 comprises SEQ ID NO: 158;

(r) HCDR1 comprises SEQ ID NO: 161,
  HCDR2 comprises SEQ ID NO: 162,
  HCDR3 comprises SEQ ID NO: 163,
  LCDR1 comprises SEQ ID NO: 164,
  LCDR2 comprises SEQ ID NO: 165, and
  LCDR3 comprises SEQ ID NO: 166;

(s) HCDR1 comprises SEQ ID NO: 169,
  HCDR2 comprises SEQ ID NO: 170,
  HCDR3 comprises SEQ ID NO: 171,
  LCDR1 comprises SEQ ID NO: 172,
  LCDR2 comprises SEQ ID NO: 173, and
  LCDR3 comprises SEQ ID NO: 174; or (t) HCDR1 comprises SEQ ID NO: 177,
  HCDR2 comprises SEQ ID NO: 178,
  HCDR3 comprises SEQ ID NO: 179,
  LCDR1 comprises SEQ ID NO: 180,
  LCDR2 comprises SEQ ID NO: 181, and
  LCDR3 comprises SEQ ID NO: 182.

2. The isolated antibody or antigen binding fragment thereof of claim 1, wherein:

(a) the VH comprises at least 90% sequence identity to any one of SEQ ID NO: 7, 15, 23, 31, 39, 47, 55, 23, 71, 79, 87, 95, 103, 111, 119, 127, 135, 143, 151, 159, 167, 175, or 183; and (b) the VL comprises at least 90% sequence identity to any one of SEQ ID NO: 8, 16, 24, 32, 40, 48, 56, 24, 72, 80, 88, 96, 104, 112, 120, 128, 136, 144, 152, 160,168, 176, or 184.

3. The isolated antibody or antigen binding fragment thereof of claim 2, wherein, (a) VH comprises SEQ ID NO: 119, and VL comprises SEQ ID NO: 120;

(b) VH comprises SEQ ID NO: 103, and VL comprises SEQ ID NO: 104;

(c) VH comprises SEQ ID NO: 135, and VL comprises SEQ ID NO: 136;

(d) VH comprises SEQ ID NO: 143, and VL comprises SEQ ID NO: 144;

(e) VH comprises SEQ ID NO: 7, and VL comprises SEQ ID NO: 8;

(f) VH comprises SEQ ID NO: 15, and VL comprises SEQ ID NO: 16;

(g) VH comprises SEQ ID NO: 31, and VL comprises SEQ ID NO: 32;

(h) VH comprises SEQ ID NO: 39, and VL comprises SEQ ID NO: 40;

(i) VH comprises SEQ ID NO: 47, and VL comprises SEQ ID NO: 48;

(j) VH comprises SEQ ID NO: 55, and VL comprises SEQ ID NO: 56;

(k) VH comprises SEQ ID NO: 23, and VL comprises SEQ ID NO: 24;

(l) VH comprises SEQ ID NO: 71, and VL comprises SEQ ID NO: 72;

(m) VH comprises SEQ ID NO: 79, and VL comprises SEQ ID NO: 80;

(n) VH comprises SEQ ID NO: 87, and VL comprises SEQ ID NO: 88;

(o) VH comprises SEQ ID NO: 95, and VL comprises SEQ ID NO: 96;

(p) VH comprises SEQ ID NO: 111, and VL comprises SEQ ID NO: 112;

(q) VH comprises SEQ ID NO: 127, and VL comprises SEQ ID NO: 128;

(r) VH comprises SEQ ID NO: 151, and VL comprises SEQ ID NO: 152;

(s) VH comprises SEQ ID NO: 159, and VL comprises SEQ ID NO: 160;

(t) VH comprises SEQ ID NO: 167, and VL comprises SEQ ID NO: 168;

(u) VH comprises SEQ ID NO: 175, and VL comprises SEQ ID NO: 176; or (v) VH comprises SEQ ID NO: 183, and VL comprises SEQ ID NO: 184.

4. The antibody or antigen binding fragment thereof of claim 1, wherein the VH of the antibody or antigen binding fragment thereof comprises heavy chain framework regions HFR1, HFR2, HFR3, HFR4, and wherein the VL of the antibody or antigen binding fragment thereof comprises light chain framework regions LFR1, LFR2, LFR3, LFR4, wherein:

(a) the HFR1 region comprises the amino acid sequence of any one of SEQ ID NOs: 185, 193, 197, 205, 213, 226, 234, 241, 250, or 269;

(b) the HFR2 region comprises the amino acid sequence of any one of SEQ ID NOs: 186, 194, 198, 206, 214, 223, 227, 232, 242, or 253;

(c) the HFR3 region comprises the amino acid sequence of any one of SEQ ID NOs: 187, 195, 199, 207, 215, 219, 224, 228, 233, 235, 243, 251, 254, 258, 259, 262, 265, 267, or 270;

(d) the HFR4 region comprises the amino acid sequence of any one of SEQ ID NOs: 188, 200, 208, 220, 229, 236, 244, or 271;

(e) the LFR1 region comprises the amino acid sequence of any one of SEQ ID NOs: 189, 201, 209, 237, 245, 255, or 260;

(f) the LFR2 region comprises the amino acid sequence of any one of SEQ ID NOs: 190, 202, 210, 216, 221, 225, 230, 238, 246, 261, 263, or 272;

(g) the LFR3 region comprises the amino acid sequence of any one of SEQ ID NOs: 191, 196, 203, 211, 217, 222, 230, 239, 247, 249, 252, 256, 264, 266, 268, or 273; and (h) the LFR4 region comprises the amino acid sequence of any one of SEQ ID NOs: 192, 204, 212, 218, 240, 248, or 257.

5. The antibody or antigen binding fragment thereof of claim 1, wherein the antibody or antigen binding fragment thereof further comprises a heavy chain constant (CH) domain and a light chain constant (CL) domain, wherein:

(a) said CH domain is selected from the group consisting of IgG, IgG1, IgG2, IgG2a, IgG2b, IgG2c, IgG3, IgG4, IgA, IgA1, IgA2, IgD, IgM, and IgE constant domains, and comprises a sequence with at least 90% sequence identity to one of SEQ ID NOs: 274-290; and (b) said CL domain is selected from the group consisting of Ig kappa and Ig lambda constant domains, and comprises a sequence with at least 90% sequence identity to one of SEQ ID NOs: 291-301.

6. The antibody or antigen binding fragment thereof of claim 1, wherein the antibody or antigen binding fragment thereof is a monoclonal antibody, a chimeric antibody, a humanized antibody, a human engineered antibody, a single chain antibody (scFv), or an antibody fragment.

7. The antibody or antigen binding fragment thereof of claim 1, wherein the antibody or antigen binding fragment thereof has reduced glycosylation, no glycosylation, or is hypofucosylated.

8. A pharmaceutical composition comprising the antibody or antigen binding fragment thereof of claim 1 and a pharmaceutically acceptable excipient.

9. A method of neutralizing a BK virus infection in a subject in need thereof, the method comprising administering an effective amount of the antibody or antigen binding fragment thereof of claim 1 to the subject.

10. The method of claim 9, wherein the subject is diagnosed with BK virus infection or BK viremia.

11. A method of treating or reducing the likelihood of a BK virus or JC virus associated disorder, the method comprising administering to a subject in need thereof an effective amount of the antibody or antigen binding fragment thereof of claim 1, wherein the BK virus or JC virus associated disorder is selected from the group consisting of transplant rejection, graft-versus-host disease (GvHD), nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, immune reconstitution inflammatory syndrome (IRIS).

12. The method of claim 11, wherein the antibody or antigen binding fragment thereof is administered via injection or infusion.

13. The method of claim 11, the method further comprising administering an additional therapeutic agent, wherein the therapeutic agent is an immunosuppressive agent.

14. The method of claim 13, wherein the immunosuppressive agent is a monophosphate dehydrogenase inhibitor, a purine synthesis inhibitor, a calcineurin inhibitor, or an mTOR inhibitor.

15. The method of claim 13, wherein the immunosuppressive agent is mycophenolate mofetil (MMF), mycophenolate sodium, azathioprine, tacrolimus, sirolimus, or cyclosporine.

16. The method of claim 11, wherein the therapeutic agent is an additional anti-VP1 antibody.

17. A nucleic acid that encodes the antibody or antigen binding fragment of claim 1.

18. A vector comprising the nucleic acid of claim 17.

19. An isolated host cell comprising the vector of claim 18.

20. A method of reducing the risk of transplant rejection in a transplant recipient receiving a donor organ, comprising (i) determining serotype of BK virus present in the donor organ, (ii) selecting an antibody or antigen binding fragment thereof of claim 1, wherein the antibody or antigen binding fragment thereof neutralizes the serotype of BK virus present in the donor organ, and (iii) administering the selected antibody or antigen binding fragment thereof to the transplant recipient via injection or infusion.

* * * * *